(12) United States Patent
Blagg et al.

(10) Patent No.: US 10,030,006 B2
(45) Date of Patent: Jul. 24, 2018

(54) COUMARIN BASED HSP90 INHIBITORS WITH UREA AND ETHER SUBSTITUENTS

(71) Applicant: University of Kansas, Lawrence, KS (US)

(72) Inventors: Brian S. J. Blagg, Lawrence, KS (US); Huiping Zhao, Lawrence, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 15/035,610

(22) PCT Filed: Nov. 11, 2014

(86) PCT No.: PCT/US2014/065059
§ 371 (c)(1),
(2) Date: May 10, 2016

(87) PCT Pub. No.: WO2015/070238
PCT Pub. Date: May 14, 2015

(65) Prior Publication Data
US 2016/0289217 A1    Oct. 6, 2016

Related U.S. Application Data

(60) Provisional application No. 61/902,517, filed on Nov. 11, 2013.

(51) Int. Cl.
| | | |
|---|---|---|
| C07D 405/12 | (2006.01) | |
| C07D 405/14 | (2006.01) | |
| C07D 413/12 | (2006.01) | |
| A61K 31/352 | (2006.01) | |
| A61K 31/4025 | (2006.01) | |
| A61K 31/453 | (2006.01) | |
| A61K 31/496 | (2006.01) | |
| A61K 31/5377 | (2006.01) | |
| A61K 45/06 | (2006.01) | |
| C07D 311/16 | (2006.01) | |
| G16H 50/50 | (2018.01) | |

(52) U.S. Cl.
CPC .......... *C07D 405/12* (2013.01); *A61K 31/352* (2013.01); *A61K 31/4025* (2013.01); *A61K 31/453* (2013.01); *A61K 31/496* (2013.01); *A61K 31/5377* (2013.01); *A61K 45/06* (2013.01); *C07D 311/16* (2013.01); *C07D 405/14* (2013.01); *C07D 413/12* (2013.01); *G16H 50/50* (2018.01)

(58) Field of Classification Search
None
See application file for complete search history.

(56) References Cited

U.S. PATENT DOCUMENTS

| | | | | |
|---|---|---|---|---|
| 3,890,297 A | * | 6/1975 | Dolak | .................. C07H 17/075 536/17.9 |
| 2009/0163709 A1 | | 6/2009 | Blagg | |
| 2012/0252745 A1 | | 10/2012 | Blagg et al. | |

FOREIGN PATENT DOCUMENTS

| | | |
|---|---|---|
| WO | WO 2010/096650 | 8/2010 |
| WO | WO 2011/041593 | 4/2011 |

OTHER PUBLICATIONS

Lubbers et al., Design, synthesis, and structure-activity relationship studies of ATP analogues as DNA gyrase inhibitors, Bioorganic & Medicinal Chemistry Letters (2000), 10(8), 821-826.*

Althaus et al., Novenamines as inhibitors of two independent enzymes during DNA replication in a toluenized *Escherichia coli* cell system, Biochemical Pharmacology, vol. 51, Issue 10, May 17, 1996, pp. 1373-1378.*

(Continued)

*Primary Examiner* — Svetlana M Ivanova
(74) *Attorney, Agent, or Firm* — Parker Highlander PLLC

(57) ABSTRACT

Compounds of the formulas: wherein: $R_1$-$R_4$, $X_1$, $Y_1$, and A are as defined herein are provided. Pharmaceutical compositions of the compounds are also provided. In some aspects, these compounds are are useful for the treatment of a disease or disorder. In some embodiments, the disease or disorder is a proliferative disease such as cancer.

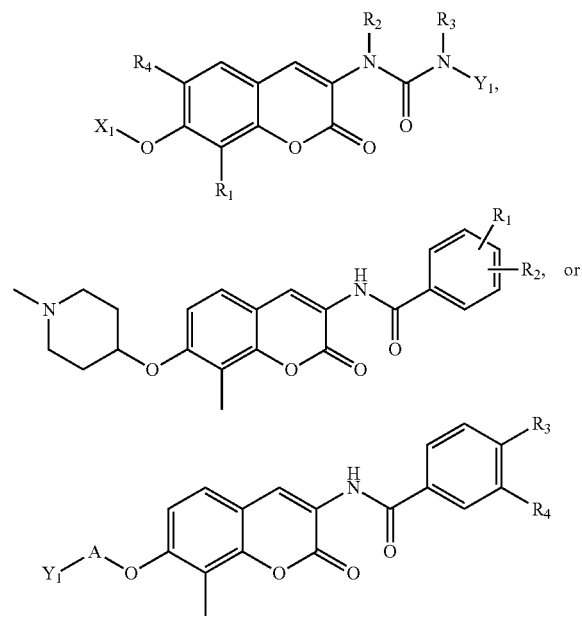

17 Claims, 4 Drawing Sheets

(56) References Cited

OTHER PUBLICATIONS

Cron et al, Semisynthetic antibiotics derived from coumermycin, Progr. Antimicrob. Anticancer Chemother., Proc. Int. Congr. Chemother., 6th (1970), Meeting Date 1969, vol. 2, 1069-82 Publisher: Univ. Park Press, Baltimore, Md. CODEN: 22PYAN, STN document No. 75:86843.*
Keil et al, Preparation of semisynthetic coumermycin A1 derivatives. IV. Aliphatic acyl and related derivatives of 3-amino-4-hydroxy-8-methyl-7-[3-0-(5-methyl-2-pyrrolylcarbonyl)noviosyloxy]coumarin, Antimicrobial Agents and Chemotherapy (1961-70) (1970), Volume Date 1969 200-8 CODEN: AACHAX; ISSN: 0074-9923, STN document No. 75:20897.*
Price et al, Semisynthetic coumermycins; structure-activity relations, Applied Microbiology (1970), 19(1), 14-26 CODEN: APMBAY; ISSN: 0003-6919, STN document No. 72:77109.*
Burlison et al., "Development of novobiocin analogues that manifest anti-proliferative activity against several cancer cell lines", *J. Org. Chem.*, 73:2130, 2008.
Burlison et al., "Novobiocin: redesigning a DNA gyrase inhibitor for selective inhibition of hsp90", *J. Am. Chem. Soc.*, 128:15529, 2006.
Donnelly, et al., "Cytotoxic sugar analogues of an optimized novobiocin scaffold," *MedChemComm*, 1(2):165-170, 2010.
Huang, et al., "Molecular Design of Anticancer Drug Leads Based on Three-Dimensional Quantitative Structure-Activity Relationship," *J. Chem. Info. Modeling*, 51(8):1999-2006, 2011.
International Preliminary Report on Patentability issued in International Application No. PCT/US2014/065059, dated May 26, 2016.
International Search Report and Written Opinion issued in International Application No. PCT/US2014/065059, dated Jun. 1, 2015.
Invitation to Pay Additional Fees and Partial Search Report issued in International Application No. PCT/US2014/065059, dated Mar. 11, 2015.
Moroni, et al., "Exploiting Conformational Dynamics in Drug Discovery: Design of C-Terminal Inhibitors of Hsp90 with Improved Activities," *J. Chem. Info. Modeling*, 54(1):195-208, 2014.

PubChem Compound Accession No. CID71716931, retrieved from NIH, dated Sep. 23, 2013.
PubChem Compound Accession No. CID71718170, retrieved from NIH, dated Sep. 23, 2013.
PubChem Compound Accession No. CID71718754, retrieved from NIH, dated Sep. 23, 2013.
PubChem Compound Accession No. CID71720592, retrieved from NIH, dated Sep. 23, 2013.
Sadikot, et al., "Development of a High-Throughput Screening Cancer Cell-Based Luciferase Refolding Assay for Identifying Hsp90 Inhibitors," *Assay and Drug Development Technologies*, 11(8):478-488, 2013.
Yu et al., "Hsp90 inhibitors identified from a library of novobiocin analogues", *J. Am. Chem. Soc.*, 127:12778, 2005.
Zhang, et al., "Simplified aminocoumarin analogues as anticancer agents: Amino isosteric replacement in the noviose moiety resulted in substantial enhancement of antiproliferative activity," *Chinese Chemical Letters*, 24(8):719-722, 2013.
Zhao and Blagg, "Novobiocin analogues with second-generation noviose surrogates," *Bioorg & Med. Chem. Lett.*, 23(2):552-557, 2013.
Zhao et al., "Engineering an antibiotic to fight cancer: optimization of the novobiocin scaffold to produce anti-proliferative agents," *Journal of Medicinal Chemistry*, 54(11):3839-3853, 2011.
Zhao et al., "Identification and initial SAR of silybin: An Hsp90 inhibitor". *Bioorg. Med. Chem. Lett.*, 21:2659-2664, 2011.
Zhao, et al.,"3-Aryleoumarin Derivatives Manifest Anti-Proliferative Activity through Hsp90 Inhibition," *ACS Med. Chem. Lett.*, 3(4):327-331, 2012.
Zhao, et al.,"3D-QSAR-Assisted Design, Synthesis, and Evaluation of Novobiocin Analogues," *ACS Med. Chem. Lett.*, 4(1):57-62, 2013.
Zhao, et al., "Identification of a New Scaffold for Hsp90 C-Terminal Inhibition," *ACS Med. Chem. Lett.*, 5(1):84-88, 2014.
Zhao, et al., "Synthesis and Evaluation of Noviose Replacements on Novobiocin That Manifest Antiproliferative Activity," *ACS Med. Chem. Lett.*, 1(7):311-315, 2010.

* cited by examiner

COUMARIN BASED HSP90 INHIBITORS WITH UREA AND ETHER SUBSTITUENTS

This application is a national phase application under 35 U.S.C. § 371 of International Application No. PCT/US2014/065059, filed Nov. 11, 2014, which claims the benefit of U.S. Provisional Application 61/902,517, filed on Nov. 11, 2013, the entire content of which are incorporated herein by reference.

This invention was made with government support under CA120458 awarded by the National Institute of Health and QH815179 awarded by the Department of Defense Prostate Cancer Research Program. The government has certain rights in the invention.

BACKGROUND OF THE INVENTION

I. Field of the Invention

The present invention relates generally to the fields of biology, chemistry, and medicine. More particularly, it concerns compounds, compositions and methods for the treatment and prevention of diseases such as cancer and other proliferative diseases.

II. Description of Related Art

The 90 kDa heat shock protein (Hsp90) is a highly conserved molecular chaperone that plays a pivotal role in the maintenance of protein homeostasis and sustains cell viability during cellular stress (Taipale, et al., 2010). Abnormal expression of Hsp90 has been implicated in a variety of disease states. In cancer, elevated Hsp90 levels are critical for the stabilization and function of oncogenic proteins distributed amongst all six hallmarks of cancer (Hanahan and Weinberg, 2011). Malignant or mutated oncogenic proteins, such as Her-2, Raf-1, Akt, CDK4, Src, Flt-3, hTert, c-Met, etc, are distributed amongst all six hallmarks of cancer and are highly dependent upon the Hsp90 protein folding machinery for their ability to promote cell survival, proliferation, and adaptation (Hanahan and Weinberg, 2011). Therefore, small molecules that inhibit the Hsp90 folding machinery can simultaneously attack multiple signaling pathways that are essential for cancer cell survival, adaptation, proliferation, and provides a unique opportunity for development of cancer therapeutics (Blagg and Kerr, 2006). In such scenarios, Hsp90 inhibition has been implicated in the simultaneous disruption of multiple oncogenic pathways and eventually leads to cancer cell death, while largely sparing normal cells.

Several small molecules that inhibit the N-terminus Hsp90 function are currently in clinical trials for the treatment of various cancers in order to demonstrate the viability of this treatment paradigm (Neckers and Workman, 2012). Unfortunately, small molecules that target the Hsp90 N-terminus have been reported to lead to the concomitant heat shock response induced upon administration of such agents compromises their efficacy and allows cancer cell survival, which may lead to resistance and metastasis (Whitesell, et al., 2012). Further studies have demonstrated the existence of a second nucleotide-binding site at the Hsp90 C-terminus and these small molecules have been shown to bind this region and induce a dose-dependent degradation of Hsp90 client proteins in a manner similar to Hsp90 N-terminal inhibitors (Marcu, et al., 2000). In contrast to N-terminal inhibitors, C-terminal inhibitors have been shown not to induce the pro-survival heat shock response, and these compounds therefore provide an alternative model for Hsp90 modulation (Eskew, et al., 2011; Shelton, et al., 2009; and Conde, et al., 2009). Because the Hsp90 C-terminus is responsible for mediating the interactions with co-chaperones such as HOP (Hsp70-Hsp90 organization protein) and the immunophilins (e.g., FK506 binding protein) to facilitate client protein maturation (Cox and Johnson, 2011, Robson and James, 2012), small molecule modulation of this region exhibits activities not observed with N-terminal inhibitors (Eskew, et al., 2011, Zhang, et al., 2012). Novobiocin was identified as the first Hsp90 C-terminal inhibitor in 2000; albeit with low efficiency (~700 µM in SKBr3 cells) (Marcu, et al., 2000). Subsequent modification to novobiocin has led to the elucidation of structure-activity relationships and analogues that exhibit superior inhibitory activity (Yu, et al., 2005; Burlison, et al., 2008; Zhao, et al., 2011; Donnelly, et al., 2010; Zhao, et al., 2011). Deletion of both the 4-hydroxy substituent on the coumarin ring and the 3'-carbamoyl group on noviose resulted in DHN2, which transformed novobiocin from a DNA gyrase inhibitor to a selective Hsp90 inhibitor (FIG. 1) (Burlison, et al., 2006). Subsequent replacement of the synthetically complex noviose sugar with readily available amines led to molecules that manifested increased anti-proliferative activity and solubility (FIG. 1, NA-1 and NA-2) (Zhao, et al., 2011). Further improvements on coumarin core to produce other Hsp90 C-terminal inhibitors are of commercial interest.

SUMMARY OF THE INVENTION

The present disclosure provides novel compounds, including novobiocin analogs with anti-proliferative properties, pharmaceutical compositions thereof, methods for their manufacture, and methods for their use.

In one aspect of the present disclosure there are provided compounds of the formula:

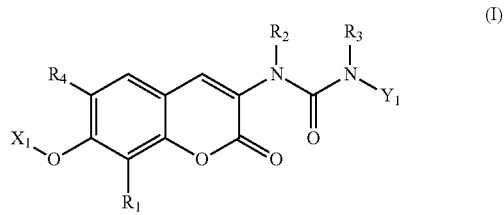

wherein: $R_1$ and $R_2$ are each independently selected from hydrogen, alkyl$_{(C \leq 12)}$, or substituted alkyl$_{(C \leq 12)}$; $R_3$ is hydrogen, alkyl$_{(C \leq 12)}$, aralkyl$_{(C \leq 12)}$, substituted alkyl$_{(C \leq 12)}$, or substituted aralkyl$_{(C \leq 12)}$; or $R_3$ and $Y_1$ are taken together as defined below; $R_4$ is hydrogen, alkyl$_{(C \leq 12)}$, alkoxy$_{(C \leq 12)}$, substituted alkyl$_{(C \leq 12)}$, or substituted alkoxy$_{(C \leq 12)}$; $X_1$ is -alkanediyl$_{(C \leq 8)}$-heterocycloalkyl$_{(C \leq 12)}$, -alkanediyl$_{(C \leq 8)}$-amino$_{(C \leq 12)}$, -alkanediyl$_{(C \leq 8)}$-alkylamino$_{(C \leq 12)}$, -alkanediyl$_{(C \leq 8)}$-dialkylamino$_{(C \leq 12)}$, heterocycloalkyl$_{(C \leq 12)}$, or a substituted version of any of these groups; and $Y_1$ is alkyl$_{(C \leq 12)}$, cycloalkyl$_{(C \leq 12)}$, adamantyl$_{(C \leq 18)}$, aryl$_{(C \leq 18)}$, aralkyl$_{(C \leq 18)}$, acyl$_{(C \leq 12)}$, -alkanediyl$_{(C \leq 8)}$-cycloalkyl$_{(C \leq 12)}$, -arenediyl$_{(C \leq 12)}$-alkene$_{(C \leq 8)}$, -arenediyl$_{(C \leq 12)}$-aryl$_{(C \leq 12)}$, -arenediyl$_{(C \leq 12)}$-aralkyl$_{(C \leq 12)}$, -arenediyl$_{(C \leq 12)}$-aryloxy$_{(C \leq 12)}$, or a substituted version of any of these groups; or $R_3$ and $Y_1$ are taken together and are alkanediyl$_{(C \leq 8)}$, alkylaminodiyl$_{(C \leq 8)}$, alkoxydiyl$_{(C \leq 8)}$, or a substituted version of any of these groups; or

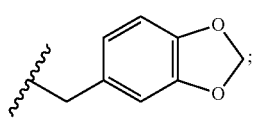 [SMILES: *Cc1ccc2c(c1)OCO2]

or a pharmaceutically acceptable salt thereof. In some embodiments, the compound is further defined as:

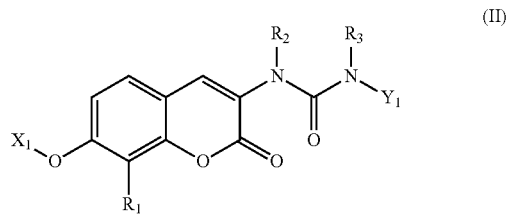

(II)

wherein: $R_1$ and $R_2$ are each independently selected from hydrogen, alkyl$_{(C \leq 12)}$, or substituted alkyl$_{(C \leq 12)}$; $R_3$ is hydrogen, alkyl$_{(C \leq 12)}$, aralkyl$_{(C \leq 12)}$, substituted alkyl$_{(C \leq 12)}$, or substituted aralkyl$_{(C \leq 12)}$; or $R_3$ and $Y_1$ are taken together as defined below; $X_1$ is -alkanediyl$_{(C \leq 8)}$-heterocycloalkyl$_{(C \leq 12)}$, -alkanediyl$_{(C \leq 8)}$-amino$_{(C \leq 12)}$, -alkanediyl$_{(C \leq 8)}$-alkylamino$_{(C \leq 12)}$, -alkanediyl$_{(C \leq 8)}$-dialkylamino$_{(C \leq 12)}$, heterocycloalkyl$_{(C \leq 12)}$, or a substituted version of any of these groups; and $Y_1$ is alkyl$_{(C \leq 12)}$, cycloalkyl$_{(C \leq 12)}$, adamantyl$_{(C \leq 18)}$, aryl$_{(C \leq 18)}$, aralkyl$_{(C \leq 18)}$, acyl$_{(C \leq 12)}$, -alkanediyl$_{(C \leq 8)}$-cycloalkyl$_{(C \leq 12)}$, -arenediyl$_{(C \leq 12)}$-alkene$_{(C \leq 8)}$, -arenediyl$_{(C \leq 12)}$-aryl$_{(C \leq 12)}$, -arenediyl$_{(C \leq 12)}$-aralkyl$_{(C \leq 12)}$, -arenediyl$_{(C \leq 12)}$-aryloxy$_{(C \leq 12)}$, or a substituted version of any of these groups; or $R_3$ and $Y_1$ are taken together and are alkanediyl$_{(C \leq 8)}$, alkylaminodiyl$_{(C \leq 8)}$, alkoxydiyl$_{(C \leq 8)}$, or a substituted version of any of these groups; or

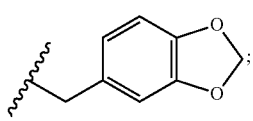 [SMILES: *Cc1ccc2c(c1)OCO2]

or a pharmaceutically acceptable salt thereof. In some embodiments, the compound is further defined as:

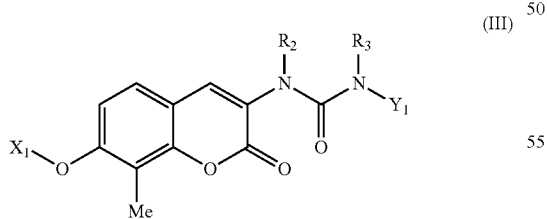

(III)

wherein: $R_2$ is hydrogen, alkyl$_{(C \leq 12)}$, or substituted alkyl$_{(C \leq 12)}$; $R_3$ is hydrogen, alkyl$_{(C \leq 12)}$, aralkyl$_{(C \leq 12)}$, substituted alkyl$_{(C \leq 12)}$, or substituted aralkyl$_{(C \leq 12)}$; or $R_3$ and $Y_1$ are taken together as defined below; $X_1$ is -alkanediyl$_{(C \leq 8)}$-heterocycloalkyl$_{(C \leq 12)}$, -alkanediyl$_{(C \leq 8)}$-amino$_{(C \leq 12)}$, -alkanediyl$_{(C \leq 8)}$-alkylamino$_{(C \leq 12)}$, -alkanediyl$_{(C \leq 8)}$-dialkylamino$_{(C \leq 12)}$, heterocycloalkyl$_{(C \leq 12)}$, or a substituted version of any of these groups; and $Y_1$ is alkyl$_{(C \leq 12)}$, cycloalkyl$_{(C \leq 12)}$, adamantyl$_{(C \leq 18)}$, aryl$_{(C \leq 18)}$, aralkyl$_{(C \leq 18)}$, acyl$_{(C \leq 12)}$, -alkanediyl$_{(C \leq 8)}$-cycloalkyl$_{(C \leq 12)}$, -arenediyl$_{(C \leq 12)}$-alkene$_{(C \leq 8)}$, -arenediyl$_{(C \leq 12)}$-aryl$_{(C \leq 12)}$, -arenediyl$_{(C \leq 12)}$-aralkyl$_{(C \leq 12)}$, -arenediyl$_{(C \leq 12)}$-aryloxy$_{(C \leq 12)}$, or a substituted version of any of these groups; or $R_3$ and $Y_1$ are taken together and are alkanediyl$_{(C \leq 8)}$, alkylaminodiyl$_{(C \leq 8)}$, alkoxydiyl$_{(C \leq 8)}$, or a substituted version of any of these groups; or

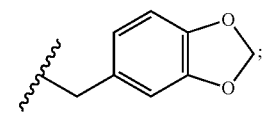 [SMILES: *Cc1ccc2c(c1)OCO2]

or a pharmaceutically acceptable salt thereof. In some embodiments, the compound is further defined as:

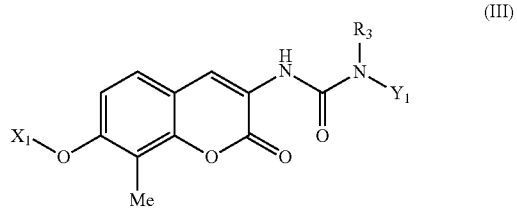

(III)

wherein: $R_3$ is hydrogen, alkyl$_{(C \leq 12)}$, aralkyl$_{(C \leq 12)}$, substituted alkyl$_{(C \leq 12)}$, or substituted aralkyl$_{(C \leq 12)}$; or $R_3$ and $Y_1$ are taken together as defined below; $X_1$ is -alkanediyl$_{(C \leq 8)}$-heterocycloalkyl$_{(C \leq 12)}$, -alkanediyl$_{(C \leq 8)}$-amino$_{(C \leq 12)}$, -alkanediyl$_{(C \leq 8)}$-alkylamino$_{(C \leq 12)}$, -alkanediyl$_{(C \leq 8)}$-dialkylamino$_{(C \leq 12)}$, heterocycloalkyl$_{(C \leq 12)}$, or a substituted version of any of these groups; and $Y_1$ is alkyl$_{(C \leq 12)}$, cycloalkyl$_{(C \leq 12)}$, adamantyl$_{(C \leq 18)}$, aryl$_{(C \leq 18)}$, aralkyl$_{(C \leq 18)}$, acyl$_{(C \leq 12)}$, -alkanediyl$_{(C \leq 8)}$-cycloalkyl$_{(C \leq 12)}$, -arenediyl$_{(C \leq 12)}$-alkene$_{(C \leq 8)}$, -arenediyl$_{(C \leq 12)}$-aryl$_{(C \leq 12)}$, -arenediyl$_{(C \leq 12)}$-aralkyl$_{(C \leq 12)}$, -arenediyl$_{(C \leq 12)}$-aryloxy$_{(C \leq 12)}$, or a substituted version of any of these groups; or $R_3$ and $Y_1$ are taken together and are alkanediyl$_{(C \leq 8)}$, alkylaminodiyl$_{(C \leq 8)}$, alkoxydiyl$_{(C \leq 8)}$, or a substituted version of any of these groups; or

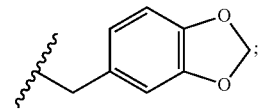 [SMILES: *Cc1ccc2c(c1)OCO2]

or a pharmaceutically acceptable salt thereof. In some embodiments, the compound is further defined as:

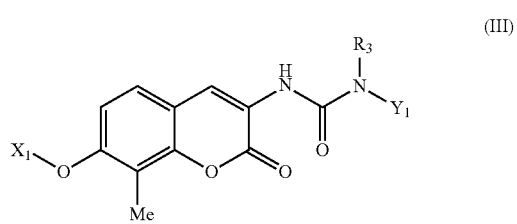

(III)

wherein: $R_3$ is hydrogen, alkyl$_{(C \leq 12)}$, substituted alkyl$_{(C \leq 12)}$, aralkyl$_{(C \leq 12)}$, or substituted aralkyl$_{(C \leq 12)}$; or $R_3$ and $Y_1$ are taken together as defined below; $X_1$ is heterocycloalkyl$_{(C \leq 12)}$ or substituted heterocycloalkyl$_{(C \leq 12)}$; and $Y_1$ is alkyl$_{(C \leq 12)}$, cycloalkyl$_{(C \leq 12)}$, adamantyl$_{(C \leq 18)}$, aryl$_{(C \leq 18)}$, aralkyl$_{(C \leq 18)}$, acyl$_{(C \leq 12)}$, -alkanediyl$_{(C \leq 8)}$-cycloalkyl$_{(C \leq 12)}$, -arenediyl$_{(C \leq 12)}$-alkene$_{(C \leq 8)}$, -arenediyl$_{(C \leq 12)}$-aryl$_{(C \leq 12)}$, -arenediyl$_{(C \leq 12)}$-aralkyl$_{(C \leq 12)}$, -arenediyl$_{(C \leq 12)}$-aryloxy$_{(C \leq 12)}$, or a substituted version of any of these groups; or $R_3$ and $Y_1$ are taken together and are alkanediyl$_{(C \leq 8)}$, alkylaminodiyl$_{(C \leq 8)}$, alkoxydiyl$_{(C \leq 8)}$, or a substituted version of any of these groups; or

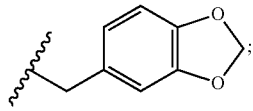 [SMILES: *Cc1ccc2c(c1)OCO2]

or a pharmaceutically acceptable salt thereof. In some embodiments, $R_3$ is hydrogen. In some embodiments, $R_3$ is alkyl$_{(C \leq 12)}$ or substituted alkyl$_{(C \leq 12)}$. In some embodiments, $R_3$ is alkyl$_{(C \leq 6)}$ or substituted alkyl$_{(C \leq 6)}$. In some embodiments, $R_3$ is alkyl$_{(C \leq 6)}$. In some embodiments, $R_3$ is methyl. In some embodiments, $R_3$ is aralkyl$_{(C \leq 12)}$ or substituted aralkyl$_{(C \leq 12)}$. In some embodiments, $R_3$ is aralkyl$_{(C \leq 8)}$ or substituted aralkyl$_{(C \leq 8)}$. In some embodiments, $R_3$ is aralkyl$_{(C \leq 8)}$. In some embodiments, $R_3$ is benzyl. In some embodiments, $X_1$ is heterocycloalkyl$_{(C \leq 8)}$ or substituted heterocycloalkyl$_{(C \leq 8)}$. In some embodiments, $X_1$ is heterocycloalkyl$_{(C \leq 8)}$. In some embodiments, $X_1$ is:

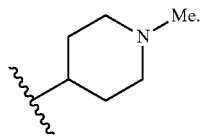 [SMILES: *C1CCN(C)CC1]

In some embodiments, $Y_1$ is alkyl$_{(C \leq 8)}$ or substituted alkyl$_{(C \leq 8)}$. In some embodiments, $Y_1$ is alkyl$_{(C \leq 8)}$. In some embodiments, $Y_1$ is t-butyl. In some embodiments, $Y_1$ is cycloalkyl$_{(C \leq 12)}$ or substituted cycloalkyl$_{(C \leq 12)}$. In some embodiments, $Y_1$ is cycloalkyl$_{(C \leq 8)}$ or substituted cycloalkyl$_{(C \leq 8)}$. In some embodiments, $Y_1$ is cycloalkyl$_{(C \leq 8)}$. In some embodiments, $Y_1$ is cyclopentyl or cyclohexyl. In some embodiments, $Y_1$ is adamantyl$_{(C \leq 18)}$ or substituted adamantyl$_{(C \leq 18)}$. In some embodiments, $Y_1$ is adamantyl$_{(C \leq 12)}$ or substituted adamantyl$_{(C \leq 12)}$. In some embodiments, $Y_1$ is adamantyl$_{(C \leq 12)}$. In some embodiments, $Y_1$ is:

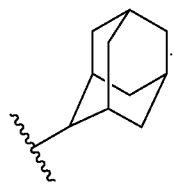 [SMILES: *C1C2CC3CC(C2)CC1C3]

In some embodiments, $Y_1$ is:

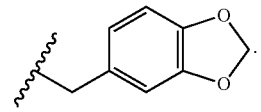 [SMILES: *Cc1ccc2c(c1)OCO2]

In some embodiments, $Y_1$ is aryl$_{(C \leq 18)}$ or substituted aryl$_{(C \leq 18)}$. In some embodiments, $Y_1$ is aryl$_{(C \leq 18)}$. In some embodiments, $Y_1$ is aryl$_{(C \leq 12)}$. In some embodiments, $Y_1$ is phenyl, 4-methylphenyl, 3-methylphenyl, 4-ethylphenyl, 3-ethylphenyl, 4-isopropylphenyl, 4-t-butylphenyl, 3,4-dimethylphenyl, 2,4-dimethylphenyl, or 3,5-dimethylphenyl. In some embodiments, $Y_1$ is biphenyl$_{(C \leq 12)}$. In some embodiments, $Y_1$ is 3-biphenyl or 4-biphenyl. In some embodiments, $Y_1$ is substituted aryl$_{(C \leq 18)}$. In some embodiments, $Y_1$ is substituted aryl$_{(C \leq 12)}$. In some embodiments, $Y_1$ is 4-trifluoromethylphenyl, 3-trifluoromethylphenyl, 4-methoxyphenyl, 3-methoxyphenyl, 4-acetoxyphenyl, 3-acetoxyphenyl, 4-hydroxyphenyl, 3-hydroxyphenyl, 4-trifluoromethoxyphenyl, 2-methoxy-5-t-butylphenyl, 3,4,5-trimethoxyphenyl, 4-dimethylaminophenyl, 4-fluorophenyl, 4-chlorophenyl, 4-bromophenyl, 4-acetylphenyl, 4-nitrophenyl, 4-cyanophenyl, 3-cyanophenyl, 4-chloro-3-methylphenyl, 3-bromo-4-methylphenyl, 3-chloro-4-methylphenyl, 3-iodo-4-methylphenyl, 3-chlorophenyl, 3-acetylphenyl, 3,4-dichlorophenyl, or 3,5-dichlorophenyl. In some embodiments, $Y_1$ is substituted biphenyl$_{(C \leq 18)}$. In some embodiments, $Y_1$ is:

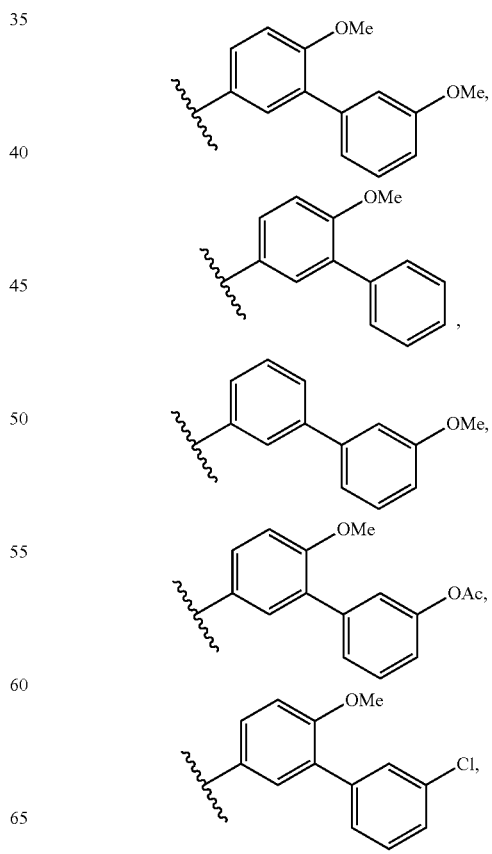

-continued

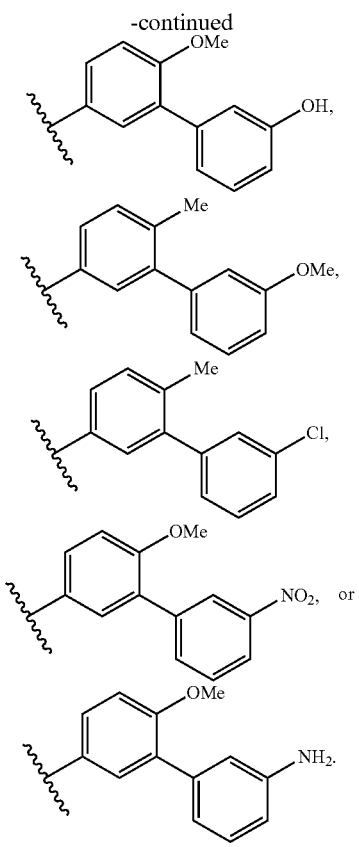

In some embodiments, $Y_1$ is aralkyl$_{(C\leq18)}$ or substituted aralkyl$_{(C\leq18)}$. In some embodiments, $Y_1$ is aralkyl$_{(C\leq12)}$. In some embodiments, $Y_1$ is benzyl, 4-methylbenzyl, and diphenylmethyl. In some embodiments, $Y_1$ is substituted aralkyl$_{(C\leq12)}$. In some embodiments, $Y_1$ is 4-chlorobenzyl, 4-methoxybenzyl, 4-trifluoromethoxybenzyl, 3,4-dichlorobenzyl, or benzo[d][1,3]dioxolylmethyl. In some embodiments, $Y_1$ is acyl$_{(C\leq12)}$ or substituted acyl$_{(C\leq12)}$. In some embodiments, $Y_1$ is acyl$_{(C\leq12)}$. In some embodiments, $Y_1$ is benzoyl. In some embodiments, $Y_1$ is -alkanediyl$_{(C\leq8)}$-cycloalkyl$_{(C\leq12)}$ or substituted -alkanediyl$_{(C\leq8)}$-cycloalkyl$_{(C\leq12)}$. In some embodiments, $Y_1$ is -alkanediyl$_{(C\leq6)}$-cycloalkyl$_{(C\leq8)}$. In some embodiments, $Y_1$ is:

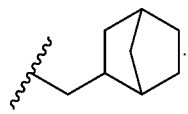 [SMILES: *CC1CC2CCC1C2]

In some embodiments, $Y_1$ is -arenediyl$_{(C\leq12)}$-alkene$_{(C\leq8)}$ or substituted -arenediyl$_{(C\leq12)}$-alkene$_{(C\leq8)}$. In some embodiments, $Y_1$ is -arenediyl$_{(C\leq8)}$-alkene$_{(C\leq6)}$. In some embodiments, the arenediyl$_{(C\leq8)}$ of $Y_1$ is:

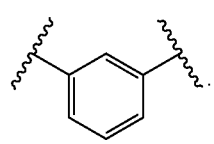 [SMILES: *c1cccc(*)c1]

In some embodiments, the alkene$_{(C\leq6)}$ of $Y_1$ is —CH$_2$CHCH(CH$_3$)$_2$. In some embodiments, $Y_1$ is:

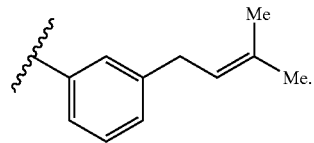 [SMILES: *c1cccc(CC=C(C)C)c1]

In some embodiments, $Y_1$ is substituted -arenediyl$_{(C\leq8)}$-alkene$_{(C\leq6)}$. In some embodiments, the substituted arenediyl$_{(C\leq8)}$ of $Y_1$ is

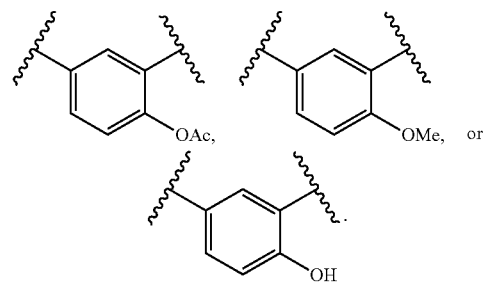

In some embodiments, the alkene$_{(C\leq6)}$ of $Y_1$ is —CH$_2$CHCH(CH$_3$)$_2$. In some embodiments, $Y_1$ is:

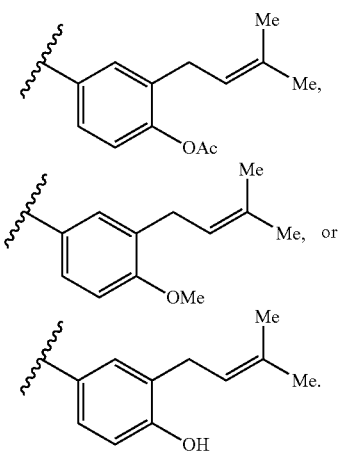

In some embodiments, $Y_1$ is -arenediyl$_{(C\leq12)}$-aryl$_{(C\leq12)}$ or substituted -arenediyl$_{(C\leq12)}$-aryl$_{(C\leq12)}$. In some embodiments, $Y_1$ is -arenediyl$_{(C\leq8)}$-aryl$_{(C\leq8)}$ or substituted -arenediyl$_{(C\leq8)}$-aryl$_{(C\leq8)}$. In some embodiments, $Y_1$ is -arenediyl$_{(C\leq8)}$-aryl$_{(C\leq8)}$. In some embodiments, the arenediyl$_{(C\leq8)}$ of $Y_1$ is:

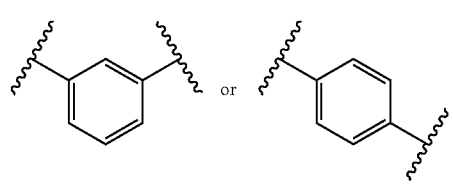

In some embodiments, the aryl$_{(C\leq8)}$ of $Y_1$ is phenyl. In some embodiments, $Y_1$ is:

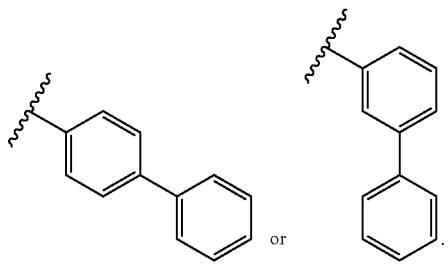 [SMILES: *c1ccc(-c2ccccc2)cc1 ; *c1cccc(-c2ccccc2)c1]

In some embodiments, $Y_1$ is substituted -arenediyl$_{(C\leq 8)}$-aryl$_{(C\leq 8)}$. In some embodiments, the arenediyl$_{(C\leq 8)}$ of $Y_1$ is:

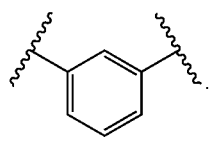 [SMILES: *c1cccc(*)c1]

In some embodiments, the substituted arenediyl$_{(C\leq 8)}$ of $Y_1$ is:

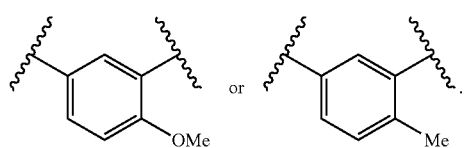 [SMILES: *c1ccc(OC)c(*)c1 ; *c1ccc(C)c(*)c1]

In some embodiments, the aryl$_{(C\leq 8)}$ of $Y_1$ is phenyl. In some embodiments, the substituted aryl$_{(C\leq 8)}$ of $Y_1$ is 3-methoxyphenyl, 3-acetoxyphenyl, 3-hydroxyphenyl, 3-chlorophenyl, 3-nitrophenyl, or 3-aminophenyl. In some embodiments, $Y_1$ is:

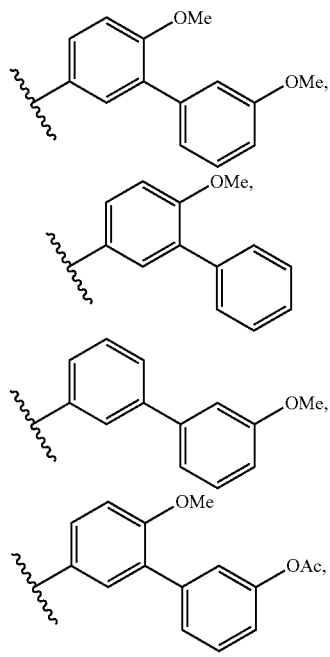

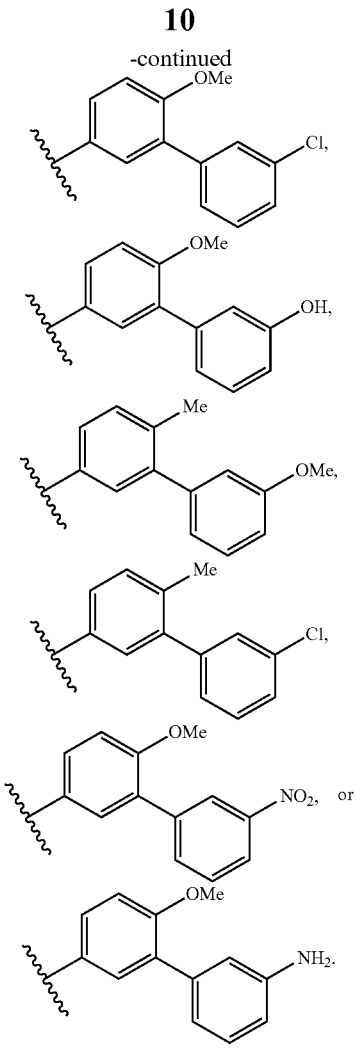

In some embodiments, $Y_1$ is -arenediyl$_{(C\leq 12)}$-aralkyl$_{(C\leq 12)}$ or substituted -arenediyl$_{(C\leq 12)}$-aralkyl$_{(C\leq 12)}$. In some embodiments, $Y_1$ is -arenediyl$_{(C\leq 8)}$-aralkyl$_{(C\leq 8)}$. In some embodiments, $Y_1$ is:

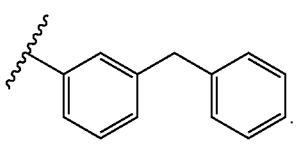 [SMILES: *c1cccc(Cc2ccccc2)c1]

In some embodiments, $Y_1$ is -arenediyl$_{(C\leq 12)}$-aryloxy$_{(C\leq 12)}$ or substituted -arenediyl$_{(C\leq 12)}$-aryloxy$_{(C\leq 12)}$. In some embodiments, the arenediyl$_{(C\leq 8)}$ of $Y_1$ is:

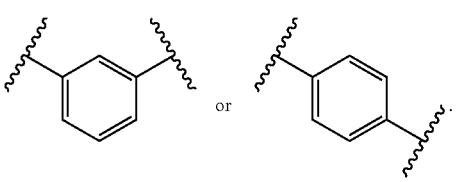 [SMILES: *c1cccc(*)c1 ; *c1ccc(*)cc1]

In some embodiments, aryloxy$_{(C\leq 12)}$ of $Y_1$ is phenyloxy. In some embodiments, $Y_1$ is:

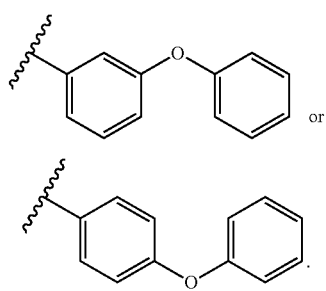

In some embodiments, $Y_1$ and $R_3$ are taken together and are alkanediyl$_{(C≤8)}$, alkoxydiyl$_{(C≤8)}$, alkylaminodiyl$_{(C≤8)}$, or a substituted version thereof. In some embodiments, $Y_1$ and $R_3$ are taken together and are alkylaminodiyl$_{(C≤8)}$ or substituted alkylaminodiyl$_{(C≤8)}$. In some embodiments, $Y_1$ and $R_3$ are taken together and are:

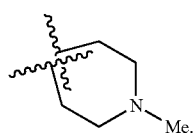 [SMILES: *CCN(C)CC*]

In some embodiments, the compound is not selected from:

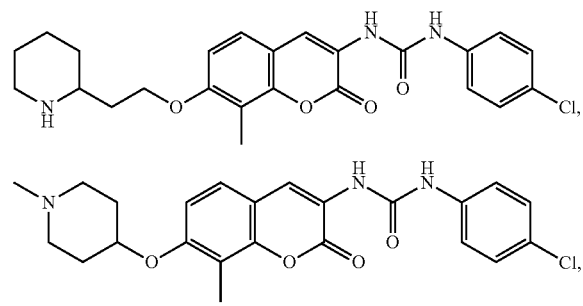

In some embodiments, the compound is not selected from:

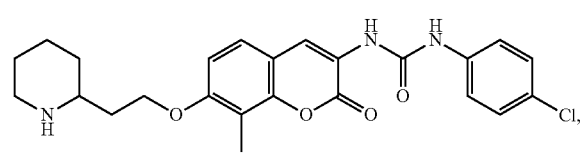

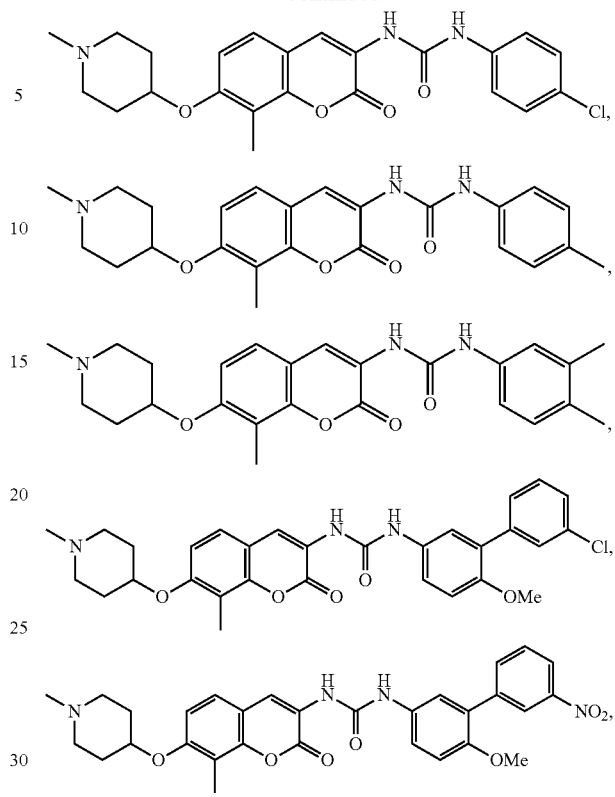

and

In some embodiments, the compound is further defined as:

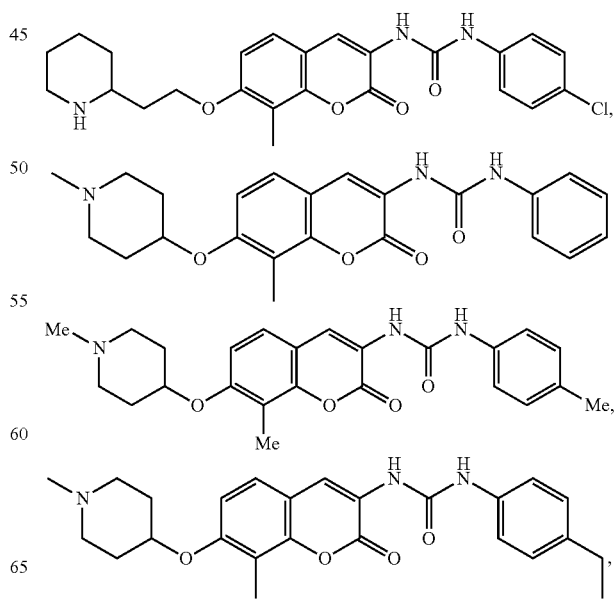

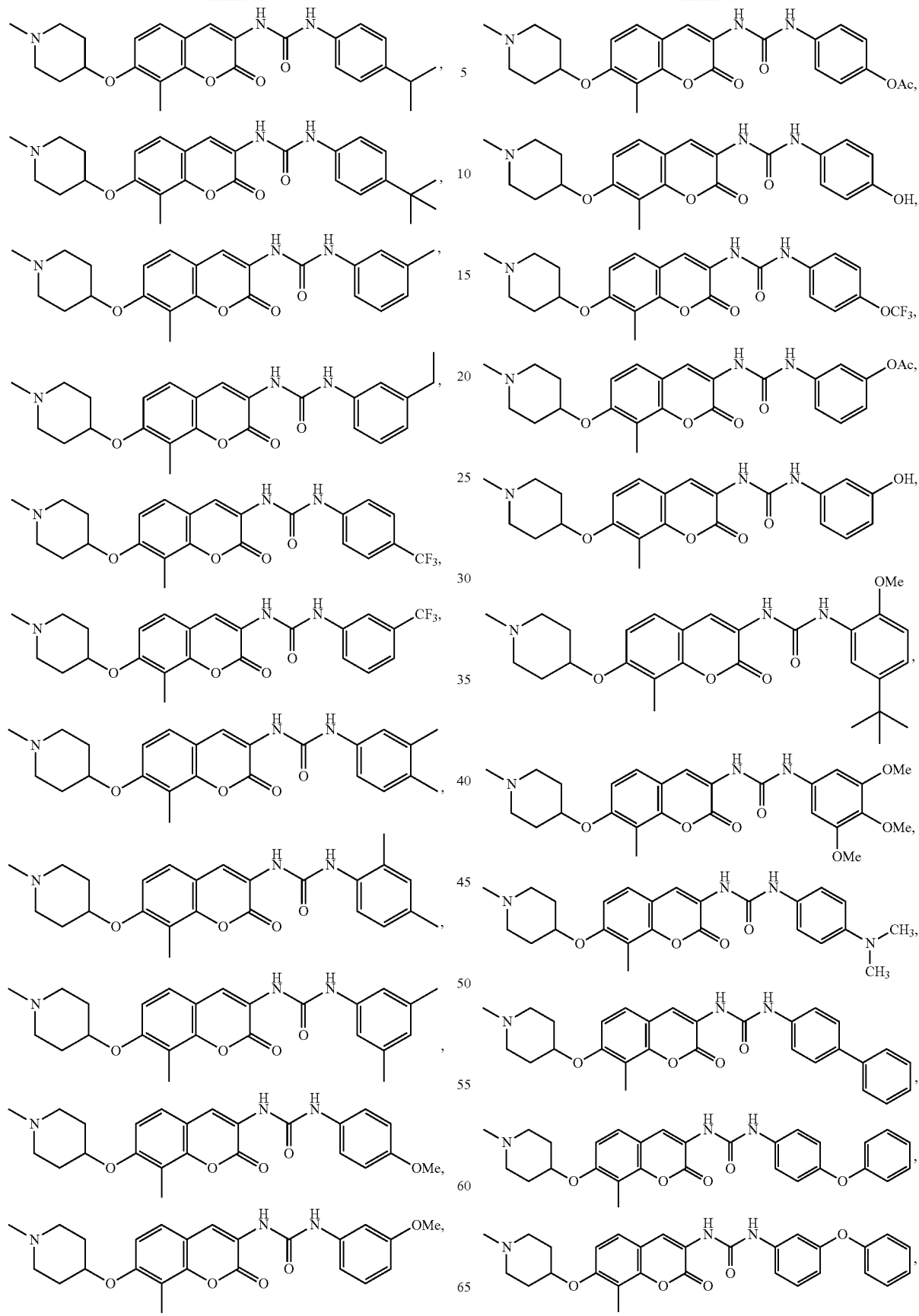

-continued
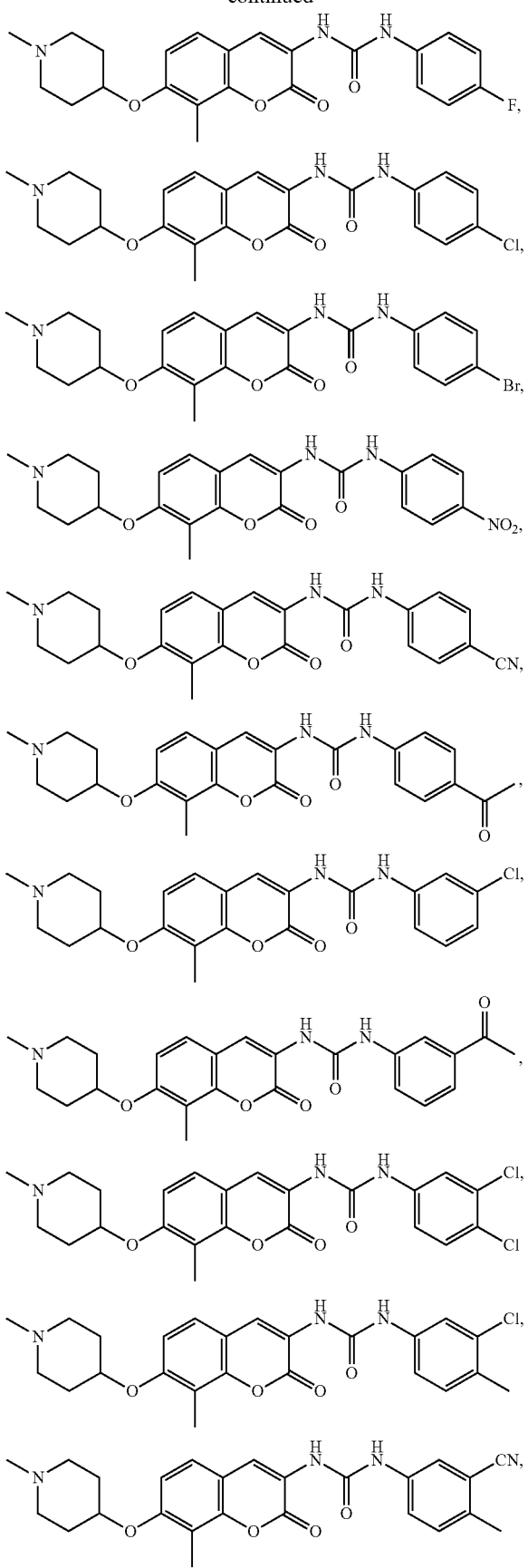
-continued
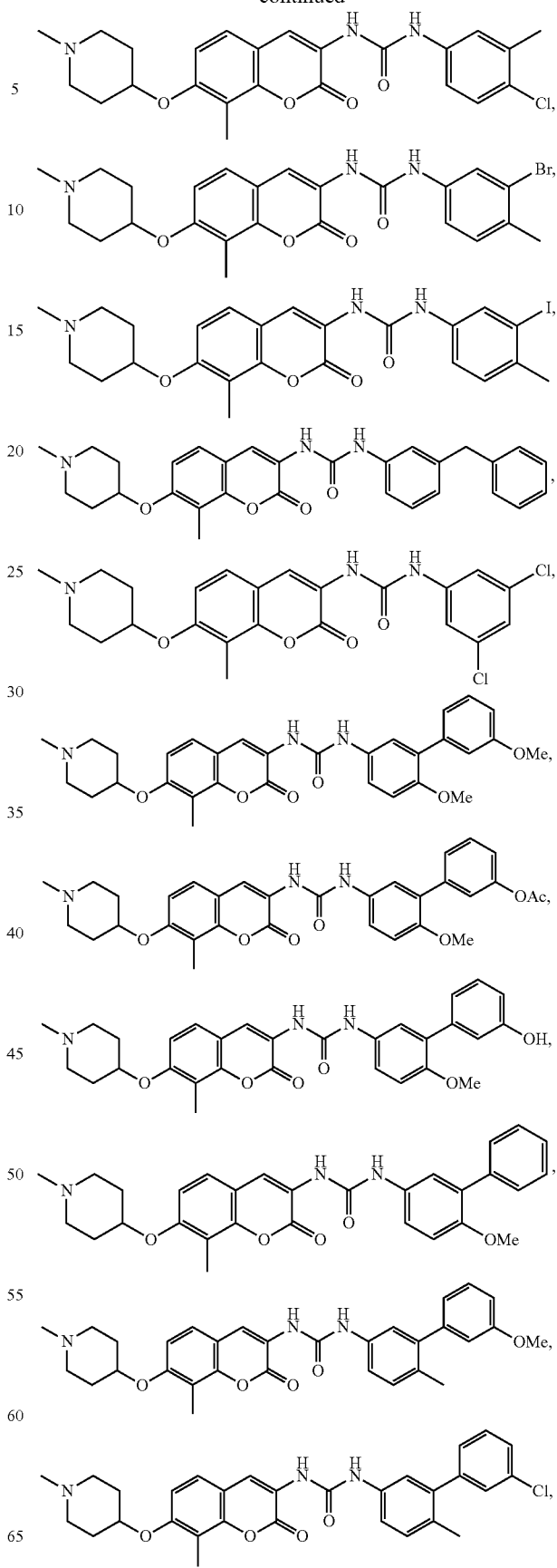

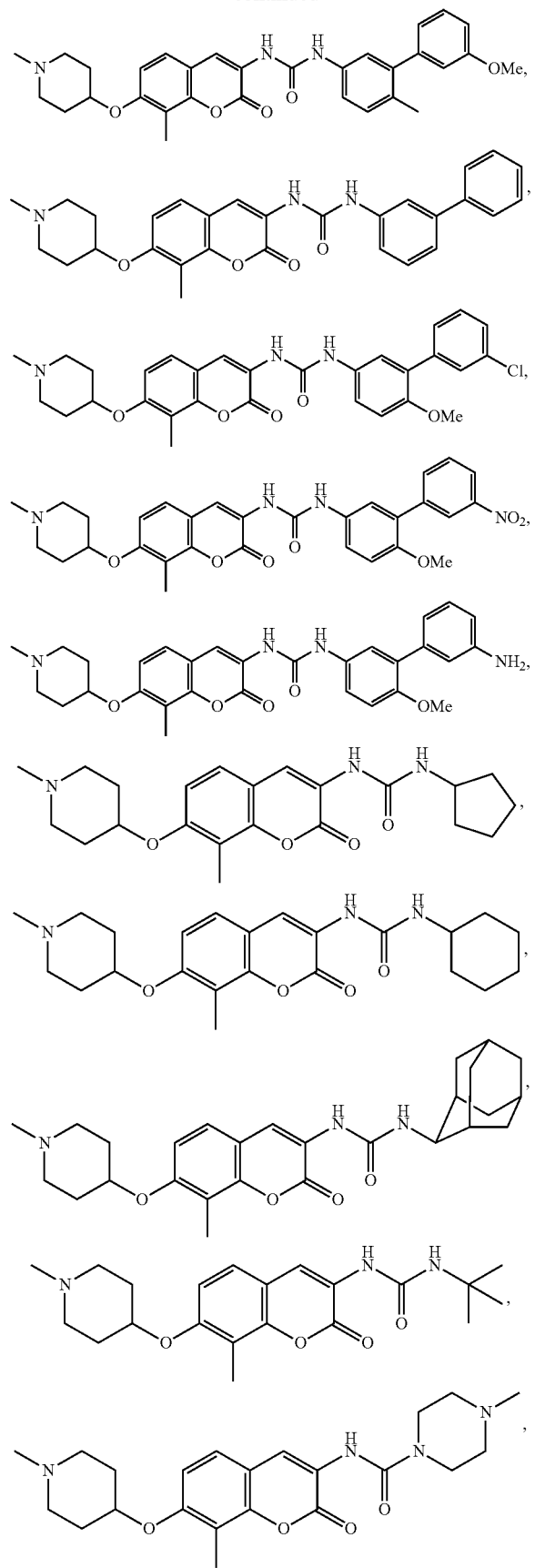
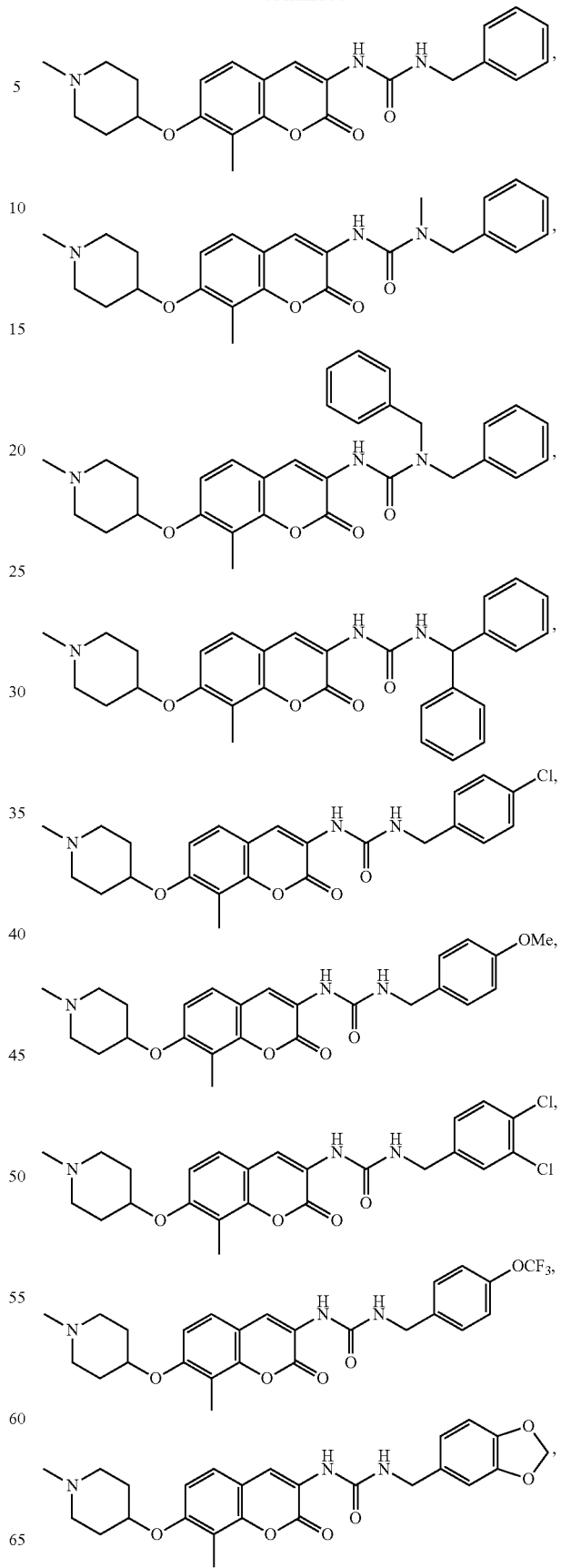

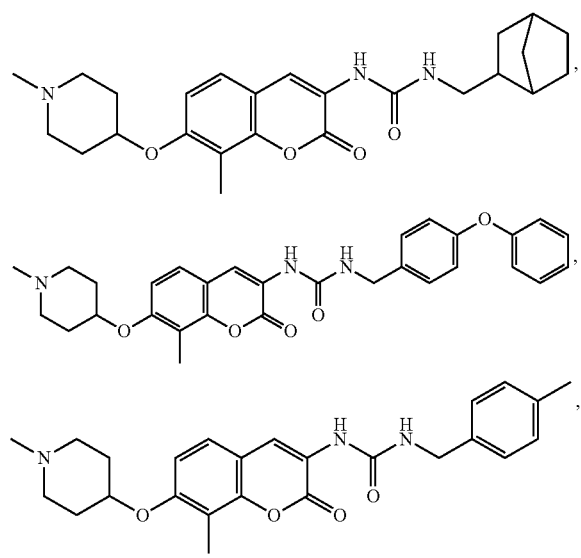

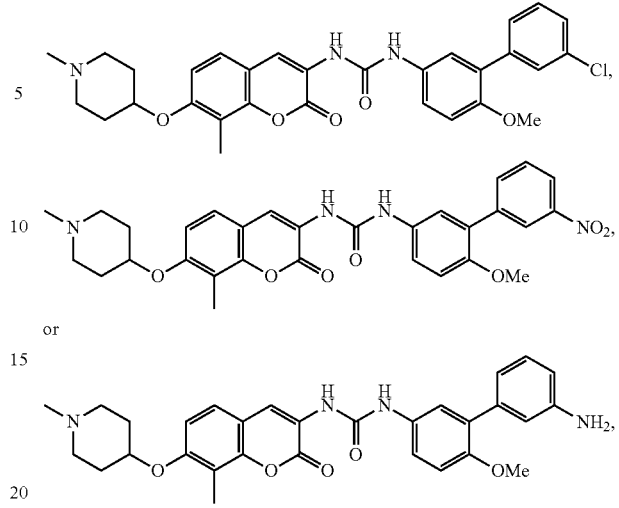

or a pharmaceutically acceptable salt thereof. In some embodiments, the compound is further defined as:

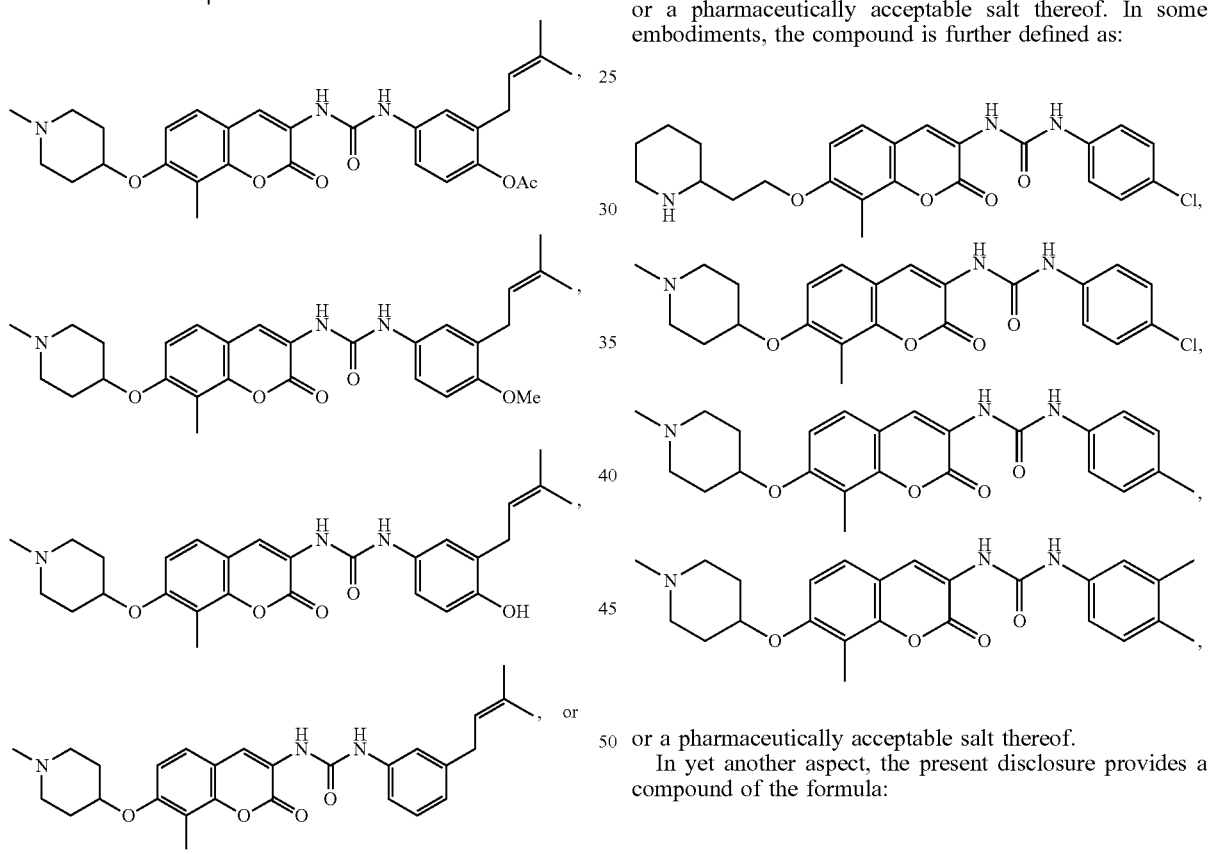

or a pharmaceutically acceptable salt thereof.

In yet another aspect, the present disclosure provides a compound of the formula:

(IV)

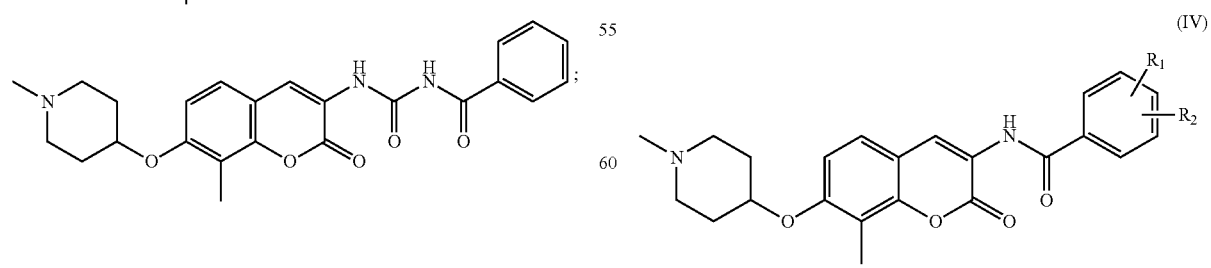

wherein: R₁ is hydrogen, hydroxy, alkoxy$_{(C\leq 12)}$, alkenyloxy$_{(C\leq 12)}$, alkynyloxy$_{(C\leq 12)}$, acyloxy$_{(C\leq 12)}$, or a subor a pharmaceutically acceptable salt thereof. In some embodiments, the compound is further defined as:

stituted version of any of the last four groups; $R_2$ is hydrogen, halo, alkyl$_{(C \leq 12)}$, alkenyl$_{(C \leq 12)}$, aryl$_{(C \leq 12)}$, or a substituted version of any of the last three groups; or

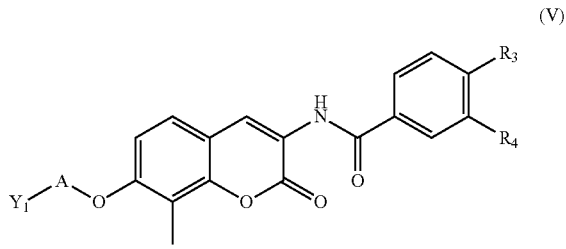

(V)

wherein: $R_3$ is hydrogen, hydroxy, alkoxy$_{(C \leq 12)}$, substituted alkoxy$_{(C \leq 12)}$, acyloxy$_{(C \leq 12)}$, or substituted acyloxy$_{(C \leq 12)}$; $R_4$ is alkyl$_{(C \leq 12)}$, alkenyl$_{(C \leq 12)}$, aryl$_{(C \leq 12)}$, or a substituted version of any of these groups; A is alkanediyl$_{(C \leq 8)}$ or substituted alkanediyl$_{(C \leq 8)}$; and $Y_1$ is heterocycloalkyl$_{(C \leq 12)}$, substituted heterocycloalkyl$_{(C \leq 12)}$, or —NR$_5$R$_6$; wherein: $R_5$ and $R_6$ are each independently selected from hydrogen, alkyl$_{(C \leq 12)}$, cycloalkyl$_{(C \leq 12)}$, aryl$_{(C \leq 12)}$, aralkyl$_{(C \leq 12)}$, adamantyl$_{(C \leq 18)}$, or a substituted version of any of the last five groups; provided that when $R_2$ is meta and —CH$_2$CHCH(CH$_3$)$_2$, then $R_1$ is not —OH, —OCH$_2$CH$_2$N(CH$_3$)$_2$, or —OCH$_2$CH$_2$CH$_2$N(CH$_3$)$_2$, and provided that when $R_3$ is —OH and $R_4$ is —CH$_2$CHCH(CH$_3$)$_2$, then A is not —CH$_2$CH$_2$CH$_2$— and $Y_1$ is not —N(CH$_3$)$_2$, —N(CH$_3$)CH$_2$CH$_3$, or —N(CH$_3$)CH(CH$_3$)$_2$; or a pharmaceutically acceptable salt thereof. In some embodiments, the formula is further defined as:

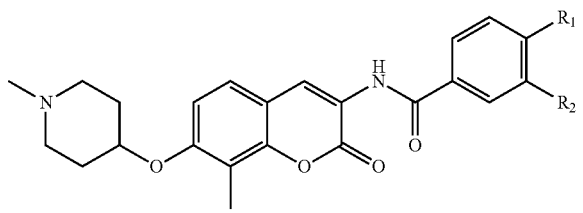

(VI)

wherein: $R_1$ is hydrogen, hydroxy, alkoxy$_{(C \leq 12)}$, alkenyloxy$_{(C \leq 12)}$, alkynyloxy$_{(C \leq 12)}$, acyloxy$_{(C \leq 12)}$, or a substituted version of any of the last four groups; and $R_2$ is hydrogen, halo, alkyl$_{(C \leq 12)}$, alkenyl$_{(C \leq 12)}$, aryl$_{(C \leq 12)}$, or a substituted version of any of the last three groups; provided that $R_2$ is —CH$_2$CHCH(CH$_3$)$_2$, then $R_1$ is not —OH, —OCH$_2$CH$_2$N(CH$_3$)$_2$, or —OCH$_2$CH$_2$CH$_2$N(CH$_3$)$_2$, or a pharmaceutically acceptable salt thereof. In some embodiments, the compound is further defined as:

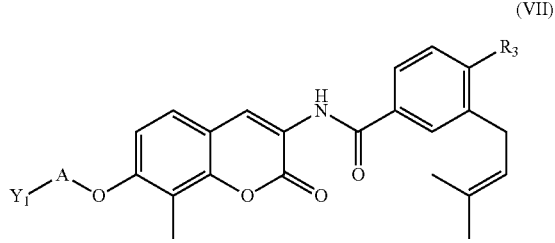

(VII)

wherein: $R_3$ is hydroxy, acyloxy$_{(C \leq 12)}$, or substituted acyloxy$_{(C \leq 12)}$; A is alkanediyl$_{(C \leq 8)}$ or substituted alkanediyl$_{(C \leq 8)}$; and $Y_1$ is heterocycloalkyl$_{(C \leq 12)}$, substituted heterocycloalkyl$_{(C \leq 12)}$, or —NR$_5$R$_6$; wherein: $R_5$ and $R_6$ are each independently selected from hydrogen, alkyl$_{(C \leq 12)}$, cycloalkyl$_{(C \leq 12)}$, aryl$_{(C \leq 12)}$, aralkyl$_{(C \leq 12)}$, adamantyl$_{(C \leq 18)}$, or a substituted version of any of the last five groups; provided that when $R_3$ is —OH, then A is not —CH$_2$CH$_2$CH$_2$— and $Y_1$ is not —N(CH$_3$)$_2$, —N(CH$_3$)CH$_2$CH$_3$, or —N(CH$_3$)CH(CH$_3$)$_2$; or a pharmaceutically acceptable salt thereof. In some embodiments, the compound is of formula IV. In some embodiments, the compound is of formula V. In some embodiments, $R_1$ is hydrogen. In some embodiments, $R_1$ is hydroxy. In some embodiments, $R_1$ is alkoxy$_{(C \leq 12)}$. In some embodiments, $R_1$ is methoxy or n-butyloxy. In some embodiments, $R_1$ is alkynyloxy$_{(C \leq 12)}$. In some embodiments, $R_1$ is —OCH$_2$C≡CH. In some embodiments, $R_1$ is acyloxy$_{(C \leq 12)}$. In some embodiments, $R_1$ is —OAc. In some embodiments, $R_2$ is hydrogen. In some embodiments, $R_2$ is halo. In some embodiments, $R_2$ is chloro. In some embodiments, $R_2$ is alkyl$_{(C \leq 12)}$. In some embodiments, $R_2$ is isobutyl or isopentyl. In some embodiments, $R_2$ is alkenyl$_{(C \leq 12)}$. In some embodiments, $R_2$ is —CH$_2$CHCH$_2$ or —CH$_2$CHCH(CH$_3$)$_2$. In some embodiments, $R_2$ is aryl$_{(C \leq 12)}$. In some embodiments, $R_2$ is phenyl. In some embodiments, $R_2$ is substituted aryl$_{(C \leq 12)}$. In some embodiments, $R_2$ is 3-hydroxyphenyl, 3-acetoxyphenyl, or 3-methoxyphenyl. In some embodiments, $R_3$ is hydroxy. In some embodiments, $R_3$ is acyloxy$_{(C \leq 12)}$. In some embodiments, $R_3$ is —OAc. In some embodiments, $R_4$ is alkenyl$_{(C \leq 12)}$. In some embodiments, $R_4$ is —CH$_2$CHCH(CH$_3$)$_2$. In some embodiments, A is alkanediyl$_{(C \leq 12)}$. In some embodiments, A is —CH$_2$—, —CH$_2$CH$_2$—, or —CH$_2$CH$_2$CH$_2$—. In some embodiments, A is —CH$_2$CH$_2$CH$_2$—. In some embodiments, $Y_1$ is heterocycloalkyl$_{(C \leq 12)}$. In some embodiments, $Y_1$ is:

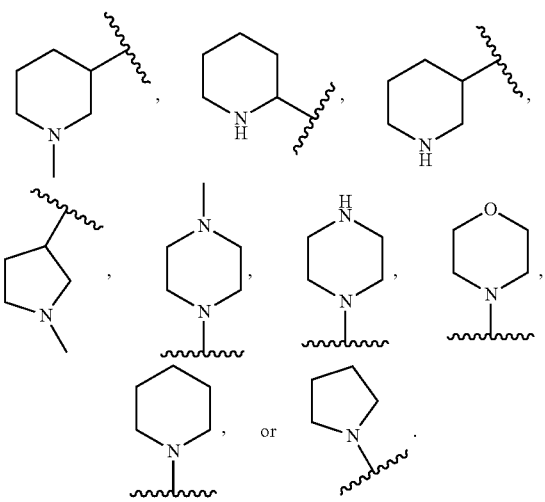

In some embodiments, $Y_1$ is —NR$_5$R$_6$; wherein: $R_5$ and $R_6$ are each independently selected from hydrogen, alkyl$_{(C \leq 12)}$, cycloalkyl$_{(C \leq 12)}$, aryl$_{(C \leq 12)}$, aralkyl$_{(C \leq 12)}$, adamantyl$_{(C \leq 18)}$, or a substituted version of any of the last five groups. In some embodiments, $R_5$ is hydrogen. In some embodiments, $R_5$ is alkyl$_{(C \leq 12)}$ or substituted alkyl$_{(C \leq 12)}$. In some embodiments, $R_5$ is alkyl$_{(C \leq 12)}$. In some embodiments, $R_5$ is methyl, ethyl, propyl, isobutyl, isopropyl, or t-butyl. In some embodiments, $R_5$ is substituted alkyl$_{(C \leq 12)}$. In some embodiments, $R_5$ is —$CH_2CO_2H$, —$CH_2CO_2Me$, —$CH_2C(O)NH_2$, or —$CH_2CH_2OH$. In some embodiments, $R_5$ is cycloalkyl$_{(C \leq 12)}$.

In some embodiments, is cyclohexyl or

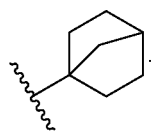 [SMILES: *C12CCC(CC1)C2]

In some embodiments, $R_5$ is aryl$_{(C \leq 12)}$ or substituted aryl$_{(C \leq 12)}$. In some embodiments, $R_5$ is phenyl. In some embodiments, $R_5$ is aralkyl$_{(C \leq 12)}$ or substituted aralkyl$_{(C \leq 12)}$. In some embodiments, $R_5$ is benzyl, 1-methyl-1-phenylethyl, or 1-phenylmethyl. In some embodiments, $R_5$ is adamantyl$_{(C \leq 12)}$ or substituted adamantyl$_{(C \leq 12)}$. In some embodiments, $R_5$ is adamantyl. In some embodiments, $R_6$ is hydrogen. In some embodiments, $R_6$ is alkyl$_{(C \leq 12)}$ or substituted alkyl$_{(C \leq 12)}$. In some embodiments, $R_6$ is alkyl$_{(C \leq 12)}$. In some embodiments, $R_6$ is methyl, ethyl, propyl, or isopropyl. In some embodiments, $R_5$ and $R_6$ are not both hydrogen. In some embodiments, the compound is not selected from:

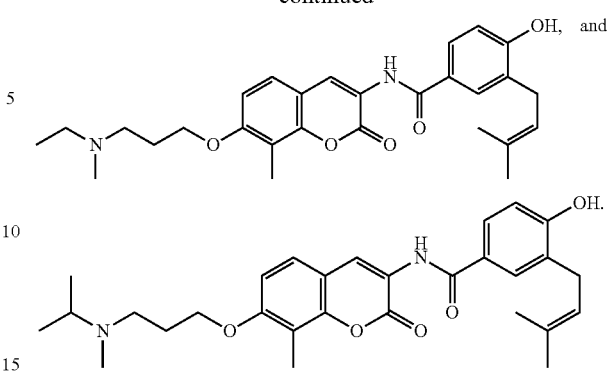

In some embodiments, the compound is further defined as:

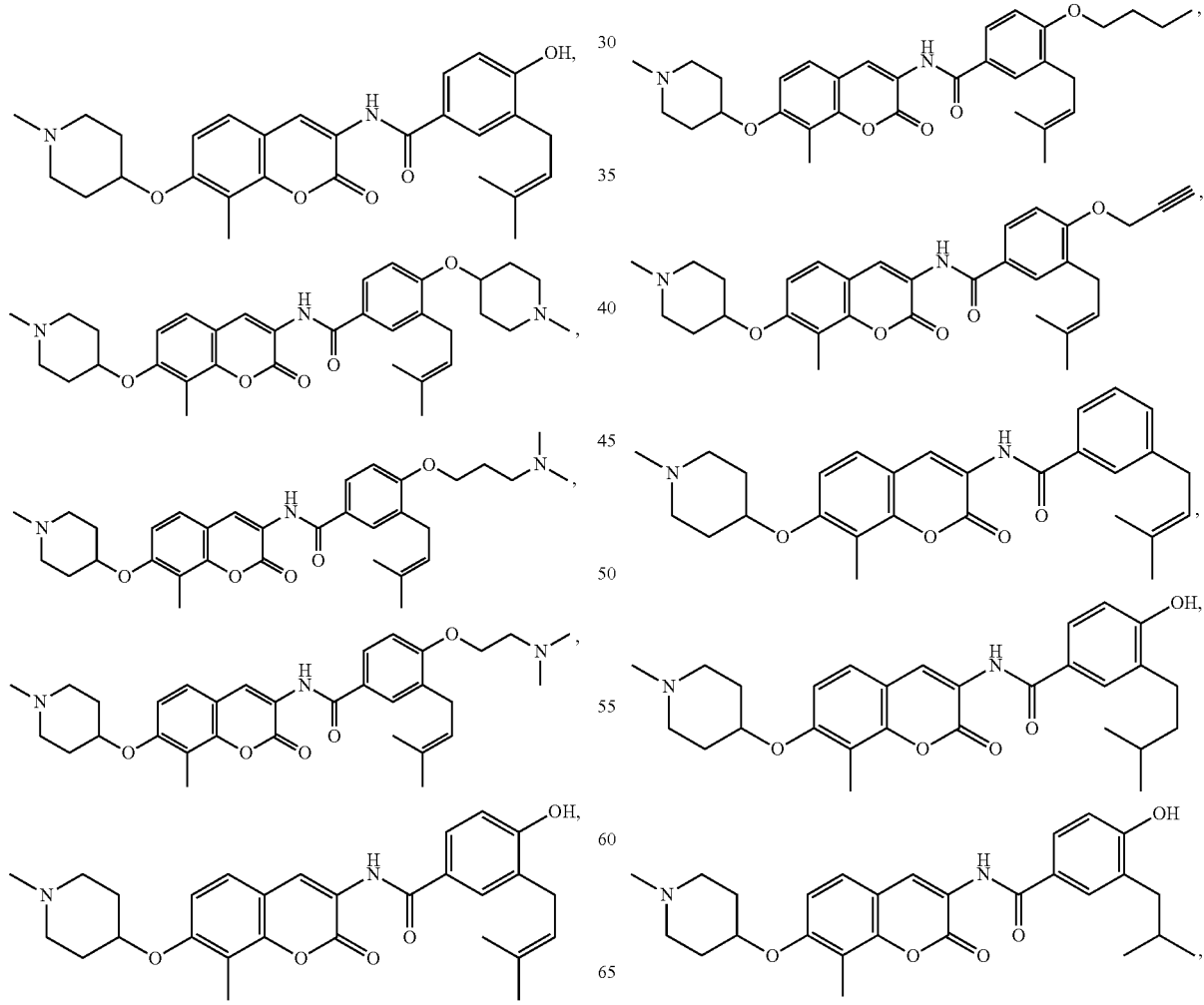

25
-continued
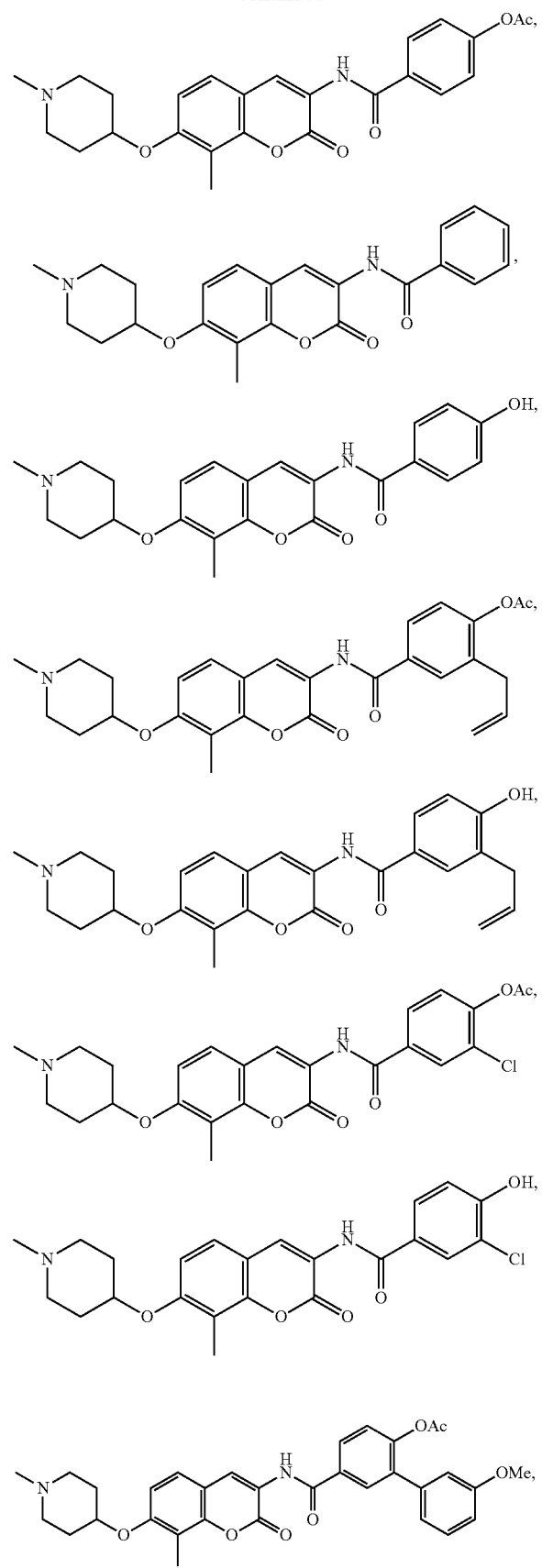
26
-continued
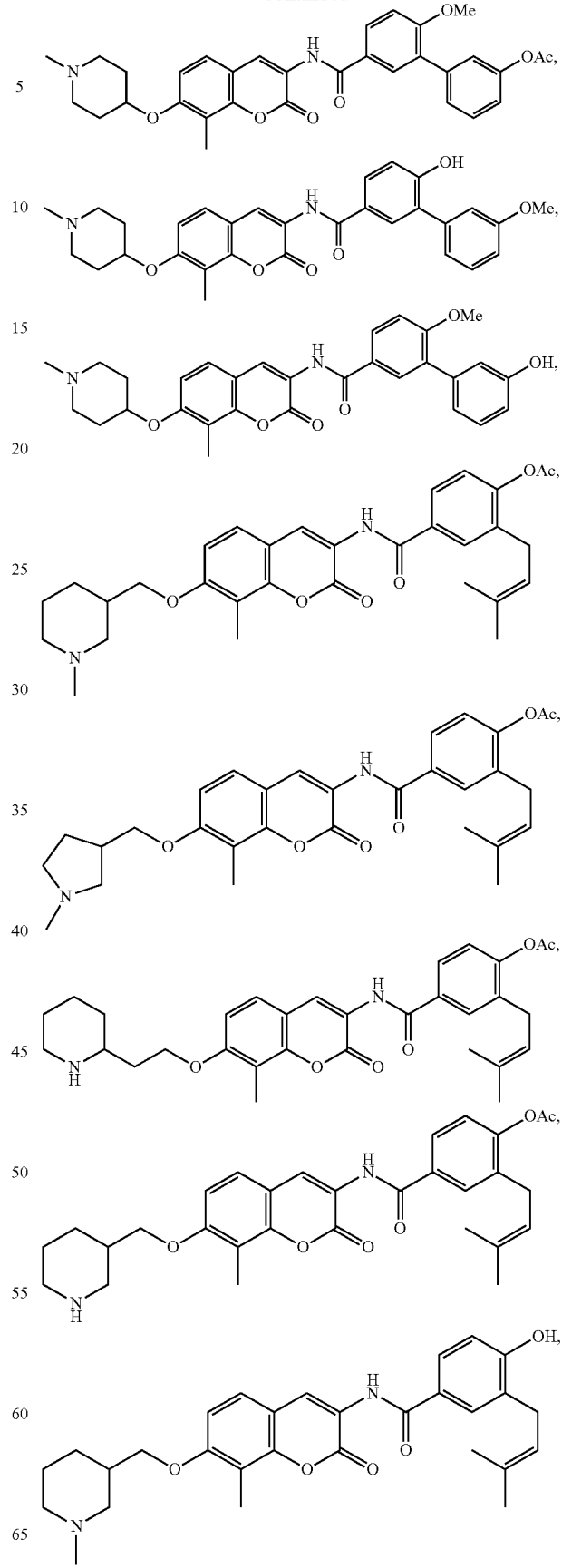

27
-continued
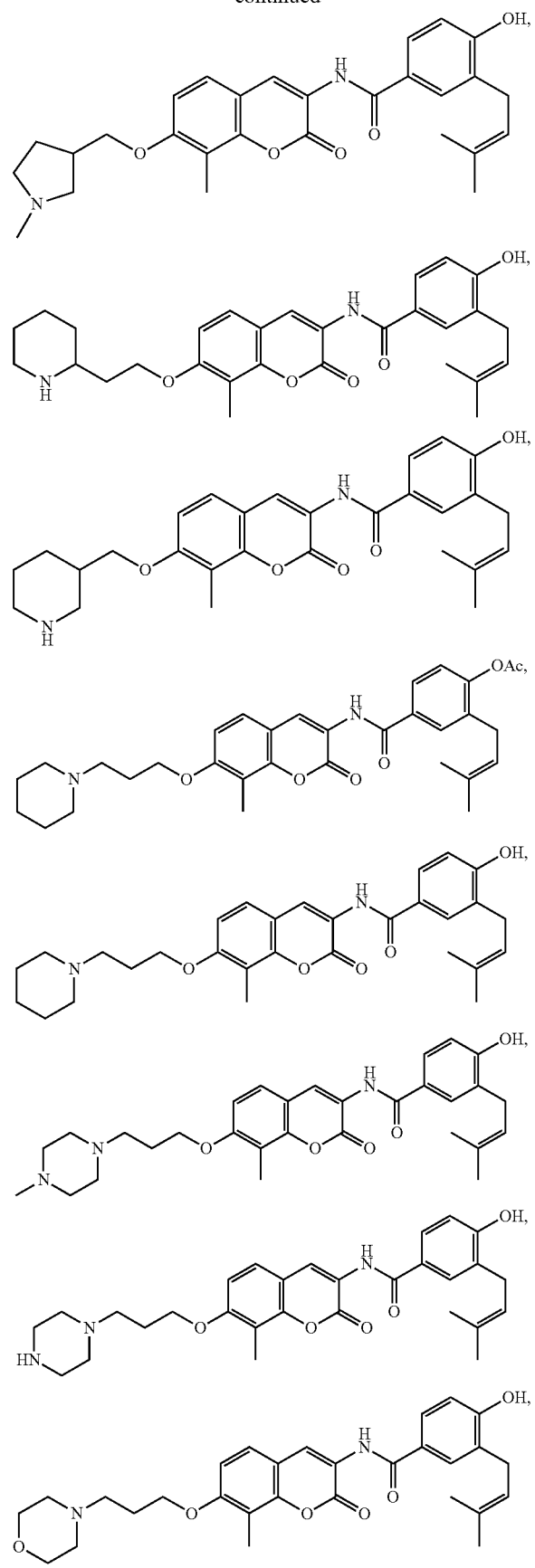
28
-continued
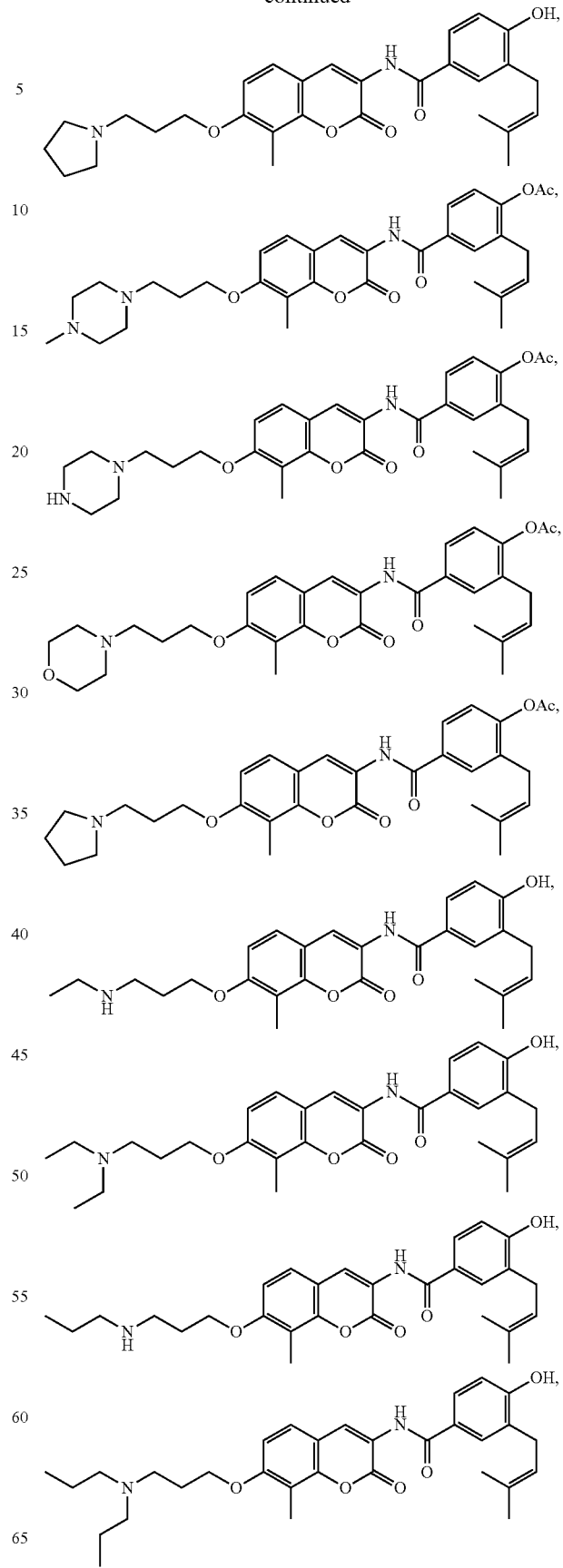

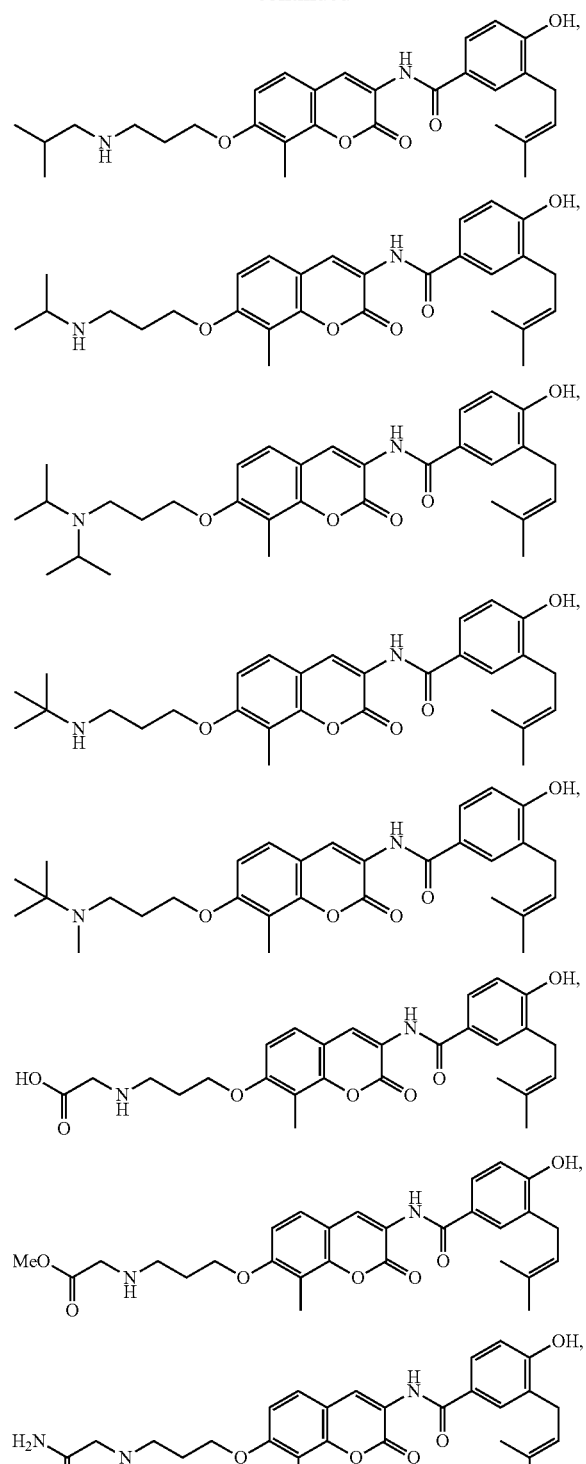
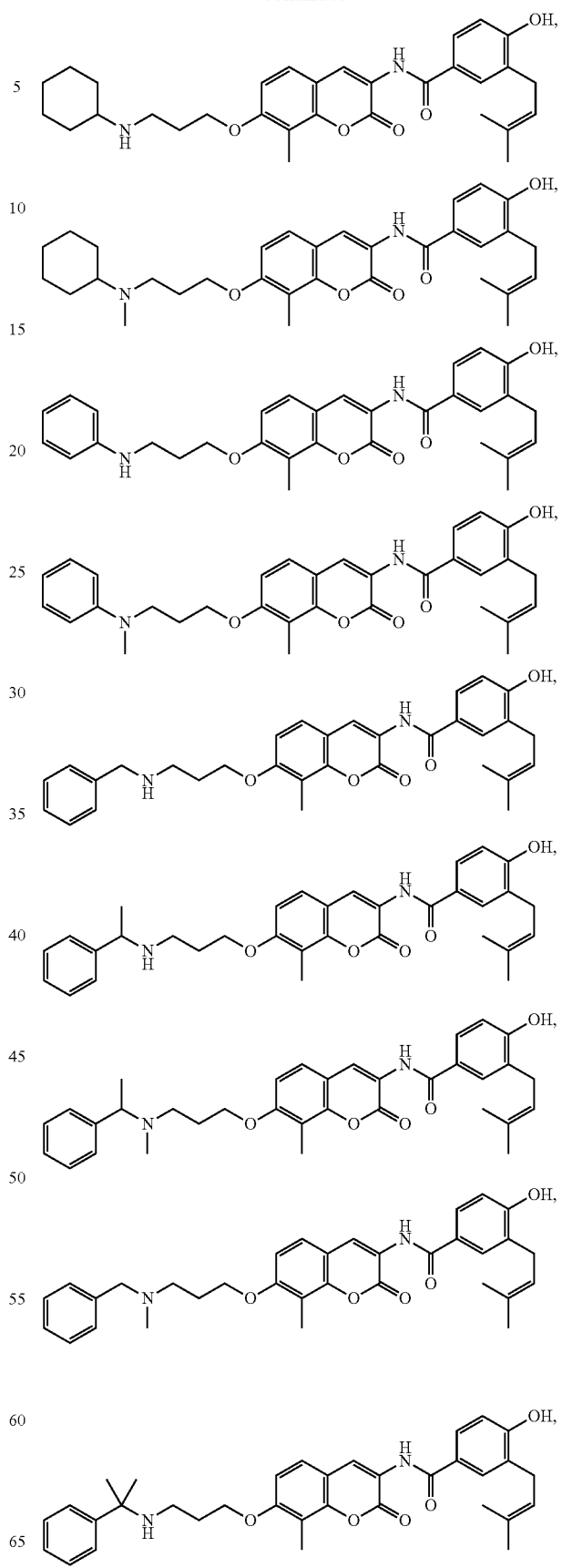

-continued

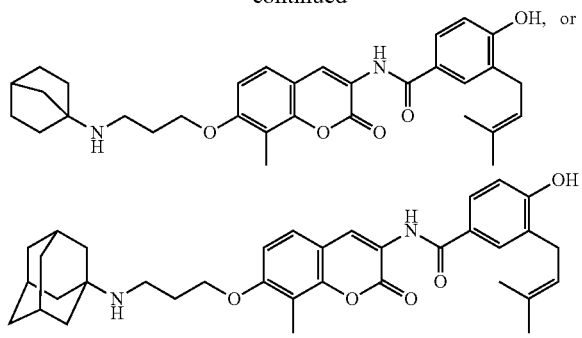

or a pharmaceutically acceptable salt thereof.

In yet another aspect, the present disclosure provides a pharmaceutical composition comprising a compound of the present disclosure and an excipient. In some embodiments, the composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion.

In still another aspect, the present disclosure provides a method for treating a disease or disorder comprising administering to a patient in need thereof a pharmaceutically acceptable amount of a compound or a pharmaceutical composition of the present disclosure. In some embodiments, the disease or disorder is cancer. In some embodiments, the cancer is a carcinoma, sarcoma, lymphoma, leukemia, melanoma, mesothelioma, multiple myeloma, or seminoma. In some embodiments, the cancer is a cancer of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is breast cancer, prostate cancer, head and neck cancer, or thyroid cancer. In some embodiments, the method further comprises administering the compound with one or more additional therapeutic agents or modalities. In some embodiments, the additional therapeutic agents or modalities are a second chemotherapeutic agent, radiotherapy, immunotherapy, or surgery. In some embodiments, the method comprises administering the compound and the second therapeutic agent or modality simultaneously. In some embodiments, the method comprises administering the compound and the second therapeutic agent or modality sequentially. In some embodiments, the method comprises administering an amount of compound sufficient to inhibit cancer cell growth, propagation, or migration.

In still yet another aspect, the present disclosure provides a method of inhibiting Hsp90 comprising administering to a patient in need thereof an effective amount of a compound or composition of the present disclosure.

In another aspect, the present disclosure provides a novobiocin analog comprising: one of the following structures or derivative thereof or salt thereof or prodrug thereof:

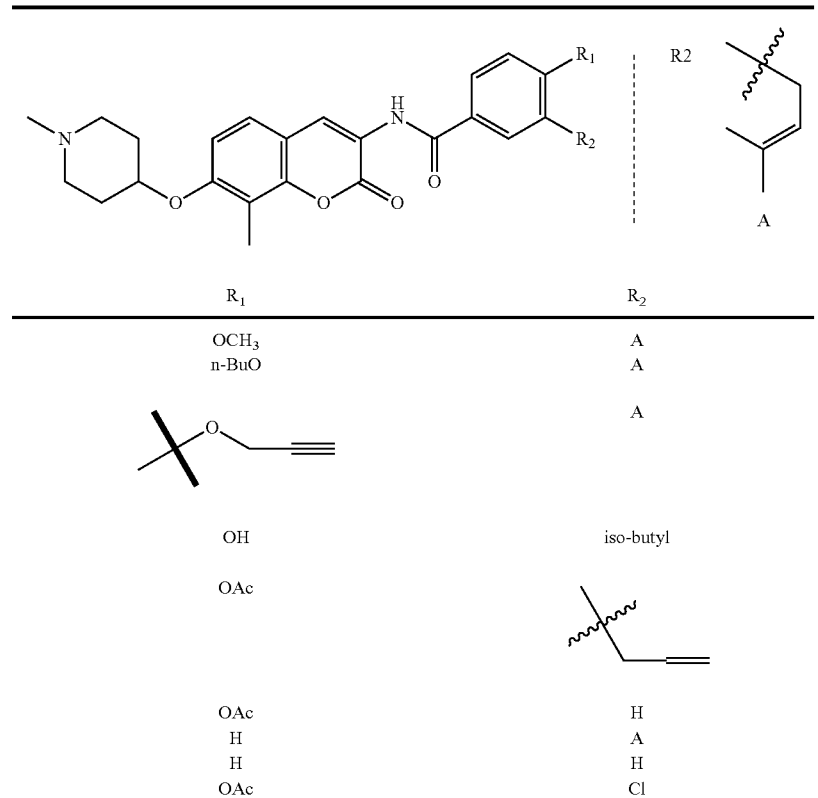

-continued
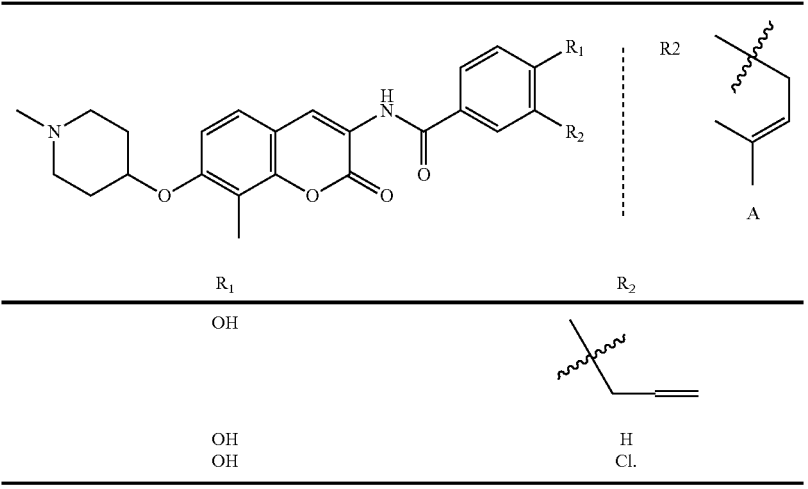
| R₁ | R₂ |
|---|---|
| OH | (allyl group) |
| OH | H |
| OH | Cl |
In yet another aspect, the present disclosure provides a novobiocin analog comprising: one of the following structures or derivative thereof or salt thereof or prodrug thereof:
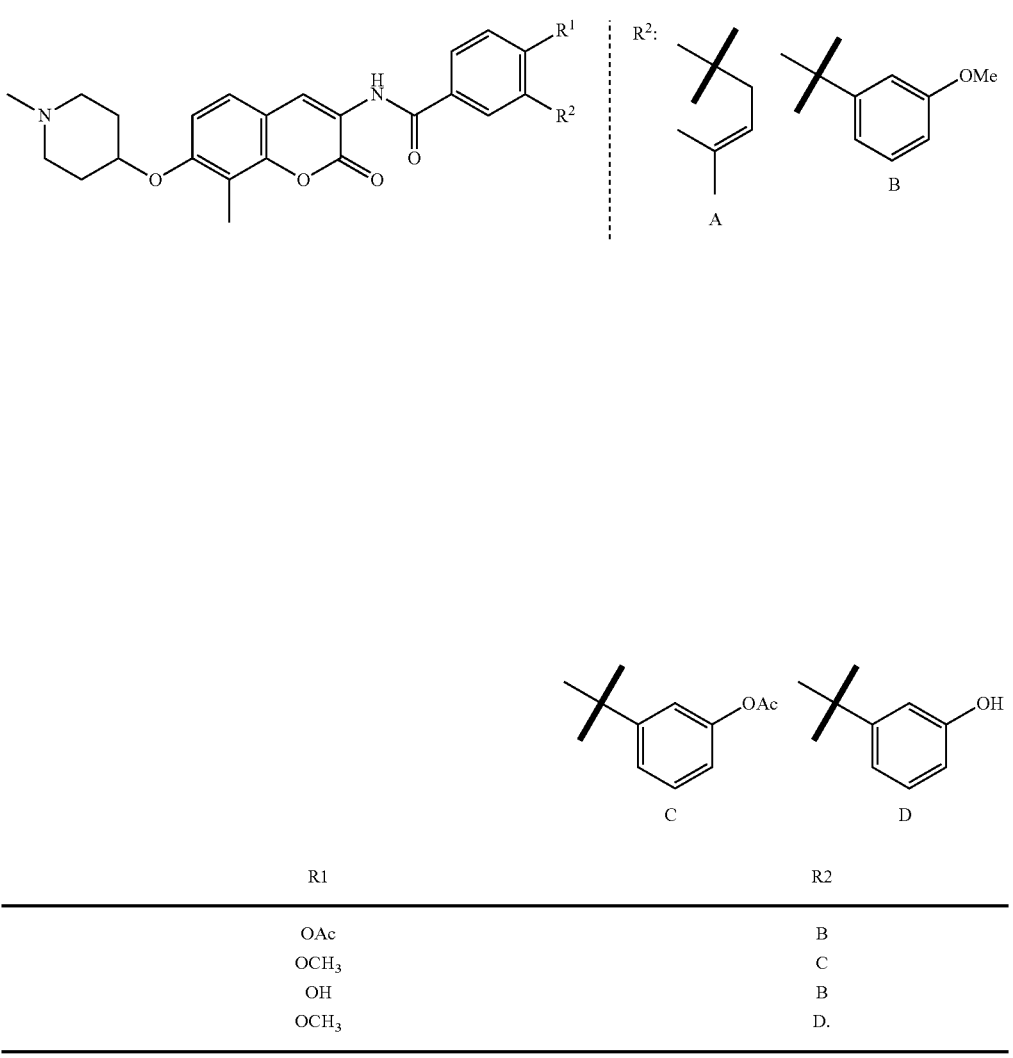
| R1 | R2 |
|---|---|
| OAc | B |
| OCH₃ | C |
| OH | B |
| OCH₃ | D |

In another aspect, the present disclosure provides a novobiocin analog comprising: one of the following structures or derivative thereof or salt thereof or prodrug thereof:

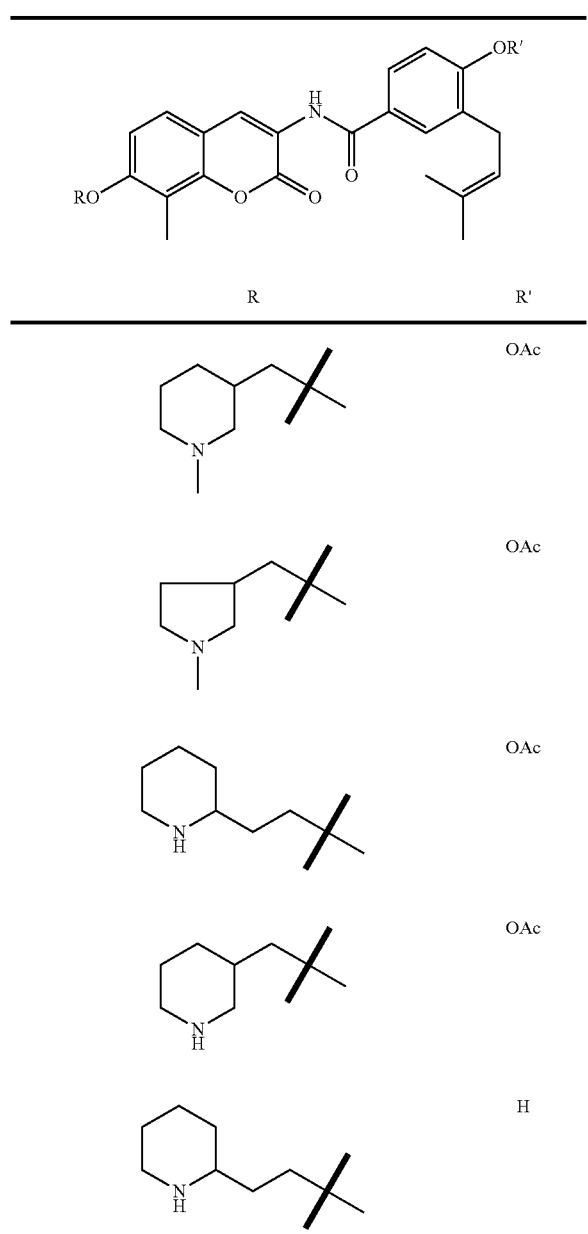

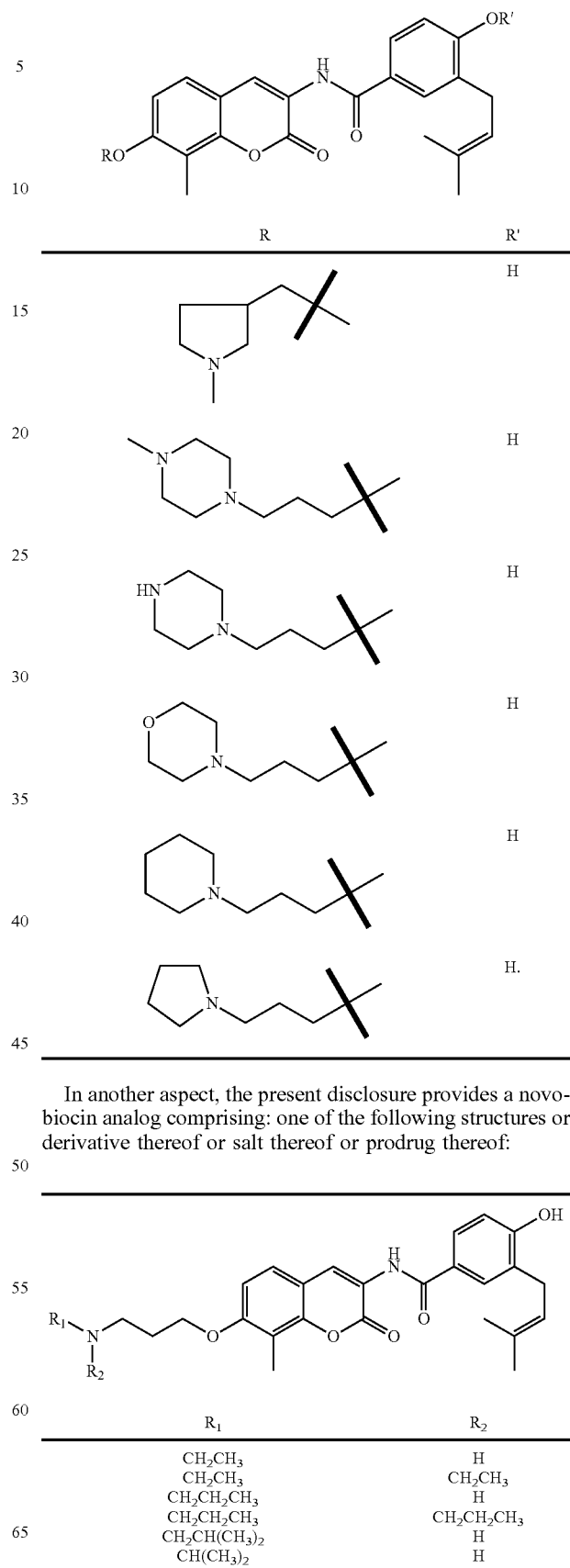

In another aspect, the present disclosure provides a novobiocin analog comprising: one of the following structures or derivative thereof or salt thereof or prodrug thereof:

| $R_1$ | $R_2$ |
|---|---|
| $CH_2CH_3$ | H |
| $CH_2CH_3$ | $CH_2CH_3$ |
| $CH_2CH_2CH_3$ | H |
| $CH_2CH_2CH_3$ | $CH_2CH_2CH_3$ |
| $CH_2CH(CH_3)_2$ | H |
| $CH(CH_3)_2$ | H |

-continued

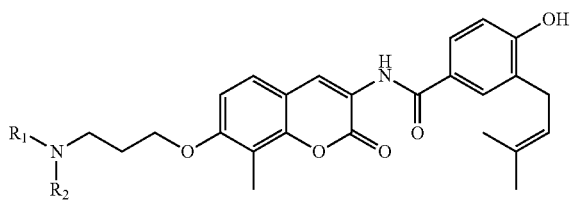

| R₁ | R₂ |
|---|---|
| CH(CH₃)₂ | CH(CH₃)₂ |
| C(CH₃)₃ | H |
| C(CH₃)₃ | CH₃ |
| CH₂COOMe | H |
| CH₂COOH | H |
| CH₂CONH₂ | H |
| CH₂CH₂OH | H |
| Cyclohexyl | H |
| Cyclohexyl | CH₃ |
| Phenyl | H |
| Phenyl | CH₃ |
| Benzyl | H |
| (R)-1-phenylethyl | H |
| Cumentyl | H |
| Benzyl | CH₃ |
| 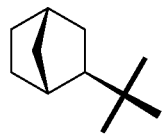 | H |
| Adamantyl | H. |

In another aspect, the present disclosure provides a novobiocin analog comprising: one of the following structures or derivative thereof or salt thereof or prodrug thereof:

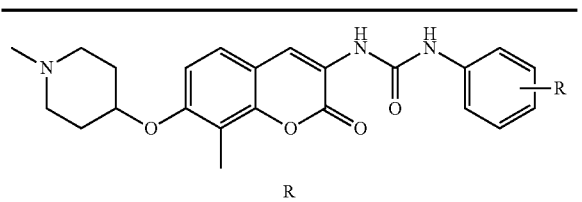

H
p-CH₃
p-CH₂CH₃
p-CH(CH₃)₂
p-C(CH₃)₃
m-CH₃
m-CH₂CH₃
p-CF₃
m-CF₃
3,4-dimethyl
2,4-dimethyl
3,5-dimethyl
p-OCH₃
m-OCH₃

-continued

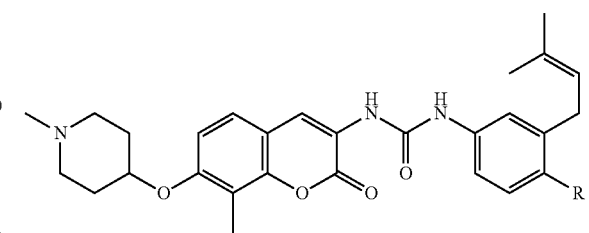

R p-OAc
p-OH
p-OCF₃
m-OAc
m-OH
2-OMe-5-t-Bu
3,4,5-trimethoxyl
p-N-dimethylamine
p-phenyl
p-phenoxyl
m-phenoxyl
p-F
p-Cl
p-Br
p-NO₂
p-CN
p-COCH₃
m-Cl
m-COCH₃
3,4-dichloro
3,5-dichloro.

In another aspect, the present disclosure provides a novobiocin analog comprising: one of the following structures or derivative thereof or salt thereof or prodrug thereof:

R

OAc
OH
OMe
H.

In another aspect, the present disclosure provides a novobiocin analog comprising: one of the following structures or derivative thereof or salt thereof or prodrug thereof:

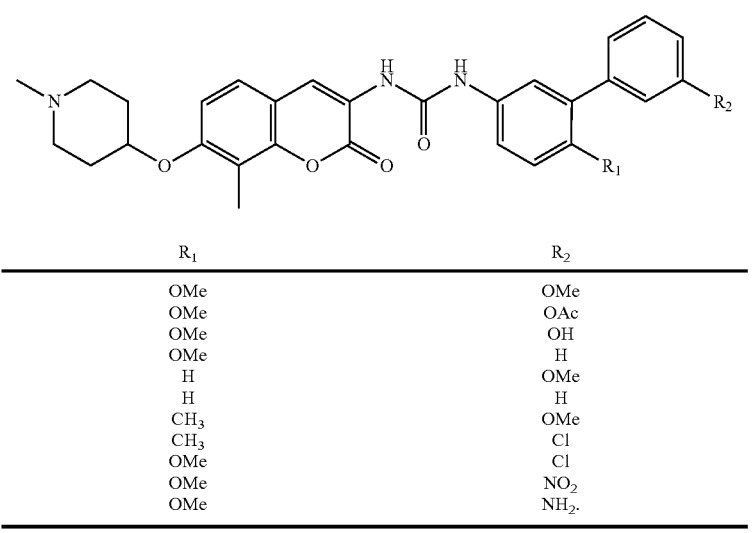
| R₁ | R₂ |
|---|---|
| OMe | OMe |
| OMe | OAc |
| OMe | OH |
| OMe | H |
| H | OMe |
| H | H |
| CH₃ | OMe |
| CH₃ | Cl |
| OMe | Cl |
| OMe | NO₂ |
| OMe | NH₂. |
In another aspect, the present disclosure provides a novobiocin analog comprising: one of the following structures or derivative thereof or salt thereof or prodrug thereof:
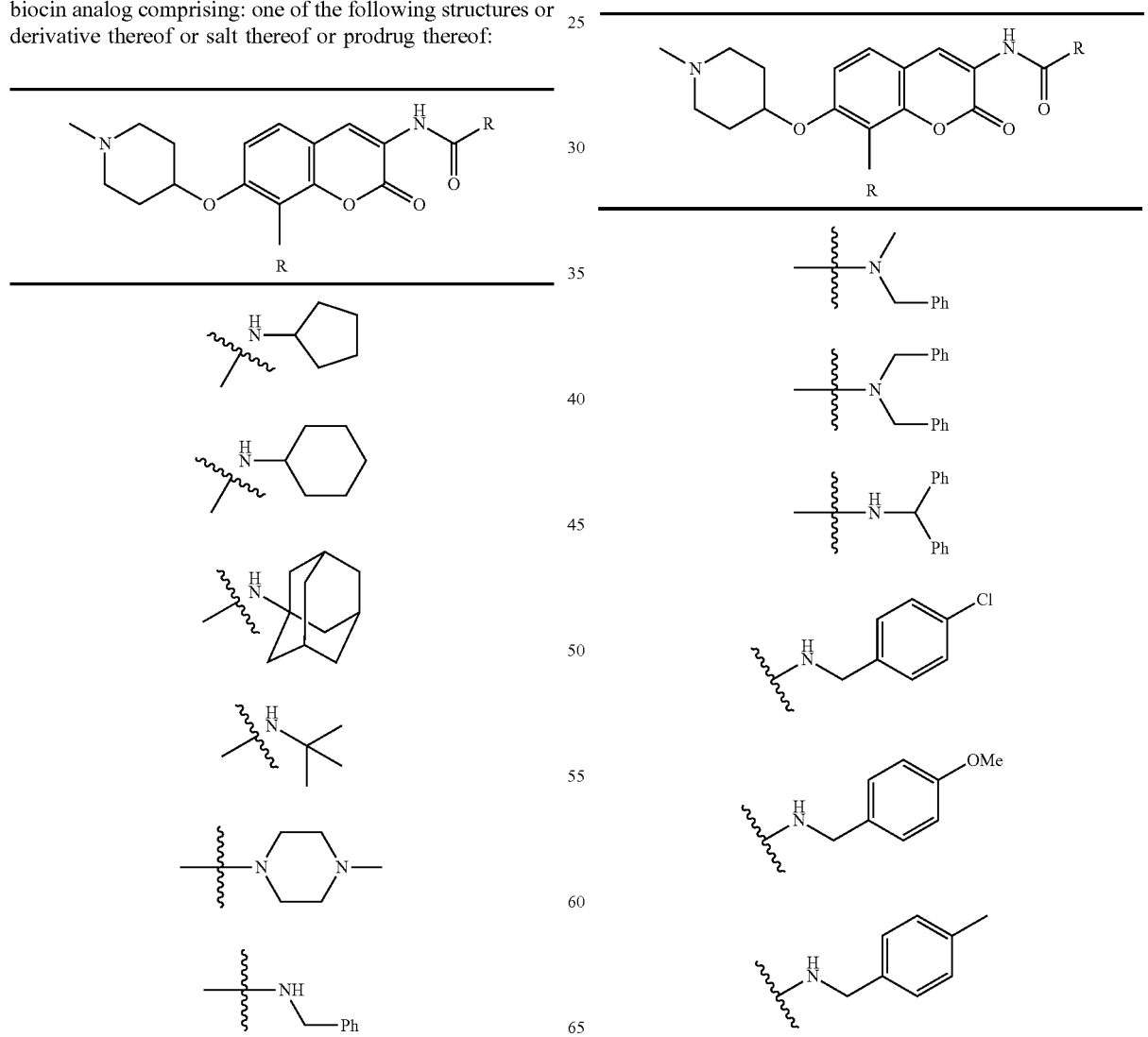

-continued

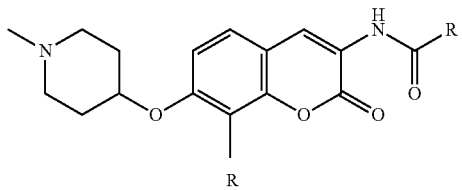

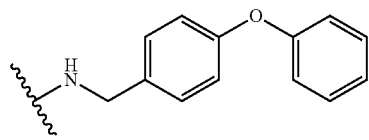 [SMILES: *NCc1ccc(Oc2ccccc2)cc1]

In yet another aspect, the present disclosure provides a method of synthesizing the novobiocin analog of the present disclosure, comprising: performing a synthesis protocol with one or more reagents in order to obtain the novobiocin analog.

In still another aspect, the present disclosure provides a method of inhibiting Hsp90, comprising:
A) providing the novobiocin analog of the present disclosure; and
B) inhibiting Hsp90 with the novobiocin analog.

In yet another aspect, the present disclosure provides a method of treating or inhibiting cancer, the method comprising:
A) providing the novobiocin analog of the present disclosure; and
B) administering the novobiocin analog in a therapeutically effective amount to a subject so as to treat or inhibit cancer.

In another aspect, the present disclosure provides a method of designing a novobiocin analog, the method comprising:
A) using a three-dimensional quantitative structure-activity relationship (3D-QSAR) of novobiocin and/or one or more derivatives thereof in order to determine chemical structure having a desired property or activity; and
B) selecting a novobiocin analog to further derivatize to obtain the novobiocin analog of the present disclosure.

In another aspect, the present disclosure provides a compound of the formula:

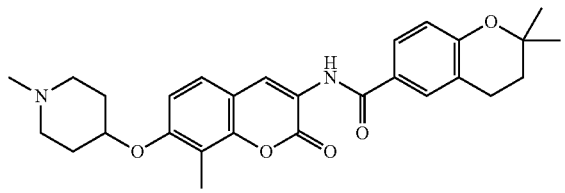

or a pharmaceutically acceptable salt thereof.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

DESCRIPTION OF ILLUSTRATIVE EMBODIMENTS

Figure 1:
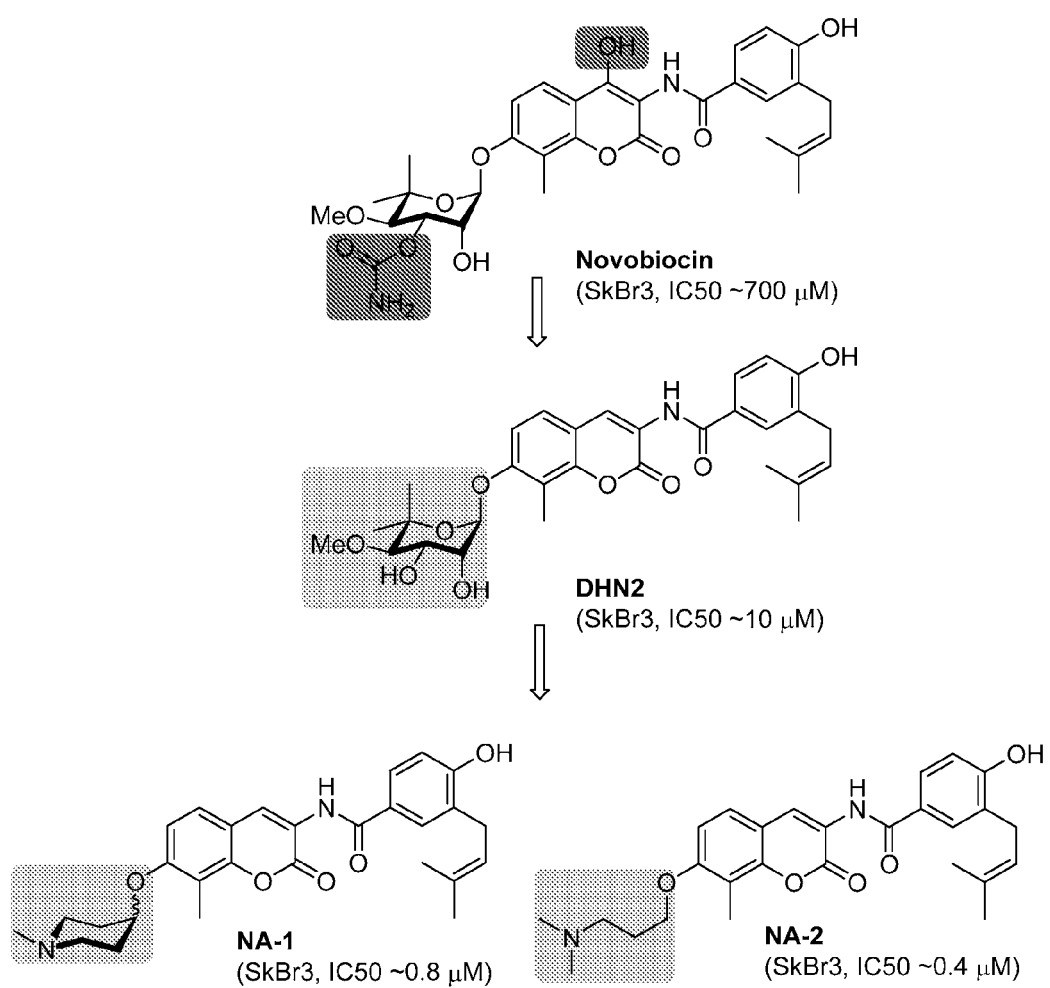
FIG. 1—Evolution of novobiocin core to increased activity in a variety of cancer cell lines.
Figure 2:
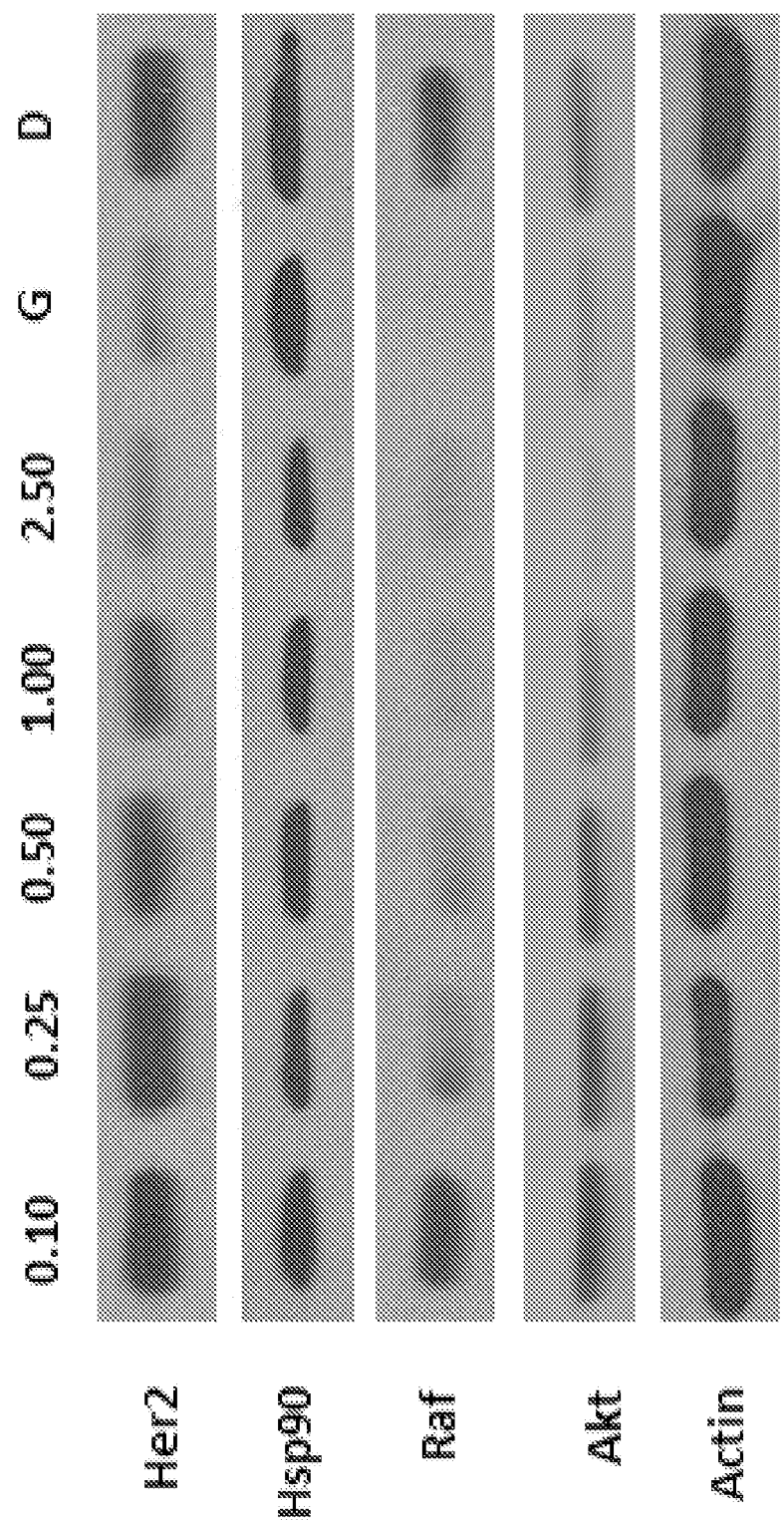
FIG. 2—Western blot analyses of MCF-7 cell lysates for Hsp90 client protein degradation after 24 h incubation. Concentrations (in µM) of 24 are indicated above each lane. Geldanamycin (G, 500 nM) and DMSO (D) were respectively employed as positive and negative controls.
Figure 3:
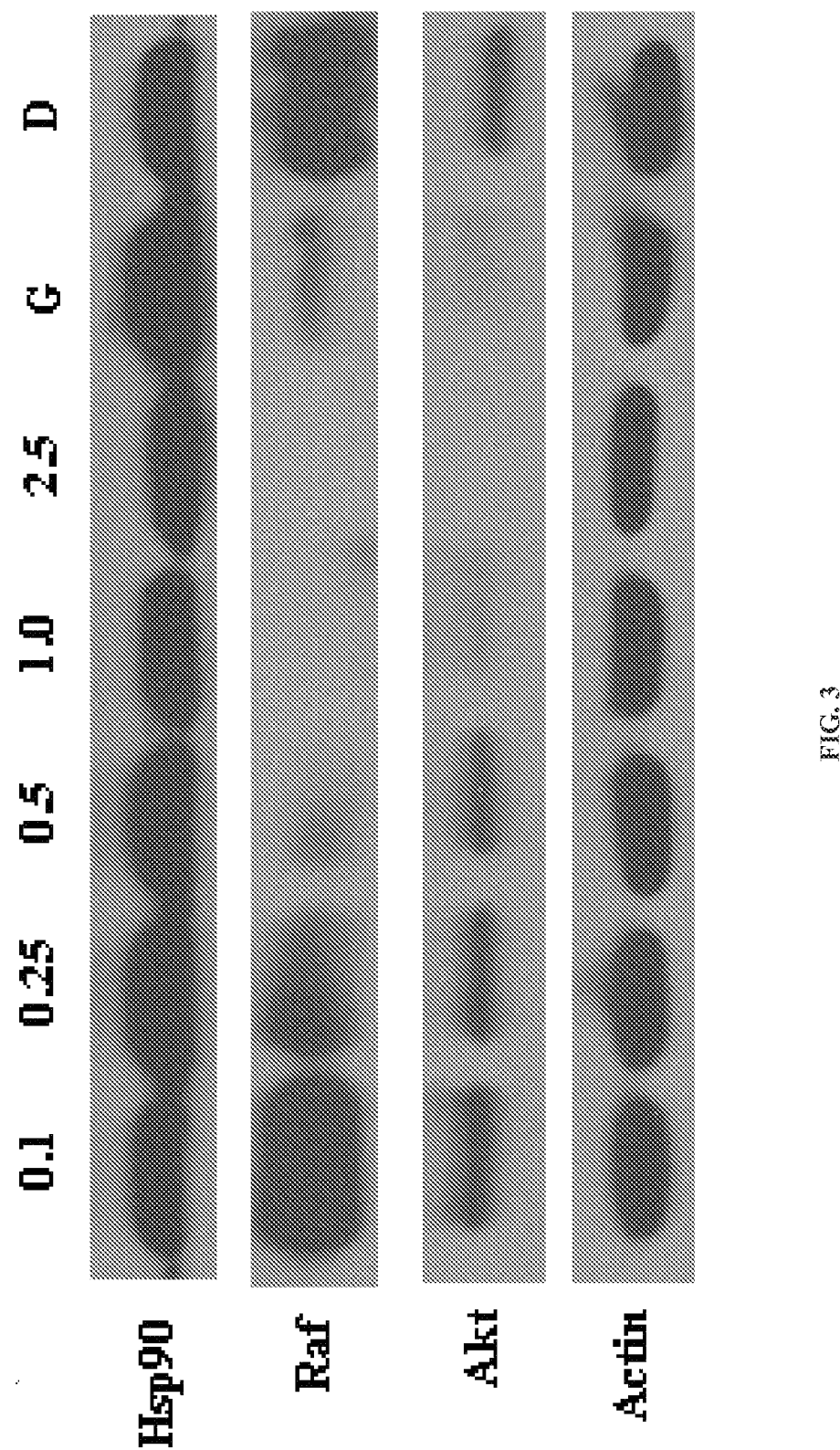
FIG. 3—Western blot analyses of MCF-7 cell lysates for Hsp90 client protein degradation after 24 h incubation. Concentrations (in µM) of 70j are indicated above each lane. Geldanamycin (G, 500 nM) and DMSO (D) were employed respectively as positive and negative controls.

The present disclosure provides new compounds which may be used to inhibit Hsp90 in some embodiments. Without being bound by theory, in some embodiments, inhibition of Hsp90 may be effected by binding to the C-terminus nucleotide binding pocket of the protein. In some embodiments, these compounds are useful in the treatment of a disease or disorder, including, for example, cancer.

I. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfato" means —S(O)$_2$OH; "sulfamido" means —S(O)$_2$NH$_2$; "sulfonyl" means —S(O)$_2$—; and "sulfinyl" means —S(O)—.

In the context of chemical formulas, the symbol "—" means a single bond, "=" means a double bond, and "≡" means triple bond. The symbol "- - - -" represents an optional bond, which if present is either single or double. The symbol "⚌" represents a single bond or a double bond. Thus, for example, the formula

includes

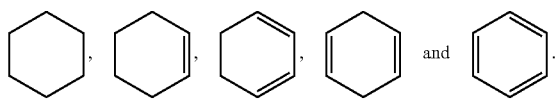

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⌇⌇⌇", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⦀⦀" means a single bond where the group attached to the thick end of the wedge is "into the page". The symbol "⌇⌇⌇" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

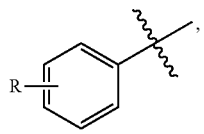

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

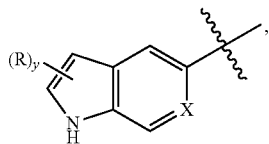

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the number of carbon atoms in the group is as indicated as follows: "Cn" defines the exact number (n) of carbon atoms in the group/class. "C≤n" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" Designates Those Alkyl Groups Having from 2 to 10 carbon atoms. Typically, the carbon number indicator follows the group it modifies, is enclosed with parentheses, and is written entirely in subscript; however, the indicator may also precede the group, or be written without parentheses, without signifying any change in meaning. Thus, the terms "C5 olefin", "C5-olefin", "olefin$_{(C5)}$", and "olefin$_{C5}$" are all synonymous.

The term "saturated" when used to modify a compound or an atom means the compound or atom has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the compound H—R, wherein R is cycloalkyl as this term is defined above. The group "adamantyl" is a subset of cycloalkyl wherein the cycloalkyl group is defined by the structure:

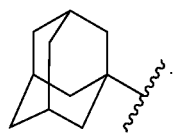 [SMILES: *C12CC3CC(CC(C3)C1)C2]

When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. A "substituted adamantyl" group is a group with the adamantyl carbon ring structure and one or more hydrogen has been replaced as defined above.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$≡CCH$_3$ are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

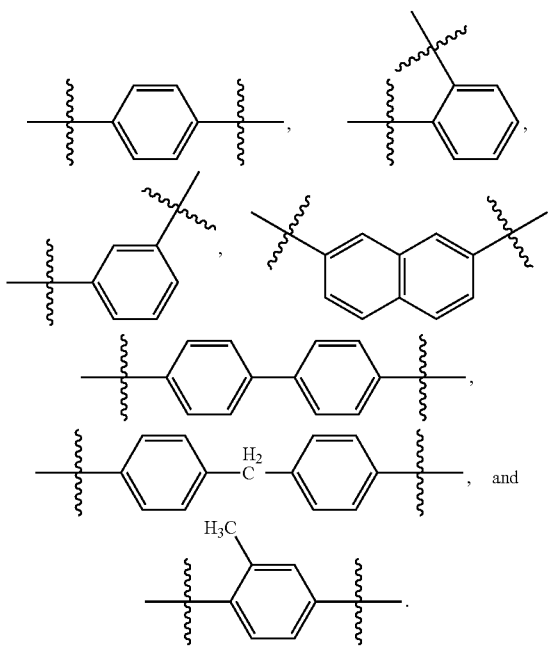

An "arene" refers to the compound H—R, wherein R is aryl as that term is defined above. Benzene and toluene are non-limiting examples of arenes. The term "biphenyl" is a subset of the term "aryl" wherein the group is defined by the aromatic ring structure:

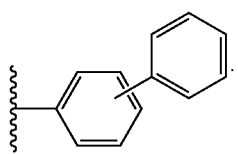

When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the compound H—R, wherein R is heteroaryl. Pyridine and quinoline are non-limiting examples of heteroarenes. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

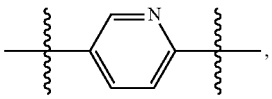

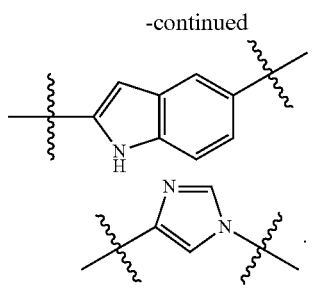 and

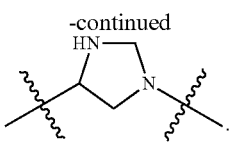

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

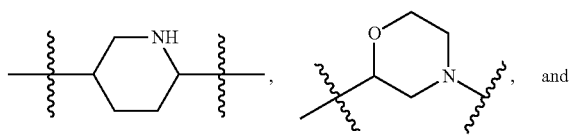 and

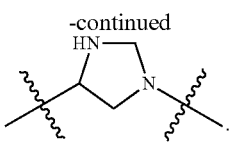

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH₃ (acetyl, Ac), —C(O)CH₂CH₃, —C(O)CH₂CH₂CH₃, —C(O)CH(CH₃)₂, —C(O)CH(CH₂)₂, —C(O)C₆H₅, —C(O)C₆H₄CH₃, —C(O)CH₂C₆H, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The groups, —C(O)CH₂CF₃, —CO₂H (carboxyl), —CO₂CH₃ (methylcarboxyl), —CO₂CH₂CH₃, —C(O)NH₂ (carbamoyl), and —CON(CH₃)₂, are non-limiting examples of substituted acyl groups.

The term "alkoxy" when used without the "substituted" modifier refers to the group —OR, in which R is an alkyl, as that term is defined above. Non-limiting examples include: —OCH₃ (methoxy), —OCH₂CH₃ (ethoxy), —OCH₂CH₂CH₃, —OCH(CH₃)₂ (isopropoxy), —OC(CH₃)₃ (tert-butoxy), —OCH(CH₂)₂, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

Other abbreviations used herein are as follows: DMSO, dimethyl sulfoxide;

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Compounds And Synthetic Methods

The compounds provided by the present disclosure are shown, for example, above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Urea analogs of novobiocin are obtained by reacting an isocyanate with the amine containing coumarin core. In some embodiments, 2~5 equivalent of an isocyanate is added to a solution of coumarin amine in dichloromethane and the resulting solution stirred at room temperature overnight. Solvent was evaporated under vacuum and the residue was purified by column chromatography ($SiO_2$, DCM: MeOH, 10:1) to obtain the desired urea as outlined in Scheme 1, wherein R is an chemical groups as described herein. In some embodiments, the group is a non-reactive group such as an alkyl, aryl, or tertiary amine group. In other embodiments, the group is a protected group such as a protected amine or a protected hydroxyl group, wherein the protected group is removed after the reaction with the coumarin amine. Removal of a protecting group is described at least in Greene and Wut's *Protecting Groups in Organic Chemistry*, which is incorporated herein by reference.

Scheme 1: General Urea Synthesis Methodology

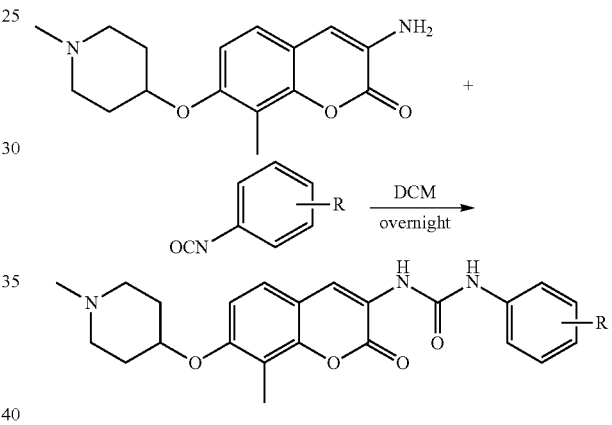

Generally, appropriate non-commerically available isocyanates are prepared as described in Scheme 2. Modification and optimization of these methodologies would be routine for a person of skill in the art.

Scheme 2: General Isocyanate Synthesis Methodology

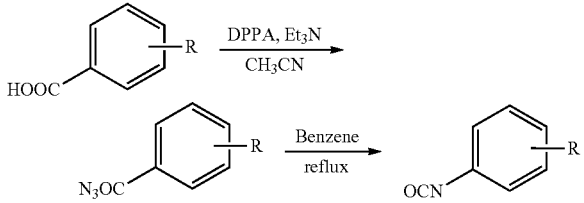

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of the compounds provided herein are within the scope of the invention. It will also be appreciated by those skilled in organic chemistry that many organic compounds can exist in more than one crystalline form. For example, crystalline form may vary from solvate to solvate. Thus, all crystalline forms of the compounds provided herein or the pharmaceutically acceptable solvates thereof are within the scope of the present invention.

III. Biological Activity

1. Anti-proliferation Assays

Cells were maintained in a 1:1 mixture of Advanced DMEM/F12 (Gibco) supplemented with non-essential amino acids, L-glutamine (2 mM), streptomycin (500 µg/mL), penicillin (100 units/mL), and 10% FBS. Cells were grown to confluence in a humidified atmosphere (37° C., 5% $CO_2$), seeded (2000/well, 100 µL) in 96-well plates, and allowed to attach overnight. Compound at varying concentrations in DMSO (1% DMSO final concentration) was added, and cells were returned to the incubator for 72 h. At 72 h, the number of viable cells was determined using an MTS/PMS cell proliferation kit (Promega) per the manufacturer's instructions. Cells incubated in 1% DMSO were used at 100% proliferation, and values were adjusted accordingly. $IC_{50}$ values were calculated from separate experiments performed in triplicate using GraphPad Prism.

2. Western Blot Analyses

MCF-7 cells were cultured as described above and treated with various concentrations of drug, GDA in DMSO (1% DMSO final concentration), or vehicle (DMSO) for 24 h. Cells were harvested in cold PBS and lysed in RIPA lysis buffer containing 1 mM PMSF, 2 mM sodium orthovanadate, and protease inhibitors on ice for 1 h. Lysates were clarified at 14000 g for 10 min at 4° C. Protein concentrations were determined using the Pierce BCA protein assay kit per the manufacturer's instructions. Equal amounts of protein (20 µg) were electrophoresed under reducing conditions, transferred to a nitrocellulose membrane, and immunoblotted with the corresponding specific antibodies. Membranes were incubated with an appropriate horseradish peroxidase-labeled secondary antibody, developed with a chemiluminescent substrate, and visualized.

IV. Hsp90 Protein And Hyperproliferative Diseases

The compound of the present disclosure may be useful in the treatment of diseases or disorders with result from the unnatural proliferation of cells. In some aspects, this disease or disorder is cancer. Without being bound by theory, the compounds of the present disclosure bind to the C terminus of the Hsp90 protein and thus prevent the binding of the natural substrate to the protein. The Hsp90 is a molecular chaperone protein, which in addition to assisting in protein folding, protein degration, and mitigating heat stress, is implicated in stabilizing a number of proteins associated with cancer. Inhibition of the Hsp90 protein has been shown to lead to apoptosis of the cancerous cells. Without being bound by theory, a number of different molecular pathways are implicated in the Hsp90 protein's role in cancer development and proliferation. For example, the protein is implicated in stabilizing mutant oncogenic proteins such as v-Src, Bcr/Abl, and p53, stabilizing several growth factors and signaling molecules such as EGFR, PI3K, and AKT proteins which leads to growth factor signaling pathway promotion, and promotes the induction of VEGF, nitric oxide synthase, and the matrix metalloproteinase MMP2 which promote angiogenesis and metathesis of the cancerous cells. Many different cancer types and subtypes rely on pathways mediated by the Hsp90 protein for proliferation and tumor development thus inhibitors of the highly conserved Hsp90 protein may be used to treat a wide variety of cancers.

The compound may be used to treat cancer cells according to the embodiments include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

V. Pharmaceutical Formulations and Routes Of Administration

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, the effective dosing amount that may be used is an amount sufficient to cause greater than 10% reduction in number of cancerous cells. In other embodiments, an effective dosing amount is sufficient to reduce the tumor volume by greater than 10% over a given time period compared to the volume before administration of the compound. In other embodiments, the effective amount is measured based upon the treatment with the compound and one or more different pharmaceutical agents or modalities.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.01% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks therebetween. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

VI. Combination Therapy

In addition to being used as a monotherapy, the compounds of the present disclosure may also be used in combination therapies. In some embodiments, effective combination therapy is achieved with a single composition or pharmacological formulation that includes both agents, or with two distinct compositions or formulations, administered at the same time, wherein one composition includes a compound of this invention, and the other includes the second agent(s). Alternatively, in other embodiments, the therapy precedes or follows the other agent treatment by intervals ranging from minutes to months.

A wide range of second therapies may be used in conjunction with the compounds of the present disclosure. Such second therapies include, but are not limited to, surgery, immunotherapy, radiotherapy, or a second chemotherapeutic agent. In some embodiments, the second chemotherapeutic agent is a N-terminus Hsp90 inhibitor such as geldanamycin, radicicol, the geldanamycin derivative 17AAG, or gamitrinib.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Compound Activity in Cancer Cell Lines

The anti-proliferative activity of these compounds is evaluated against two breast cancer cell lines, SKBr3 (estrogen receptor negative, Her2 over-expressing breast cancer cells) and MCF-7 (estrogen receptor positive breast cancer cells). As shown in Table 1, alkylation of the 4'-phenol (16-18) results in decreased anti-proliferative activity against both cell lines. Saturation of the double bond (19) produces no effect on inhibitory activity; while intramolecular cyclization (20), the removal of two terminal methyl groups on the prenyl chain (21a and 22a), and removal of the prenyl group (21b and 22b) results in decreased anti-proliferative activities. Compound 21c, in which the phenol was removed, results in a two-fold lower activity. Removal of both the phenol and prenyl group (21d) resulted in significantly decreased activity. Likewise, replacement of the prenyl group with electron-withdrawing substituents (21e and 22e vs 21b and 22b) results in diminished activity.

TABLE 1

Modified Benzamide Coumarin Derivatives

| Compound ID | Structure | SKBr3 (μM) | MCF-7 (μM) |
|---|---|---|---|
| 2 | 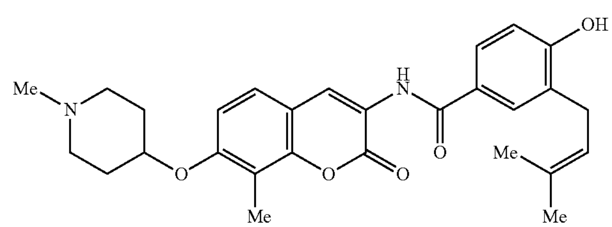 [SMILES: CC(C)=CCc1cc(C(=O)Nc2cc3ccc(OC4CCN(C)CC4)c(C)c3oc2=O)ccc1O] | 0.76 ± 0.17 | 1.09 ± 0.10 |
| 16 | 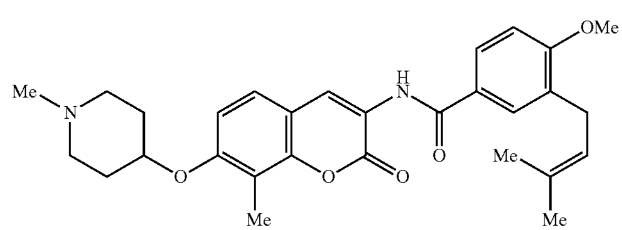 [SMILES: COc1ccc(C(=O)Nc2cc3ccc(OC4CCN(C)CC4)c(C)c3oc2=O)cc1CC=C(C)C] | 1.41 ± 0.20 | 1.58 ± 0.09 |
| 17 | 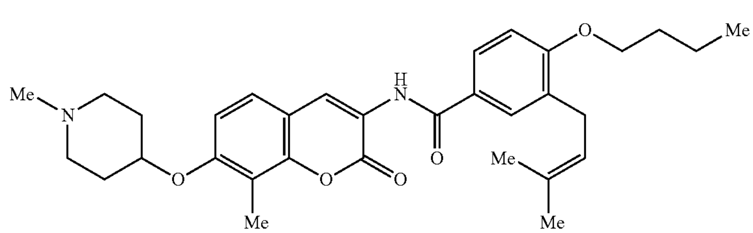 [SMILES: CCCCOc1ccc(C(=O)Nc2cc3ccc(OC4CCN(C)CC4)c(C)c3oc2=O)cc1CC=C(C)C] | 1.40 ± 0.07 | 1.44 ± 0.05 |

TABLE 1-continued

Modified Benzamide Coumarin Derivatives

| Compound ID | Structure | SKBr3 (μM) | MCF-7 (μM) |
|---|---|---|---|
| 18 | 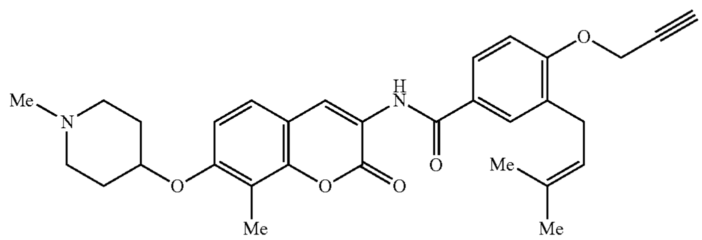 [SMILES: C#CCOc1ccc(C(=O)Nc2cc3ccc(OC4CCN(C)CC4)c(C)c3oc2=O)cc1CC=C(C)C] | 1.40 ± 0.11 | 1.12 ± 0.16 |
| 19 | 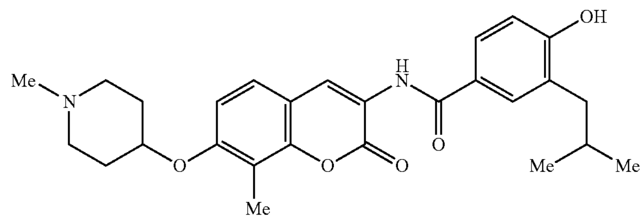 [SMILES: Cc1c(OC2CCN(C)CC2)ccc2cc(NC(=O)c3ccc(O)c(CC(C)C)c3)c(=O)oc12] | 0.60 ± 0.01 | 1.25 ± 0.39 |
| 20 | 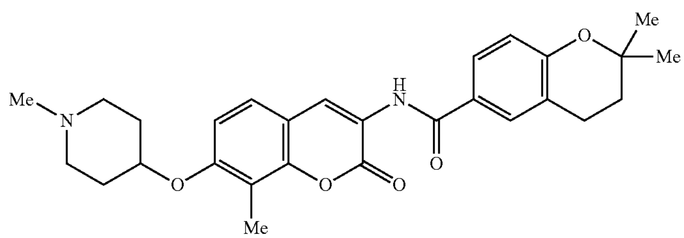 [SMILES: Cc1c(OC2CCN(C)CC2)ccc2cc(NC(=O)c3ccc4c(c3)CCC(C)(C)O4)c(=O)oc12] | 3.46 ± 0.02 | 5.01 ± 0.01 |
| 21a | 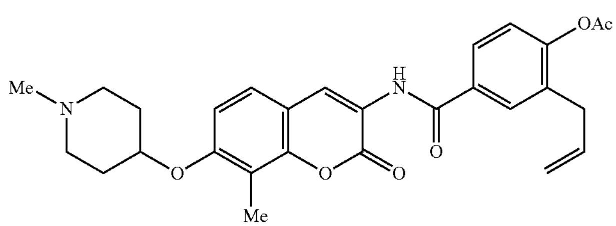 [SMILES: C=CCc1cc(C(=O)Nc2cc3ccc(OC4CCN(C)CC4)c(C)c3oc2=O)ccc1OC(C)=O] | 2.26 ± 0.12 | 2.00 ± 0.18 |
| 21b | 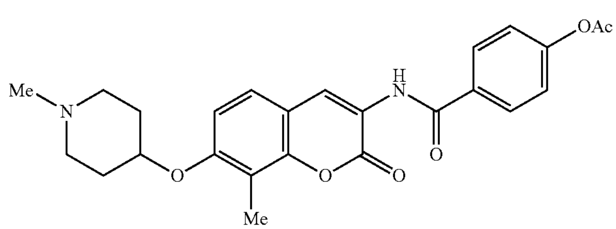 [SMILES: CC(=O)Oc1ccc(C(=O)Nc2cc3ccc(OC4CCN(C)CC4)c(C)c3oc2=O)cc1] | 1.67 ± 0.20 | 1.62 ± 0.04 |
| 21c | 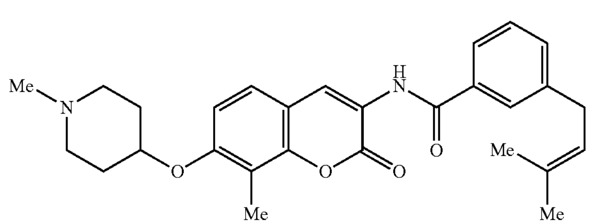 [SMILES: CC(C)=CCc1cccc(C(=O)Nc2cc3ccc(OC4CCN(C)CC4)c(C)c3oc2=O)c1] | 1.68 ± 0.12 | 2.10 ± 0.08 |

TABLE 1-continued

Modified Benzamide Coumarin Derivatives

| Compound ID | Structure | SKBr3 (μM) | MCF-7 (μM) |
|---|---|---|---|
| 21d | 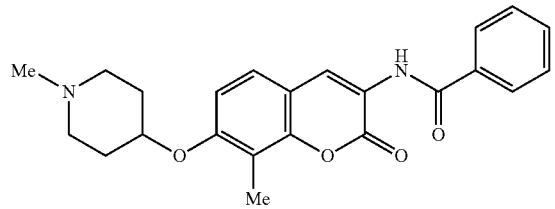 [SMILES: Cc1c(OC2CCN(C)CC2)ccc2cc(NC(=O)c3ccccc3)c(=O)oc12] | 11.5 ± 2.0 | 11.7 ± 1.0 |
| 21e | 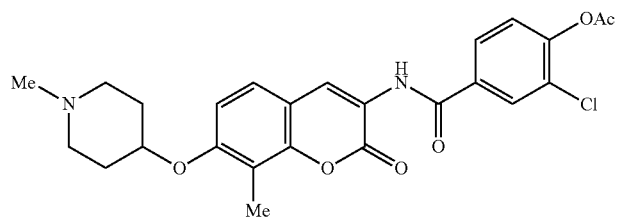 [SMILES: CC(=O)Oc1ccc(C(=O)Nc2cc3ccc(OC4CCN(C)CC4)c(C)c3oc2=O)cc1Cl] | 3.50 ± 0.01 | 1.61 ± 0.16 |
| 22a | 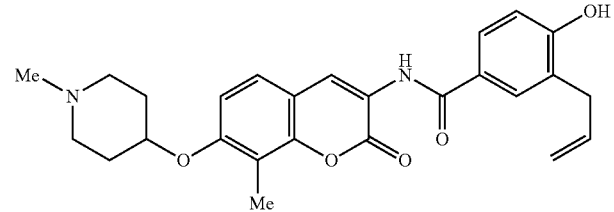 [SMILES: C=CCc1cc(C(=O)Nc2cc3ccc(OC4CCN(C)CC4)c(C)c3oc2=O)ccc1O] | 2.43 ± 0.04 | 2.17 ± 0.11 |
| 22b | 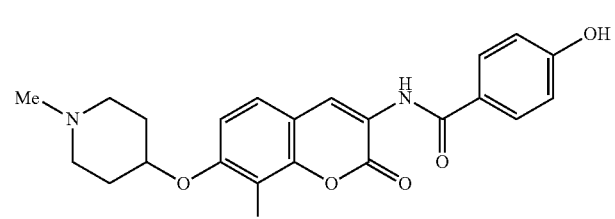 | 0.84 ± 0.18 | 1.43 ± 0.08 |
| 22e | 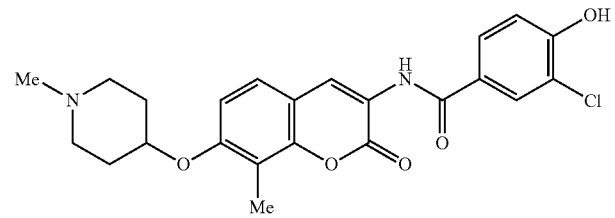 [SMILES: Cc1c(OC2CCN(C)CC2)ccc2cc(NC(=O)c3ccc(O)c(Cl)c3)c(=O)oc12] | 2.30 ± 0.57 | 1.48 ± 0.14 |

Therefore, dual functionalities were installed on the benzamide side chain to potentially optimize binding affinity. The first approach towards this investigation requires alkylation of the 4'-phenol with an alkyl tertiary amine. The activity of these compounds is described in Table 2. Additionally, previous studies demonstrated that replacing the flexible prenyl side-chain with an aromatic ring leads to improved inhibitory activity (Zhao, et al., 2012). Therefore, installation of two additional functionalities by the use of biaryl analogues, 33a and 33b is explored herein.

Evaluation of these benzamide analogues against breast cancer cell lines is described in Table 2. These data demonstrated that tethering the phenol to alkyl amines (23-25) leads to increased anti-proliferative activity. For biaryl analogues (32 and 33), replacement of the prenyl group with a substituted phenyl ring maintains inhibitory activity (32a and 33a), however, switching the phenol from the first to the second benzene ring increases activity almost three-fold (32b and 33b).

TABLE 2
Modified Benzamide and Biphenylamide Derivatives (in μM)
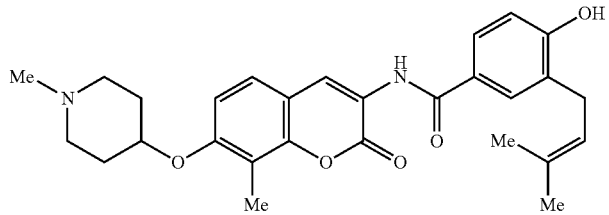 [SMILES: CC(C)=CCc1cc(C(=O)Nc2cc3ccc(OC4CCN(C)CC4)c(C)c3oc2=O)ccc1O]
| Compound ID | Structure | SKBr3 | MCF-7 |
|---|---|---|---|
| 2 | 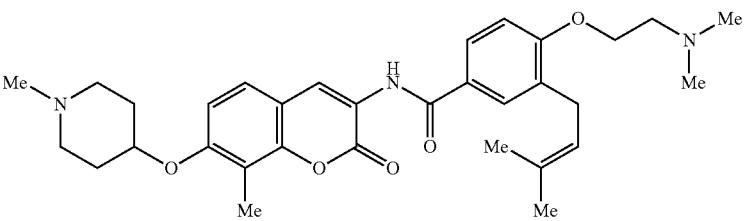 [SMILES: CC(C)=CCc1cc(C(=O)Nc2cc3ccc(OC4CCN(C)CC4)c(C)c3oc2=O)ccc1OCCN(C)C] | 0.76 ± 0.17 | 1.09 ± 0.10 |
| 23 | 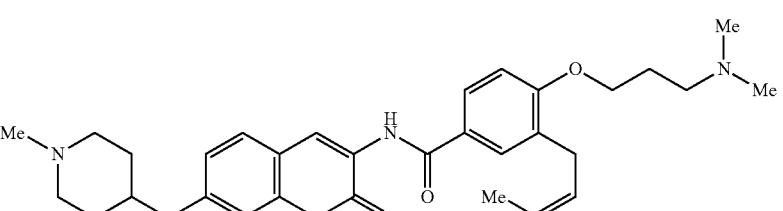 | 0.33 ± 0.00 | 0.72 ± 0.08 |
| 24 | 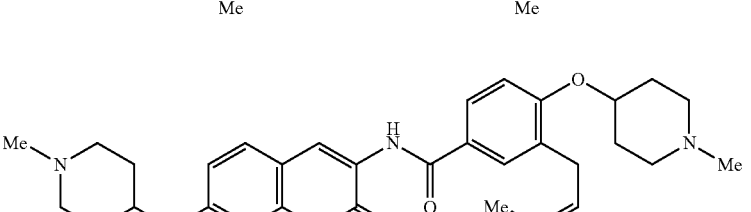 | 0.25 ± 0.02 | 0.46 ± 0.05 |
| 25 | 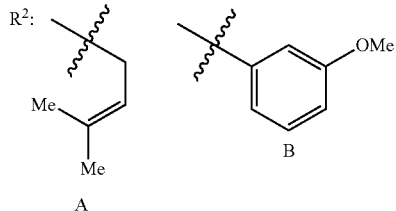 | 0.21 ± 0.00 | 0.47 ± 0.081 |

TABLE 2-continued

Modified Benzamide and Biphenylamide Derivatives (in μM)

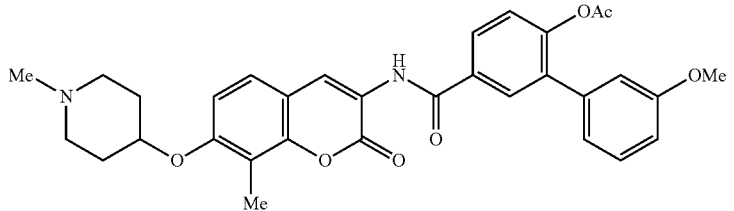 [SMILES: COc1cccc(-c2cc(C(=O)Nc3cc4ccc(OC5CCN(C)CC5)c(C)c4oc3=O)ccc2OC(C)=O)c1]

| Compound ID | Structure | SKBr3 | MCF-7 |
|---|---|---|---|
| 32a | 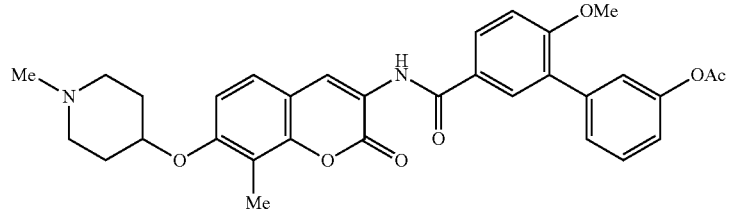 | 0.92 ± 0.06 | 0.91 ± 0.00 |
| 32b | 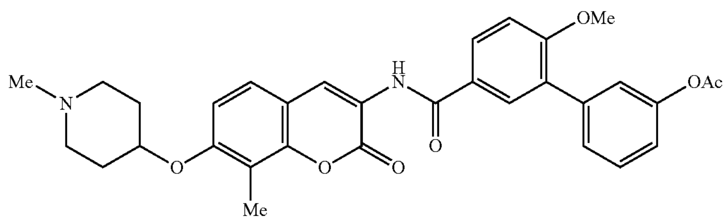 [SMILES: COc1ccc(C(=O)Nc2cc3ccc(OC4CCN(C)CC4)c(C)c3oc2=O)cc1-c1cccc(OC(C)=O)c1] | 0.29 ± 0.01 | 0.36 ± 0.06 |
| 33a | 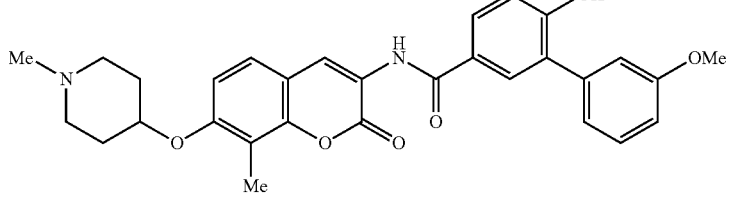 | 0.86 ± 0.16 | 0.81 ± 0.14 |
| 33b | 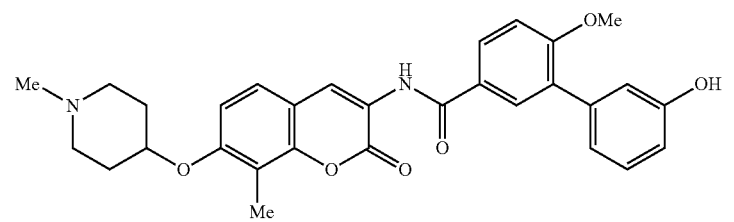 [SMILES: COc1ccc(C(=O)Nc2cc3ccc(OC4CCN(C)CC4)c(C)c3oc2=O)cc1-c1cccc(O)c1] | 0.31 ± 0.04 | 0.38 ± 0.08 |

Upon construction of the C- and N-linked heterocyclic novobiocin analogues, the compounds are subject to biological evaluation by measuring the anti-proliferative activity against SKBr3 (estrogen receptor negative, Her2 overexpressing breast cancer cells) and MCF-7 (estrogen receptor positive breast cancer cells) cell lines. As shown in Table 1, the anti-proliferative activities manifest by C-linked heterocyclic analogues (44-53) are similar to the N-methylpiperidine derivative. Although piperizine analogues (62 and 63) maintain activity comparable to the N-methylpiperidine derivative, compounds 64 and 65 are inactive at the highest concentrations tested. It appears that shrinking the ring size (66) restores activity.

TABLE 3

Anti-proliferative Activities of Cycloamine Analogues

| R | R' | SKBr3 (μM) | MCF-7 (μM) |
|---|---|---|---|
| N-methylpiperidin-4-yl | H | 0.76 ± 0.17 | 1.09 ± 0.10 |
| N-methylpiperidin-3-yl-methyl | OAc | 0.74 ± 0.01 | 1.65 ± 0.11 |
| N-methylpyrrolidin-3-yl-methyl | OAc | 0.88 ± 0.09 | 1.88 ± 0.45 |
| piperidin-2-yl-ethyl | OAc | 0.64 ± 0.06 | 0.71 ± 0.03 |
| piperidin-3-yl-methyl | OAc | 0.62 ± 0.04 | 0.82 ± 0.07 |
| piperidin-2-yl-ethyl | H | 0.64 ± 0.06 | 0.71 ± 0.03 |
| N-methylpiperidin-3-yl-methyl | H | 1.30 ± 0.63 | 2.64 ± 0.45 |
| piperidin-3-yl-methyl | H | 0.60 ± 0.01 | 0.79 ± 0.10 |

TABLE 3-continued

Anti-proliferative Activities of Cycloamine Analogues

| R | R' | SKBr3 (μM) | MCF-7 (μM) |
|---|---|---|---|
| N-methylpyrrolidin-3-yl-methyl | H | 0.92 ± 0.56 | 1.55 ± 0.04 |
| 4-methylpiperazin-1-yl-propyl | H | 1.01 ± 0.03 | 1.20 ± 0.12 |
| piperazin-1-yl-propyl | H | 0.82 ± 0.02 | 0.93 ± 0.21 |
| morpholin-4-yl-propyl | H | >50 | >50 |
| piperidin-1-yl-propyl | H | >50 | >50 |
| pyrrolidin-1-yl-propyl | H | 0.72 ± 0.01 | 0.99 ± 0.04 |

Anti-proliferative activity manifested by these analogues is evaluated against SKBr3 and MCF-7 cell lines. As shown in Table 4, one relatively bulky group (up to 3 linear carbons, 68a, 68b, 68d, and 68f-68k except 68i) is generally well-tolerated in the binding site. The one bulky group can be linear (68a, 68b, and 68d) or branched alkyl chains (68f-68h, 68j and 68k). Diethylamine (68c) and diisopropylamine (68i) analogues exhibit decreased anti-proliferative activity against SKBr3 cells while dipropylamine amine analogue did not show any activity at the highest concentration (68e). Glycine analogues (68l, 68m and 68n) exhibit decreased anti-proliferative activity while the alcoholic analogue (68o) retains activity.

TABLE 4

Anti-proliferative Activities of Alkylamino Analogues

| Compound ID | $R_1$ | $R_2$ | SKBr3 (µM) | MCF-7 (µM) |
|---|---|---|---|---|
|  | $CH_3$ | $CH_3$ | 0.44 ± 0.02 | 1.35 ± 0.38 |
| 68a | $CH_2CH_3$ | H | 0.72 ± 0.34 | 0.98 ± 0.35 |
| 68b | $CH_2CH_3$ | $CH_3$ | 0.73 ± 0.06 | 2.19 ± 0.50 |
| 68c | $CH_2CH_3$ | $CH_2CH_3$ | 4.90 ± 0.42 | 6.39 ± 0.04 |
| 68d | $CH_2CH_2CH_3$ | H | 0.99 ± 0.03 | 0.98 ± 0.00 |
| 68e | $CH_2CH_2CH_3$ | $CH_2CH_2CH_3$ | >50 | >50 |
| 68f | $CH_2CH(CH_3)_2$ | H | 1.03 ± 0.02 | 1.32 ± 0.06 |
| 68g | $CH(CH_3)_2$ | H | 0.75 ± 0.26 | 0.74 ± 0.16 |
| 68h | $CH(CH_3)_2$ | $CH_3$ | 0.57 ± 0.13 | 1.05 ± 0.06 |
| 68i | $CH(CH_3)_2$ | $CH(CH_3)_2$ | 1.60 ± 0.02 | 1.31 ± 0.39 |
| 68j | $C(CH_3)_3$ | H | 0.66 ± 0.06 | 0.95 ± 0.10 |
| 68k | $C(CH_3)_3$ | $CH_3$ | 0.88 ± 0.10 | 1.14 ± 0.11 |
| 68l | $CH_2COOMe$ | H | 1.06 ± 0.11 | 2.82 ± 0.27 |
| 68m | $CH_2COOH$ | H | 7.57 ± 2.86 | 18.11 ± 5.35 |
| 68n | $CH_2CONH_2$ | H | 2.29 ± 0.47 | 1.46 ± 0.35 |
| 68o | $CH_2CH_2OH$ | H | 0.61 ± 0.06 | 1.56 ± 0.09 |

Table 5 shows that cyclohexyl (70a and 70b), benzyl (70e) or substituted benzyl (70f and 70g) and three dimensional alkyls (70i and 37j) are well tolerated in the binding site. Aniline analogues are inactive (70c and 70d). Compound 70h, tertiary amine analogue with a small N-methyl group, shows greatly decreased activity. Compound 70j, containing an N-adamantyl substitution, manifests good anti-proliferative activity in both SKBr3 and MCF-7 breast cancer cell lines.

TABLE 5

Anti-proliferative Activity of Alkylether Derivatives with Cyclic N-Substitutions

| Compound ID | $R_1$ | $R_2$ | SKBr3 (µM) | MCF-7 (µM) |
|---|---|---|---|---|
| 70a | Cyclohexyl | H | 0.66 ± 0.12 | 1.07 ± 0.35 |
| 70b | Cyclohexyl | $CH_3$ | 0.97 ± 0.03 | 1.08 ± 0.07 |
| 70c | Phenyl | H | >50 | >50 |
| 70d | Phenyl | $CH_3$ | >50 | >50 |
| 70e | Benzyl | H | 0.47 ± 0.16 | 0.91 ± 0.01 |
| 70f | (R)-1-phenylethyl | H | 1.00 ± 0.31 | 1.45 ± 0.20 |
| 70g | Cumenyl | H | 0.96 ± 0.01 | 1.07 ± 0.01 |
| 70h | Benzyl | $CH_3$ | 10.73 ± 0.49 | 11.52 ± 4.16 |
| 70i | (norbornyl-gem-dimethyl) | H | 0.77 ± 0.13 | 1.03 ± 0.12 |
| 70j | Adamantyl | H | 0.31 ± 0.04 | 0.32 ± 0.03 |

Additional studies were carried out exploring the substitution of the benzamide group with a urea linkage. Tables 6-9 describes the activity of these compounds. In particular, the urea linkage manifests anti-proliferative activity in a variety of cell lines including breast, prostate, head and neck squamous cell carcinoma, triple negative breast, and thyroid cancer. As can be seen when comparing the amide linkage to the urea linkage, the phenyl amide exhibits an $IC_{50}$ of 11.5 µM and 11.7 µM for SKBr3 and MCF-3, while the phenyl urea linkage exhibits an $IC_{50}$ of 0.77 µM and 0.89 µM for those two cell lines. The change in inhibitory concentration represents an increase in inhibition of almost 15 fold. Similarly, the hydroxy prenyl benzamide compound exhibits an $IC_{50}$ of 0.76 µM and 1.09 µM, while the urea linkage exhibits lower inhibitory concentrations with $IC_{50}$ values of 0.39 µM and 0.37 µM for the two breast cancer cell lines which represents an approximately 2-3 fold change in inhibition.

TABLE 6

Substituted Phenyl Urea Derivatives ($IC_{50}$ in µM)

| | Breast Cancer | | Prostate Cancer | | | HSNCC | | Tri-Neg | Thyroid | | Normal | |
|---|---|---|---|---|---|---|---|---|---|---|---|---|
| R | SKBr3 | MCF-3 | HCT-116 | PC-3 | A-549 | MDA1986 | JMAR | MDAMB231 | DRO81-1 | BCPAP | MRC5 | HMLE |
| H | 0.77 ± 0.01 | 0.89 ± 0.00 | 0.44 ± 0.01 | 0.25 ± 0.01 | 0.24 ± 0.00 | 1.3 | 16.6 | 2.5 | 15.1 |  | 3.6 | 3.7 |
| p-$CH_3$ | 0.27 ± 0.04 | 0.29 ± 0.02 | 0.059 ± 0.010 | 0.81 ± 0.42 | 0.017 ± 0.001 | 3.2 | 3.5 | 0.91 | 16.3 |  | 6.6 | 3.3 |
| p-$CH_2CH_3$ | 0.58 ± 0.16 | 0.56 ± 0.04 | 0.53 ± 0.15 | 0.41 ± 0.00 | 0.49 ± 0.09 | 1.4 | 1.03 | 0.69 | 0.29 | 4.36 | 2.6 | 1.2 |
| p-$CH(CH_3)_2$ | 0.67 ± 0.12 | 0.82 ± 0.23 | 1.06 ± 1.18 | 0.13 ± 0.01 | 0.16 ± 0.03 | 1.11 | 0.88 | 0.61 | 0.3 |  | 1.9 | 6.4 |
| p-$C(CH_3)_3$ | 0.93 ± 0.02 | 0.96 ± 0.08 | 0.21 ± 0.06 | 0.14 ± 0.01 | 0.092 ± 0.028 | 0.57 | 0.49 | 0.5 | 0.71 |  | 1.8 | 14.5 |
| m-$CH_3$ | 0.84 ± 0.12 | 0.55 ± 0.06 | 1.11 ± 0.03 | 0.84 ± 0.09 | 1.21 ± 0.05 | 2.02 | 1.8 | 3.5 | 0.54 | 3.54 | 4.3 | 3.1 |
| m-$CH_2CH_3$ | 0.44 ± 0.05 | 0.50 ± 0.01 | 0.34 ± 0.05 | 0.41 ± 0.00 | 0.40 ± 0.02 | 1.32 | 0.63 | 1.9 | 0.67 | 5.59 | 5.3 | >25 |

TABLE 6-continued

Substituted Phenyl Urea Derivatives (IC$_{50}$ in µM)

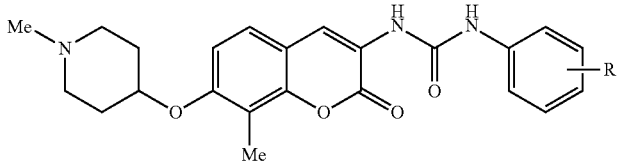

| | Breast Cancer | | Prostate Cancer | | | HSNCC | | Tri-Neg | Thyroid | | Normal | |
|---|---|---|---|---|---|---|---|---|---|---|---|---|
| R | SKBr3 | MCF-3 | HCT-116 | PC-3 | A-549 | MDA1986 | JMAR | MDAMB231 | DRO81-1 | BCPAP | MRC5 | HMLE |
| p-CF$_3$ | 0.35 ± 0.04 | 0.47 ± 0.03 | 0.80 ± 0.59 | 0.060 ± 0.012 | 0.13 ± 0.00 | 0.9 | 3.6 | 0.43 | 0.64 | | 3.1 | 15.5 |
| m-CF$_3$ | 0.26 ± 0.08 | 0.28 ± 0.04 | N/A | 0.043 ± 0.00 | 0.046 | 0.15 | 1.7 | 0.55 | 7.3 | | 1.6 | 16.8 |
| 3,4-dimethyl | 0.31 ± 0.09 | 0.33 ± 0.05 | 0.066 ± 0.019 | 1.33 ± 0.02 | 0.063 ± 0.028 | 1.3 | 1.7 | 1.9 | 8.1 | | 2.7 | 0.9 |
| 2,4-dimethyl | 3.79 ± 0.22 | 1.11 ± 0.02 | 0.77 ± 0.44 | 0.27 ± 0.13 | 0.43 ± 0.07 | 1.9 | 1.1 | 2.6 | 2.3 | | 3.6 | >25 |
| 3,5-dimethyl | 0.30 ± 0.03 | 0.34 ± 0.04 | 0.17 ± 0.04 | 1.35 ± 0.18 | 0.052 ± 0.002 | 0.09 | 3.4 | 0.65 | 8.4 | | 5.9 | 13.8 |
| p-OCH$_3$ | 0.86 ± 0.07 | 0.96 ± 0.35 | 0.25 ± 0.07 | 0.52 ± 0.20 | 1.09 ± 0.00 | 2.6 | 8.4 | 2.4 | 29 | | 2.7 | 0.74 |
| m-OCH$_3$ | 1.15 ± 0.30 | 0.96 ± 0.01 | | | | | | | | | | |
| p-OAc | 1.48 ± 0.16 | 1.72 ± 0.10 | 2.61 ± 1.14 | 1.15 ± 0.24 | 1.51 ± 0.24 | 1.98 | 3.5 | 0.85 | 3.7 | 5.53 | 15.5 | 15.9 |
| p-OH | 1.38 ± 0.06 | 1.34 ± 0.14 | | | | | | | | | | |
| p-OCF$_3$ | 0.41 ± 0.06 | 0.40 ± 0.16 | 0.27 ± 0.14 | 0.16 ± 0.02 | 0.31 ± 0.08 | 0.87 | 3.6 | 0.69 | 0.23 | 0.87 | 3.3 | 4.1 |
| m-OAc | 2.37 ± 0.85 | 1.41 ± 0.13 | 12.1 ± 0.48 | 1.91 ± 0.50 | 1.91 ± 0.50 | 6.82 | 3.85 | 4.1 | 2.7 | 2.82 | >25 | 13.6 |
| m-OH | 2.37 ± 0.33 | 2.73 ± 0.70 | >100 | 10.9 ± 7.76 | 10.9 ± 7.76 | 21.9 | 6.5 | 1.3 | >25 | 0.27 | >25 | 11.9 |
| 2-OMe-5-t-Bu | 3.87 ± 0.04 | 1.53 ± 0.22 | 1.24 ± 0.01 | 3.82 ± 0.24 | 0.84 ± 0.47 | 0.09 | 3.8 | 0.91 | 6.1 | | 2.65 | 6.1 |
| 3,4,5-tri-methoxyl | 4.26 ± 0.39 | 1.30 ± 0.26 | 209 | 4.50 ± 0.50 | 13.0 ± 0.40 | 9.1 | 1.7 | 2.9 | 14.7 | 1.32 | >25 | >25 |
| p-N-dimethyl-amine | 1.11 ± 0.23 | 1.00 ± 0.01 | 9.34 ± 4.81 | 7.96 ± 9.51 | 2.70 ± 1.51 | 17.5 | 0.77 | 1.4 | >25 | 0.74 | 14.4 | 0.96 |
| p-phenyl | 0.36 ± 0.04 | 0.70 ± 0.16 | 0.15 ± 0.01 | 0.052 ± 0.001 | 0.066 ± 0.022 | 0.85 | 0.93 | 0.37 | 0.27 | | 2 | 3.6 |
| p-phenoxyl | 0.40 ± 0.11 | 0.70 ± 0.16 | 0.24 ± 0.00 | 0.15 ± 0.00 | 0.18 ± 0.03 | 6 | 5.3 | 2.2 | 1.8 | | 11.3 | >25 |
| m-phenoxyl | 0.19 ± 0.07 | 0.28 ± 0.09 | N/A | 2.16 ± 0.00 | 1.02 ± 0.35 | 0.57 | 2.4 | 0.28 | 3.1 | | 2.2 | 5.2 |
| p-F | 0.48 ± 0.03 | 0.96 ± 0.06 | 0.061 ± 0.002 | 3.32 ± 0.57 | 1.06 ± 1.21 | 0.01 | 8.6 | 0.05 | 19.9 | | >25 | >25 |
| p-Cl | 0.17 ± 0.01 | 0.36 ± 0.01 | 0.42 ± 0.04 | 2.30 ± 0.48 | 0.16 ± 0.13 | >25 | 6.1 | >25 | 15.8 | | >25 | >25 |
| p-Br | 0.65 ± 0.04 | 1.04 ± 0.04 | 0.24 ± 0.09 | 0.18 ± 0.05 | 0.11 ± 0.01 | 3.5 | 3.6 | 2.6 | 3.5 | | 5.5 | 6 |
| p-NO$_2$ | 0.58 ± 0.04 | 4.24 ± 0.31 | 2.83 ± 1.24 | 1.06 ± 0.31 | 0.95 ± 0.25 | 6.6 | 7.3 | 2.1 | 11.5 | | >25 | >25 |
| p-CN | 0.37 ± 0.08 | 0.43 ± 0.11 | 0.57 ± 0.70 | 0.048 ± 0.001 | 0.043 ± 0.003 | 1.62 | 3.7 | 0.44 | 0.28 | | 5.7 | 4 |
| p-COCH$_3$ | 1.52 ± 0.01 | 1.72 ± 0.03 | 0.25 ± 0.11 | 2.75 ± 1.53 | 0.24 ± 0.09 | 3.4 | 11.9 | 0.75 | 13.3 | | 7.7 | 8 |
| m-Cl | 0.30 ± 0.06 | 0.52 ± 0.02 | 0.22 ± 0.07 | 1.82 ± 0.57 | 0.063 ± 0.017 | 1.7 | 1.7 | 0.57 | 3.8 | | 3.1 | 22 |
| m-COCH$_3$ | 0.83 ± 0.04 | 1.17 ± 0.54 | 0.72 ± 0.09 | 1.23 ± 0.17 | 0.54 ± 0.05 | 21 | 15.7 | 0.61 | 13.6 | 0.27 | >25 | 1.9 |
| 3,4-dichloro | 0.64 ± 0.16 | 1.78 ± 0.62 | 17.0 ± 6.52 | 2.04 ± 0.00 | 1.82 ± 0.73 | 2.6 | 6.7 | 2.9 | 13.2 | | 2.1 | 1.5 |
| 3,5-dichloro | 0.51 ± 0.02 | 0.49 ± 0.01 | 1.21 ± 0.35 | 0.16 ± 0.01 | 0.20 ± 0.04 | 7.5 | 6.2 | 3.6 | 0.77 | | >25 | >25 |

TABLE 7

Prenylated Phenyl Urea Derivatives (IC$_{50}$ in μM)

| | Breast Cancer | | Prostate Cancer | | | HSNCC | | Tri-Neg | Thyroid | | Normal | |
|---|---|---|---|---|---|---|---|---|---|---|---|---|
| R | SKBr3 | MCF-3 | HCT-116 | PC-3 | A-549 | MDA1986 | JMAR | MDAMB231 | DRO81-1 | BCPAP | MRC5 | HMLE |
| H | 0.77 ± 0.01 | 0.89 ± 0.00 | 0.44 ± 0.01 | 0.25 ± 0.01 | 0.24 ± 0.00 | 1.3 | 16.6 | 2.5 | 15.1 | | 3.6 | 3.7 |
| OAc | 0.54 ± 0.13 | 0.49 ± 0.04 | 0.34 ± 0.01 | 0.38 ± 0.00 | 0.38 ± 0.00 | 1.32 | 0.87 | 0.75 | 0.53 | 0.129 | 1.8 | 7.2 |
| OH | 0.39 ± 0.06 | 0.37 ± 0.05 | 0.39 ± 0.10 | 0.29 ± 0.07 | 0.25 ± 0.03 | 1.36 | 0.91 | 0.66 | 1.1 | 0.99 | 4.02 | 4.8 |
| OMe | 0.51 ± 0.06 | 0.37 ± 0.08 | 0.30 ± 0.11 | 0.23 ± 0.00 | 0.23 ± 0.00 | 0.85 | 0.8 | 0.83 | 0.21 | 1.34 | 2.64 | 6.5 |
| H | 0.73 ± 0.05 | 0.55 ± 0.02 | | | | | | | | | | |

TABLE 8

Activity of Biphenyl Urea Derivatives (IC$_{50}$ in μM)

| | | Breast Cancer | | Prostate Cancer | | | HSNCC | | Tri-Neg | Thyroid | | Normal |
|---|---|---|---|---|---|---|---|---|---|---|---|---|
| R$_1$ | R$_2$ | SKBr3 | MCF-3 | HCT-116 | PC-3 | A-549 | MDA1986 | JMAR | MDAMB231 | DRO81-1 | BCPAP | MRC5 | HMLE |
| OMe | OMe | 0.17 ± 0.07 | 0.20 ± 0.03 | 0.46 ± 0.04 | 0.47 ± 0.08 | 0.47 ± 0.08 | 1.39 | 0.5 | 0.61 | 0.48 | 0.39 | 4.3 | 1.6 |
| OMe | OAc | 0.26 ± 0.02 | 0.27 ± 0.03 | 3.39 ± 0.45 | 1.04 ± 0.03 | 0.54 ± 0.31 | 0.85 | 2.2 | 0.39 | 0.26 | 0.016 | 3.1 | 1 |
| OMe | OH | 0.39 ± 0.10 | 0.29 ± 0.01 | 0.42 ± 0.22 | 0.60 ± 0.21 | 0.41 ± 0.05 | 2.8 | 0.96 | 0.095 | 1.2 | 1.94 | 9.8 | 3.7 |
| OMe | H | 0.45 ± 0.02 | 0.93 ± 0.04 | | | | | | | | | | |
| H | OMe | 0.44 ± 0.02 | 0.37 ± 0.06 | | | | | | | | | | |
| H | H | 0.38 ± 0.06 | 0.32 ± 0.02 | | | | | | | | | | |
| CH$_3$ | OMe | 0.25 ± 0.01 | 0.21 ± 0.04 | | | | | | | | | | |
| CH$_3$ | Cl | 0.44 ± 0.02 | 0.50 ± 0.01 | | | | | | | | | | |
| OMe | Cl | 0.13 ± 0.11 | 0.47 ± 0.05 | | | | | | | | | | |
| OMe | NO$_2$ | 0.16 ± 0.01 | 0.36 ± 0.06 | | | | | | | | | | |
| OMe | NH$_2$ | 0.36 ± 0.01 | 0.67 ± 0.09 | | | | | | | | | | |

TABLE 9

Activity in Cancer Cell of Non-Aryl Ureas (IC$_{50}$ in μM)

[Structure: 1-methylpiperidin-4-yloxy substituted coumarin with 8-Me and 3-NHC(O)R group]

| R | Breast Cancer | | Prostate Cancer | | | HSNCC | | Tri-Neg | Thyroid | |
|---|---|---|---|---|---|---|---|---|---|---|
| | SKBr3 | MCF-3 | HCT-116 | PC-3 | A-549 | MDA 1986 | JMAR | MDAM-B231 | DRO81-1 | BCPAP |
| HN-cyclopentyl | 2.39 ± 0.35 | 3.83 ± 0.33 | 7.87 ± 7.97 | 2.16 ± 1.17 | 1.24 ± 0.94 | >25 | >25 | 0.65 | 8.8 | |
| HN-cyclohexyl | 3.83 ± 0.33 | 3.84 ± 0.31 | 9.21 ± 6.54 | 1.67 ± 0.00 | >100 | >25 | >25 | >25 | >25 | |
| HN-adamantyl | 0.36 ± 0.18 | 0.64 ± 0.18 | 0.082 ± 0.035 | 0.019 ± 0.003 | 0.010 ± 0.010 | 5.9 | 6.2 | 3 | 18.7 | |
| HN-C(Me)$_3$ | 3.96 ± 0.14 | 1.77 ± 0.26 | 12.1 ± 0.61 | 4.54 ± 0.46 | 4.85 ± 0.29 | 21.5 | 2.1 | 3.8 | >25 | 2.57 |
| N-piperazinyl-N'-Me | >50 | 32.10 ± 4.78 | >100 | 115 | 18.3 ± 12.0 | >25 | >25 | >25 | >25 | >25 |
| -N(H)-CH$_2$Ph | 0.71 ± 0.10 | 0.58 ± 0.13 | 0.66 ± 0.15 | 0.87 ± 0.33 | 0.28 ± 0.03 | 14.4 | >25 | 7.9 | 14.6 | 0.045 |
| -N(Me)-CH$_2$Ph | 6.70 ± 0.21 | 3.80 ± 0.16 | 183 | 28.7 ± 24.6 | 138 | 13.4 | 7.5 | >25 | 19.5 | 0.0084 |
| -N(CH$_2$Ph)$_2$ | 1.21 ± 0.02 | 3.36 ± 0.16 | 5.95 ± 2.92 | 1.27 ± 0.09 | 3.57 ± 0.55 | 3.65 | 0.7 | 2.8 | 1.9 | 1.81 |
| -NH-CHPh$_2$ | 0.49 ± 0.07 | 0.54 ± 0.01 | 0.96 ± 0.16 | 1.12 ± 0.05 | 0.87 ± 0.21 | 7.1 | 5.9 | 4.3 | 1.3 | 5.76 |
| -NH-CH$_2$-(4-Cl-C$_6$H$_4$) | 1.04 ± 0.07 | 1.05 ± 0.07 | | | | | | | | |
| -NH-CH$_2$-(4-OMe-C$_6$H$_4$) | 0.68 ± 0.06 | 0.65 ± 0.11 | | | | | | | | |

TABLE 9-continued
Activity in Cancer Cell of Non-Aryl Ureas (IC$_{50}$ in μM)
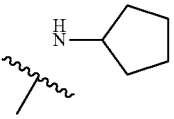
| | | |
|---|---|---|
| 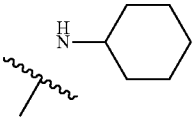 | 0.56 ± 0.07 | 0.55 ± 0.02 |
| 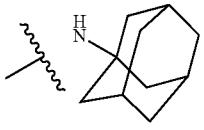 | 0.23 ± 0.08 | 0.38 ± 0.04 |
| R | Normal | |
| | MRC5 | HMLE |
|---|---|---|
| 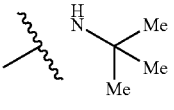 | >25 | >25 |
| 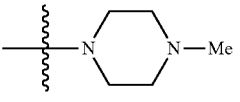 | >25 | >25 |
| 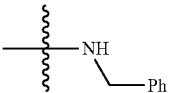 | 3.8 | >25 |
| 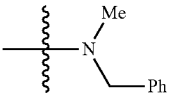 | 21.1 | >25 |
| 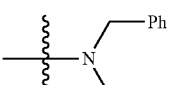 | >25 | >25 |
| 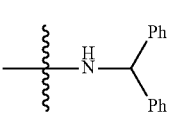 | 20.9 | >25 |
| 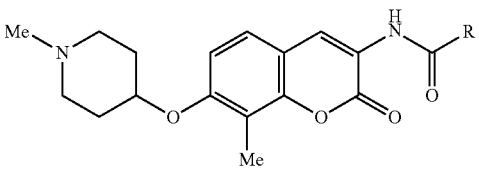 | >25 | >25 |
| 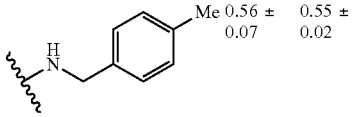 | 20.9 | 7.1 |
| 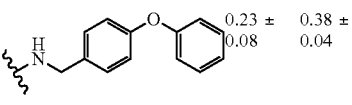 | 15.5 | 1.6 |

TABLE 9-continued

Activity in Cancer Cell of Non-Aryl Ureas (IC$_{50}$ in μM)

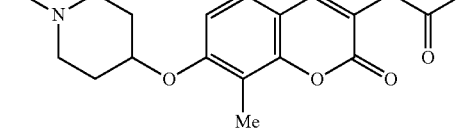

Initial Compounds for Structure Optimization from Modified Sugar to N-Methylpiperidine to Urea Modification

TABLE 10

Modified Initial Novobiocin Analog Activity

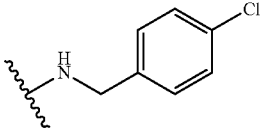 [SMILES: *NCc1ccc(Cl)cc1]

1: Y = CH$_3$, R = A
3: Y = CH$_3$, R = B
4: Y = CH$_3$, R = C
5: Y = OCH$_3$, R = B

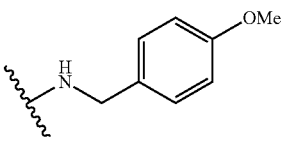 [SMILES: *NCc1ccc(OC)cc1]

2: R = A
6: R = B
7: R = C

TABLE 10-continued

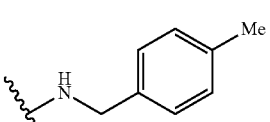

8: R$^1$ = H, R$^2$ = Cl
9: R$^1$ = H, R$^2$ = CH$_3$
10: R$^1$ = CH$_3$, R$^2$ = CH$_3$

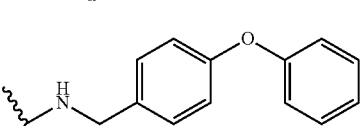

11: R$^1$ = H, R$^2$ = Cl

| | SkBr3, IC$_{50}$ [μM] |
|---|---|
| 1 | 10.86 ± 0.47 |
| 2 | 0.76 ± 0.17 |
| 3 | 7.5 ± 1.0 |
| 4 | 2.9 ± 1.2 |
| 5 | 13.9 ± 1.2 |
| 6 | 1.34 ± 0.22 |
| 7 | 0.31 ± 0.00 |
| 8 | 0.17 ± 0.01 |
| 9 | 0.27 ± 0.04 |
| 10 | 0.31 ± 0.09 |
| 11 | 0.21 ± 0.06 |

TABLE 10-continued

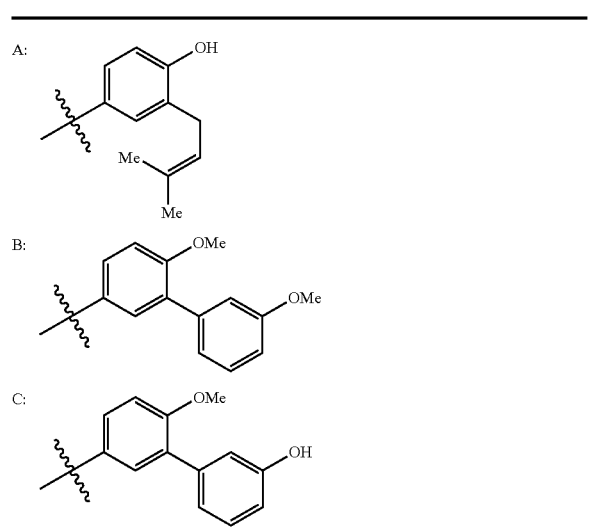

Example 2

Compounds and Synthesis i. Modified Benzamide Derivatives

Preparation of benzamide analogues is described in Scheme 3. Preparation of coumarin core has been described previously in Zhao, et al., 2011, which is incorporated herein by reference. This coumarin core is then modified under Mitsunobu coupling conditions to attach the methyl-piperidine by converting the phenol on the ether with 4-hydroxy-N-methylpiperidine. The amine on the coumarin core is then transforms into the amide of the final product using an appropriate acid chloride in the presence of a base. The coumarin core is then modified as described in Scheme 3. As described in Scheme 4, methylation of the benzamide 4'-phenol occurred upon treatment of 2 with sodium hydride followed by iodomethane to give methylether 16 in good yield. Similar etherifications occurred by Mitsunobo reactions between 2 and n-butanol or prop-2-yn-1-ol to afford 17 or 18, respectively. Hydrogenation of 2 gave the saturated prenyl group found in 19, while exposure to acid resulted in cyclization to give ether 20. Amide coupling between aniline 12 and carboxylic acid chlorides prepared from 13a-e afforded compounds 21a-e, which upon solvolysis provided 22a, 22b and 22e, respectively.

Scheme 3: Synthesis of Substituted Benzylamide

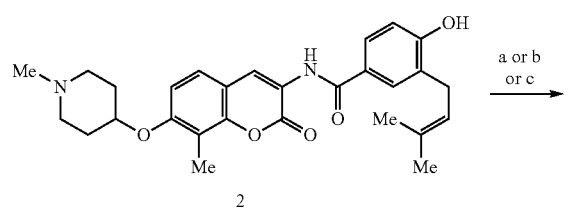

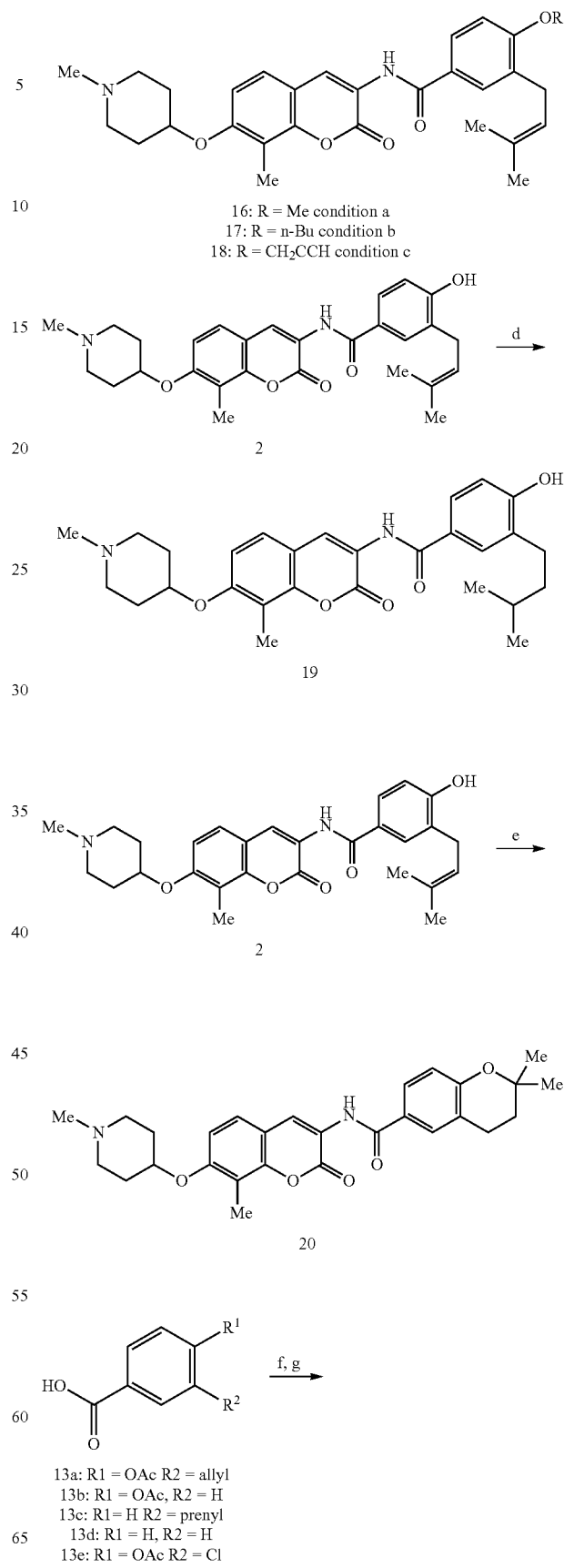

87

-continued

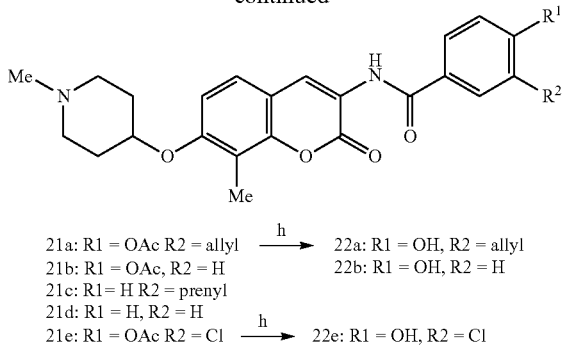

21a: R1 = OAc R2 = allyl  →h  22a: R1 = OH, R2 = allyl
21b: R1 = OAc, R2 = H            22b: R1 = OH, R2 = H
21c: R1= H R2 = prenyl
21d: R1 = H, R2 = H           h
21e: R1= OAc R2 = Cl  →  22e: R1 = OH, R2 = Cl Reagents and conditions: a MeI, NaH, DMF. b n-BuOH, Ph₃P, DIAD, THF, c CH₂OHCCH, Ph₃P, DIAD, THF, d Pd/C, H₂, THF, e HCl/Dioxane f SOCl₂, THF, g 12, pyridine, DCM, h Et₃N, MeOH.

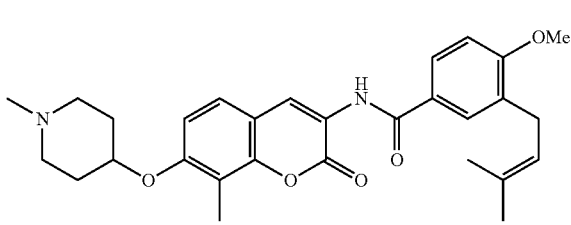 [SMILES: COc1ccc(C(=O)Nc2cc3ccc(OC4CCN(C)CC4)c(C)c3oc2=O)cc1CC=C(C)C]

4-methoxy-N-(8-methyl-7-(1-methylpiperidin-4-yloxy)-2-oxo-2H-chromen-3-yl)-3-(3-methylbut-2-enyl)benzamide (16)

Sodium hydride (4.2 mg, 60% in mineral oil, 0.10 mmol) was added to a solution of 2 (50 mg, 0.10 mmol) in DMF (2 mL) at 0° C., followed by iodomethane (14 mg, 0.10 mmol). The resulting solution was stirred at 0° C. for 4 hours, quenched with saturated aqueous ammonium chloride solution and extracted with ethyl acetate (3×10 mL). The combined organic layers were dried (MgSO₄), filtered, and concentrated. The residue was purified by column chromatography (SiO₂; 10:1, CH₂Cl₂:MeOH) to afford methylether 16 as light brown amorphorous solid (13 mg, 27%): $^1$H NMR (500 MHz, DMSO-d₆) δ 9.39 (s, 1H), 8.47 (s, 1H), 7.85 (d, J=8.5 Hz, 1H), 7.73 (s, 1H), 7.12 (d, J=8.6 Hz, 1H), 7.00 (d, J=8.6 Hz, 1H), 5.29~5.17 (m, 1H), 4.34~5.30 (m, 1H), 4.61 (m, 1H), 3.89 (s, 3H), 3.30 (d, J=7.1 Hz, 2H), 2.66 (m, 2H), 2.42 (s, 3H), 2.29 (s, 3H), 2.25 (s, 3H), 1.99~1.96 (m, 2H), 1.77~1.74 (m, 2H), 1.66 (s, 3H), 1.65 (s, 3H). $^{13}$C NMR (125 MHz, DMSO-d₆) δ 165.1, 159.9, 158.2, 156.6, 149.5, 132.1, 129.2, 128.6, 128.5, 127.1, 126.0, 125.2, 121.9, 121.2, 113.4, 112.6, 110.6, 110.2, 71.6, 55.7, 51.6, 45.2, 29.8, 28.0, 25.4, 17.6, 8.1. HRMS (ESI⁺) m/z [M+H⁺] calcd for C₂₉H₃₅N₂O₅ 491.2546, found 491.2541.

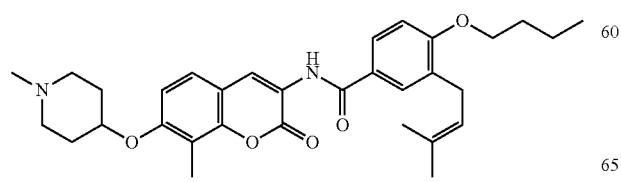

88

4-butoxy-N-(8-methyl-7-(1-methylpiperidin-4-yloxy)-2-oxo-2H-chromen-3-yl)-3-(3-methylbut-2-enyl)benzamide (17)

$^1$H NMR (500 MHz, CDCl₃) δ 8.79 (s, 1H), 8.67 (s, 1H), 7.74 (d, J=8.5 Hz, 1H), 7.71 (s, 1H), 7.32 (d, J=8.6 Hz, 1H), 6.90 (d, J=8.6 Hz, 1H), 6.87 (d, J=8.7 Hz, 1H), 4.34~5.30 (m, 1H), 4.54 (m, 1H), 4.05 (t, J=6.3 Hz, 2H), 3.38 (d, J=6.3 Hz, 2H), 2.80~2.77 (m, 2H), 2.62 (m, 2H), 2.45 (s, 3H), 2.35 (s, 3H), 2.18~2.14 (m, 2H), 2.03~1.98 (m, 2H), 1.85~1.80 (m, 2H), 1.77 (s, 3H), 1.74 (s, 3H), 1.56~1.52 (m, 2H), 1.00 (t, J=7.4 Hz, 3H). $^{13}$C NMR (125 MHz, CDCl₃) δ 166.1, 160.5, 159.7, 156.7, 147.6, 133.5, 131.0, 128.7, 126.7, 125.8, 125.5, 124.1, 122.1, 121.9, 115.3, 113.8, 110.7, 110.6, 71.6, 68.1, 52.0, 45.9, 31.5, 30.1, 28.8, 26.0, 19.5, 18.1, 14.1, 8.6. HRMS (ESI⁺) m/z [M+H⁺] calcd for C₃₂H₄₁N₂O₅ Exact Mass: 533.3015, found 533.3021.

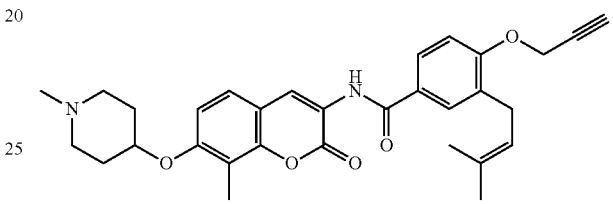

N-(8-methyl-7-(1-methylpiperidin-4-yloxy)-2-oxo-2H-chromen-3-yl)-3-(3-methylbut-2-enyl)-4-(prop-2-ynyloxy)benzamide (18)

$^1$H NMR (500 MHz, CDCl₃) δ 8.69 (s, 1H), 7.71 (d, J=8.4 Hz, 2H), 7.66 (s, 1H), 7.30 (d, J=8.7 Hz, 1H), 7.27 (s, 1H), 6.99 (d, J=8.7 Hz, 1H), 6.83 (d, J=8.4 Hz, 1H), 5.26~5.23 (m, 1H), 4.55 (m, 1H), 3.32 (d, J=7.3 Hz, 1H), 2.80~2.75 (m, 4H), 2.54 (s, 1H), 2.46 (s, 3H), 2.28 (s, 3H), 2.12 (m, 2H), 1.99~1.97 (m, 2H), 1.70 (s, 3H), 1.67 (s, 3H). $^{13}$C NMR (125 MHz, CDCl₃) δ 166.2, 159.6, 158.8, 156.4, 149.5, 133.8, 131.5, 128.8, 126.44, 126.39, 125.9, 124.6, 121.7, 121.3, 115.1, 113.7, 111.5, 110.4, 78.1, 76.1, 70.1, 56.1, 51.3, 45.1, 19.1, 28.4, 25.8, 17.9, 8.4. HRMS (ESI⁺) m/z [M+H⁺] calcd for C₃₁H₃₅N₂O₅ 515.2546, found 515.2539.

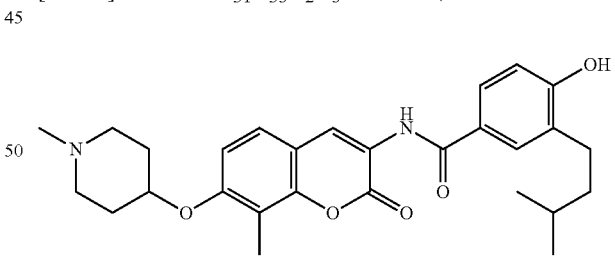

4-hydroxy-3-isopentyl-N-(8-methyl-7-(1-methylpiperidin-4-yloxy)-2-oxo-2H-chromen-3-yl)benzamide (19)

Palladium on carbon (10%, 5 mg) was added to a solution of 2 (48 mg, 0.10 mmol) in anhydrous THF (3 mL) and the solution was placed under an atmosphere of hydrogen. After 12 h, the solution was filtered through SiO₂ (10:1, CH₂Cl₂: methanol) and the eluent was concentrated to afford 19 as a colorless amorphous solid (42 mg, 88%): $^1$H NMR (400 MHz, CDCl₃/MeOD) δ 8.44 (s, 1H), 7.41 (s, 1H), 7.34 (d, J=8.4 Hz, 1H), 7.10 (d, J=8.0 Hz, 1H), 6.67 (d, J=8.1 Hz, 1H), 6.61 (d, J=8.0 Hz, 1H), 4.46 (m, 1H), 2.55~2.45 (m, 2H), 2.40~2.38 (m, 2H), 2.36~2.31 (m, 2H), 2.14 (s, 3H), 2.07 (s, 3H), 1.84~1.78 (m, 2H), 1.72~1.70 (m, 2H), 1.40~1.37 (m, 1H), 1.29~1.23 (m, 2H), 0.71 (s, 3H), 0.69 (s, 3H). $^{13}$C NMR (100 MHz, CDCl$_3$/MeOD) δ 165.5, 159.5, 156.7, 152.2, 149.6, 136.1, 131.7, 129.6, 125.89, 125.85, 124.67, 123.1, 121.7, 115.3, 113.6, 110.5, 71.1, 51.7, 45.6, 39.3, 29.7, 28.3, 28.1, 22.6, 21.1, 8.6. HRMS (ESI$^+$) m/z [M+Na$^+$] calcd for C$_{28}$H$_{34}$N$_2$NaO$_5$ 501.5697, found 501.5694.

65%). $^1$H NMR (400 MHz, CDCl$_3$) δ 8.78 (s, 1H), 8.65 (s, 1H, NH), 7.75 (s, 1H), 7.44 (d, J=8.4 Hz, 1H), 7.34 (d, J=8.0 Hz, 1H), 6.97 (d, J=8.1 Hz, 1H), 6.85 (d, J=8.0 Hz, 1H), 5.95~6.04 (m, 1H), 5.09 (d, J=12.0 Hz, 2H), 4.61 (m, 1H), 3.48 (d, J=7.6 Hz, 2H), 2.91~2.80 (m, 4H), 2.56 (s, 3H), 2.32 (s, 3H), 2.29~2.11 (m, 2H), 2.12~2.02 (m, 2H). $^{13}$C NMR (125 MHz, CDCl$_3$) δ 169.0, 165.5, 159.6, 157.2, 152.3, 149.7, 135.1, 133.2, 131.9, 129.9, 126.6, 125.9, 124.9, 123.3, 121.6, 117.3, 115.5, 113.5, 110.7, 72.1, 52.3, 46.3, 34.9, 30.6, 21.2, 8.6. HRMS (ESI$^+$) m/z [M+H$^+$] calcd for C$_{28}$H$_{31}$N$_2$O$_6$ 491.5555, found 491.5557.

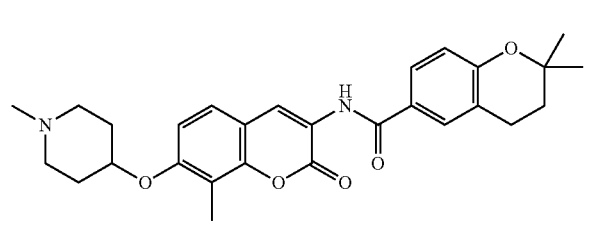

2,2-dimethyl-N-(8-methyl-7-(1-methylpiperidin-4-yloxy)-2-oxo-2H-chromen-3-yl)chroman-6-carboxamide (20)

1 mL of 6 M hydrochloride in dioxane was added to a solution of 2 (25 mg, 0.05 mmol) in dioxane (2 mL) and the resulting solution was stirred at room temperature for 48 hours. The solvent was evaporated and residues was purified (SiO$_2$; 10:1, CH$_2$Cl$_2$:methanol) to afford 20 as a colorless amorphous solid (17 mg, 68%): $^1$H NMR (500 MHz, CDCl$_3$) δ 8.53 (s, 1H), 7.59 (s, 1H), 7.51 (d, J=8.4 Hz, 1H), 7.25 (d, J=8.7 Hz, 1H), 6.79 (d, J=8.7 Hz, 1H), 6.76 (d, J=8.4 Hz, 1H), 4.49 (m, 1H), 2.78~2.74 (m, 4H), 2.64 (m, 2H), 2.38 (s, 3H), 2.23 (s, 3H), 2.05~2.01 (m, 2H), 1.98~1.91 (, 4H), 1.55 (s, 6H). $^{13}$C NMR (125 MHz, CDCl$_3$) δ 166.5, 159.7, 159.5, 156.5, 149.4, 129.4, 129.0, 126.7, 125.8, 124.7, 124.4, 121.6, 115.0, 114.9, 113.6, 110.4, 77.2, 70.9, 51.4, 45.4, 45.1, 32.3, 29.2, 26.2, 8.2. HRMS (ESI$^+$) m/z [M+H$^+$] calcd for C$_{28}$H$_{33}$N$_2$O$_5$ 477.2389, found 477.2394.

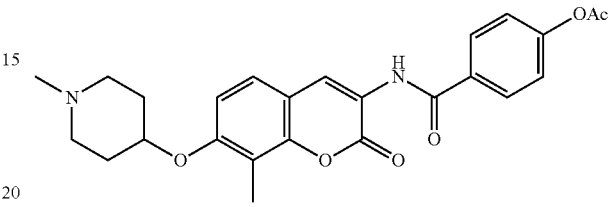

4-(8-methyl-7-(1-methylpiperidin-4-yloxy)-2-oxo-2H-chromen-3-ylcarbamoyl)phenyl acetate (21b)

$^1$H NMR (500 MHz, DMSO-d$_6$) δ 9.73 (s, 1H), 8.52 (s, 1H), 8.02 (d, J=8.7 Hz, 2H), 7.61 (d, J=8.7 Hz, 1H), 7.31 (d, J=8.7 Hz, 2H), 7.17 (d, J=7.8 Hz, 1H), 4.92 (m, 1H), 3.46~3.12 (m, 4H), 2.76 (s, 3H), 2.31 (s, 3H), 2.25~2.18 (m, 2H), 2.05 (m, 2H). $^{13}$C NMR (125 MHz, DMSO-d$_6$) δ 169.0, 165.1, 158.1, 153.3, 149.8, 131.1, 129.3, 126.3, 122.1, 121.3, 113.6, 113.0, 110.5, 66.9, 48.7, 42.3, 28.4, 20.9, 8.2. HRMS (ESI$^+$) m/z [M+H$^+$] calcd for C$_{25}$H$_{27}$N$_2$O$_6$ 451.1869, found 451.1875.

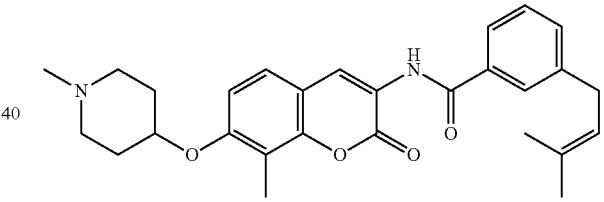

N-(8-methyl-7-((1-methylpiperidin-4-yl)oxy)-2-oxo-2H-chromen-3-yl)-3-(3-methylbut-2-en-1-yl)benzamide (21c)

$^1$H NMR (400 MHz, CDCl$_3$) δ 8.77 (s, 1H), 8.71 (s, 1H, NH), 7.70~7.68 (m, 2H), 7.40~7.38 (m, 2H), 7.31 (d, J=8.0 Hz, 1H), 6.85 (d, J=8.1 Hz, 1H), 5.32 (m, 1H), 4.61 (m, 1H), 3.41 (d, J=7.6 Hz, 2H), 2.77 (m, 2H), 2.62 (m, 2H), 2.44 (s, 3H), 2.32 (s, 3H), 2.15 (m, 2H), 1.98 (m, 2H). 1.76 (s, 3H), 1.73 (s, 3H). HRMS (ESI$^+$) m/z [M+H$^+$] calcd for C$_{28}$H$_{33}$N$_2$O$_4$ 461.5726, found 461.5729.

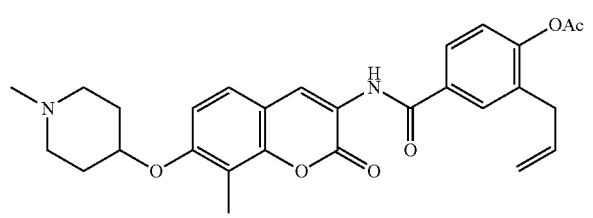 [SMILES: C=CCc1cc(C(=O)Nc2cc3ccc(OC4CCN(C)CC4)c(C)c3oc2=O)ccc1OC(C)=O]

2-allyl-4-((8-methyl-7-((1-methylpiperidin-4-yl)oxy)-2-oxo-2H-chromen-3-yl)carbamoyl)phenyl acetate (21a)

Freshly prepared acid chloride from carboxylic acid 13a (44 mg, 0.2 mmol) was added to a solution of amine 12 (29 mg, 0.1 mmol) in dichloromethane, followed by pyridine (100 μL). The resulting solution was stirred at room temperature for 4 hours, quenched with water and extracted with ethyl acetate; combined organic fractions were dried (MgSO$_4$), filtered, and concentrated. The residue was purified by column chromatography (SiO$_2$, 10:1 CH$_2$Cl$_2$:MeOH) to afford 21a as colorless amorphous solid (32 mg,

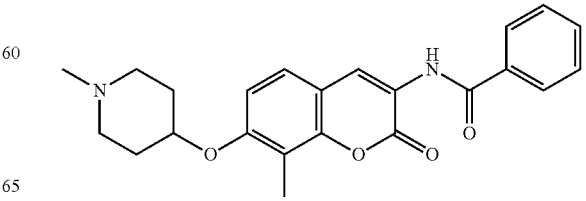

N-(8-methyl-7-(1-methylpiperidin-4-yloxy)-2-oxo-2H-chromen-3-yl)benzamide (21d)

$^1$H NMR (400 MHz, DMSO-d$_6$) δ 9.58 (s, 1H), 8.45 (s, 1H), 7.94 (d, J=6.9 Hz, 2H), 7.61 (m, 1H), 7.54 (m, 3H), 7.09 (d, J=8.2 Hz, 2H), 4.54 (m, 1H), 2.67 (m, 2H), 2.46 (m, 2H), 2.29 (s, 3H), 2.21 (s, 3H), 1.96 (m, 2H), 1.76 (m, 2H). $^{13}$C NMR (125 MHz, DMSO-d$_6$) δ 166.1, 158.4, 156.6, 150.0, 133.7, 132.4, 129.7, 128.9, 127.8, 126.5, 121.4, 113.9, 113.1, 110.8, 70.0, 50.8, 43.5, 28.3, 8.3. HRMS (ESI$^+$) m/z [M+H$^+$] calcd for C$_{23}$H$_{25}$N$_2$O$_4$ 393.1814, found 393.1819.

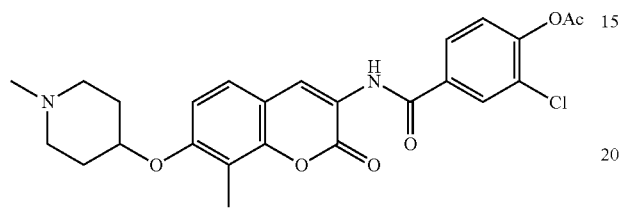

2-chloro-4-(8-methyl-7-(1-methylpiperidin-4-yloxy)-2-oxo-2H-chromen-3-ylcarbamoyl)phenyl acetate (21e)

$^1$H NMR (500 MHz, CDCl$_3$) δ 8.69 (s, 1H), 7.99 (s, 1H), 7.80 (d, J=8.7 Hz, 2H), 7.32 (d, J=8.7 Hz, 1H), 7.26 (d, J=8.7 Hz, 2H), 6.86 (d, J=7.8 Hz, 1H), 4.56 (m, 1H), 2.78 (m, 2H), 2.67 (m, 2H), 2.43 (s, 3H), 2.35 (s, 3H), 2.28 (s, 3H), 2.13~2.08 (m, 2H), 1.95~1.93 (m, 2H). $^{13}$C NMR (125 MHz, CDCl$_3$) δ 168.4, 164.3, 159.4, 156.9, 150.1, 149.6, 132.8, 129.7, 129.6, 127.9, 126.7, 126.0, 125.9, 124.2, 121.1, 115.1, 113.3, 110.4, 70.6, 51.5, 45.3, 29.4, 20.5, 8.2. HRMS (ESI$^+$) m/z [M+H$^+$] calcd for C$_{25}$H$_{26}$ClN$_2$O$_6$ 485.1479, found 485.1486.

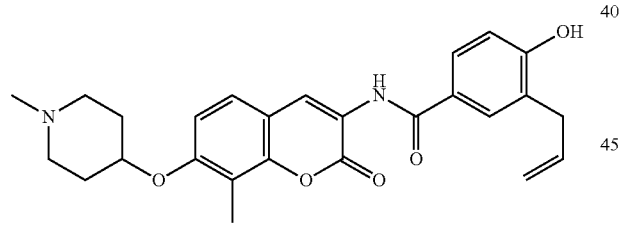

3-allyl-4-hydroxy-N-(8-methyl-7-((1-methylpiperidin-4-yl)oxy)-2-oxo-2H-chromen-3-yl)benzamide (22a)

Triethylamine (0.1 mL) was added to a solution of 21a (18 mg, 0.037 mmol) in methanol (1 mL). The solution was stirred at room temperature overnight and concentrated. The residue was purified by column chromatography on silica by using methylene chloride and methanol (10:1) to give 22a as a white, amorphous solid (13 mg, 79%). $^1$H NMR (500 MHz, CDCl$_3$/MeOD) δ 8.68 (s, 1H), 7.64 (s, 1H), 7.60 (d, J=8.7 Hz, 1H), 7.30 (d, J=8.7 Hz, 1H), 6.86 (d, J=8.7 Hz, 2H), 6.84 (d, J=7.8 Hz, 1H), 6.03~5.95 (m, 1H), 5.07~5.05 (m, 2H), 4.50 (m, 1H), 3.39 (d, J=7.6 Hz, 2H), 2.69 (m, 2H), 2.52 (m, 2H), 2.35 (s, 3H), 2.29 (s, 3H), 2.03~2.01 (m, 2H), 1.93~1.92 (m, 2H). $^{13}$C NMR (125 MHz, CDCl$_3$) δ 166.4, 159.7, 159.2, 156.6, 149.3, 136.0, 129.4, 127.3, 126.9, 125.7, 124.7, 124.4, 121.5, 115.9, 115.0, 114.9, 113.4, 110.5, 71.7, 51.7, 45.6, 34.0, 29.8, 29.6, 8.2. HRMS (ESI$^+$) m/z [M+H$^+$] calcd for C$_{26}$H$_{29}$N$_2$O$_5$ 449.2076, found 449.2074.

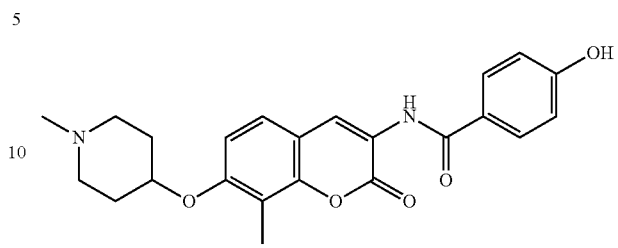

4-hydroxy-N-(8-methyl-7-(1-methylpiperidin-4-yloxy)-2-oxo-2H-chromen-3-yl)benzamide (22b)

$^1$H NMR (500 MHz, DMSO-d$_6$) δ 9.28 (s, 1H), 8.48 (s, 1H), 7.83 (d, J=8.7 Hz, 2H), 7.54 (d, J=8.7 Hz, 1H), 7.11 (d, J=8.7 Hz, 2H), 6.88 (d, J=7.8 Hz, 1H), 4.59 (m, 1H), 2.62 (m, 2H), 2.37 (m, 2H), 2.25 (s, 3H), 2.23 (s, 3H), 1.97~1.94 (m, 2H), 1.75~1.73 (m, 2H). $^{13}$C NMR (125 MHz, DMSO-d$_6$) δ 165.2, 161.1, 158.3, 156.6, 149.5, 129.6, 127.9, 126.0, 124.1, 121.3, 115.2, 113.4, 112.7, 110.7, 71.9, 51.7, 45.5, 30.0, 8.1. HRMS (ESI$^+$) m/z [M+H$^+$] calcd for C$_{23}$H$_{25}$N$_2$O$_5$ 409.1763, found 409.1776.

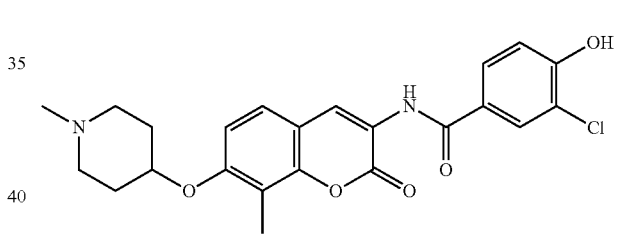

3-chloro-4-hydroxy-N-(8-methyl-7-(1-methylpiperidin-4-yloxy)-2-oxo-2H-chromen-3-yl)benzamide (22e)

$^1$H NMR (400 MHz, DMSO-d$_6$) δ 8.45 (s, 1H), 7.96 (s, 1H), 7.77 (d, J=8.7 Hz, 2H), 7.51 (d, J=8.7 Hz, 1H), 7.09~7.06 (m, 2H), 4.56 (m, 1H), 2.59 (m, 2H), 2.32 (m, 2H), 2.24 (s, 3H), 2.23 (s, 3H), 1.97~1.94 (m, 2H), 1.79~1.68 (m, 2H). $^{13}$C NMR (125 MHz, DMSO-d$_6$) δ 164.3, 158.2, 157.0, 156.9, 149.8, 129.7, 129.4, 128.2, 126.1, 124.8, 121.1, 119.8, 116.4, 113.4, 112.6, 110.8, 72.3, 52.0, 25.9, 30.4, 8.2. HRMS (ESI$^+$) m/z [M+H$^+$] calcd for C$_{23}$H$_{24}$ClN$_2$O$_5$ 443.1374, found 443.1371.

Additional modifications include introducing amines onto the carbon chain of the phenyl ether. Three amines (2-(dimethylamino)ethanol, 3-(dimethylamino)propan-1-ol and 1-methylpiperidin-4-ol) were attached to the 4'-phenol benzamide side chain of 2 via Mitsunobu etherification to afford compounds 23-25 (Scheme 4).

Scheme 4: Synthesis of Amine Substituted Phenolamide

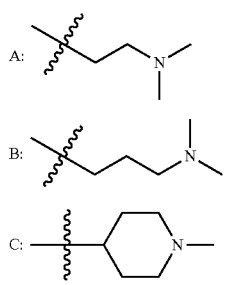

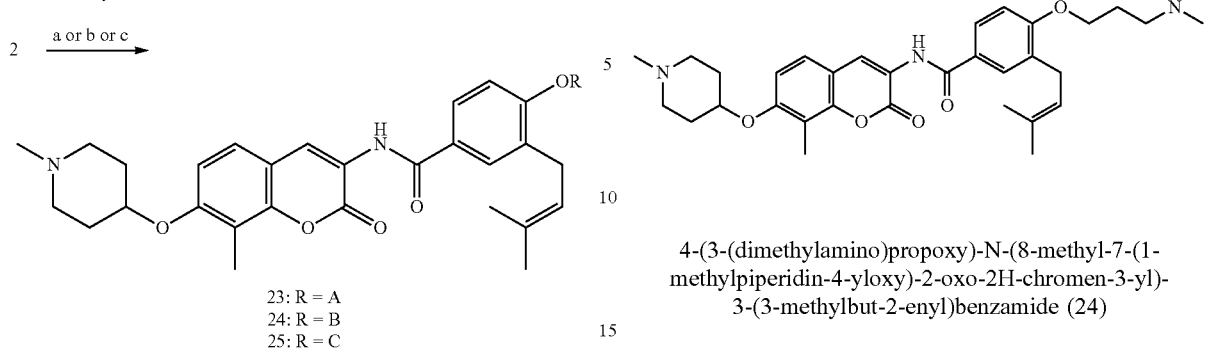

23: R = A
24: R = B
25: R = C

A: (structure)
B: (structure)
C: (structure)

Reagents and conditions: a 2-(dimethylamino)ethanol, Ph₃P, DIAD, THF
b 3-(dimethylamino)propan-1-ol, Ph₃P, DIAD, THF
c 1-methylpiperidin-4-ol, PPh₃, DIAD, THF

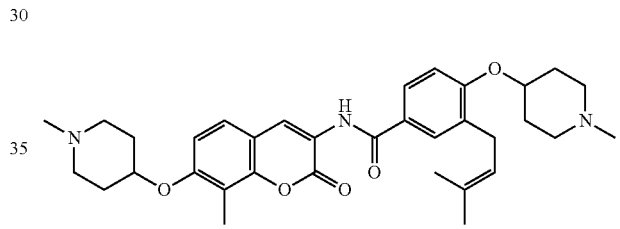

4-(3-(dimethylamino)propoxy)-N-(8-methyl-7-(1-methylpiperidin-4-yloxy)-2-oxo-2H-chromen-3-yl)-3-(3-methylbut-2-enyl)benzamide (24)

$^1$H NMR (500 MHz, CDCl$_3$) δ 8.79 (s, 1H), 8.68 (s, 1H), 7.74 (d, J=8.5 z, H), 7.72 (s, 1H), 7.32 (d, J=8.6 Hz, 1H), 6.92 (d, J=8.6 Hz, 1H), 6.88 (d, J=8.7 Hz, 1H), 5.34~5.31 (m, 1H), 4.47 (m, 1H), 4.11 (t, J=4.6 Hz, 2H), 3.38 (d, J=7.2 Hz, 2H), 2.66 (m, 2H), 2.50 (t, J=4.6 Hz, 2H), 2.48~2.42 (m, 2H), 2.41 (s, 3H), 2.33 (s, 3H), 2.28 (s, 6H), 2.05~1.99 (m, 4H), 1.94~1.87 (m, 2H), 1.77 (s, 3H), 1.75 (s, 3H). $^{13}$C NMR (125 MHz, CDCl$_3$) δ 166.1, 160.3, 159.8, 157.1, 149.6, 133.5, 131.0, 128.7, 126.7, 125.6, 124.3, 124.2, 121.9, 121.8, 115.5, 113.6, 110.8, 110.7, 72.8, 66.6, 56.6, 52.6, 46.5, 45.8, 31.0, 28.8, 27.7, 26.0, 18.1, 8.7. HRMS (ESI$^+$) m/z [M+H$^+$] calcd for C$_{33}$H$_{44}$N$_3$O$_5$ 562.7196, found 562.7194.

N-(8-methyl-7-(1-methylpiperidin-4-yloxy)-2-oxo-2H-chromen-3-yl)-3-(3-methylbut-2-enyl)-4-(1-methylpiperidin-4-yloxy)benzamide (25)

$^1$H NMR (500 MHz, CDCl$_3$) δ 8.78 (s, 1H), 8.66 (s, 1H), 7.74~7.72 (m, 2H), 7.31 (d, J=8.6 Hz, 1H), 6.90 (d, J=8.6 Hz, 1H), 6.87 (d, J=8.7 Hz, 1H), 5.35~5.31 (m, 1H), 4.47 (m, 2H), 3.38 (d, J=7.2 Hz, 2H), 2.70~2.65 (m, 4H), 2.38~2.36 (m, 4H), 2.34 (s, 3H), 2.32 (s, 6H), 2.05~2.00 (m, 4H), 1.93~1.88 (m, 4H), 1.76 (s, 3H), 1.74 (s, 3H). $^{13}$C NMR (125 MHz, CDCl$_3$) δ 166.1, 159.8, 159.7, 157.1, 149.6, 133.4, 131.8, 129.1, 126.6, 125.7, 124.3, 122.0 (2C), 121.9, 115.5, 113.6, 112.0, 110.7, 72.7, 72.0, 53.5, 52.6, 46.5, 46.3, 31.0, 30.9, 28.9, 26.0, 18.2, 8.6. HRMS (ESI$^+$) m/z [M+H$^+$] calcd for C$_{34}$H$_{44}$N$_3$O$_5$ 574.7303, found 574.7306.

Additionally, the benzamide was modified into a biphenyl group and modifications were made to both rings to explore the effects of these modifications on activity. As described in Scheme 5, Suzuki coupling between 26 and phenyl boronic acid 27 gave biaryl ester 28 in good yield. Upon hydrolysis and subsequent esterification, compound 28 was converted to the corresponding acid, 29. Subsequent coupling of 12 with acyl chloride 31 afforded amides 32a and 32b in modest yield. Finally, basic solvolysis occurred upon treatment with triethylamine in methanol to give 33a or 33b.

4-(2-(dimethylamino)ethoxy)-N-(8-methyl-7-(1-methylpiperidin-4-yloxy)-2-oxo-2H-chromen-3-yl)-3-(3-methylbut-2-enyl)benzamide (23)

Diisopropylazodicarboxylate (17 mg, 0.08 mmol) was added to a solution of 2-(dimethylamino)ethanol (3.7 mg, 0.04 mmol), phenol 2 (20 mg, 0.04 mmol) and triphenylphosphine (22 mg, 0.08 mmol) in anhydrous THF (5 mL). After 2 h, the solvent was concentrated and the residue purified via column chromatography (SiO$_2$, 10:1 CH$_2$Cl$_2$:methanol) to afford compound 23 as a colorless amorphous solid (18 mg, 78%). $^1$H NMR (500 MHz, CDCl$_3$) δ 8.79 (s, 1H), 8.68 (s, 1H), 7.75 (d, J=8.5 Hz, 1H), 7.72 (s, 1H), 7.32 (d, J=8.6 Hz, 1H), 6.92 (d, J=8.6 Hz, 1H), 6.89 (d, J=8.7 Hz, 1H), 5.34~5.30 (m, 1H), 4.47 (m, 1H), 4.17 (t, J=4.6 Hz, 2H), 3.39 (d, J=7.3 Hz, 2H), 2.81 (t, J=4.6 Hz, 2H), 2.65 (m, 2H), 2.38 (s, 6H), 2.38~2.35 (m, 2H), 2.35 (s, 3H), 2.32 (s, 3H), 2.05~2.01 (m, 2H), 1.93~1.89 (m, 2H), 1.77 (s, 3H), 1.74 (s, 3H). $^{13}$C NMR (125 MHz, CDCl$_3$) δ 166.1, 160.1, 159.8, 157.1, 149.6, 133.7, 131.1, 128.8, 126.7, 125.9, 125.7, 124.3, 121.9, 121.8, 115.5, 113.6, 110.9, 110.7, 72.7, 67.2, 58.4, 52.6, 46.5, 46.4, 31.0, 28.6, 26.0, 18.1, 8.6. HRMS (ESI$^+$) m/z [M+H$^+$] calcd for C$_{32}$H$_{42}$N$_3$O$_5$ 548.6930, found 548.6931.

Scheme 5: Synthesis of Biphenyl Substituted Amide

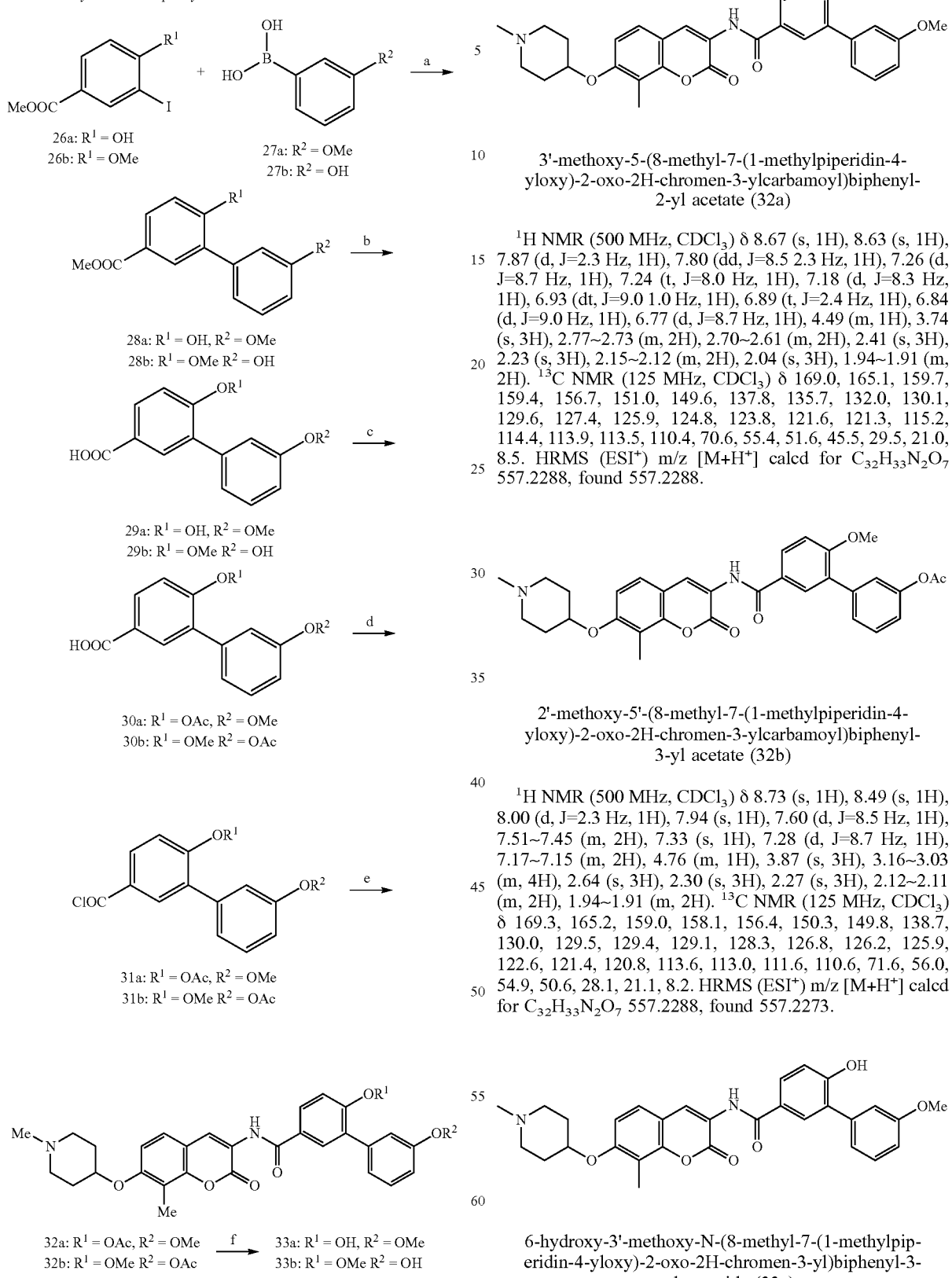

Reagents and conditions: a Pd(dppf)₂, K₂CO₃, Dioxane/H₂O b LiOH, THF/H₂O/MeOH. c Ac₂O, pyridine d SOCl2, THF e 12, pyridine, THF f Et₃N, MeOH 3'-methoxy-5-(8-methyl-7-(1-methylpiperidin-4-yloxy)-2-oxo-2H-chromen-3-ylcarbamoyl)biphenyl-2-yl acetate (32a)

$^1$H NMR (500 MHz, CDCl$_3$) δ 8.67 (s, 1H), 8.63 (s, 1H), 7.87 (d, J=2.3 Hz, 1H), 7.80 (dd, J=8.5 2.3 Hz, 1H), 7.26 (d, J=8.7 Hz, 1H), 7.24 (t, J=8.0 Hz, 1H), 7.18 (d, J=8.3 Hz, 1H), 6.93 (dt, J=9.0 1.0 Hz, 1H), 6.89 (t, J=2.4 Hz, 1H), 6.84 (d, J=9.0 Hz, 1H), 6.77 (d, J=8.7 Hz, 1H), 4.49 (m, 1H), 3.74 (s, 3H), 2.77~2.73 (m, 2H), 2.70~2.61 (m, 2H), 2.41 (s, 3H), 2.23 (s, 3H), 2.15~2.12 (m, 2H), 2.04 (s, 3H), 1.94~1.91 (m, 2H). $^{13}$C NMR (125 MHz, CDCl$_3$) δ 169.0, 165.1, 159.7, 159.4, 156.7, 151.0, 149.6, 137.8, 135.7, 132.0, 130.1, 129.6, 127.4, 125.9, 124.8, 123.8, 121.6, 121.3, 115.2, 114.4, 113.9, 113.5, 110.4, 70.6, 55.4, 51.6, 45.5, 29.5, 21.0, 8.5. HRMS (ESI$^+$) m/z [M+H$^+$] calcd for C$_{32}$H$_{33}$N$_2$O$_7$ 557.2288, found 557.2288.

2'-methoxy-5'-(8-methyl-7-(1-methylpiperidin-4-yloxy)-2-oxo-2H-chromen-3-ylcarbamoyl)biphenyl-3-yl acetate (32b)

$^1$H NMR (500 MHz, CDCl$_3$) δ 8.73 (s, 1H), 8.49 (s, 1H), 8.00 (d, J=2.3 Hz, 1H), 7.94 (s, 1H), 7.60 (d, J=8.5 Hz, 1H), 7.51~7.45 (m, 2H), 7.33 (s, 1H), 7.28 (d, J=8.7 Hz, 1H), 7.17~7.15 (m, 2H), 4.76 (m, 1H), 3.87 (s, 3H), 3.16~3.03 (m, 4H), 2.64 (s, 3H), 2.30 (s, 3H), 2.27 (s, 3H), 2.12~2.11 (m, 2H), 1.94~1.91 (m, 2H). $^{13}$C NMR (125 MHz, CDCl$_3$) δ 169.3, 165.2, 159.0, 158.1, 156.4, 150.3, 149.8, 138.7, 130.0, 129.5, 129.4, 129.1, 128.3, 126.8, 126.2, 125.9, 122.6, 121.4, 120.8, 113.6, 113.0, 111.6, 110.6, 71.6, 56.0, 54.9, 50.6, 28.1, 21.1, 8.2. HRMS (ESI$^+$) m/z [M+H$^+$] calcd for C$_{32}$H$_{33}$N$_2$O$_7$ 557.2288, found 557.2273.

6-hydroxy-3'-methoxy-N-(8-methyl-7-(1-methylpiperidin-4-yloxy)-2-oxo-2H-chromen-3-yl)biphenyl-3-carboxamide (33a)

$^1$H NMR (500 MHz, DMSO-d$_6$) δ 9.51 (s, 1H), 8.47 (s, 1H), 7.91 (d, J=2.3 Hz, 1H), 7.81 (dd, J=8.5 2.3 Hz, 1H), 7.56 (d, J=8.7 Hz, 1H), 7.36 (t, J=8.0 Hz, 1H), 7.19~7.16 (m, 2H0, 7.13 (d, J=8.9 Hz, 1H), 7.07 (d, J=8.5 Hz, 1H), 6.92 (dd, J=8.5 2.3 Hz, 1H), 4.62 (m, 1H), 3.80 (s, 3H), 2.71 (m, 2H), 2.49 (m, 2H), 2.32 (s, 3H), 2.24 (s, 3H), 1.99 (m, 2H), 1.78 (m, 2H). $^{13}$C NMR (125 MHz, DMSO-d$_6$) δ 165.3, 159.0, 158.3, 158.0, 156.6, 149.7, 139.1, 130.3, 129.1, 128.9, 128.7, 127.4, 126.1, 124.5, 121.6, 121.3, 116.0, 115.1, 113.5, 112.8, 112.3, 110.7, 71.6, 55.1, 51.5, 45.1, 29.8, 8.2. HRMS (ESI$^+$) m/z [M+H$^+$] calcd for C$_{30}$H$_{31}$N$_2$O$_6$ 515.2182, found 515.2188.

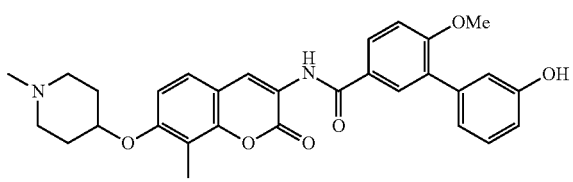 [SMILES: COc1ccc(C(=O)Nc2cc3ccc(OC4CCN(C)CC4)c(C)c3oc2=O)cc1-c1cccc(O)c1]

3'-hydroxy-6-methoxy-N-(8-methyl-7-(1-methylpiperidin-4-yloxy)-2-oxo-2H-chromen-3-yl)biphenyl-3-carboxamide (33b)

$^1$H NMR (500 MHz, DMSO-d$_6$) δ 9.67 (s, 1H), 9.47 (s, 1H), 7.91 (d, J=2.3 Hz, 1H), 8.48 (s, 1H), 7.99 (dd, J=8.5 2.1 Hz, 1H), 7.89 (d, J=2.3 Hz, 1H), 7.57 (d, J=8.7 Hz, 1H), 7.26~7.22 (m, 2H), 7.15 (d, J=8.9 Hz, 1H), 6.96~6.94 (m, 2H), 6.77 (dd, J=8.6 2.1 Hz, 1H), 4.66 (m, 1H), 3.86 (s, 3H), 2.80 (m, 2H), 2.41~2.37 (m, 2H), 2.32 (s, 3H), 2.25 (s, 3H), 2.01 (m, 2H), 1.82 (m, 2H). $^{13}$C NMR (125 MHz, DMSO-d$_6$) δ 165.2, 159.1, 158.2, 157.0, 149.8, 138.6, 129.9, 129.7, 129.5, 129.1, 128.9, 126.2, 125.7, 121.3, 120.1, 116.3, 114.2, 113.5, 111.5, 110.7, 71.8, 55.9, 54.9, 48.6, 29.9, 8.2. HRMS (ESI$^+$) m/z [M+H$^+$] calcd for C$_{30}$H$_{31}$N$_2$O$_6$ 515.2182, found 515.2179.

ii. Amine Containing Ether Derivatives

These amines were assembled with coumarin core in a modular sequence by utilizing the Boc-protected secondary amines (34 and 36) or tertiary amines (35 and 37), which underwent Mitsunobu esterification with phenol 38 to afford 39-42. Subsequent hydrogenolysis to unmask the amine allowed for amide coupling with 4-(chlorocarbonyl)-2-(3-methylbut-2-en-1-yl)phenyl acetate (43) in the presence of pyridine to afford novobiocin C-linked heterocycle derivatives 44-47. Acid-catalyzed deprotection of 44 and 46 resulted in the secondary amines, 48 and 49. Finally, hydrolysis of ester, 45 and 47-49, generated phenols 50-53 (Scheme 6).

Scheme 6: Synthesis of C-linked Heterocycle Derivatives of Novobiocin

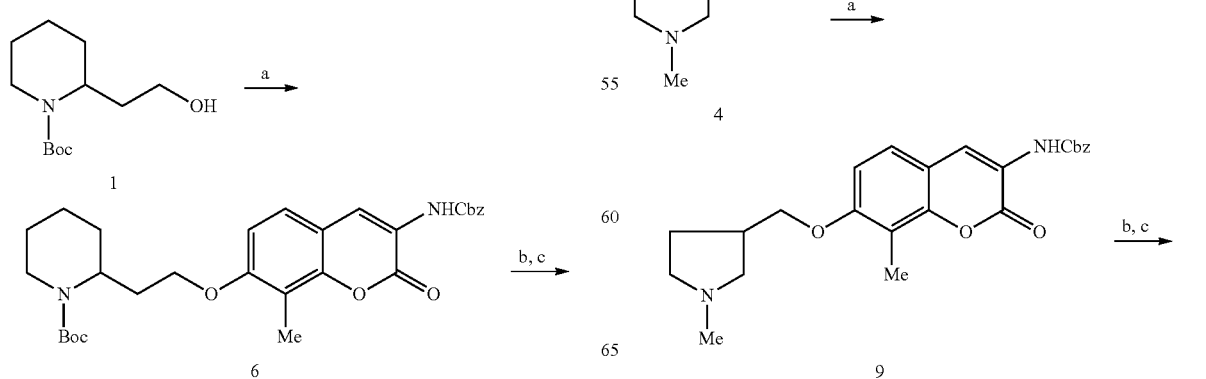

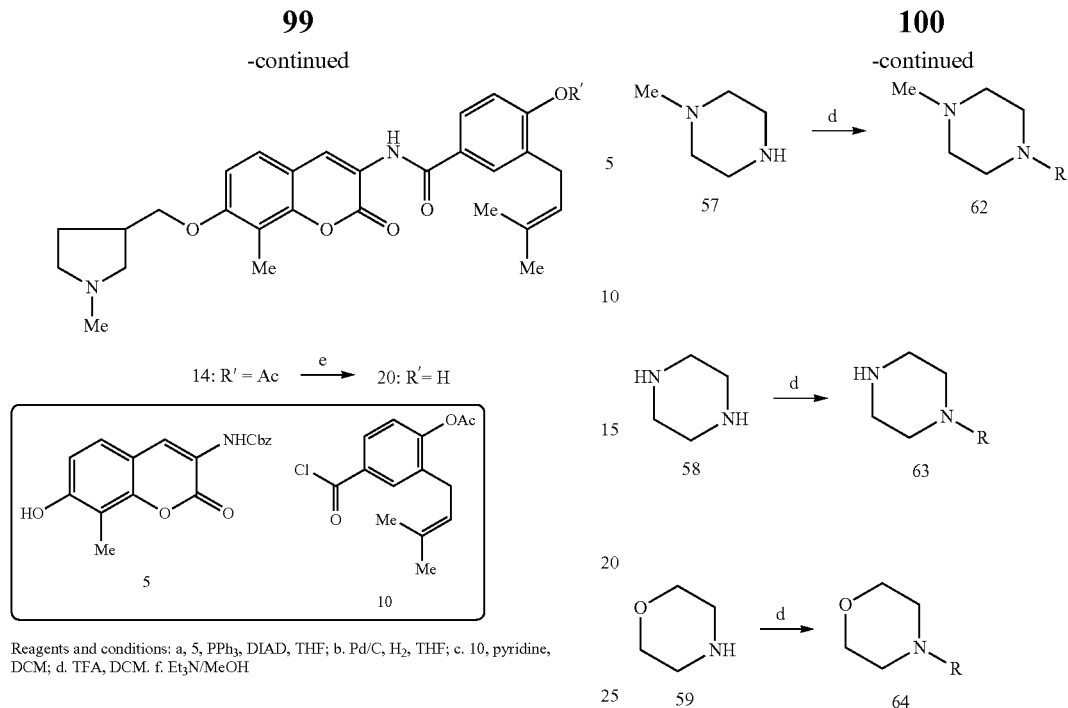

Reagents and conditions: a, 5, PPh₃, DIAD, THF; b. Pd/C, H₂, THF; c. 10, pyridine, DCM; d. TFA, DCM. f. Et₃N/MeOH Along with the C-linked heterocycle derivatives (45, 47, 48-53), N-linked heterocycles (62-66) were also synthesized (Scheme 7). Compound 56 was regarded as a versatile intermediate and prepared in 3 steps: benzyl (7-hydroxy-8-methyl-2-oxo-2H-chromen-3-yl)carbamate reacted with 10 equivalents of 1,3-dibromopropane (54) in the presence of potassium carbonate to afford compound 55. Subsequent hydrogenolysis in the presence of palladium on carbon and hydrogen followed by amide coupling with acid chloride produced compound 56. Final substitution of bromide 56 with amines 57-61 in N,N-dimethylformamide and simultaneously ester hydrolysis generated compound 62-66.

Scheme 7: Synthesis of Terminal Cycloamine Derivatives of Novobiocin

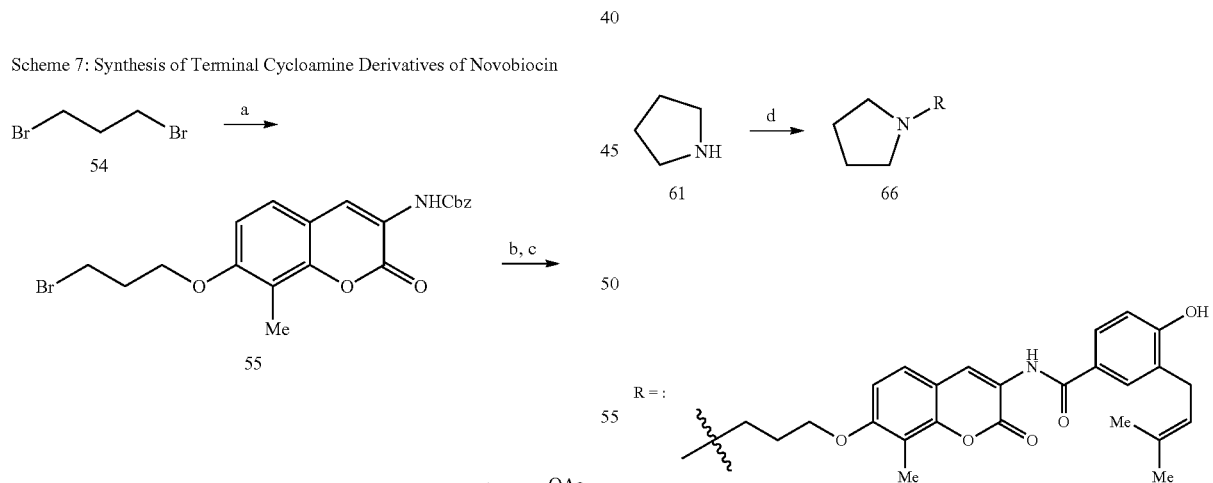

Reagents and conditions: a. phenolcoumarin, sealed tube, reflux, 48 h; b, Pd/C, THF, H₂; c. 3-prenyl-4-acetylbenzylcarbonyl chloride, pyridine, DCM. d. 56, DMF, room temperature, overnight.

As shown in Scheme 8, primary and secondary amines (67a-67o) that contain increasing linear or branched steric bulk were reacted with 56 in DMF to produce the corresponding secondary and tertiary amine derivatives (68a-68o) to explore the binding pocket.

Scheme 8: Synthesis of Alkylamine Analogues with Linear and Branched N-substitutions
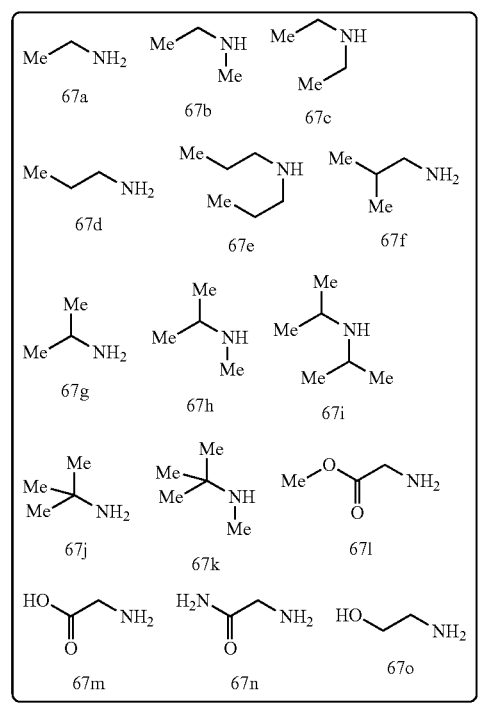
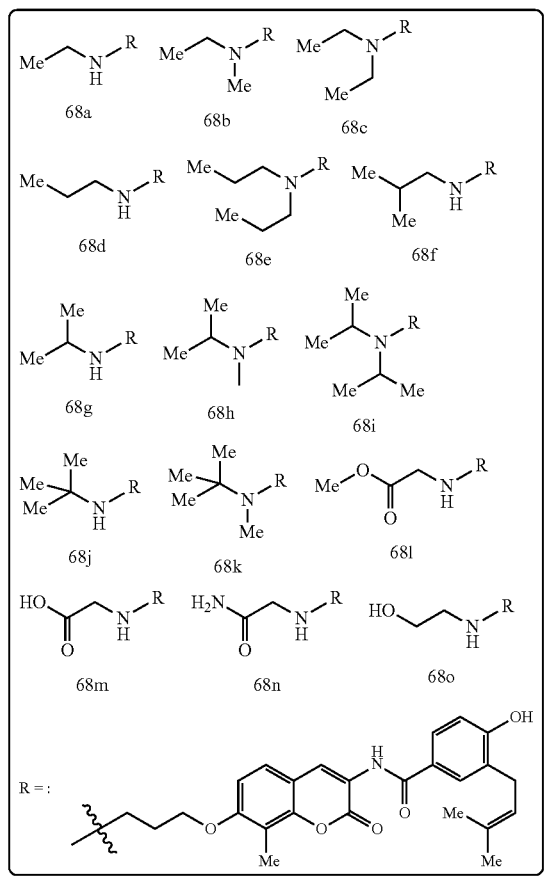

Although none of the first two sets of compounds showed significantly improved anti-proliferative activity, it is clear that a variety of steric bulk is well-tolerated in the mainly hydrophobic binding site. To evaluate the limit of tolerated bulk in the binding site, a set of alkylamine derivatives with N-cyclic substitutions (70a-70j) were prepared in a similar synthetic sequence, as described in Scheme 9.

Scheme 9: Synthesis of Alkylamine Derivatives with Cyclic N-substitutions

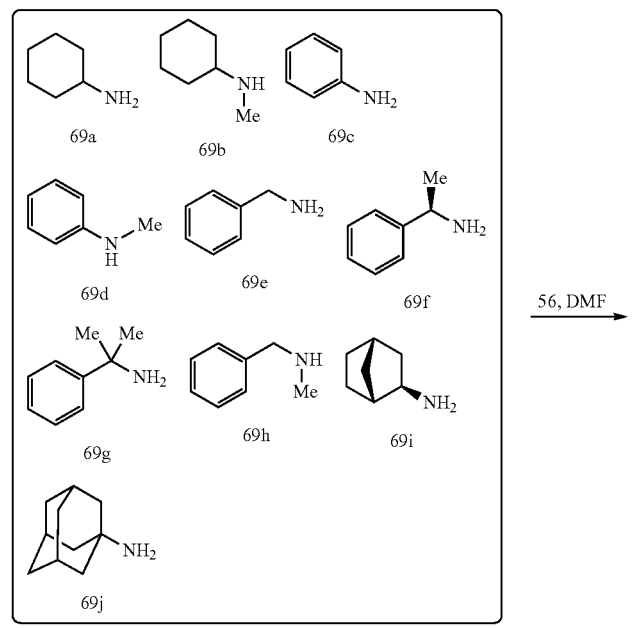

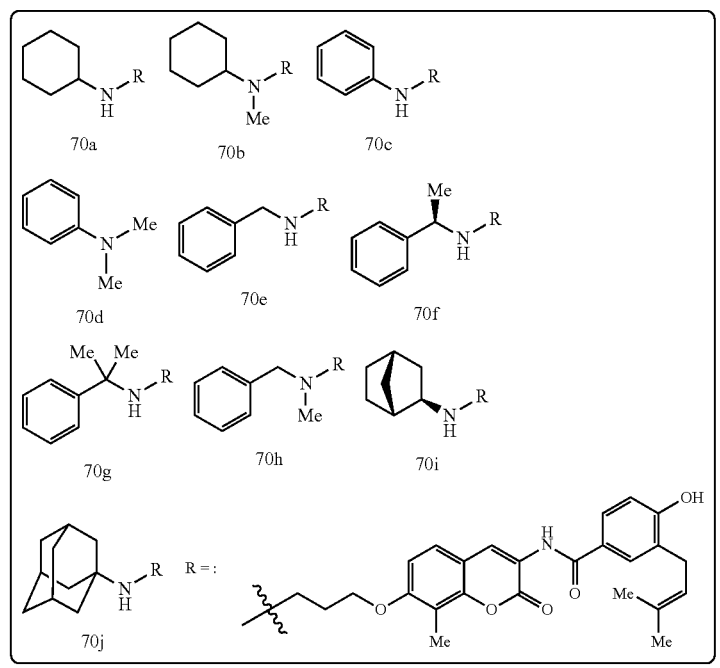

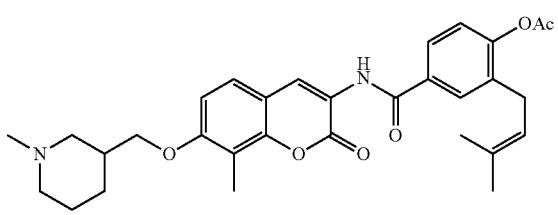 [SMILES: CC(=O)Oc1ccc(C(=O)Nc2cc3ccc(OCC4CCCN(C)C4)c(C)c3oc2=O)cc1CC=C(C)C]

4-((8-methyl-7-((1-methylpiperidin-3-yl)methoxy)-2-oxo-2H-chromen-3-yl)carbamoyl)-2-(3-methylbut-2-en-1-yl)phenyl acetate 1H NMR (500 MHz, CDCl$_3$) δ 8.79 (s, 1H), 8.67 (s, 1H, NH), 7.81 (s, 1H), 7.76 (d, J=8.5 Hz, 1H), 7.36 (d, J=8.6 Hz, 1H), 7.19 (d, J=8.6 Hz, 1H), 6.84 (d, J=8.7 Hz, 1H), 5.21~5.19 (m, 1H), 4.08~3.99 (m, 2H), 3.61~3.49 (m, 2H), 3.33 (d, J=6.3 Hz, 2H), 2.93~2.91 (m, 1H), 2.84 (s, 3H), 2.75~2.69 (m, 2H), 2.36 (s, 3H), 2.33 (s, 3H), 2.32~2.30 (m, 1H), 2.06~2.00 (m, 2H), 1.78 (s, 3H), 1.74 (s, 3H), 1.61~1.54 (m, 1H). $^{13}$C NMR (126 MHz, CDCl$_3$) δ 169.11, 165.64, 159.56, 157.93, 152.29, 149.34, 134.85, 134.53, 131.76, 129.55, 126.12, 126.06, 124.63, 123.11, 121.85, 120.81, 114.29, 113.94, 108.89, 70.33, 57.79, 55.41, 44.93, 34.81, 29.00, 25.94, 25.42, 23.04, 21.10, 18.15, 8.47. HRMS (ESI$^+$) m/z [M+H$^+$] calcd for C$_{31}$H$_{37}$N$_2$O$_6$ 533.2652, found 533.2655.

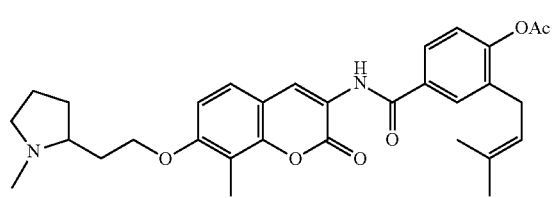 [SMILES: CC(=O)Oc1ccc(C(=O)Nc2cc3ccc(OCCC4CCCN4C)c(C)c3oc2=O)cc1CC=C(C)C]

4-((8-methyl-7-(2-(1-methylpyrrolidin-2-yl)ethoxy)-2-oxo-2H-chromen-3-yl)carbamoyl)-2-(3-methylbut-2-en-1-yl)phenyl acetate $^{13}$C NMR (126 MHz, CDCl$_3$+CH$_3$OH) δ 169.37, 165.84, 159.50, 158.07, 152.04, 149.17, 134.60, 134.21, 131.46, 129.28, 126.01, 125.88, 125.36, 122.85, 121.19, 120.51, 113.79, 113.41, 108.80, 65.73, 65.58, 56.43, 39.59, 31.22, 30.17, 28.69, 25.46, 21.52, 20.62, 17.67, 7.94. HRMS (ESI$^+$) m/z [M+H$^+$] calcd for C$_{31}$H$_{37}$N$_2$O$_6$ 533.2652, found 533.2655.

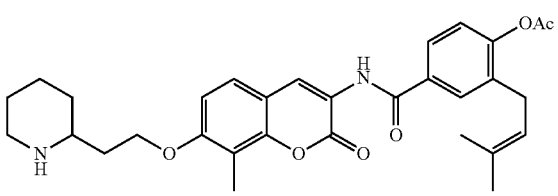 [SMILES: CC(=O)Oc1ccc(C(=O)Nc2cc3ccc(OCCC4CCCCN4)c(C)c3oc2=O)cc1CC=C(C)C]

4-((8-methyl-2-oxo-7-(2-(piperidin-2-yl)ethoxy)-2H-chromen-3-yl)carbamoyl)-2-(3-methylbut-2-en-1-yl) phenyl acetate $^{13}$C NMR (126 MHz, CDCl$_3$) δ 169.06, 165.39, 159.47, 157.85, 152.25, 149.25, 134.76, 134.45, 131.57, 129.53, 126.05, 126.01, 124.46, 123.05, 121.71, 120.86, 114.13, 113.81, 108.69, 64.28, 54.97, 45.08, 33.17, 29.02, 28.63, 25.89, 22.59, 22.35, 21.08, 18.15, 8.31. HRMS (ESI$^+$) m/z [M+H$^+$] calcd for C$_{31}$H$_{37}$N$_2$O$_6$ 533.2652, found 533.2650.

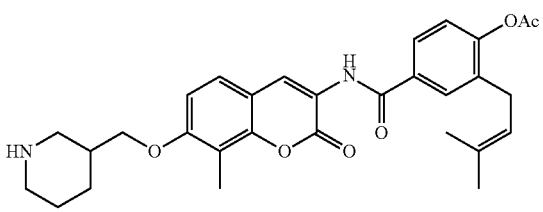 [SMILES: CC(=O)Oc1ccc(C(=O)Nc2cc3ccc(OCC4CCCNC4)c(C)c3oc2=O)cc1CC=C(C)C]

4-((8-methyl-2-oxo-7-(piperidin-3-ylmethoxy)-2H-chromen-3-yl)carbamoyl)-2-(3-methylbut-2-en-1-yl) phenyl acetate $^{13}$C NMR (126 MHz, CDCl$_3$) δ 169.06, 165.56, 159.41, 157.77, 152.31, 149.28, 134.80, 134.40, 131.71, 129.55, 126.09, 126.05, 124.43, 123.09, 121.86, 120.85, 114.34, 113.96, 108.80, 70.15, 46.75, 44.41, 34.11, 29.02, 25.94, 25.78, 21.98, 21.10, 18.21, 8.23.

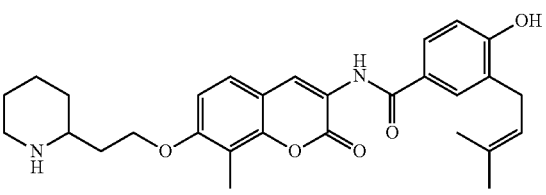 [SMILES: CC(C)=CCc1cc(C(=O)Nc2cc3ccc(OCCC4CCCCN4)c(C)c3oc2=O)ccc1O]

4-hydroxy-N-(8-methyl-2-oxo-7-(2-(piperidin-2-yl)ethoxy)-2H-chromen-3-yl)-3-(3-methylbut-2-en-1-yl)benzamide $^{13}$C NMR (126 MHz, CDCl$_3$+CH$_3$OH) δ 166.65, 162.69, 162.40, 159.64, 157.64, 148.94, 128.78, 126.33, 125.83, 124.53, 124.20, 121.54, 121.46, 117.49, 115.18, 114.71, 113.71, 108.85, 64.17, 54.67, 44.80, 32.88, 28.54, 27.94, 25.34, 22.02, 21.69, 17.45, 7.72. HRMS (ESI$^+$) m/z [M+H$^+$] calcd for C$_{29}$H$_{35}$N$_2$O$_5$ 491.2546, found 491.2544.

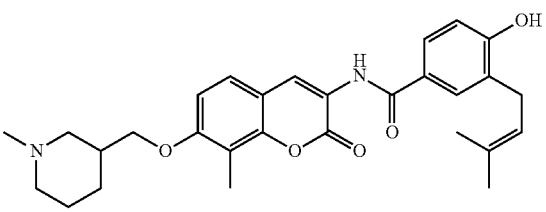 [SMILES: CC(C)=CCc1cc(C(=O)Nc2cc3ccc(OCC4CCCN(C)C4)c(C)c3oc2=O)ccc1O]

4-hydroxy-N-(8-methyl-7-((1-methylpiperidin-3-yl)methoxy)-2-oxo-2H-chromen-3-yl)-3-(3-methylbut-2-en-1-yl)benzamide $^{13}$C NMR (126 MHz, CDCl$_3$+CH$_3$OH) δ 166.67, 159.73, 159.19, 157.68, 148.96, 133.47, 128.81, 126.37, 125.85, 124.47, 124.27, 121.58, 121.48, 114.76, 113.87, 113.75, 108.80, 69.97, 58.78, 57.24, 54.93, 44.21, 34.88, 28.07, 25.59, 24.85, 17.58, 8.48. HRMS (ESI+) m/z [M+H+] calcd for $C_{29}H_{35}N_2O_5$ 491.2546, found 491.2545.

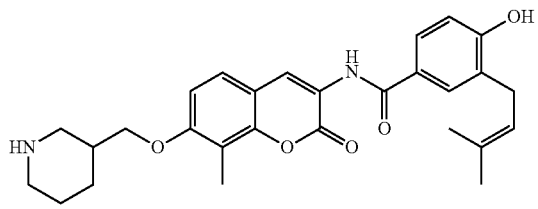 [SMILES: CC(C)=CCc1cc(C(=O)Nc2cc3ccc(OCC4CCCNC4)c(C)c3oc2=O)ccc1O]

4-hydroxy-N-(8-methyl-2-oxo-7-(piperidin-3-yl-methoxy)-2H-chromen-3-yl)-3-(3-methylbut-2-en-1-yl)benzamide 13C NMR (126 MHz, CDCl3+CH3OH) δ 166.56, 159.64, 159.18, 157.56, 148.92, 133.42, 128.78, 126.34, 125.81, 124.40, 124.21, 121.56, 121.47, 114.74, 113.84, 113.74, 108.71, 69.87, 46.36, 44.10, 33.96, 28.04, 25.51, 25.27, 21.71, 17.51, 7.75.

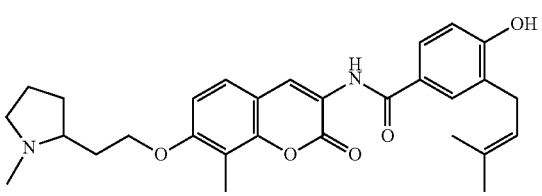 [SMILES: CC(C)=CCc1cc(C(=O)Nc2cc3ccc(OCCC4CCCN4C)c(C)c3oc2=O)ccc1O]

4-hydroxy-N-(8-methyl-7-(2-(1-methylpyrrolidin-2-yl)ethoxy)-2-oxo-2H-chromen-3-yl)-3-(3-methylbut-2-en-1-yl)benzamide 13C NMR (126 MHz, CDCl3+CH3OH) δ 166.66, 159.65, 159.18, 157.68, 148.97, 133.46, 128.80, 126.36, 125.87, 124.44, 124.26, 121.55, 121.48, 114.81, 113.71, 108.75, 77.43, 66.12, 65.45, 56.29, 39.39, 30.69, 29.99, 28.07, 25.55, 21.50, 17.59, 7.95.

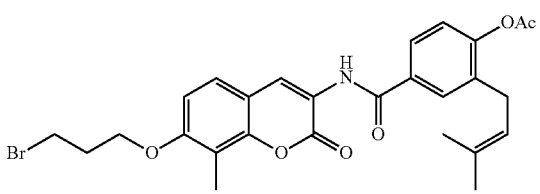 [SMILES: CC(=O)Oc1ccc(C(=O)Nc2cc3ccc(OCCCBr)c(C)c3oc2=O)cc1CC=C(C)C]

4-((7-(3-bromopropoxy)-8-methyl-2-oxo-2H-chromen-3-yl)carbamoyl)-2-(3-methylbut-2-en-1-yl)phenyl acetate 1H NMR (400 MHz, CDCl3) δ 8.80 (s, 1H), 8.70 (s, 1H), 7.80 (s, 1H), 7.76 (d, J=8.3 Hz, 1H) 7.35 (d, J=8.6 Hz, 1H), 7.17 (d, J=8.3 Hz, 1H), 6.89 (d, J=8.6 Hz, 1H), 5.29-5.16 (m, 1H), 4.20 (t, J=5.7 Hz, 2H), 3.64 (t, J=6.4 Hz, 2H), 3.32 (d, J=7.0 Hz, 2H), 2.45-2.35 (m, 5H), 2.34 (s, 1H), 2.32 (s, 1H), 1.77 (s, 3H), 1.73 (s, 3H). 13C NMR (101 MHz, CDCl3) δ 169.03, 165.48, 159.53, 158.24, 152.20, 149.32, 134.74, 134.42, 131.71, 129.47, 126.00, 125.93, 124.65, 123.03, 121.60, 120.79, 114.32, 113.60, 109.02, 66.20, 32.40, 29.95, 28.95, 25.89, 21.04, 18.09, 8.27. HRMS (ESI+) m/z [M+H+] calcd for $C_{27}H_{29}BrNO_6$ 542.1178, found 542.1174.

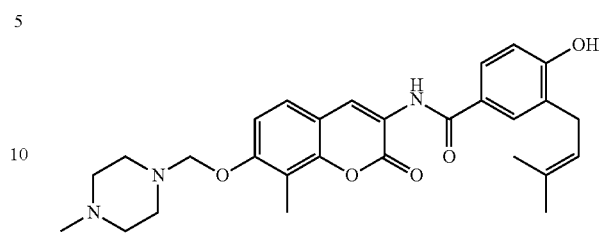

4-hydroxy-N-(8-methyl-7-(3-(4-methylpiperazin-1-yl)propoxy)-2-oxo-2H-chromen-3-yl)-3-(3-methyl-but-2-en-1-yl)benzamide 13C NMR (126 MHz, DMSO) δ 165.33, 158.75, 158.39, 158.09, 149.28, 131.85, 129.19, 128.08, 127.66, 126.86, 126.15, 123.99, 122.29, 121.25, 114.56, 112.72, 112.40, 109.19, 66.73, 54.50, 54.24, 52.39, 45.38, 27.93, 26.16, 25.55, 17.71, 7.94. HRMS (ESI+) m/z [M+H+] calcd for $C_{30}H_{38}N_3O_5$ 520.2811, found 520.2806.

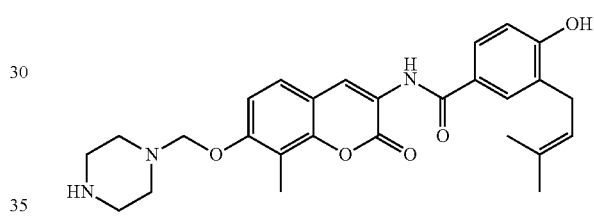

4-hydroxy-N-(8-methyl-2-oxo-7-(3-(piperazin-1-yl)propoxy)-2H-chromen-3-yl)-3-(3-methylbut-2-en-1-yl)benzamide 13C NMR (126 MHz, CDCl3) δ 166.59, 159.69, 159.13, 158.20, 148.98, 133.31, 128.72, 127.57, 126.28, 125.69, 124.66, 124.20, 121.44, 121.25, 114.66, 113.69, 113.29, 108.84, 66.18, 54.43, 49.48, 43.46, 27.96, 26.24, 25.42, 17.46, 7.75. HRMS (ESI+) m/z [M+H+] calcd for $C_{29}H_{36}N_2O_5$ 506.2655, found 506.2664.

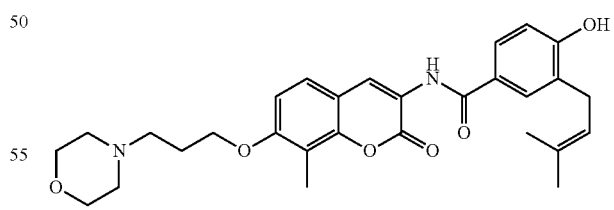

4-hydroxy-N-(8-methyl-7-(3-morpholinopropoxy)-2-oxo-2H-chromen-3-yl)-3-(3-methylbut-2-en-1-yl)benzamide 13C NMR (101 MHz, CDCl3) δ 166.35, 159.79, 158.94, 158.37, 149.17, 134.01, 129.14, 128.72, 126.55, 125.78, 124.91, 124.47, 121.62, 121.55, 115.06, 114.06, 113.49, 108.94, 66.85, 55.70, 53.75, 31.02, 28.55, 26.34, 25.88, 17.95, 8.17. HRMS (ESI⁺) m/z [M+H⁺] calcd for C₂₉H₃₅N₂O₆ 507.2495, found 507.2490.

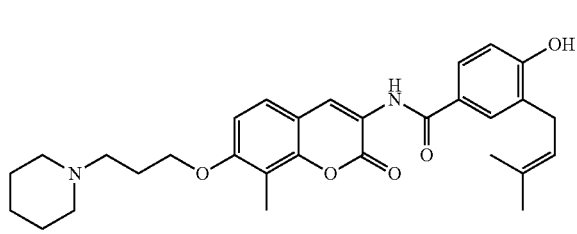 [SMILES: CC(C)=CCc1cc(C(=O)Nc2cc3ccc(OCCCN4CCCCC4)c(C)c3oc2=O)ccc1O]

4-hydroxy-N-(8-methyl-2-oxo-7-(3-(piperidin-1-yl) propoxy)-2H-chromen-3-yl)-3-(3-methylbut-2-en-1-yl)benzamide ¹³C NMR (126 MHz, DMSO) δ 165.36, 158.79, 158.35, 157.67, 149.25, 131.86, 129.19, 128.00, 127.67, 126.87, 126.17, 123.96, 122.29, 121.43, 114.57, 112.99, 112.49, 109.18, 65.88, 53.46, 52.29, 27.93, 25.55, 23.52, 22.75, 21.35, 17.72, 8.02. HRMS (ESI⁺) m/z [M+H⁺] calcd for C₃₀H₃₇N₂O₅ 505.2702, found 505.2702.

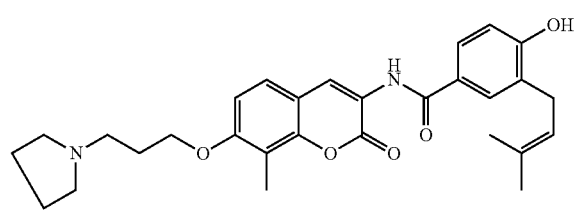 [SMILES: CC(C)=CCc1cc(C(=O)Nc2cc3ccc(OCCCN4CCCC4)c(C)c3oc2=O)ccc1O]

4-hydroxy-N-(8-methyl-2-oxo-7-(3-(pyrrolidin-1-yl) propoxy)-2H-chromen-3-yl)-3-(3-methylbut-2-en-1-yl)benzamide ¹³C NMR (126 MHz, DMSO) δ 165.36, 158.78, 158.34, 157.66, 149.25, 131.86, 129.19, 128.01, 127.67, 126.87, 126.16, 123.96, 122.29, 121.42, 114.56, 112.98, 112.49, 109.15, 65.68, 53.31, 51.36, 27.93, 25.55, 22.64, 17.71, 8.03. HRMS (ESI⁺) m/z [M+H⁺] calcd for C₂₉H₃₅N₂O₅ 491.2546, found 491.2550.

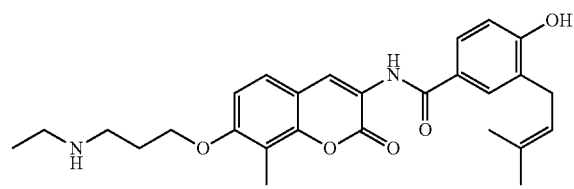 [SMILES: CCNCCCOc1ccc2cc(NC(=O)c3ccc(O)c(CC=C(C)C)c3)c(=O)oc2c1C]

N-(7-(3-(ethylamino)propoxy)-8-methyl-2-oxo-2H-chromen-3-yl)-4-hydroxy-3-(3-methylbut-2-en-1-yl)benzamide HRMS (ESI⁺) m/z [M+H⁺] calcd for C₂₇H₃₃N₂O₅ 465.2389, found 465.2389.

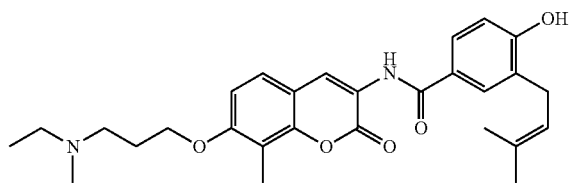 [SMILES: CCN(C)CCCOc1ccc2cc(NC(=O)c3ccc(O)c(CC=C(C)C)c3)c(=O)oc2c1C]

N-(7-(3-(ethyl(methyl)amino)propoxy)-8-methyl-2-oxo-2H-chromen-3-yl)-4-hydroxy-3-(3-methylbut-2-en-1-yl)benzamide HRMS (ESI⁺) m/z [M+H⁺] calcd for C₂₈H₃₅N₂O₅ 479.2546, found 479.2542.

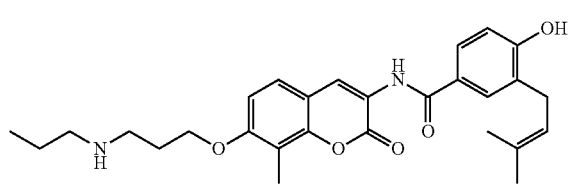 [SMILES: CCCNCCCOc1ccc2cc(NC(=O)c3ccc(O)c(CC=C(C)C)c3)c(=O)oc2c1C]

4-hydroxy-N-(8-methyl-2-oxo-7-(3-(propylamino) propoxy)-2H-chromen-3-yl)-3-(3-methylbut-2-en-1-yl)benzamide HRMS (ESI⁺) m/z [M+H⁺] calcd for C₂₈H₃₅N₂O₅ 479.2546, found 479.2542.

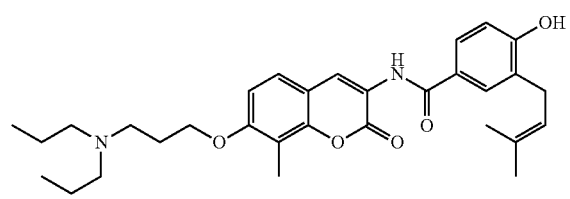 [SMILES: CCCN(CCC)CCCOc1ccc2cc(NC(=O)c3ccc(O)c(CC=C(C)C)c3)c(=O)oc2c1C]

N-(7-(3-(dipropylamino)propoxy)-8-methyl-2-oxo-2H-chromen-3-yl)-4-hydroxy-3-(3-methylbut-2-en-1-yl)benzamide ¹³C NMR (126 MHz, CDCl₃) δ 166.59, 159.63, 159.18, 157.53, 148.95, 133.45, 128.80, 127.65, 126.36, 125.90, 124.42, 124.24, 121.61, 121.47, 114.74, 113.80, 113.64, 108.81, 65.40, 54.55, 50.19, 28.06, 25.53, 23.93, 17.57, 17.09, 10.86, 7.87. HRMS (ESI⁺) m/z [M+H⁺] calcd for C₃₁H₄₁N₂O₅ 521.3015, found 521.3012.

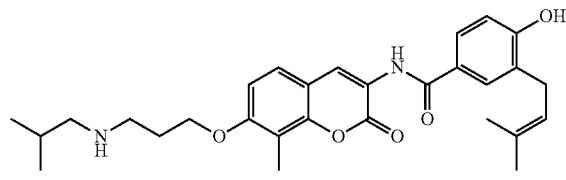 [SMILES: CC(C)=CCc1cc(C(=O)Nc2cc3ccc(OCCCNCC(C)C)c(C)c3oc2=O)ccc1O]

4-hydroxy-N-(7-(3-(isobutylamino)propoxy)-8-methyl-2-oxo-2H-chromen-3-yl)-3-(3-methylbut-2-en-1-yl)benzamide HRMS (ESI+) m/z [M+H+] calcd for $C_{29}H_{37}N_2O_5$ 493.2702, found 493.2711.

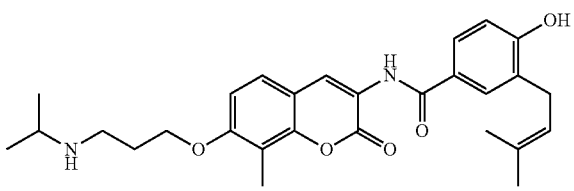 [SMILES: CC(C)=CCc1cc(C(=O)Nc2cc3ccc(OCCCNC(C)C)c(C)c3oc2=O)ccc1O]

4-hydroxy-N-(7-(3-(isopropylamino)propoxy)-8-methyl-2-oxo-2H-chromen-3-yl)-3-(3-methylbut-2-en-1-yl)benzamide $^{13}$C NMR (126 MHz, CDCl$_3$+CH$_3$OH) δ 166.58, 159.61, 159.16, 157.65, 148.91, 133.35, 128.75, 128.73, 126.30, 125.83, 124.49, 124.16, 121.49, 121.44, 114.68, 113.64, 113.59, 108.81, 65.41, 50.58, 42.33, 27.99, 26.18, 25.45, 18.70, 17.49, 7.74. HRMS (ESI+) m/z [M+H+] calcd for $C_{28}H_{35}N_2O_5$ 479.2546, found 479.2561.

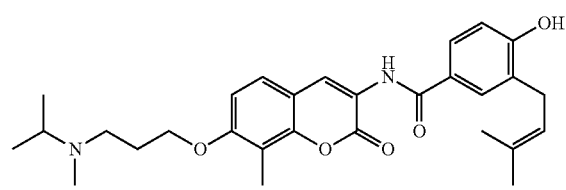

4-hydroxy-N-(7-(3-(isopropyl(methyl)amino)propoxy)-8-methyl-2-oxo-2H-chromen-3-yl)-3-(3-methylbut-2-en-1-yl)benzamide HRMS (ESI+) m/z [M+H+] calcd for $C_{29}H_{37}N_2O_5$ 493.2702, found 493.2683.

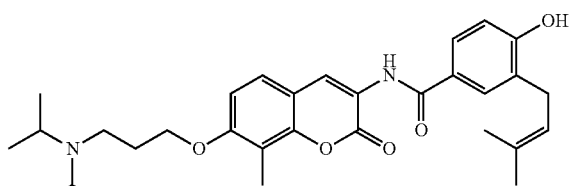 [SMILES: CC(C)=CCc1cc(C(=O)Nc2cc3ccc(OCCCN(C)C(C)C)c(C)c3oc2=O)ccc1O]

N-(7-(3-(diisopropylamino)propoxy)-8-methyl-2-oxo-2H-chromen-3-yl)-4-hydroxy-3-(3-methylbut-2-en-1-yl)benzamide $^{13}$C NMR (126 MHz, CDCl$_3$+CH$_3$OH) δ 166.54, 159.69, 159.19, 157.58, 149.03, 133.69, 128.93, 128.84, 126.47, 126.03, 124.44, 124.36, 121.74, 121.54, 114.89, 113.91, 113.60, 108.80, 65.60, 55.01, 45.08, 28.24, 27.50, 25.72, 17.86, 17.77, 8.09. HRMS (ESI+) m/z [M+H+] calcd for $C_{31}H_{41}N_2O_5$ 521.3015, found 521.3018.

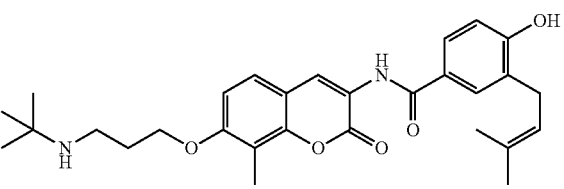

N-(7-(3-(tert-butylamino)propoxy)-8-methyl-2-oxo-2H-chromen-3-yl)-4-hydroxy-3-(3-methylbut-2-en-1-yl)benzamide $^{13}$C NMR (126 MHz, CDCl$_3$+CH$_3$OH) δ 166.51, 159.65, 159.16, 157.68, 148.94, 133.51, 128.82, 128.79, 126.37, 125.90, 124.41, 124.28, 121.55, 121.50, 114.79, 113.70, 113.63, 108.89, 65.51, 57.05, 38.92, 28.11, 26.47, 25.60, 25.54, 17.65, 7.88. HRMS (ESI+) m/z [M+H+] calcd for $C_{29}H_{37}N_2O_5$ 493.2702, found 493.2701.

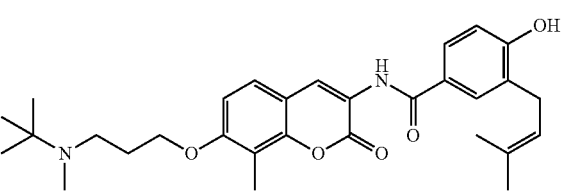 [SMILES: CC(C)=CCc1cc(C(=O)Nc2cc3ccc(OCCCN(C)C(C)(C)C)c(C)c3oc2=O)ccc1O]

N-(7-(3-(tert-butyl(methyl)amino)propoxy)-8-methyl-2-oxo-2H-chromen-3-yl)-4-hydroxy-3-(3-methylbut-2-en-1-yl)benzamide HRMS (ESI+) m/z [M+H+] calcd for $C_{30}H_{39}N_2O_5$ 507.2859, found 507.2853.

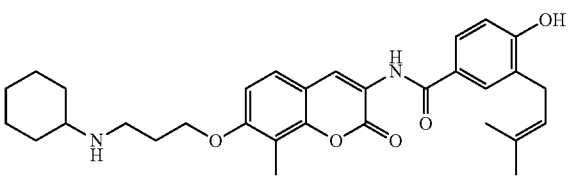 [SMILES: CC(C)=CCc1cc(C(=O)Nc2cc3ccc(OCCCNC4CCCCC4)c(C)c3oc2=O)ccc1O]

N-(7-(3-(cyclohexylamino)propoxy)-8-methyl-2-oxo-2H-chromen-3-yl)-4-hydroxy-3-(3-methylbut-2-en-1-yl)benzamide HRMS (ESI+) m/z [M+H+] calcd for $C_{31}H_{39}N_2O_5$ 519.2859, found 519.2858.

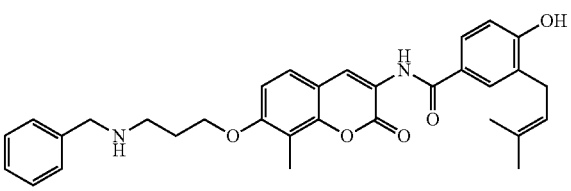

N-(7-(3-(benzylamino)propoxy)-8-methyl-2-oxo-2H-chromen-3-yl)-4-hydroxy-3-(3-methylbut-2-en-1-yl)benzamide $^{13}$C NMR (126 MHz, CDCl$_3$+CH$_3$OH) δ 166.57, 159.69, 159.14, 158.09, 148.94, 137.05, 133.33, 128.75, 128.74, 128.57, 128.46, 127.70, 126.60, 126.28, 125.71, 124.64, 124.20, 121.45, 121.28, 114.66, 113.68, 113.34, 108.79, 66.63, 53.05, 51.09, 45.59, 43.29, 28.30, 27.99, 25.45, 22.20, 17.48, 7.72. HRMS (ESI$^+$) m/z [M+H$^+$] calcd for C$_{32}$H$_{35}$N$_2$O$_5$ 527.2546. found 527.2546.

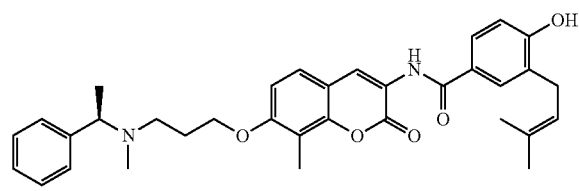 [SMILES: CC(C)=CCc1cc(C(=O)Nc2cc3ccc(OCCCN(C)[C@H](C)c4ccccc4)c(C)c3oc2=O)ccc1O]

(R)-4-hydroxy-N-(8-methyl-7-(3-(methyl(1-phenylethyl)amino)propoxy)-2-oxo-2H-chromen-3-yl)-3-(3-methylbut-2-en-1-yl)benzamide HRMS (ESI$^+$) m/z [M+H$^+$] calcd for C$_{33}$H$_{37}$N$_2$O$_5$ 541.2702, found 541.2700.

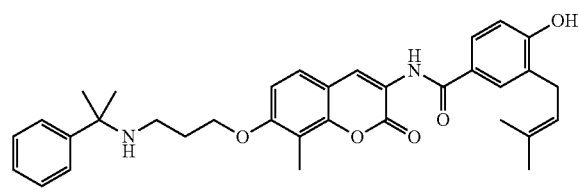 [SMILES: CC(C)=CCc1cc(C(=O)Nc2cc3ccc(OCCCNC(C)(C)c4ccccc4)c(C)c3oc2=O)ccc1O]

4-hydroxy-N-(8-methyl-2-oxo-7-(3-((2-phenylpropan-2-yl)amino)propoxy)-2H-chromen-3-yl)-3-(3-methylbut-2-en-1-yl)benzamide $^{13}$C NMR (126 MHz, CDCl$_3$+CH$_3$OH) δ 166.60, 159.77, 159.16, 158.04, 149.00, 133.57, 133.54, 128.87, 128.82, 128.60, 127.27, 126.40, 125.77, 125.51, 124.63, 124.38, 121.52, 121.41, 114.80, 113.77, 113.43, 108.79, 66.41, 57.71, 40.09, 28.67, 28.15, 27.77, 25.64, 17.67, 7.84. HRMS (ESI$^+$) m/z [M+H$^+$] calcd for C$_{34}$H$_{39}$N$_2$O$_5$ 555.2859, found 555.2864.

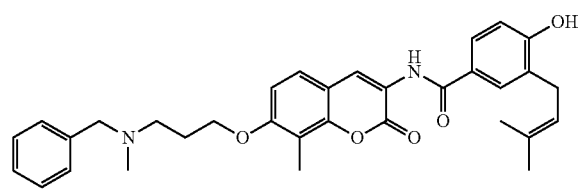 [SMILES: CC(C)=CCc1cc(C(=O)Nc2cc3ccc(OCCCN(C)Cc4ccccc4)c(C)c3oc2=O)ccc1O]

N-(7-(3-(benzyl(methyl)amino)propoxy)-8-methyl-2-oxo-2H-chromen-3-yl)-4-hydroxy-3-(3-methylbut-2-en-1-yl)benzamide HRMS (ESI$^+$) m/z [M+H$^+$] calcd for C$_{33}$H$_{37}$N$_2$O$_5$ 541.2702, found 541.2714.

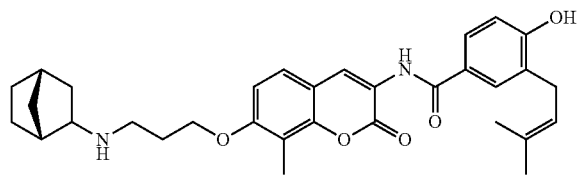 [SMILES: CC(C)=CCc1cc(C(=O)Nc2cc3ccc(OCCCNC4C[C@H]5CC[C@@H]4C5)c(C)c3oc2=O)ccc1O]

N-(7-(3-(((1R,4S)-bicyclo[2.2.1]heptan-2-ylamino)propoxy)-8-methyl-2-oxo-2H-chromen-3-yl)-4-hydroxy-3-(3-methylbut-2-en-1-yl)benzamide HRMS (ESI$^+$) m/z [M+H$^+$] calcd for C$_{34}$H$_{39}$N$_2$O$_5$ 555.2859, found 555.2847.

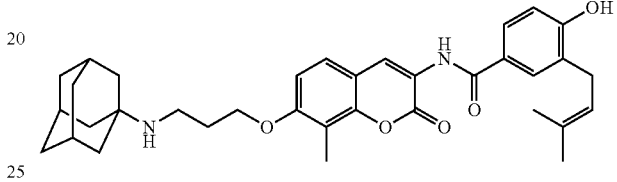

N-(7-(3-((3S,5S,7S)-adamantan-1-ylamino)propoxy)-8-methyl-2-oxo-2H-chromen-3-yl)-4-hydroxy-3-(3-methylbut-2-en-1-yl)benzamide $^{13}$C NMR (126 MHz, CDCl$_3$+CH$_3$OH) δ 166.58, 159.73, 159.18, 157.78, 149.02, 133.62, 128.90, 128.83, 126.44, 125.95, 124.47, 124.40, 121.63, 121.53, 114.84, 113.76, 113.72, 108.95, 65.73, 57.15, 38.61, 37.06, 35.54, 29.01, 28.19, 26.62, 25.68, 17.72, 8.02. HRMS (ESI$^+$) m/z [M+H$^+$] calcd for C$_{35}$H$_{43}$N$_2$O$_5$ 571.3172, found 571.3173.

iii. Synthesis of Urea Derivatives

Figure 4:
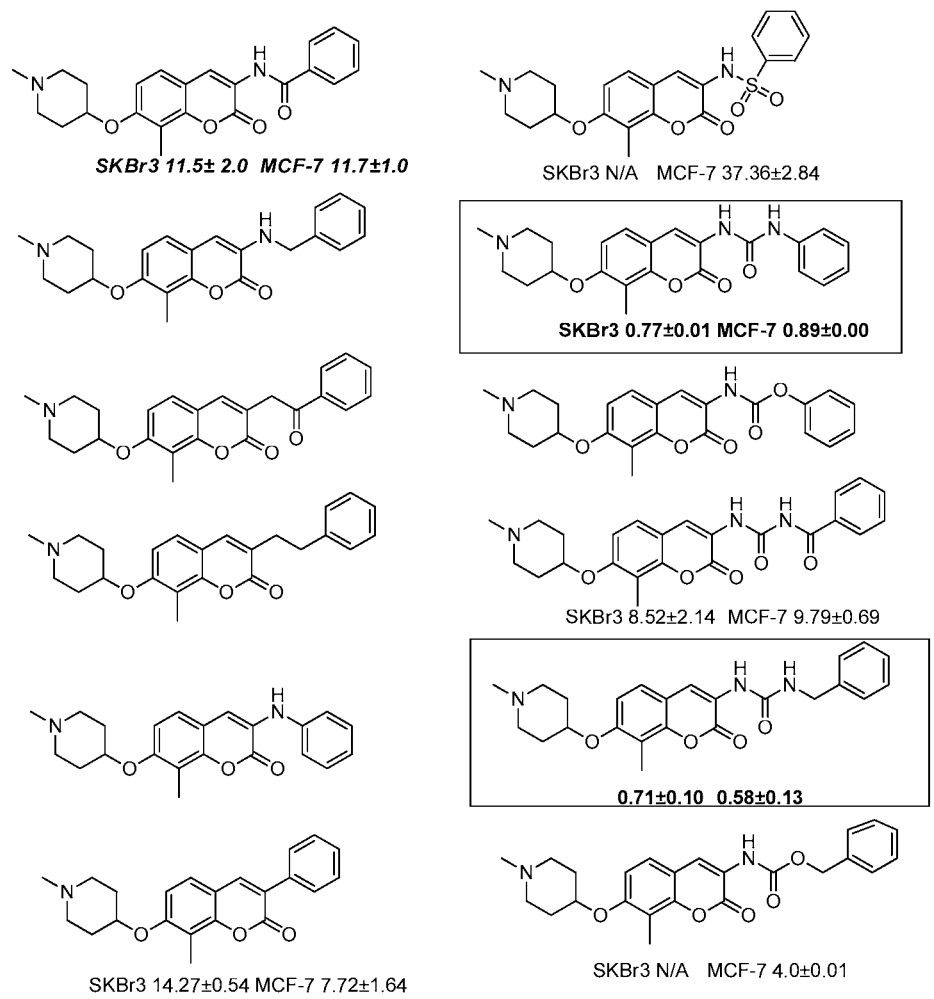
FIG. 4—Different envisioned linkers between the coumarin core and the phenyl group attached to the C3 position of the coumarin core.

Different linkers between the coumarin core and the attached phenyl group were explored to determine the optimal linker. Some examples of different linkers are explored in FIG. 4. The urea derivatives described herein are produced by reacting the aminocoumarin compound with an isocyanate in DCM to produce the urea derivative. This method is described in greater detail above. The characterization of the compounds is detailed below.

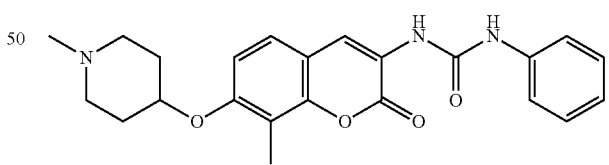

1-(8-methyl-7-((1-methylpiperidin-4-yl)oxy)-2-oxo-2H-chromen-3-yl)-3-phenylurea $^1$H NMR (400 MHz, CDCl$_3$) δ 8.75 (s, 1H, NH), 8.52 (s, 1H, NH), 8.42 (s, 1H), 7.54 (d, J=7.7 Hz, 2H), 7.23-7.12 (m, 3H), 6.93 (t, J=7.3 Hz, 1H), 6.80 (d, J=8.8 Hz, 1H), 4.39 (m, 1H), 2.70~2.62 (m, 1H), 2.40~2.33 (m, 2H), 2.32 (s, 3H), 2.32 (s, 3H), 2.06-1.82 (m, 2H), 1.90~1.88 (m, 2H). $^{13}$C NMR (126 MHz, DMSO) δ 158.31, 155.48, 152.28, 148.17, 139.27, 128.93, 125.25, 122.61, 122.21, 120.39, 117.99, 113.45, 113.40, 110.96, 71.60, 51.58, 45.14, 29.77, 8.16. HRMS (ESI⁺) m/z [M+H⁺] calcd for C₂₃H₂₆N₃O₄ 408.1923; found 408.1919.

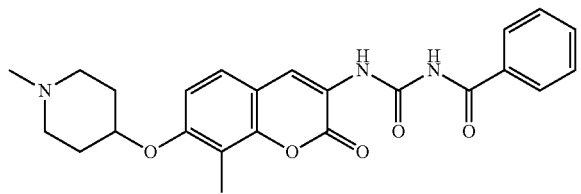 [SMILES: Cc1c(OC2CCN(C)CC2)ccc2cc(NC(=O)NC(=O)c3ccccc3)c(=O)oc12]

N-((8-methyl-7-((1-methylpiperidin-4-yl)oxy)-2-oxo-2H-chromen-3-yl)carbamoyl)benzamide ¹H NMR (500 MHz, CDCl₃) δ 8.82 (s, 1H), 8.76 (s, 1H, NH), 7.93 (d, J=7.1 Hz, 1H), 7.60 (m, 1H), 7.55-7.49 (m, 1H), 7.34 (d, J=8.6 Hz, 1H), 6.88 (d, J=8.7 Hz, 1H), 4.52 (m, 1H), 2.74 (m, 2H), 2.54 (m, 2H), 2.48 (s, 3H), 2.35 (s, 3H), 2.14 (m 2H), 1.96 (m, 2H). ¹³C NMR (126 MHz, CDCl₃) δ 166.20, 159.64, 157.04, 149.71, 133.95, 132.60, 129.12, 127.32, 125.85, 124.77, 121.71, 115.43, 113.54, 110.63, 71.86, 52.19, 46.14, 30.47, 8.61. HRMS (ESI⁺) m/z [M+H⁺] calcd for C₂₄H₂₆N₃O₅ 436.1872; found 436.1876.

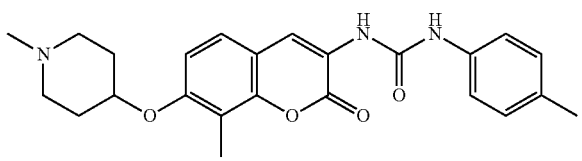

1-(8-methyl-7-((1-methylpiperidin-4-yl)oxy)-2-oxo-2H-chromen-3-yl)-3-(p-tolyl)urea ¹H NMR (500 MHz, DMSO) δ 9.37 (s, 1H, NH), 8.65 (s, 1H, NH), 8.40 (s, 1H), 7.48 (d, J=8.7 Hz, 1H), 7.34 (d, J=8.4 Hz, 2H), 7.10 (d, J=8.3 Hz, 2H), 7.08 (d, J=8.8 Hz, 1H), 4.60 (m, 1H), 2.76 (m, 2H), 2.54 (m, 2H), 2.37 (s, 3H), 2.25 (s, 3H), 2.24 (s, 3H), 1.99 (m, 2H), 1.80 (m, 2H). ¹³C NMR (126 MHz, DMSO) δ 158.27, 155.33, 152.24, 148.08, 136.64, 131.02, 129.26, 125.16, 122.65, 120.17, 118.02, 117.92, 113.42, 110.90, 70.95, 51.37, 44.76, 29.51, 20.32, 8.11. HRMS (ESI⁺) m/z [M+H⁺] calcd for C₂₄H₂₈N₃O₄ 422.2080; found 422.2084.

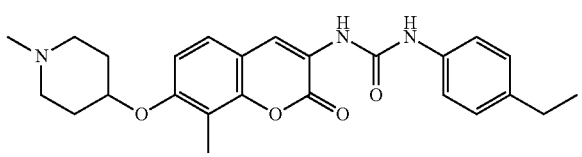 [SMILES: CCc1ccc(NC(=O)Nc2cc3ccc(OC4CCN(C)CC4)c(C)c3oc2=O)cc1]

1-(4-ethylphenyl)-3-(8-methyl-7-((1-methylpiperidin-4-yl)oxy)-2-oxo-2H-chromen-3-yl)urea ¹H NMR (400 MHz, CDCl₃) δ 8.37 (s, 1H), 7.36 (d, J=8.4 Hz, 2H), 7.14 (d, J=8.6 Hz, 1H), 6.98 (d, J=8.3 Hz, 2H), 6.74 (d, J=8.8 Hz, 1H), 4.40 (m, 1H), 2.67 (m, 2H), 2.55-2.40 (m, 4H), 2.33 (s, 3H), 2.21 (s, 3H), 2.02 (m, 2H), 1.90 (m, 2H), 13 (t, J=7.6 Hz, 3H). ¹³C NMR (126 MHz, DMSO) δ 158.28, 155.43, 152.24, 148.08, 137.51, 136.85, 128.06, 125.14, 122.60, 120.18, 118.07, 113.37, 113.34, 110.91, 71.86, 51.69, 45.40, 30.01, 27.48, 15.74, 8.09. HRMS (ESI⁺) m/z [M+H⁺] calcd for C₂₅H₃₀N₃O₄ 436.2236; found 436.2240.

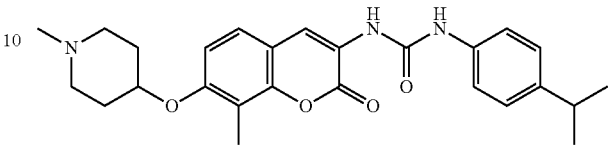

1-(4-isopropylphenyl)-3-(8-methyl-7-((1-methylpiperidin-4-yl)oxy)-2-oxo-2H-chromen-3-yl)urea ¹H NMR (400 MHz, CDCl₃) δ 8.23 (s, 1H), 7.20 (d, J=8.5 Hz, 2H), 7.12 (d, J=8.6 Hz, 1H), 6.99 (d, J=8.5 Hz, 2H), 6.71 (d, J=8.8 Hz, 1H), 4.36 (m, 1H), 2.73 (m, 1H), 2.59 (m, 2H), 2.41 (m, 2H), 2.23 9s, 3H), 2.13 (s, 3H), 1.91 (m, 2H), 1.79 (m, 2H), 1.06 (s, 3H), 1.04 (s, 3H). ¹³C NMR (126 MHz, DMSO) δ 158.28, 155.38, 152.24, 148.08, 142.22, 136.91, 126.59, 125.17, 122.63, 120.16, 118.07, 117.97, 113.40, 110.92, 71.76, 51.52, 45.12, 32.75, 29.69, 23.98, 8.11. HRMS (ESI⁺) m/z [M+H⁺] calcd for C₂₆H₃₂N₃O₄ 450.2393; found 450.2390.

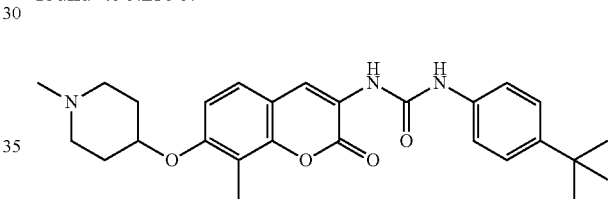

1-(4-(tert-butyl)phenyl)-3-(8-methyl-7-((1-methylpiperidin-4-yl)oxy)-2-oxo-2H-chromen-3-yl)urea ¹H NMR (400 MHz, CDCl₃) δ 8.62 (s, 1H), 8.32 (s, 1H, NH), 8.29 (s, 1H, NH), 7.55 (d, J=8.7 Hz, 2H), 7.37 (d, J=8.7 Hz, 2H), 7.33 (d, J=8.7 Hz, 1H), 6.90 (d, J=8.8 Hz, 1H), 4.50 (m, 1H), 2.75 (m, 2H), 2.50 (m, 2H), 2.41 (s, 3H), 2.40 (s, 3H), 2.11 (m, 2H), 1.98 (m, 2H), 1.34 (s, 9H). ¹³C NMR (126 MHz, CDCl₃) δ 160.85, 156.56, 152.90, 148.84, 146.27, 136.37, 127.99, 126.03, 125.43, 122.86, 119.09, 115.11, 114.21, 111.20, 72.84, 52.58, 46.42, 34.77, 31.65, 30.99, 8.49. HRMS (ESI⁺) m/z [M+H⁺] calcd for C₂₇H₃₄N₃O₄ 464.2549; found 464.2953.

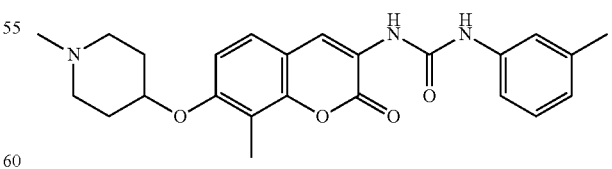

1-(8-methyl-7-((1-methylpiperidin-4-yl)oxy)-2-oxo-2H-chromen-3-yl)-3-(m-tolyl)urea ¹H NMR (500 MHz, CDCl₃) δ 8.38 (s, 1H), 7.29 (s, 1H), 7.26 (d, J=8.0 Hz, 1H), 7.19 (d, J=8.0 Hz, 1H), 7.13 (t, J=8.0

Hz, 1H), 6.85 (d, J=8.0 hz, 1H), 6.82 (d, J=8.0 Hz, 1H), 4.61 (m, 1H), 2.98 (m, 4H), 2.59 (s, 3H), 2.29 (s, 3H), 2.28 (s, 3H), 2.21 (m, 2H), 2.06 (m, 2H). $^{13}$C NMR (126 MHz, CDCl$_3$) δ 159.51, 155.27, 153.20, 148.65, 138.71, 138.44, 128.63, 125.12, 123.77, 122.71, 121.66, 119.61, 116.09, 114.60, 114.25, 110.25, 69.44, 50.94, 44.35, 28.50, 21.20, 8.02. HRMS (ESI$^+$) m/z [M+H$^+$] calcd for C$_{24}$H$_{28}$N$_3$O$_4$ 422.2080; found 422.2074.

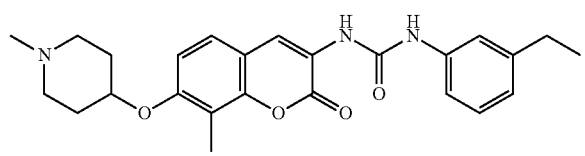 [SMILES: CCc1cccc(NC(=O)Nc2cc3ccc(OC4CCN(C)CC4)c(C)c3oc2=O)c1]

1-(3-ethylphenyl)-3-(8-methyl-7-((1-methylpiperidin-4-yl)oxy)-2-oxo-2H-chromen-3-yl)urea $^1$H NMR (500 MHz, DMSO) δ 9.41 (s, 1H, NH), 8.67 (s, 1H, NH), 8.41 (s, 1H), 7.48 (d, J=8.6 Hz, 1H), 7.36 (s, 1H), 7.27-7.12 (m, 2H), 7.08 (d, J=8.8 Hz, 1H), 6.88-6.74 (m, 1H), 4.55 (m, 1H), 2.63 (m, 2H), 2.62 (q, J=7.6 Hz, 2H), 2.36 (m, 2H), 2.26 (s, 3H), 2.22 (s, 3H), 1.96 (m, 2H), 1.73 (m, 2H), 1.18 (t, J=7.6 Hz, 3H). $^{13}$C NMR (126 MHz, DMSO) δ 205.03, 158.34, 155.52, 152.29, 148.16, 144.50, 139.26, 128.82, 125.23, 122.60, 121.76, 120.38, 117.37, 115.45, 113.42, 113.39, 110.98, 71.83, 51.79, 45.51, 30.11, 28.32, 15.58, 8.16. HRMS (ESI$^+$) m/z [M+H$^+$] calcd for C$_{25}$H$_{30}$N$_3$O$_4$ 436.2236; found 436.2240.

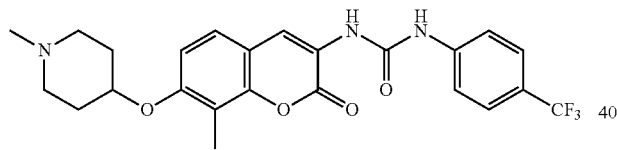

1-(8-methyl-7-((1-methylpiperidin-4-yl)oxy)-2-oxo-2H-chromen-3-yl)-3-(4-(trifluoromethyl)phenyl)urea $^1$H NMR (500 MHz, CDCl$_3$+CH$_3$OH) δ 8.18 (s, 1H), 7.36 (d, J=8.6 Hz, 2H), 7.29 (d, J=8.6 Hz, 2H), 7.06 (d, J=8.6 Hz, 1H), 6.65 (d, J=8.6 Hz, 1H), 4.28 (s, 1H), 2.53-2.49 (m, 2H), 2.33-2.29 (m, 2H), 2.15 (s, 3H), 2.07 (s, 3H), 1.87-1.79 (m, 2H), 1.74-1.70 (s, 2H). $^{13}$C NMR (126 MHz, CDCl$_3$+CH$_3$OH) δ 159.47, 155.97, 152.72, 148.74, 142.10, 125.90, 125.87, 125.04, 124.14 (q), 122.26, 122.08, 117.95, 114.64, 113.65, 110.39, 70.98, 51.62, 45.32, 29.72, 7.89. HRMS (ESI$^+$) m/z [M+H$^+$] calcd for C$_{24}$H$_{25}$F$_3$N$_3$O$_4$ 476.1797; found 476.1801.

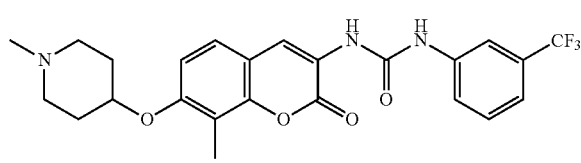 [SMILES: Cc1c(OC2CCN(C)CC2)ccc2cc(NC(=O)Nc3cccc(C(F)(F)F)c3)c(=O)oc12]

1-(8-methyl-7-((1-methylpiperidin-4-yl)oxy)-2-oxo-2H-chromen-3-yl)-3-(3-(trifluoromethyl)phenyl)urea $^1$H NMR (500 MHz, CDCl$_3$) δ 8.39 (s, 1H), 7.82 (s, 1H), 7.56 (d, J=8.0 Hz, 1H), 7.36 (d, J=8.0 Hz, 1H), 7.35~7.21 (m, 2H), 6.83 (d, J=8.0 Hz, 1H), 4.50 (m, 1H), 2.75 (m, 2H), 2.59 (m, 2H), 2.40 (s, 3H), 2.26 (s, 3H), 2.09 (m, 2H), 1.94 (m, 2H). $^{13}$C NMR (126 MHz, CDCl$_3$+CH$_3$OH) δ 159.70, 155.94, 152.78, 148.73, 139.48, 131.13 (q), 129.27, 125.18, 122.90, 122.36, 122.21, 121.57, 119.10, 115.03, 114.69, 113.82, 110.48, 70.85, 51.61, 45.30, 29.56, 8.04. HRMS (ESI$^+$) m/z [M+H$^+$] calcd for C$_{24}$H$_{25}$N$_3$O$_4$ 476.1797; found 476.1794.

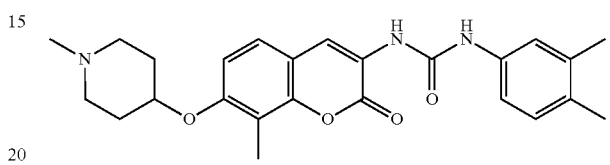

1-(3,4-dimethylphenyl)-3-(8-methyl-7-((1-methylpiperidin-4-yl)oxy)-2-oxo-2H-chromen-3-yl)urea $^1$H NMR (500 MHz, CDCl$_3$) δ 8.34 (s, 1H), 7.20~7.16 (m, 2H), 7.07 (d, J=8.0 Hz, 1H), 6.96 (d, J=8.0 Hz, 1H), 6.76 (d, J=8.0 Hz, 1H), 4.44 (m, 1H), 2.68 (m, 2H), 2.56 (m, 2H), 2.33 (s, 3H), 2.22 (s, 3H), 2.16 (s, 3H), 2.12 (s, 3H), 2.00 (m, 2H), 1.89 (m, 2H). $^{13}$C NMR (126 MHz, CDCl$_3$+CH$_3$OH) δ 159.83, 155.78, 153.29, 148.73, 137.20, 136.23, 131.44, 129.95, 125.11, 122.67, 121.87, 120.63, 116.77, 114.79, 114.12, 110.54, 70.93, 51.76, 45.69, 29.67, 19.82, 18.99, 8.35. HRMS (ESI$^+$) m/z [M+H$^+$] calcd for C$_{25}$H$_{30}$N$_3$O$_4$ 436.2236; found 436.2242.

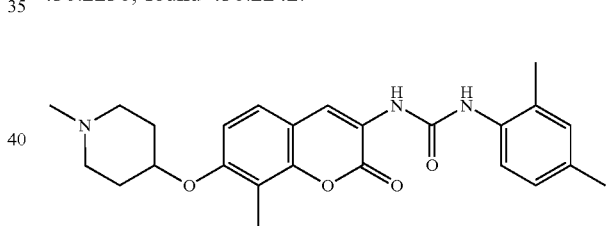

1-(2,4-dimethylphenyl)-3-(8-methyl-7-((1-methylpiperidin-4-yl)oxy)-2-oxo-2H-chromen-3-yl)urea $^1$H NMR (500 MHz, CDCl$_3$) δ 8.79 (s, 1H), 7.54 (d, J=8.0 Hz, 1H), 7.27 (d, J=8.0 Hz, 1H), 7.06 (m, 2H), 6.86 (d, J=8.0 Hz, 1H), 4.51 (m, 1H), 2.76 (m, 2H), 2.56 (m, 2H), 2.43 (s, 3H), 2.39 (s, 3H), 2.33 (s, 3H), 2.30 (s, 3H), 2.14 (m, 2H), 1.97 (m, 2H). $^{13}$C NMR (126 MHz, CDCl$_3$) δ 160.30, 156.24, 153.69, 148.98, 138.91, 135.30, 133.19, 131.67, 127.63, 125.42, 124.40, 122.96, 122.79, 115.09, 114.22, 110.85, 71.88, 52.33, 46.03, 30.32, 21.11, 18.37, 8.71. HRMS (ESI$^+$) m/z [M+H$^+$] calcd for C$_{25}$H$_{30}$N$_3$O$_4$ 436.2236; found 436.2232.

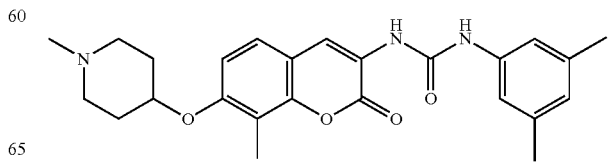

1-(3,5-dimethylphenyl)-3-(8-methyl-7-((1-methylpiperidin-4-yl)oxy)-2-oxo-2H-chromen-3-yl)urea $^1$H NMR (500 MHz, CDCl$_3$) δ 8.40 (s, 1H), 7.24 (d, J=8.0 Hz, 1H), 7.06 (s, 2H), 7.00 (s, 1H), 6.82 (d, J=8.0 Hz, 1H), 6.65 (s, 1H), 4.49 (m, 1H), 2.75 (m, 2H), 2.59 (m, 2H), 2.39 (s, 3H), 2.27 (s, 3H), 2.26 (s, 6H), 2.06 (m, 2H), 1.94 (m, 2H). $^{13}$C NMR (126 MHz, CDCl$_3$+CH$_3$OH) δ 159.77, 155.74, 153.18, 148.68, 138.58, 138.50, 138.45, 125.08, 124.77, 124.48, 122.56, 121.90, 116.98, 116.76, 114.71, 114.07, 110.48, 70.37, 51.45, 45.33, 29.61, 21.17, 8.22. Extra peaks HRMS (ESI$^+$) m/z [M+H$^+$] calcd for C$_{25}$H$_{30}$N$_3$O$_4$ 436.2236; found 436.2235.

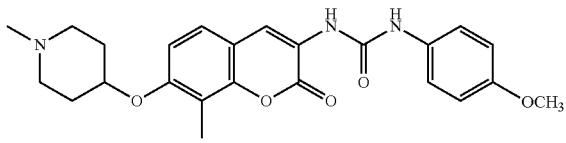 [SMILES: COc1ccc(NC(=O)Nc2cc3ccc(OC4CCN(C)CC4)c(C)c3oc2=O)cc1]

1-(4-methoxyphenyl)-3-(8-methyl-7-((1-methylpiperidin-4-yl)oxy)-2-oxo-2H-chromen-3-yl)urea $^1$H NMR (400 MHz, CDCl$_3$) δ 8.33 (s, 1H), 7.29 (d, J=8.0 Hz, 2H), 7.21 (d, J=8.0 Hz, 1H), 6.80 (d, J=8.0 Hz, 2H), 4.51 (m, 1H), 3.71 (s, 3H), 2.80 (m, 4H), 2.46 (s, 3H), 2.23 (s, 3H), 2.10 (m, 2H), 1.97 (m, 2H). $^{13}$C NMR (126 MHz, DMSO) δ 196.22, 158.19, 155.67, 151.92, 148.23, 143.74, 130.68, 129.69, 125.31, 122.17, 120.94, 116.97, 113.36, 113.14, 110.88, 71.98, 51.80, 45.60, 30.17, 26.33, 8.07. HRMS (ESI$^+$) m/z [M+H$^+$] calcd for C$_{25}$H$_{28}$N$_3$O$_5$ 450.2029; found 450.2031.

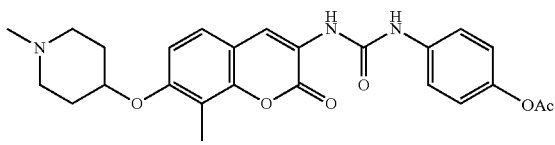 [SMILES: CC(=O)Oc1ccc(NC(=O)Nc2cc3ccc(OC4CCN(C)CC4)c(C)c3oc2=O)cc1]

4-(3-(8-methyl-7-((1-methylpiperidin-4-yl)oxy)-2-oxo-2H-chromen-3-yl)ureido)phenyl acetate $^1$H NMR (500 MHz, CDCl$_3$+CH$_3$OH) δ 8.22 (s, 1H), 7.28 (d, J=9.0 Hz, 2H), 7.09 (d, J=8.6 Hz, 1H), 6.82 (d, J=8.9 Hz, 2H), 6.68 (d, J=8.8 Hz, 1H), 4.34 (m, 1H), 2.58 (m, 2H), 2.42 (m, 2H), 2.23 (s, 3H), 2.11 (s, 3H), 2.09 (s, 3H), 1.89 (m, 2H), 1.78 (m, 2H). $^{13}$C NMR (126 MHz, CDCl$_3$+CH$_3$OH) δ 170.31, 159.62, 155.78, 153.02, 148.69, 145.74, 136.51, 129.21, 125.06, 121.95, 121.77, 119.63, 114.67, 113.90, 110.43, 70.83, 51.52, 45.36, 29.55, 20.71, 8.03. HRMS (ESI$^+$) m/z [M+H$^+$] calcd for C$_{25}$H$_{28}$N$_3$O$_6$ 466.1978; found 466.1981.

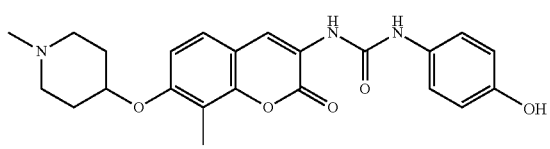 [SMILES: Cc1c(OC2CCN(C)CC2)ccc2cc(NC(=O)Nc3ccc(O)cc3)c(=O)oc12]

1-(4-hydroxyphenyl)-3-(8-methyl-7-((1-methylpiperidin-4-yl)oxy)-2-oxo-2H-chromen-3-yl)urea $^1$H NMR (400 MHz, CDCl$_3$) δ 8.15 (s, 1H), 7.04 (d, J=8.7 Hz, 1H), 7.02 (d, J=8.7 Hz, 2H), 6.67 (d, J=8.8 Hz, 1H), 6.56 (d, J=8.7 Hz, 2H), 4.31 (m, 1H), 2.57 (m, 2H), 2.39 (m, 2H), 2.20 (s, 3H), 2.09 (s, 3H), 1.85 (m, 2H), 1.76 (m, 2H). $^{13}$C NMR (126 MHz, DMSO) δ 158.32, 155.36, 152.73, 152.38, 148.02, 130.63, 125.07, 122.76, 120.04, 119.87, 115.25, 113.41, 113.38, 110.95, 71.93, 51.83, 45.47, 30.09, 8.11. HRMS (ESI$^+$) m/z [M+H$^+$] calcd for C$_{23}$H$_{26}$N$_3$O$_5$ 424.1872; found 424.1871.

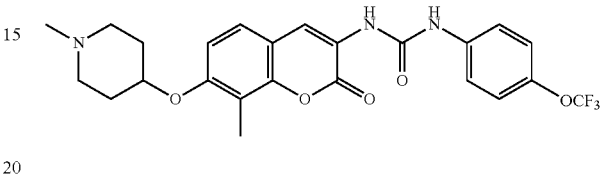

1-(8-methyl-7-((1-methylpiperidin-4-yl)oxy)-2-oxo-2H-chromen-3-yl)-3-(4-(trifluoromethoxy)phenyl)urea $^1$H NMR (500 MHz, DMSO) δ 9.67 (s, 1H, NH), 8.71 (s, 1H, NH), 8.40 (s, 1H), 7.56 (d, J=9.1 Hz, 1H), 7.49 (d, J=8.6 Hz, 1H), 7.31 (d, J=8.4 Hz, 1H), 7.09 (d, J=8.9 Hz, 1H), 4.56 (m, 1H), 2.64 (m, 2H), 2.38 (m, 2H), 2.27 (s, 3H), 2.22 (s, 3H), 1.95 (m, 2H), 1.74 (m, 2H). $^{13}$C NMR (126 MHz, DMSO) δ 158.23, 155.56, 152.16, 148.17, 142.76, 138.49, 125.25, 122.35, 121.84, 121.15, 120.64, 119.11, 113.38, 113.22, 110.89, 71.83, 51.68, 45.39, 30.00, 8.08. HRMS (ESI$^+$) m/z [M+H$^+$] calcd for C$_{24}$H$_{25}$F$_3$N$_3$O$_5$ 492.1746; found 492.1743.

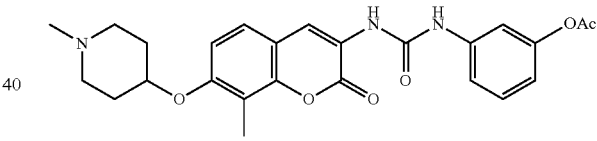

3-(3-(8-methyl-7-((1-methylpiperidin-4-yl)oxy)-2-oxo-2H-chromen-3-yl)ureido)phenyl acetate $^1$H NMR (500 MHz, CDCl$_3$) δ 8.87 (s, 1H), 8.54 (s, 1H), 8.44 (s, 1H), 7.48 (s, 1H), 7.31-7.28 (d, J=8.0 Hz, 1H), 7.22-7.19 (d, J=8.7 Hz, 1H), 7.18-7.12 (t, J=8.0 Hz, 1H), 6.85-6.79 (d, J=8.8 Hz, 1H), 6.71-6.65 (dd, J=8.0, 2.0 Hz, 1H), 4.45 (m, 1H), 2.74 (m, 2H), 2.52 (m, 2H), 2.41 (s, 3H), 2.29 (s, 3H), 2.27 (s, 3H), 2.10 (m, 2H), 1.94 (m, 2H). $^{13}$C NMR (126 MHz, CDCl$_3$) δ 169.61, 160.74, 156.40, 152.31, 151.32, 148.65, 140.60, 129.42, 125.55, 123.02, 122.60, 115.72, 115.65, 114.76, 114.17, 111.54, 111.14, 72.24, 52.28, 46.13, 30.54, 21.32, 8.38. HRMS (ESI$^+$) m/z [M+H$^+$] calcd for C$_{25}$H$_{28}$N$_3$O$_6$ 466.1978; found 466.1975.

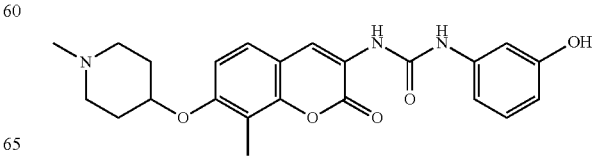

1-(3-hydroxyphenyl)-3-(8-methyl-7-((1-methylpiperidin-4-yl)oxy)-2-oxo-2H-chromen-3-yl)urea $^1$H NMR (500 MHz, CDCl$_3$+CH$_3$OH) δ 8.19 (s, 1H), 7.11 (d, J=8.6 Hz, 1H), 6.93 (t, J=8.1 Hz, 1H), 6.81 (t, J=2.1 Hz, 1H), 6.76-6.63 (m, 2H), 6.33 (dd, J=8.1, 2.3, Hz, 1H), 4.42 (m, 1H), 2.74 (m, 2H), 2.64 (m, 2H), 2.36 (s, 3H), 2.13 (s, 3H), 1.98 (m, 2H), 1.86 (m, 2H). $^{13}$C NMR (126 MHz, CDCl$_3$+CH$_3$OH) δ 159.46, 157.24, 155.47, 153.11, 148.66, 139.62, 129.59, 125.01, 122.53, 121.66, 114.62, 114.03, 110.30, 110.22, 110.04, 105.96, 70.21, 51.18, 44.63, 28.89, 7.94. HRMS (ESI$^-$) m/z [M+H$^-$] C$_{23}$H$_{24}$N$_3$O$_5$ 422.1716; found 422.1715.

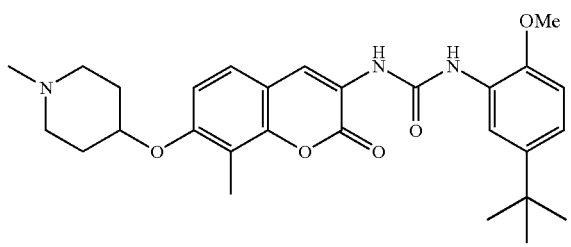 [SMILES: COc1ccc(C(C)(C)C)cc1NC(=O)Nc1cc2ccc(OC3CCN(C)CC3)c(C)c2oc1=O]

1-(5-(tert-butyl)-2-methoxyphenyl)-3-(8-methyl-7-((1-methylpiperidin-4-yl)oxy)-2-oxo-2H-chromen-3-yl)urea $^1$H NMR (400 MHz, CDCl$_3$) δ 8.25 (s, 1H), 7.98 (s, 1H), 7.12 (d, J=8.0 Hz, 1H), 6.84 (d, J=8.0 Hz, 1H), 6.69 (d, J=8.0 Hz, 1H), 6.64 (d, J=8.0 Hz, 1H), 4.39 (m, 1H), 3.68 (s, 3H), 2.69~2.67 (m, 2H), 2.54~2.50 (m, 2H), 2.31 (s, 3H), 2.15 (s, 3H), 1.99~1.94 (m, 2H), 1.85~1.83 (m, 2H), 1.13 (s, 9H). $^{13}$C NMR (126 MHz, CDCl$_3$+CH$_3$OH) δ 159.48, 155.48, 153.36, 148.68, 146.57, 143.68, 127.13, 124.99, 122.65, 121.99, 119.54, 117.44, 114.54, 114.04, 110.26, 109.76, 70.18, 55.47, 51.29, 44.81, 34.13, 31.20, 29.11, 7.93. HRMS (ESI$^+$) m/z [M+H$^+$] calcd for C$_{28}$H$_{36}$N$_3$O$_5$ 494.2655; found 494.2650.

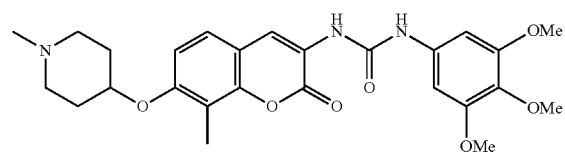 [SMILES: COc1cc(NC(=O)Nc2cc3ccc(OC4CCN(C)CC4)c(C)c3oc2=O)cc(OC)c1OC]

1-(8-methyl-7-((1-methylpiperidin-4-yl)oxy)-2-oxo-2H-chromen-3-yl)-3-(3,4,5-trimethoxyphenyl)urea $^1$H NMR (500 MHz, DMSO) δ 9.46 (s, 1H), 8.62 (s, 1H), 8.42 (s, 1H), 7.52 (d, J=8.6 Hz, 1H), 7.09 (d, J=8.9 Hz, 1H), 6.78 (s, 2H), 4.55 (m, 1H), 3.76 (s, 2H), 3.62 (s, 3H), 2.61 (m, 2H), 2.36 (m, 2H), 2.24 (s, 3H), 2.23 (s, 3H), 1.94 (m, 2H), 1.73 (m, 2H). $^{13}$C NMR (126 MHz, DMSO) δ 158.29, 155.50, 152.90, 152.18, 148.12, 135.36, 132.57, 125.22, 122.44, 120.32, 113.34, 113.31, 110.94, 95.50, 71.99, 60.08, 55.60, 51.81, 45.58, 30.17, 8.10. HRMS (ESI$^+$) m/z [M+H$^+$] calcd for C$_{26}$H$_{32}$N$_3$O$_7$ 498.2240; found 498.2244.

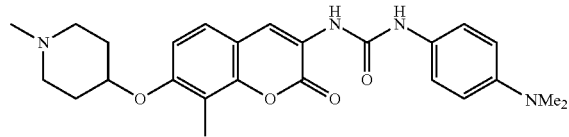 [SMILES: Cc1c(OC2CCN(C)CC2)ccc2cc(NC(=O)Nc3ccc(N(C)C)cc3)c(=O)oc12]

1-(4-(dimethylamino)phenyl)-3-(8-methyl-7-((1-methylpiperidin-4-yl)oxy)-2-oxo-2H-chromen-3-yl)urea $^1$H NMR (500 MHz, CDCl$_3$) δ 8.54 (s, 1H), 7.40 (d, J=9.0 Hz, 2H), 7.28 (d, J=8.6 Hz, 1H), 6.90-6.80 (d, J=8.7 Hz, 1H), 6.73 (d, J=9.0 Hz, 2H). 4.46 (m, 1H), 2.93 (s, 6H), 2.71 (m, 2H), 2.47 (m, 2H), 2.37 (s, 3H), 2.34 (s, 3H), 2.06 (m, 2H), 1.93 (m, 2H). $^{13}$C NMR (126 MHz, CDCl$_3$) δ 160.40, 156.23, 153.57, 148.83, 148.08, 129.46, 125.29, 122.93, 122.21, 120.56, 115.06, 114.28, 113.68, 110.93, 72.10, 52.42, 46.21, 41.27, 30.63, 8.50. HRMS (ESI$^+$) m/z [M+H$^+$] calcd for C$_{25}$H$_{31}$N$_4$O$_4$ 451.2345; found 451.2347.

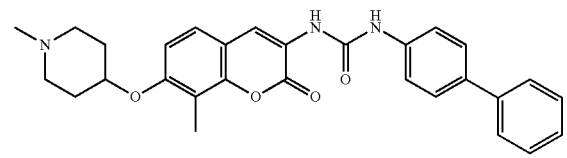 [SMILES: Cc1c(OC2CCN(C)CC2)ccc2cc(NC(=O)Nc3ccc(-c4ccccc4)cc3)c(=O)oc12]

1-([1,1'-biphenyl]-4-yl)-3-(8-methyl-7-((1-methylpiperidin-4-yl)oxy)-2-oxo-2H-chromen-3-yl)urea $^1$H NMR (500 MHz, DMSO) δ 9.59 (s, 1H, NH), 8.73 (s, 1H, NH), 8.43 (s, 1H), 7.67-7.60 (m, 4H), 7.59-7.54 (m, 2H), 7.49 (d, J=8.6 Hz, 1H), 7.45 (t, J=7.7 Hz, 2H), 7.35-7.29 (m, 1H), 7.09 (d, J=8.9 Hz, 1H), 4.57 (M, 1H), 2.65 (m, 2H), 2.40 (m, 2H), 2.28 (s, 3H), 2.23 (s, 3H), 1.96 (m, 2H), 1.76 (m, 2H). $^{13}$C NMR (126 MHz, DMSO) δ 158.27, 155.50, 152.18, 148.14, 139.70, 138.72, 133.86, 128.85, 127.09, 126.09, 125.21, 122.50, 120.43, 118.42, 118.29, 113.39, 113.31, 110.91, 71.84, 51.69, 45.35, 29.94, 8.10. HRMS (ESI$^+$) m/z [M+H$^+$] C$_{29}$H$_{30}$N$_3$O$_4$ 484.2236; found 484.2239.

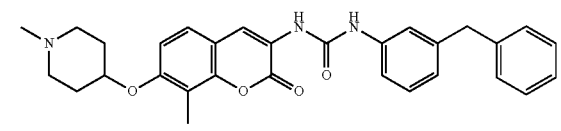 [SMILES: Cc1c(OC2CCN(C)CC2)ccc2cc(NC(=O)Nc3cccc(Cc4ccccc4)c3)c(=O)oc12]

1-(3-benzylphenyl)-3-(8-methyl-7-((1-methylpiperidin-4-yl)oxy)-2-oxo-2H-chromen-3-yl)urea $^1$H NMR (500 MHz, DMSO) δ 9.42 (s, 1H, NH), 8.64 (s, 1H, NH), 8.40 (s, 1H), 7.48 (d, J=8.0 Hz, 1H), 7.32~7.18 (m, 8H), 7.09 (d, J=8.0 Hz, 1H), 6.89 (d, J=8.0 Hz, 1H), 4.56 (m, 1H), 3.92 (s, 2H), 2.64 (m, 2H), 2.51 (m, 2H), 2.37 (s, 3H), 2.26 (s, 3H), 1.97 (m, 2H), 1.74 (m, 2H). $^{13}$C NMR (126 MHz, DMSO) δ 158.31, 155.53, 152.22, 148.17, 142.05, 141.14, 139.37, 128.98, 128.73, 128.45, 126.02, 125.24, 122.72, 122.55, 120.39, 118.20, 115.71, 113.42, 113.36, 110.98, 72.02, 51.78, 45.52, 41.22, 30.10, 8.15. HRMS (ESI⁺) m/z [M+H⁺] calcd for $C_{30}H_{32}N_3O_4$ 498.2393; found 498.2390.

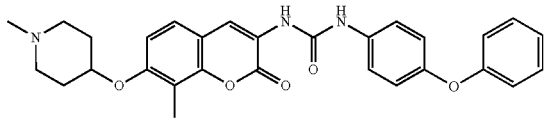 [SMILES: Cc1c(OC2CCN(C)CC2)ccc2cc(NC(=O)Nc3ccc(Oc4ccccc4)cc3)c(=O)oc12]

1-(8-methyl-7-((1-methylpiperidin-4-yl)oxy)-2-oxo-2H-chromen-3-yl)-3-(4-phenoxyphenyl)urea ¹H NMR (500 MHz, CDCl₃+CH₃OH) δ 8.27 (s, 1H), 7.29 (d, J=8.0 Hz, 1H), 7.18~7.14 (m, 3H), 6.92 (t, J=8.0 Hz, 1H), 6.84~6.81 (m, 4H), 6.73 (d, J=8.0 Hz, 1H), 4.37 (m, 1H), 2.57 (m, 2H), 2.38 (m, 2H), 2.22 (s, 3H), 2.16 (s, 3H), 1.90 (m, 2H), 1.80 (m, 2H). ¹³C NMR (126 MHz, CDCl₃+CH₃OH) δ 159.70, 157.77, 155.89, 153.31, 152.31, 148.71, 134.31, 129.58, 125.03, 122.76, 122.43, 122.00, 120.76, 119.76, 117.97, 114.74, 113.89, 110.52, 71.20, 51.66, 45.58, 29.79, 8.04. HRMS (ESI⁺) m/z [M+H⁺] calcd for $C_{29}H_{30}N_3O_5$ 500.2185; found 500.2187.

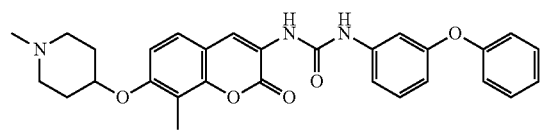 [SMILES: Cc1c(OC2CCN(C)CC2)ccc2cc(NC(=O)Nc3cccc(Oc4ccccc4)c3)c(=O)oc12]

1-(8-methyl-7-((1-methylpiperidin-4-yl)oxy)-2-oxo-2H-chromen-3-yl)-3-(3-phenoxyphenyl)urea ¹H NMR (500 MHz, DMSO) δ 9.57 (s, 1H, NH), 8.65 (s, 1H, NH), 8.36 (s, 1H), δ 7.50-7.46 (d, J=8.7 Hz, 1H), 7.44-7.39 (m, 2H), 7.33-7.27 (m, 2H), 7.19-7.14 (t, J=7.4 Hz, 1H), 7.10-7.02 (m, 4H), 6.68-6.63 (dd, J=8.1, 1.8 Hz, 1H), 4.56 (m, 1H), 2.64 (m, 2H), 2.37 (m, 2H), 2.26 (s, 3H), 2.22 (s, 3H), 1.94 (m, 2H), 1.74 (m, 2H). ¹³C NMR (126 MHz, DMSO) δ 158.24, 157.23, 156.40, 155.54, 152.06, 148.15, 140.79, 130.24, 130.03, 125.26, 123.53, 122.33, 120.55, 118.81, 113.36, 113.24, 112.78, 112.19, 110.92, 107.73, 71.74, 51.74, 45.33, 30.04, 8.09. HRMS (ESI⁺) m/z [M+H⁺] calcd for $C_{29}H_{30}N_3O_5$ 500.2185; found 500.2181.

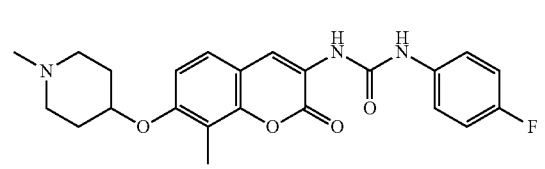 [SMILES: Cc1c(OC2CCN(C)CC2)ccc2cc(NC(=O)Nc3ccc(F)cc3)c(=O)oc12]

1-(4-fluorophenyl)-3-(8-methyl-7-((1-methylpiperidin-4-yl)oxy)-2-oxo-2H-chromen-3-yl)urea ¹H NMR (500 MHz, CDCl₃) δ 8.25 (s, 1H), 7.27 (m, 2H), 7.11 (d, J=8.0 Hz, 1H), 6.80 (m, 2H), 6.71 (d, J=8.0 Hz, 1H), 4.36 (m, 1H), 2.61 (m, 2H), 2.43 (m, 2H), 2.27 (s, 3H), 2.13 (s, 3H), 1.96~1.92 (m, 2H), 1.83~1.82 (m, 2H). ¹³C NMR (126 MHz, CDCl₃+CH₃OH) δ 159.80, 159.42, 157.51, 155.87, 152.90, 148.57, 134.71, 125.08, 122.33, 122.02, 120.18, 115.30, 115.12, 114.54, 113.85, 110.45, 71.23, 51.68, 45.47, 30.01, 8.05. HRMS (ESI+) m/z [M+H⁺] calcd for $C_{23}H_{25}FN_3O_4$ 426.1829; found 426.1817.

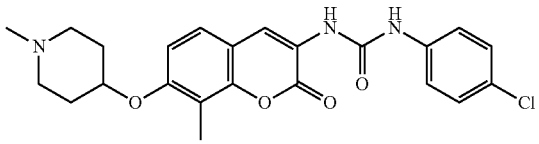 [SMILES: Cc1c(OC2CCN(C)CC2)ccc2cc(NC(=O)Nc3ccc(Cl)cc3)c(=O)oc12]

1-(4-chlorophenyl)-3-(8-methyl-7-((1-methylpiperidin-4-yl)oxy)-2-oxo-2H-chromen-3-yl)urea ¹H NMR (500 MHz, CDCl₃) δ 8.24 (s, 1H), 7.23 (d, J=8.7 Hz, 2H), 7.07 (d, J=8.6 Hz, 1H), 7.00 (d, J=8.7 Hz, 2H), 6.67 (d, J=8.7 Hz, 1H), 4.37 (m, 1H), 2.65 (m, 2H), 2.48 (m, 2H), 2.30 (s, 3H), 2.11 (s, 3H), 1.96 (m, 2H), 1.84 (m, 2H). ¹³C NMR (126 MHz, CDCl₃+CH₃OH) δ 159.84, 155.92, 152.48, 148.51, 137.45, 128.55, 127.24, 125.16, 122.17, 119.39, 116.48, 114.43, 113.78, 110.41, 70.94, 51.70, 45.45, 29.73, 7.97. HRMS (ESI⁺) m/z [M+H⁺] calcd for $C_{23}H_{25}ClN_3O_4$ 442.1534; found 442.1535.

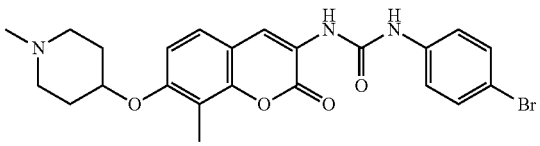 [SMILES: Cc1c(OC2CCN(C)CC2)ccc2cc(NC(=O)Nc3ccc(Br)cc3)c(=O)oc12]

1-(4-bromophenyl)-3-(8-methyl-7-((1-methylpiperidin-4-yl)oxy)-2-oxo-2H-chromen-3-yl)urea ¹H NMR (500 MHz, CDCl₃) δ 8.21 (s, 1H), 7.21 (d, J=8.0 Hz, 2H), 7.19~7.16 (m, 4H), 7.12 (d, J=8.0 Hz, 1H), 6.72 (d, J=8.0 Hz, 2H), 4.41 (m, 1H), 2.70 (m, 2H), 2.69 (m, 2H), 2.33 (s, 3H), 2.12 (s, 3H), 1.96 (m, 2H), 1.84 (m, 2H). ¹³C NMR (126 MHz, CDCl₃+CH₃OH) δ 159.43, 155.61, 152.92, 148.69, 137.86, 131.61, 127.55, 125.00, 122.35, 121.77, 120.29, 115.03, 113.92, 110.30, 70.22, 51.18, 44.75, 29.06, 7.92. HRMS (ESI+) m/z [M+H⁺] calcd for $C_{23}H_{25}BrN_3O_4$ 486.1028; found 486.1025.

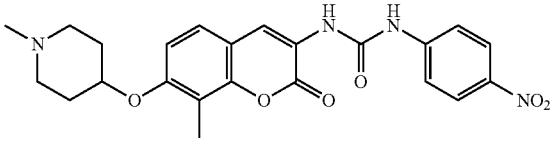 [SMILES: Cc1c(OC2CCN(C)CC2)ccc2cc(NC(=O)Nc3ccc([N+](=O)[O-])cc3)c(=O)oc12]

1-(8-methyl-7-((1-methylpiperidin-4-yl)oxy)-2-oxo-2H-chromen-3-yl)-3-(4-nitrophenyl)urea ¹H NMR (500 MHz, CDCl₃) δ 8.17 (s, 1H), 7.92 (d, J=9.1 Hz, 2H), 7.29 (d, J=9.0 Hz, 2H), 7.11 (d, J=8.5 Hz, 1H), 6.70 (d, J=8.7 Hz, 0H), 3.90 (m, 1H), 2.6 (m, 2H), 2.4 (m, 2H) 2.20 (s, 3H), 2.05 (s, 3H), 1.88 (m, 2H), 1.76 (m, 2H). ¹³C NMR (126 MHz, CDCl₃+CH₃OH) δ 159.41, 152.42, 149.17, 148.95, 145.49, 142.14, 127.60, 125.28, 125.00, 122.64, 117.57, 114.69, 113.83, 110.39, 70.64, 51.51, 45.18, 29.58, 8.07. HRMS (ESI+) m/z [M+H$^+$] calcd for C$_{24}$H$_{25}$N$_4$O$_4$ 433.1876; found 433.1879.

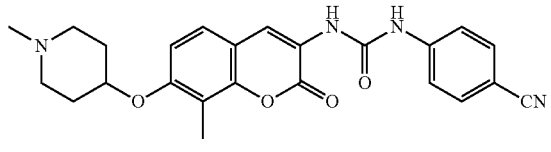 [SMILES: Cc1c(OC2CCN(C)CC2)ccc2cc(NC(=O)Nc3ccc(C#N)cc3)c(=O)oc12]

1-(4-cyanophenyl)-3-(8-methyl-7-((1-methylpiperidin-4-yl)oxy)-2-oxo-2H-chromen-3-yl)urea $^1$H NMR (500 MHz, DMSO) δ 9.95 (s, 1H, NH), 8.82 (s, 1H, NH), 8.39 (s, 1H), 7.75 (d, J=8.8 Hz, 2H), 7.62 (d, J=8.8 Hz, 2H), 7.49 (d, J=8.6 Hz, 1H), 7.09 (d, J=8.9 Hz, 1H), 4.56 (s, 1H), 2.63 (m, 2H), 2.37 (m, 2H), 2.26 (s, 3H), 2.22 (s, 3H), 1.96 (m, 2H), 1.74 (m, 2H). $^{13}$C NMR (126 MHz, DMSO) δ 158.21, 155.76, 151.91, 148.33, 143.64, 133.42, 125.42, 122.11, 121.20, 119.22, 117.89, 113.43, 113.14, 110.93, 103.70, 71.89, 51.77, 45.49, 30.08, 8.13. HRMS (ESI+) m/z [M+H$^+$] calcd for C$_{24}$H$_{25}$N$_4$O$_4$ 433.1876; found 433.1878.

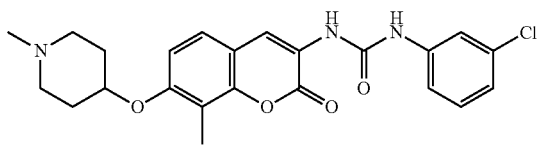 [SMILES: Cc1c(OC2CCN(C)CC2)ccc2cc(NC(=O)Nc3cccc(Cl)c3)c(=O)oc12]

1-(3-chlorophenyl)-3-(8-methyl-7-((1-methylpiperidin-4-yl)oxy)-2-oxo-2H-chromen-3-yl)urea $^1$H NMR (500 MHz, CDCl$_3$+CH$_3$OH) δ 8.12 (s, 1H), 7.19 (s, 1H), 6.94 (d, J=8.0 Hz, 1H), 6.91 (d, J=8.0 Hz, 1H), 6.79 (m, 1H), 6.63 (d, J=8.0 Hz, 1H), 6.58 (d, J=8.0 Hz, 1H), 4.38 (m, 1H), 2.75 (m, 2H), 2.59 (m, 2H), 2.42 (s, 3H), 2.03 (m, 2H), 2.00 (s, 3H), 1.89 (m, 2H). $^{13}$C NMR (126 MHz, CDCl$_3$+CH$_3$OH) δ 159.56, 155.61, 151.53, 147.94, 139.70, 133.76, 128.91, 124.87, 122.01, 121.57, 121.51, 116.92, 115.38, 113.91, 113.33, 110.03, 70.40, 51.45, 44.98, 29.43, 7.70. HRMS (ESI+) m/z [M+H$^+$] calcd for C$_{23}$H$_{25}$ClN$_3$O$_4$ 442.1534; found 442.1538.

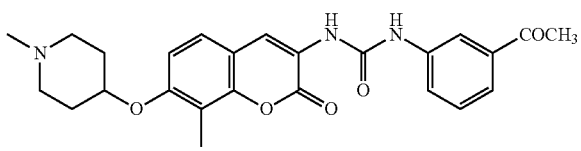 [SMILES: CC(=O)c1cccc(NC(=O)Nc2cc3ccc(OC4CCN(C)CC4)c(C)c3oc2=O)c1]

1-(3-acetylphenyl)-3-(8-methyl-7-((1-methylpiperidin-4-yl)oxy)-2-oxo-2H-chromen-3-yl)urea $^1$H NMR (500 MHz, DMSO) δ 9.69 (s, 1H, NH), 8.72 (s, 1H, NH), 8.44 (s, 1H), 8.14 (s, 1H), 7.61 (t, J=8.0 Hz, 2H), 7.51 (d, J=8.6 Hz, 1H), 7.47 (t, J=7.9 Hz, 1H), 7.10 (d, J=8.9 Hz, 1H), 4.57 (m, 1H), 2.64 (m, 2H), 2.62 (s, 3H), 2.39 (m, 2H), 2.27 (s, 3H), 2.23 (s, 3H), 1.97 (m, 2H), 1.75 (m, 2H). $^{13}$C NMR (126 MHz, DMSO) δ 211.94, 197.62, 158.26, 155.56, 152.23, 148.18, 139.62, 137.43, 129.29, 125.28, 122.44, 122.36, 122.28, 120.68, 116.95, 113.37, 113.27, 110.93, 72.12, 51.69, 45.38, 30.01, 26.74, 8.10. HRMS (ESI+) m/z [M+H$^+$] calcd for C$_{25}$H$_{28}$N$_3$O$_5$ 450.2029; found 450.2033.

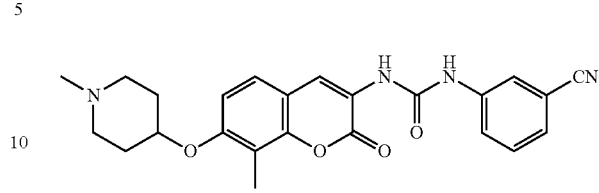

1-(3-cyanophenyl)-3-(8-methyl-7-((1-methylpiperidin-4-yl)oxy)-2-oxo-2H-chromen-3-yl)urea $^1$H NMR (500 MHz, DMSO) δ 9.79 (s, 1H), 8.78 (s, 1H), 8.40 (s, 1H), 8.01 (s, 1H), 7.68-7.55 (m, 1H), 7.55-7.38 (m, 3H), 7.18-6.98 (d, J=8.8 Hz, 1H), 4.58-4.33 (s, 1H), 2.69-2.50 (m, 2H), 2.38-2.27 (m, 2H), 2.23 (s, 3H), 2.22 (s, 3H), 2.00-1.81 (m, 2H), 1.80-1.60 (m, 2H). $^{13}$C NMR (126 MHz, DMSO) δ 158.19, 155.69, 152.15, 148.24, 140.06, 130.29, 125.66, 125.31, 122.61, 122.14, 121.01, 120.44, 118.74, 113.36, 113.12, 111.69, 110.90, 71.98, 51.79, 45.60, 30.17, 8.08. HRMS (ESI+) m/z [M+H$^+$] calcd for C$_{24}$H$_{25}$N$_4$O$_4$ 433.1876; found 433.1879.

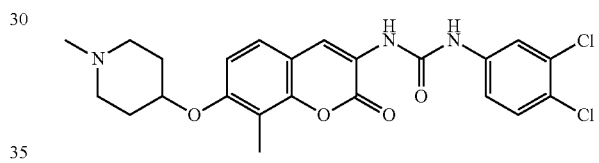

1-(3,4-dichlorophenyl)-3-(8-methyl-7-((1-methylpiperidin-4-yl)oxy)-2-oxo-2H-chromen-3-yl)urea $^1$H NMR (500 MHz, MeOD) δ 8.17 (s, 1H), 7.52 (s, 1H), 7.10~7.08 (m, 2H), 7.03 (m, 1H), 6.68 (d, J=8.7 Hz, 1H), 4.34 (m, 1H), 2.60 (m, 2H), 2.43 (m, 2H), 2.23 (s, 3H), 2.08 (s, 3H), 1.88 (m, 2H), 1.76 (m, 2H). $^{13}$C NMR (126 MHz, CDCl$_3$+CH$_3$OH) δ 159.37, 155.83, 152.63, 148.70, 138.46, 132.28, 130.11, 127.49, 125.36, 125.03, 122.11, 119.95, 117.81, 114.58, 113.68, 110.32, 70.52, 51.41, 45.01, 29.45, 7.80. HRMS (ESI+) m/z [M+H$^+$] calcd for C$_{23}$H$_{24}$Cl$_2$N$_3$O$_4$ 476.1144; found 476.1148.

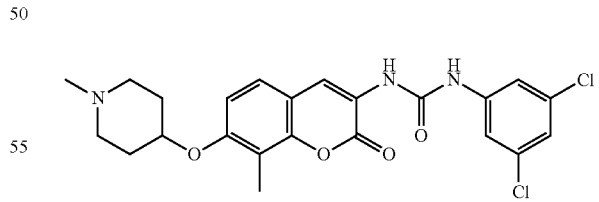

1-(3,5-dichlorophenyl)-3-(8-methyl-7-((1-methylpiperidin-4-yl)oxy)-2-oxo-2H-chromen-3-yl)urea $^1$H NMR (500 MHz, DMSO) δ 9.85 (s, 1H, NH), 8.76 (s, 1H, NH), 8.38 (s, 1H), 7.49 (s, 1H), 7.48 (s, 1H), 7.46 (d, J=8.0 Hz, 1H), 7.18 (s, 1H), 7.08 (d, J=8.0 Hz, 1H), 4.55 (m, 1H), 2.63 (m, 2H), 2.37 (m, 2H), 2.26 (s, 3H), 2.20 (s, 3H), 1.97~1.93 (m, 2H), 1.74~1.72 (2H). $^{13}$C NMR (126 MHz, DMSO) δ 158.13, 155.69, 151.93, 148.25, 141.64, 134.15, 125.33, 121.99, 121.20, 121.18, 115.98, 113.34, 113.08, 110.83, 71.71, 51.70, 45.41, 30.01, 8.05. (ESI+) m/z [M+H⁺] calcd for C₂₃H₂₄Cl₂N₃O₄ 476.1144; found 476.1141.

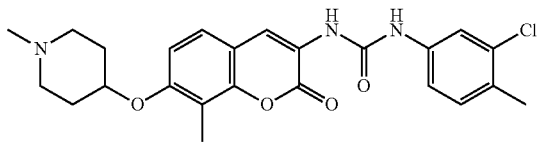

1-(3-chloro-4-methylphenyl)-3-(8-methyl-7-((1-methylpiperidin-4-yl)oxy)-2-oxo-2H-chromen-3-yl)urea ¹H NMR (500 MHz, DMSO) δ 9.56 (s, 1H), 8.69 (s, 1H), 8.40 (s, 1H), 7.73 (d, J=2.2 Hz, 1H), 7.47 (d, J=8.6 Hz, 1H), 7.26 (d, J=8.6 Hz, 1H), 7.13 (dd, J=8.2, 2.2 Hz, 1H), 7.08 (d, J=8.8 Hz, 1H), 4.53 (s, 1H), 2.54 (m, 2H), 2.27 (s, 3H), 2.25 (m, 2H), 2.22 (s, 3H), 2.18 (s, 3H), 1.92 (m, 2H), 1.71 (m, 2H). ¹³C NMR (126 MHz, DMSO) δ 158.24, 155.64, 152.13, 148.17, 138.34, 133.18, 131.25, 128.60, 125.22, 122.30, 120.68, 117.83, 116.67, 113.35, 113.18, 110.94, 72.31, 51.95, 45.90, 30.42, 18.81, 8.08. HRMS (ESI⁺) m/z [M+H⁺] calcd for C₂₄H₂₇N₃O₄ 456.1690; found 456.1693.

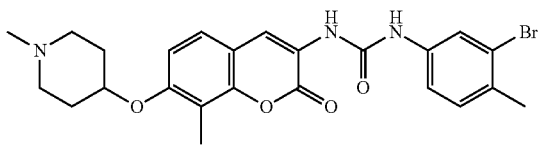

1-(3-bromo-4-methylphenyl)-3-(8-methyl-7-((1-methylpiperidin-4-yl)oxy)-2-oxo-2H-chromen-3-yl)urea ¹H NMR (500 MHz, DMSO) δ 9.54 (s, 1H, NH), 8.69 (s, 1H, NH), 8.41 (s, 1H), 7.93 (d, J=2.2 Hz, 1H), 7.49 (d, J=8.6 Hz, 1H), 7.27 (d, J=8.3 Hz, 1H), 7.17 (dd, J=8.2, 2.2 Hz, 1H), 7.10 (d, J=8.8 Hz, 1H), 4.56 (m, 1H), 2.64 (m, 2H), 2.37 (m, 2H), 2.29 (s, 3H), 2.23 (s, 3H), 2.15 (s, 3H), 1.96 (m, 2H), 1.74 (m, 2H). ¹³C NMR (126 MHz, DMSO) δ 156.53, 153.87, 150.41, 146.47, 136.65, 129.35, 128.75, 123.54, 122.28, 120.62, 119.26, 118.98, 115.55, 111.67, 111.54, 109.23, 70.27, 50.07, 43.90, 28.40, 19.87, 6.39. HRMS (ESI⁺) m/z [M+H⁺] calcd for C₂₄H₂₇BrN₃O₄ 500.1185; found 500.1187.

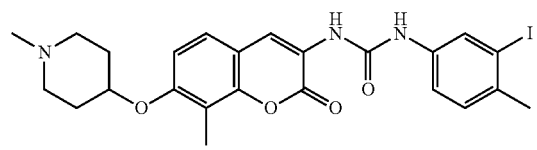

1-(3-iodo-4-methylphenyl)-3-(8-methyl-7-((1-methylpiperidin-4-yl)oxy)-2-oxo-2H-chromen-3-yl)urea ¹H NMR (500 MHz, DMSO) δ 9.51 (s, 1H, NH), 8.65 (s, 1H, NH), 8.38 (s, 1H), 8.15 (s, 1H), 7.45 (d, J=8.6 Hz, 1H), 7.24-7.16 (m, 2H), 7.06 (d, J=8.9 Hz, 1H), 4.53 (m, 1H), 2.63 (m, 2H), 2.30 (m, 2H), 2.26 (s, 3H), 2.20 (s, 3H), 1.97~1.93 (m, 2H), 1.74~1.72 (m, 2H). ¹³C NMR (126 MHz, DMSO) δ 158.19, 155.50, 152.06, 148.12, 138.07, 134.04, 129.69, 127.34, 125.17, 122.31, 120.57, 117.91, 113.33, 113.24, 110.83, 101.10, 71.79, 51.68, 45.38, 29.99, 26.59, 8.07. HRMS (ESI⁺) m/z [M+H⁺] calcd for C₂₄H₂₇IN₃O₄ 548.1046; 548.1049.

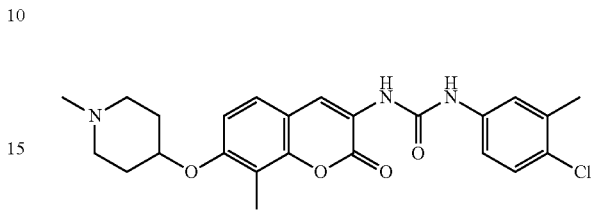

1-(4-chloro-3-methylphenyl)-3-(8-methyl-7-((1-methylpiperidin-4-yl)oxy)-2-oxo-2H-chromen-3-yl)urea ¹H NMR (500 MHz, DMSO) δ 9.49 (s, 1H, NH), 8.68 (s, 1H, NH), 8.38 (s, 1H), 7.58~7.36 (m, 2H), 7.39~7.13 (m, 2H), 7.19-6.92 (d, J=8.8 Hz, 1H), 4.56 (m, 1H), 2.64 (m, 2H), 2.40 (m, 2H), 2.27 (s, 3H), 2.22 (s, 3H), 1.96~1.94 (m, 2H), 1.74~1.73 (m, 2H). ¹³C NMR (126 MHz, DMSO) δ 158.27, 155.54, 152.16, 148.15, 138.04, 135.77, 129.11, 126.08, 125.23, 122.34, 120.67, 120.33, 117.14, 113.43, 113.22, 110.95, 71.77, 51.62, 45.31, 29.88, 19.81, 8.07. HRMS (ESI) m/z [M+H⁺] calcd for C₂₄H₂₇N₃O₄ 456.1690; found 456.1691.

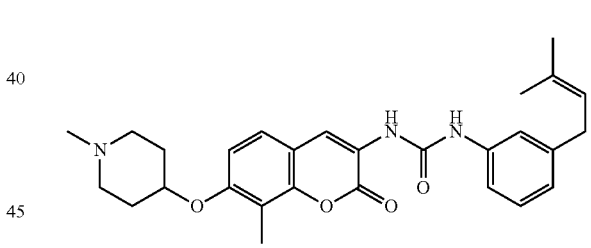

1-(8-methyl-7-((1-methylpiperidin-4-yl)oxy)-2-oxo-2H-chromen-3-yl)-3-(3-(3-methylbut-2-en-1-yl)phenyl)urea ¹H NMR (500 MHz, CDCl₃) δ 8.67 (s, 1H, NH), 8.54 (s, 1H), 8.43 (s, 1H, NH), 7.47 (s, 1H), 7.32 (d, J=8.1 Hz, 1H), 7.27 (d, J=8.1 Hz, 1H), 7.19 (t, J=7.8 Hz, 2H), 6.86 (d, J=7.5 Hz, 1H), 6.80 (d, J=8.8 Hz, 1H). 5.33 (m, 1H), 4.59 (m, 1H), 3.32 (d, J=5.2 Hz, 2H), 3.31 (m, 4H), 2.63 (s, 3H), 2.31 (m, 2H), 2.29 (s, 3H), 2.08 (m, 2H), 1.73 (s, 3H), 1.71 (s, 3H). ¹³C NMR (126 MHz, CDCl₃) δ 169.67, 160.52, 153.09, 150.47, 148.77, 139.82, 130.32, 129.43, 129.00, 127.25, 125.35, 122.93, 122.87, 122.61, 120.34, 115.10, 114.30, 112.18, 71.26, 56.22, 52.01, 45.78, 29.89, 21.44 (2C), 8.24. HRMS (ESI⁺) m/z [M+H⁺] calcd for C₂₈H₃₄N₃O₄ 476.2549; found 476.2552.

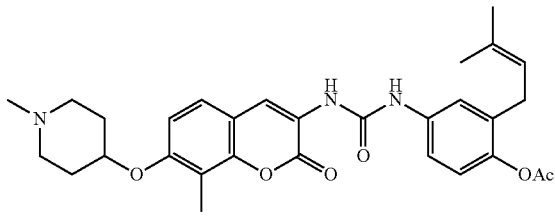 [SMILES: CC(=O)Oc1ccc(NC(=O)Nc2cc3ccc(OC4CCN(C)CC4)c(C)c3oc2=O)cc1CC=C(C)C]

4-(3-(8-methyl-7-((1-methylpiperidin-4-yl)oxy)-2-oxo-2H-chromen-3-yl)ureido)-2-(3-methylbut-2-en-1-yl)phenyl acetate $^1$H NMR (500 MHz, CDCl$_3$) δ 8.60 (s, 1H, NH), 8.59 (s, 1H, NH), 8.42 (s, 1H, NH) 7.33 (dd, J=8.7, 2.6 Hz, 1H), 7.30 (d, J=8.6 Hz, 1H), 6.95 (d, J=8.6 Hz, 1H), 6.88 (d, J=8.8 Hz, 1H), 5.33-4.96 (m, 1H), 4.51 (m, 1H), 3.23 (d, J=6.9 Hz, 2H), 2.76 (m, 2H), 2.56 (m, 2H), 2.43 (s, 3H), 2.34 (s, 3H), 2.32 (s, 3H), 2.13 (m, 2H), 1.97 (m, 2H), 1.96, 1.73 (s, 3H), 1.72 (s, 3H). $^{13}$C NMR (126 MHz, CDCl$_3$) δ 170.27, 160.64, 156.31, 152.78, 148.81, 144.41, 137.05, 134.43, 132.89, 125.49, 122.86, 122.83, 122.72, 122.09, 120.75, 117.94, 114.94, 114.26, 111.02, 71.66, 52.15, 46.03, 29.79, 25.91, 21.13, 18.17, 8.59. HRMS (ESI$^+$) m/z [M+H$^+$] calcd for C$_{30}$H$_{36}$N$_3$O$_6$ 534.2604; found 534.2601.

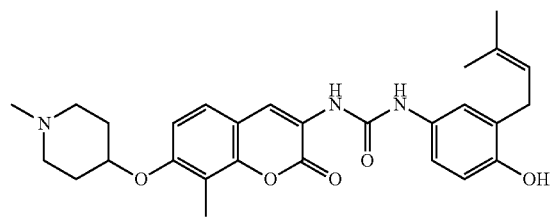 [SMILES: CC(C)=CCc1cc(NC(=O)Nc2cc3ccc(OC4CCN(C)CC4)c(C)c3oc2=O)ccc1O]

1-(4-hydroxy-3-(3-methylbut-2-en-1-yl)phenyl)-3-(8-methyl-7-((1-methylpiperidin-4-yl)oxy)-2-oxo-2H-chromen-3-yl)urea $^1$H NMR (500 MHz, CDCl$_3$+CH$_3$OH) δ 8.30 (s, 1H), δ 7.19 (d, J=8.6 Hz, 1H), 7.04 (dd, J=8.5, 2.5 Hz, 1H), 6.97 (d, J=2.5 Hz, 1H), 6.77 (d, J=8.7 Hz, 1H), 6.66 (d, J=8.5 Hz, 1H), 4.45 (m, 1H), 3.22 (d, J=7.2 Hz, 2H), 2.70 (m, 2H), 2.54 (m, 2H), 2.35 (s, 3H), 2.22 (s, 3H), 2.01 (m, 2H), 1.91 (m, 2H), 1.64 (s, 3H), 1.62 (s, 3H). $^{13}$C NMR (126 MHz, CDCl$_3$+CH$_3$OH) δ 159.76, 155.71, 153.76, 148.74, 144.17, 136.04, 132.99, 128.72, 128.32, 125.47, 125.09, 122.70, 122.20, 121.71, 115.24, 114.82, 114.15, 110.49, 70.78, 51.75, 45.36, 29.63, 28.52, 25.66, 17.68, 8.22. HRMS (ESI) m/z [M+H$^-$] calcd for C$_{28}$H$_{32}$N$_3$O$_5$ 490.2342; found 490.2345.

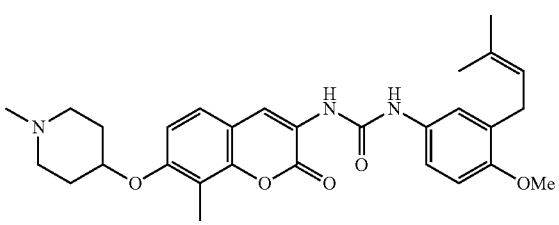 [SMILES: COc1ccc(NC(=O)Nc2cc3ccc(OC4CCN(C)CC4)c(C)c3oc2=O)cc1CC=C(C)C]

1-(4-methoxy-3-(3-methylbut-2-en-1-yl)phenyl)-3-(8-methyl-7-((1-methylpiperidin-4-yl)oxy)-2-oxo-2H-chromen-3-yl)urea $^1$H NMR (500 MHz, CDCl$_3$) δ 8.57 (s, 1H), 7.35 (m, 2H), 7.27 (d, J=8.0 Hz, 1H), 6.86 (d, J=8.0 hz, 1H), 6.80 (d, J=8.0 Hz, 1H), 5.29 (m, 1H), 4.48 (m, 1H), 3.31 (d, J=5.0 Hz, 1H), 2.74 (m, 2H), 2.52 (m, 2H), 2.41 (s, 3H), 2.34 (s, 3H), 2.11 (m, 2H), 1.96 (m, 2H), 1.72 (s, 3H), 1.71 (s, 3H). $^{13}$C NMR (126 MHz, CDCl$_3$) δ 160.49, 156.23, 154.09, 153.33, 148.81, 132.51, 131.43, 131.25, 125.36, 122.92, 122.78, 122.51, 122.30, 119.18, 115.00, 114.28, 111.04, 110.94, 72.08, 56.06, 52.12, 46.12, 30.52, 29.09, 26.01, 18.14, 8.70. HRMS (ESI$^-$) m/z [M+H$^-$] calcd for C$_{29}$H$_{36}$N$_3$O$_5$ 506.2655; found 506.2652.

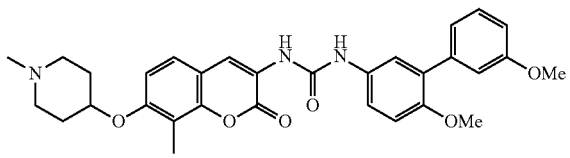 [SMILES: COc1cccc(-c2cc(NC(=O)Nc3cc4ccc(OC5CCN(C)CC5)c(C)c4oc3=O)ccc2OC)c1]

1-(3',6-dimethoxy-[1,1'-biphenyl]-3-yl)-3-(8-methyl-7-((1-methylpiperidin-4-yl)oxy)-2-oxo-2H-chromen-3-yl)urea $^1$H NMR (500 MHz, CDCl$_3$+CH$_3$OH) δ 8.26 (s, 1H), 7.33~7.29 (m, 2H), 7.19~7.14 (m, 2H), 6.97~6.95 (m, 2H), 6.82 (d, J=8.8 Hz, 1H), 6.74 (d, J=8.1 Hz, 2H), 4.39 (m, 1H), 3.70 (s, 3H), 3.65 (s, 3H), 2.60 (m, 2H), 2.40 (m, 2H), 2.25 (s, 3H), 2.17 (s, 3H), 1.91 (m, 2H), 1.81 (m, 2H). $^{13}$C NMR (126 MHz, CDCl$_3$+CH$_3$OH) δ 159.62, 159.02, 155.78, 153.52, 152.56, 148.66, 139.45, 131.64, 130.85, 128.82, 124.95, 122.57, 122.49, 121.91, 121.75, 120.06, 115.08, 114.68, 113.90, 112.45, 111.94, 110.44, 55.79, 55.04, 51.66, 45.41, 29.78, 7.97. HRMS (ESI$^+$) m/z [M+H$^+$] calcd for C$_{31}$H$_{34}$N$_3$O$_6$ 544.2448; found 544.2443.

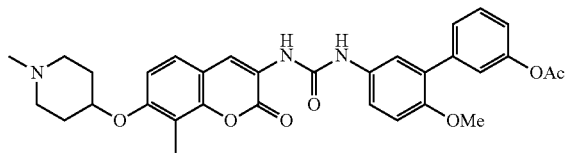 [SMILES: COc1ccc(NC(=O)Nc2cc3ccc(OC4CCN(C)CC4)c(C)c3oc2=O)cc1-c1cccc(OC(C)=O)c1]

2'-methoxy-5'-(3-(8-methyl-7-((1-methylpiperidin-4-yl)oxy)-2-oxo-2H-chromen-3-yl)ureido)-[1,1'-biphenyl]-3-yl acetate $^1$H NMR (500 MHz, CDCl$_3$+CH$_3$OH) δ 8.33 (s, 1H), 7.39-7.34 (dd, J=8.8, 2.7 Hz, 1H), 7.33-7.29 (m, 2H), 7.27 (d, J=2.5 Hz, 1H), 7.21-7.17 (m, 2H), 6.98-6.93 (m, 1H), 6.88-6.84 (d, J=8.9 Hz, 1H), 6.79-6.74 (d, J=8.8 Hz, 1H), 4.42 (m, 1H), 2.64 (m, 2H), 2.45 (m, 2H), 2.29 (s, 3H), 2.22 (m, 3H), 1.96 (m, 2H), 1.86 (m, 2H). $^{13}$C NMR (126 MHz, CDCl$_3$+CH$_3$OH) δ 170.14, 159.79, 155.88, 153.45, 152.61, 150.23, 148.77, 139.69, 131.87, 129.93, 128.90, 127.09, 125.09, 122.64, 122.60, 122.48, 121.90, 120.43, 120.12, 114.85, 114.04, 112.08, 110.56, 70.94, 55.96, 51.77, 45.63, 29.86, 21.09, 8.20. HRMS (ESI$^+$) m/z [M+H$^+$] calcd for C$_{32}$H$_{34}$N$_3$O$_7$ 572.2397; found 572.2394.

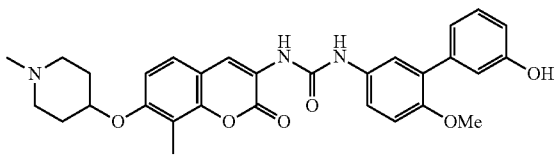 [SMILES: COc1ccc(NC(=O)Nc2cc3ccc(OC4CCN(C)CC4)c(C)c3oc2=O)cc1-c1cccc(O)c1]

1-(3'-hydroxy-6-methoxy-[1,1'-biphenyl]-3-yl)-3-(8-methyl-7-((1-methylpiperidin-4-yl)oxy)-2-oxo-2H-chromen-3-yl)urea $^1$H NMR (400 MHz, CDCl$_3$) δ 8.29 (s, 1H), 7.32 (dd, J=8.8, 2.7 Hz, 1H), 7.22 (d, J=2.7 Hz, 1H), 7.17 (d, J=8.7 Hz, 1H), 7.11 (t, J=7.9 Hz, 1H), 6.91 (d, J=7.7 Hz, 1H), 6.89 (t, J=1.9 Hz, 1H), 6.83 (d, J=8.9 Hz, 1H), 6.74 (d, J=8.8 Hz, 1H), 6.69 (dd, J=8.1, 1.7 Hz, 1H), 4.42 (m, 1H), 3.66 (s, 3H), 2.66 (m, 2H), 2.49 (m, 2H), 2.31 (s, 3H), 2.19 (s, 3H), 1.97 (m, 2H), 1.86 (m, 2H). $^{13}$C NMR (126 MHz, CDCl$_3$) δ 159.89, 156.48, 155.91, 153.51, 152.85, 148.81, 139.48, 131.66, 131.27, 129.05, 125.15, 122.83, 122.65, 122.03, 121.15, 120.17, 116.43, 114.96, 114.21, 114.11, 112.19, 110.66, 70.88, 56.07, 51.78, 45.64, 29.80, 8.27. HRMS (ESI$^+$) m/z [M+H$^+$] calcd for C$_{30}$H$_{32}$N$_3$O$_6$ 530.2291; found 530.2288.

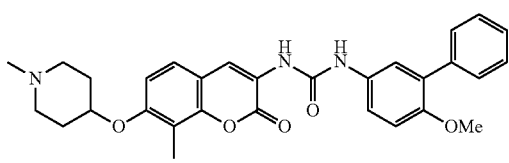 [SMILES: COc1ccc(NC(=O)Nc2cc3ccc(OC4CCN(C)CC4)c(C)c3oc2=O)cc1-c1ccccc1]

1-(6-methoxy-[1,1'-biphenyl]-3-yl)-3-(8-methyl-7-((1-methylpiperidin-4-yl)oxy)-2-oxo-2H-chromen-3-yl)urea $^1$H NMR (500 MHz, CDCl$_3$) δ 8.60 (s, 1H), 8.43 (s, broad, 2H, NH), 7.60 (dd, J=8.8, 2.6 Hz, 1H), 7.55-7.50 (m, 3H), 7.39 (t, J=7.5 Hz, 2H), 7.35-7.31 (m, 1H), 7.25 (d, J=8.6 Hz, 1H), 6.93 (d, J=8.9 Hz, 1H), 6.83 (d, J=8.8 Hz, 1H), 4.42 (m, 1H), 3.79 (s, 3H), 2.68 (m, 2H), 2.42 (m, 2H), 2.38 (s, 3H), 2.09 (s, 3H), 2.04 (m, 2H), 1.91 (m, 2H). $^{13}$C NMR (126 MHz, CDCl$_3$+CH$_3$OH) δ 159.65, 155.85, 153.56, 152.57, 148.66, 138.05, 131.68, 131.04, 129.29, 127.81, 126.87, 124.91, 122.60, 122.43, 121.77, 119.91, 114.68, 113.83, 111.90, 110.45, 71.37, 55.75, 51.76, 45.52, 29.90, 7.96. HRMS (ESI$^+$) m/z [M+H$^+$] calcd for C$_{30}$H$_{32}$N$_3$O$_5$ 514.2342; found 514.2339.

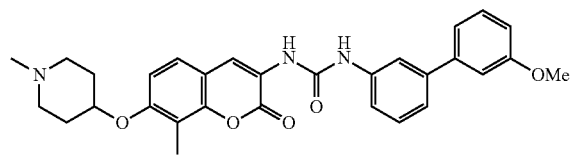 [SMILES: COc1cccc(-c2cccc(NC(=O)Nc3cc4ccc(OC5CCN(C)CC5)c(C)c4oc3=O)c2)c1]

1-(3'-methoxy-[1,1'-biphenyl]-3-yl)-3-(8-methyl-7-((1-methylpiperidin-4-yl)oxy)-2-oxo-2H-chromen-3-yl)urea $^1$H NMR (500 MHz, DMSO) δ 9.59 (s, 1H, NH), 8.73 (s, 1H, NH), 8.44 (s, 1H), 7.84 (s, 1H), 7.52-7.49 (d, J=8.6 Hz, 1H), 7.43-7.35 (m, 3H), 7.32-7.28 (dt, J=7.0, 1.8 Hz, 1H), 7.22-7.18 (m, 1H), 7.16-7.13 (t, J=2.1 Hz, 1H), 7.11-7.07 (d, J=8.9 Hz, 1H), 6.99-6.94 (dd, J=8.2, 2.5 Hz, 1H), 4.55 (m, 1H), 3.83 (s, 3H), 2.60 (m, 2H), 2.33 (m, 2H), 2.24 (s, 3H), 2.23 (s, 3H), 1.96~1.92 (m, 2H), 1.73~1.72 (m, 2H). $^{13}$C NMR (126 MHz, DMSO) δ 159.66, 158.29, 155.54, 152.30, 148.15, 141.71, 140.80, 139.74, 130.00, 129.43, 125.23, 122.46, 120.73, 120.50, 118.95, 117.19, 116.27, 113.36, 113.29, 112.95, 112.24, 110.93, 71.99, 55.10, 51.80, 45.60, 30.17, 8.10. HRMS (ESI$^+$) m/z [M+H$^+$] calcd for C$_{30}$H$_{32}$N$_3$O$_5$ 514.2342; found 514.2346.

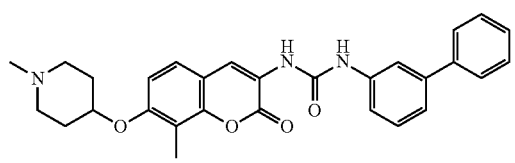 [SMILES: Cc1c(OC2CCN(C)CC2)ccc2cc(NC(=O)Nc3cccc(-c4ccccc4)c3)c(=O)oc12]

1-([1,1'-biphenyl]-3-yl)-3-(8-methyl-7-((1-methylpiperidin-4-yl)oxy)-2-oxo-2H-chromen-3-yl)urea $^1$H NMR (500 MHz, DMSO) δ 9.60 (s, 1H, NH), 8.73 (s, 1H, NH), 8.44 (s, 1H), 7.88 (s, 1H), 7.65-7.61 (dd, J=8.3, 1.1 Hz, 2H), 7.52-7.47 (m, 2H), 7.42-7.37 (m, 2H), 7.36-7.32 (m, 1H), 7.31-7.27 (dt, J=7.6, 1.3 Hz, 1H), 7.11-7.06 (d, J=8.9 Hz, 1H). 4.54 (m, 1H), 2.59 (m, 2H), 2.31 (m, 2H), 2.23 (s, 3H), 2.22 (s, 3H), 1.95 (m, 2H), 1.73 (m, 2H). $^{13}$C NMR (126 MHz, DMSO) δ 158.29, 155.55, 152.31, 148.14, 140.93, 140.19, 139.81, 129.48, 128.93, 127.54, 126.61, 125.21, 122.46, 120.62, 120.49, 117.04, 116.17, 113.35, 113.28, 110.93, 72.06, 51.83, 45.66, 30.23, 8.09. HRMS (ESI$^+$) m/z [M+H$^+$] calcd for C$_{29}$H$_{30}$N$_3$O$_4$ 484.2236; found 484.2232.

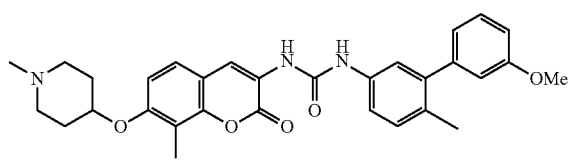 [SMILES: COc1cccc(-c2cc(NC(=O)Nc3cc4ccc(OC5CCN(C)CC5)c(C)c4oc3=O)ccc2C)c1]

1-(3'-methoxy-6-methyl-[1,1'-biphenyl]-3-yl)-3-(8-methyl-7-((1-methylpiperidin-4-yl)oxy)-2-oxo-2H-chromen-3-yl)urea $^1$H NMR (500 MHz, DMSO) δ 9.45 (s, 1H, NH), 8.66 (s, 1H, NH), 8.40 (s, 1H), 7.45 (d, J=8.6 Hz, 1H), 7.41 (d, J=2.3 Hz, 1H), 7.37 (t, J=7.9 Hz, 1H), 7.27 (m, 1H), 7.20 (m, 1H), 7.08 (d, J=8.9 Hz, 1H), 6.95 (ddd, J=8.3, 2.6, 0.8 Hz, 1H), 6.90 (dt, J=7.5, 1.1 Hz, 1H), 6.86 (dd, J=2.4, 1.6 Hz, 1H), 4.56 (m, 1H), 3.79 (s, 3H), 2.67 (m, 2H), 2.64 (m, 2H), 2.42 (s, 3H), 2.29 (s, 3H), 2.22 (s, 3H), 1.97 (m, 2H), 1.75 (m, 2H). $^{13}$C NMR (126 MHz, DMSO) δ 158.98, 158.27, 155.42, 152.26, 148.10, 142.69, 141.46, 136.99, 130.70, 129.27, 128.32, 125.14, 122.54, 121.10, 120.34, 119.08, 117.06, 114.41, 113.38, 113.36, 112.41, 110.92, 71.38, 55.06, 51.58, 45.22, 29.87, 19.45, 8.09. HRMS (ESI$^+$) m/z [M+H$^+$] calcd for C$_{31}$H$_{34}$N$_3$O$_5$ 528.2498; found 528.2495.

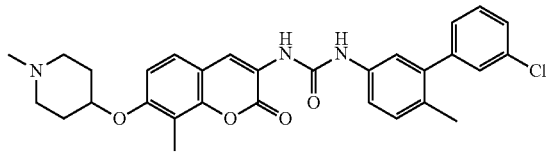 [SMILES: Cc1ccc(NC(=O)Nc2cc3ccc(OC4CCN(C)CC4)c(C)c3oc2=O)cc1-c1cccc(Cl)c1]

1-(3'-chloro-6-methyl-[1,1'-biphenyl]-3-yl)-3-(8-methyl-7-((1-methylpiperidin-4-yl)oxy)-2-oxo-2H-chromen-3-yl)urea $^1$H NMR (500 MHz, DMSO) δ 9.47 (s, 1H, NH), 8.66 (s, 1H, NH), 8.41 (s, 1H), 7.51-7.44 (m, 3H), 7.40-7.38 (t, J=1.7 Hz, 1H), 7.34-7.30 (dt, J=7.3, 1.5 Hz, 1H), 7.27-7.20 (m, 2H), 7.10-7.06 (d, J=8.9 Hz, 1H), 4.54 (m, 1H), 2.63 (m, 2H), 2.36 (m, 2H), 2.25 (s, 3H), 2.22 (s, 3H), 2.17 (s, 3H), 1.96~1.93 (m, 2H), 1.73~1.71 (m, 2H). $^{13}$C NMR (126 MHz, DMSO) δ 158.27, 155.49, 152.26, 148.11, 143.38, 140.03, 137.16, 132.88, 130.88, 130.10, 128.45, 128.32, 127.65, 126.98, 125.16, 122.48, 120.41, 119.01, 117.50, 113.37, 113.31, 110.93, 51.74, 45.48, 30.08, 19.32, 8.09. HRMS (ESI$^+$) m/z [M+H$^+$] calcd for $C_{30}H_{31}ClN_3O_4$ 532.2003; found 532.2005.

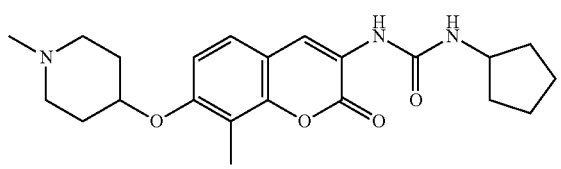 [SMILES: Cc1c(OC2CCN(C)CC2)ccc2cc(NC(=O)NC3CCCC3)c(=O)oc12]

1-cyclopentyl-3-(8-methyl-7-((1-methylpiperidin-4-yl)oxy)-2-oxo-2H-chromen-3-yl)urea $^1$H NMR (500 MHz, CDCl$_3$+CH$_3$OH) δ 8.17 (s, 1H), 7.10 (d, J=8.6 Hz, 1H), 6.71 (d, J=8.7 Hz, 1H), 4.34 (m, 1H), 3.92 (m, 1H), 2.54 (m, 2H), 2.34 (m, 2H), 2.19 (s, 3H), 2.13 (s, 3H), 1.87~1.80 (m, 6H), 1.57~1.54 (m, 2H), 1.47~1.44 (m, 2H), 1.34, 1.34~1.30 (m, 2H). $^{13}$C NMR (126 MHz, CDCl$_3$+CH$_3$OH) δ 159.82, 155.65, 155.57, 148.47, 124.79, 122.77, 121.16, 114.63, 114.02, 110.52, 71.60, 51.77, 51.42, 45.53, 33.02, 29.91, 23.44, 8.00. HRMS (ESI$^+$) m/z [M+H$^+$] calcd for $C_{22}H_{30}N_3O_4$ 400.2236; found 400.2231.

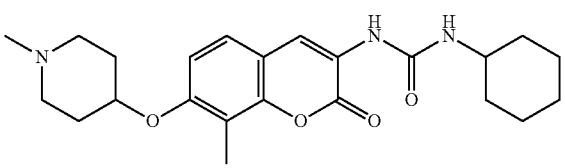 [SMILES: Cc1c(OC2CCN(C)CC2)ccc2cc(NC(=O)NC3CCCCC3)c(=O)oc12]

1-cyclohexyl-3-(8-methyl-7-((1-methylpiperidin-4-yl)oxy)-2-oxo-2H-chromen-3-yl)urea $^1$H NMR (500 MHz, CDCl$_3$) δ 8.45 (s, 1H), 7.80 (s, 1H, NH), 7.23 (d, J=8.0 Hz, 1H), 6.83 (d, J=8.0 Hz, 1H), 5.90 (d, J=5.0, 1H, NH), 4.42 (m, 1H), 3.78 (m, 1H), 2.66 (m, 2H), 2.41 (m, 2H), 2.34 (s, 3H), 2.32 (s, 3H), 2.20~2.01 (m, 4H), 1.98~1.90 (m, 2H), 1.76~1.72 (m, 2H), 1.62~1.58 (m, 1H), 1.42~1.35 (m, 2H), 1.31~1.19 (m, 3H). $^{13}$C NMR (126 MHz, CDCl$_3$) δ 160.50, 156.09, 154.76, 148.69, 125.15, 123.26, 121.59, 115.02, 114.41, 110.96, 72.24, 52.44, 49.06, 46.29, 33.74, 30.75, 25.93, 25.00, 8.46. HRMS (ESI$^+$) m/z [M+H$^+$] calcd for $C_{23}H_{32}N_3O_4$ 414.2393; found 414.2394.

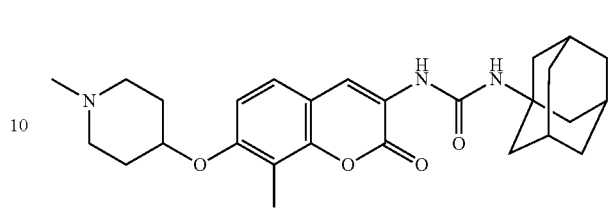

1-((3s,5s,7s)-adamantan-1-yl)-3-(8-methyl-7-((1-methylpiperidin-4-yl)oxy)-2-oxo-2H-chromen-3-yl)urea $^1$H NMR (500 MHz, CDCl$_3$) δ 8.42 (s, 1H), 7.63 (s, 1H, NH), 7.20 (d, J=8.0 Hz, 1H), 6.81 (d, J=8.0 hz, 1H), 5.61 (s, 1H, NH), 4.41 (m, 1H), 2.65 (m, 2H), 2.39 (m, 2H), 2.37 (s, 1H), 2.31 (s, 2H), 2.29 (s, 3H), 2.26 (s, 3H), 2.09 (m, 2H), 2.04 (m, 2H), 1.72~1.60 (m, 12H). $^{13}$C NMR (126 MHz, CDCl$_3$) δ 160.50, 156.10, 154.22, 148.66, 125.04, 123.23, 121.34, 115.05, 114.42, 110.98, 72.24, 52.49, 51.66, 46.37, 42.40, 36.66, 30.86, 29.77, 8.41. HRMS (ESI$^+$) m/z [M+H$^+$] calcd for $C_{27}H_{36}N_3O_4$ 466.2706; found 466.2705.

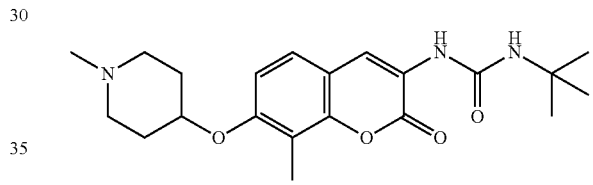

1-(tert-butyl)-3-(8-methyl-7-((1-methylpiperidin-4-yl)oxy)-2-oxo-2H-chromen-3-yl)urea $^1$H NMR (500 MHz, CDCl$_3$) δ 8.14 (s, 1H), 7.10 (d, J=8.0 Hz, 1H), 6.70 (d, J=8.0 Hz, 1H), 4.37 (m, 1H), 2.62 (m, 2H), 2.45 (m, 2H), 2.26 (s, 3H), 2.14 (s, 3H), 1.90 (m, 2H), 1.83 (m, 2H), 1.21 (s, 9H). $^{13}$C NMR (126 MHz, CDCl$_3$) δ 159.82, 155.41, 155.03, 148.43, 124.74, 122.99, 120.86, 120.77, 114.61, 114.21, 110.45, 51.62, 50.20, 45.27, 29.54, 28.83, 8.02. HRMS (ESI$^+$) m/z [M+H$^+$] calcd for $C_{21}H_{30}N_3O_4$ 388.2236; found 388.2234.

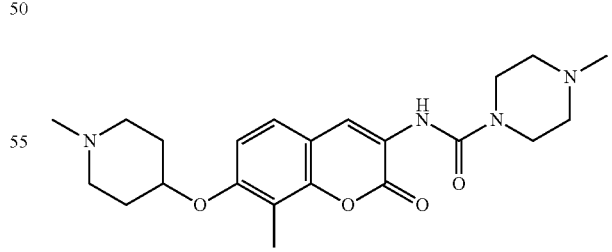

4-methyl-N-(8-methyl-7-((1-methylpiperidin-4-yl)oxy)-2-oxo-2H-chromen-3-yl)piperazine-1-carboxamide $^1$H NMR (400 MHz, CDCl$_3$) δ 8.34 (s, 1H), 7.34 9s, 1H, NH), 7.20 (d, J=8.6 Hz, 1H), 6.80 (d, J=8.7 Hz, 1H), 4.41

(m, 1H), 3.51 (t, J=5.0 Hz, 4H), 2.77 (m, 2H), 2.64 (m, 2H), 2.42 (t, J=5.0 Hz, 4H), 2.41 (s, 3H), 2.31 (s, 3H), 2.29 (s, 3H), 2.04~1.98 (m, 2H), 1.89~1.87 (m, 2H). $^{13}$C NMR (126 MHz, DMSO) δ 158.55, 155.89, 154.25, 148.77, 125.34, 124.62, 122.51, 113.31, 113.04, 110.76, 72.15, 54.26, 51.85, 45.74, 45.65, 43.53, 30.28, 8.12. HRMS (ESI$^+$) m/z [M+H$^+$] calcd for $C_{22}H_{31}N_4O_4$ 415.2345; found 415.2342.

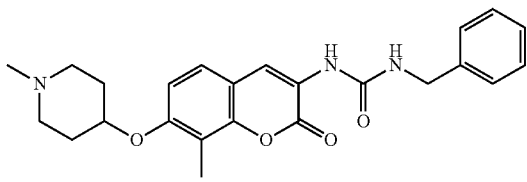 [SMILES: Cc1c(OC2CCN(C)CC2)ccc2cc(NC(=O)NCc3ccccc3)c(=O)oc12]

1-benzyl-3-(8-methyl-7-((1-methylpiperidin-4-yl)oxy)-2-oxo-2H-chromen-3-yl)urea $^1$H NMR (500 MHz, DMSO) δ 8.52 (s, 1H, NH), 8.34 (s, 1H), 7.49~7.24 (m, 7H), 7.06 (d, J=8.8 Hz, 0H), 4.52 (m, 1H), 4.32 (d, J=5.8 Hz, 1H), 2.55 (m, 2H), 2.25 (m, 2H), 2.24 (s, 3H), 2.19 (s, 3H), 1.93 (m, 2H), 1.70 (m, 2H). $^{13}$C NMR (126 MHz, DMSO) δ 158.28, 155.29, 154.97, 147.96, 139.77, 128.34, 127.09, 126.82, 124.89, 123.02, 119.56, 113.41, 113.31, 110.92, 72.35, 51.94, 45.85, 42.65, 30.40, 8.11. HRMS (ESI$^+$) m/z [M+H$^+$] calcd for $C_{24}H_{28}N_3O_4$ 422.2080; found 422.2079.

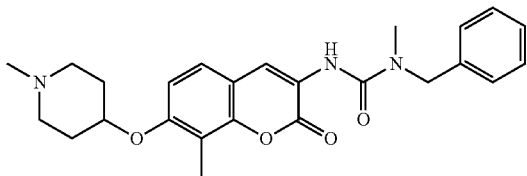 [SMILES: Cc1c(OC2CCN(C)CC2)ccc2cc(NC(=O)N(C)Cc3ccccc3)c(=O)oc12]

1-benzyl-1-methyl-3-(8-methyl-7-((1-methylpiperidin-4-yl)oxy)-2-oxo-2H-chromen-3-yl)urea $^1$H NMR (500 MHz, CDCl$_3$) δ 8.45 (s, 1H), 7.42~7.36 (m, 3H), 7.32~7.28 (m, 2H), 7.26 (d, J=8.0 Hz, 1H) 6.85 (d, J=8.0 Hz, 1H), 4.65 (s, 2H), 4.44 (m, 1H), 3.07 (s, 3H), 2.68 (m, 2H), 2.41 (m, 2H), 2.35 (s, 3H), 2.33 (s, 3H), 2.07 (m, 2H), 1.93 (m, 2H). $^{13}$C NMR (126 MHz, CDCl$_3$) δ 160.00, 156.31, 155.21, 148.96, 137.20, 128.98, 127.81, 127.63, 125.13, 122.69, 121.85, 115.25, 113.92, 110.68, 72.39, 52.43, 52.35, 46.33, 34.70, 30.82, 8.43. HRMS (ESI$^+$) m/z [M+H$^+$] calcd for $C_{25}H_{30}N_3O_4$ 436.2236; found 436.2238.

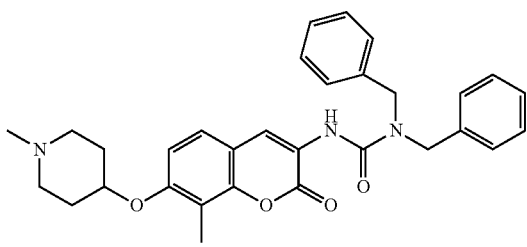 [SMILES: Cc1c(OC2CCN(C)CC2)ccc2cc(NC(=O)N(Cc3ccccc3)Cc3ccccc3)c(=O)oc12]

1,1-dibenzyl-3-(8-methyl-7-((1-methylpiperidin-4-yl)oxy)-2-oxo-2H-chromen-3-yl)urea $^1$H NMR (500 MHz, CDCl$_3$) δ 8.39 (s, 1H), 7.40 (s, 1H, NH), 7.36~7.31 (m, 4H), 7.28~7.27 (m, 6H), 7.21 (d, J=8.0 Hz, 1H), 6.78 (d, J=8.0 Hz, 1H), 4.58 (s, 4H), 4.38 (m, 1H), 2.61 (m, 2H), 2.33 (m, 2H), 2.28 (s, 3H), 2.24 (s, 3H), 1.96 (m, 2H), 1.85 (m, 2H). $^{13}$C NMR (126 MHz, CDCl$_3$) δ 159.85, 156.39, 155.45, 149.01, 136.81, 129.18, 128.10, 127.68, 125.16, 122.75, 121.98, 115.28, 113.91, 110.69, 72.69, 52.54, 50.90, 46.74, 30.82, 8.48. HRMS (ESI$^+$) m/z [M+H$^+$] calcd for $C_{31}H_{34}N_3O_4$ 512.2549; found 512.2551.

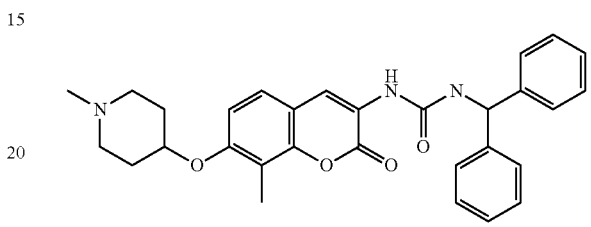

1-benzhydryl-3-(8-methyl-7-((1-methylpiperidin-4-yl)oxy)-2-oxo-2H-chromen-3-yl)urea $^1$H NMR (500 MHz, DMSO) δ 8.62 (s, 1H), 8.30 (s, 1H), 8.06 (d, J=8.0 Hz, 1H), 7.39~7.31 (m, 8H), 7.27~7.24 (m, 2H), 7.06 (d, J=8.8 Hz, 1H), 5.97 (s, 2H), 5.95 (s, 2H), 4.54 (m, 1H), 2.66 (m, 2H), 2.64 (m, 2H), 2.37 (s, 3H), 2.28 (s, 3H), 2.21, 1.94 (m, 2H), 1.74 (m, 2H). $^{13}$C NMR (126 MHz, DMSO) δ 158.30, 155.27, 154.12, 148.01, 142.96, 128.54, 127.01, 126.82, 124.96, 123.01, 119.56, 113.49, 113.41, 110.93, 71.81, 56.98, 51.69, 45.34, 29.97, 8.15. HRMS (ESI$^+$) m/z [M+H$^+$] calcd for $C_{30}H_{32}N_3O_4$ 498.2393; found 498.2397.

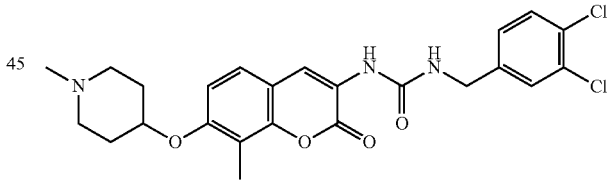

1-(3,4-dichlorobenzyl)-3-(8-methyl-7-((1-methylpiperidin-4-yl)oxy)-2-oxo-2H-chromen-3-yl)urea $^1$H NMR (500 MHz, CDCl$_3$+CH$_3$OH) δ 8.16 (s, 1H), δ 7.26 (d, J=2.0 Hz, 1H), 7.24 (d, J=8.2 Hz, 1H), 7.09 (d, J=8.6 Hz, 1H), 7.02 (dd, J=8.3, 2.1 Hz, 1H), 6.70 (d, J=8.7 Hz, 1H). 4.33 (m, 1H), 4.23 (s, 2H), 2.52 (m, 2H), 2.31 (m, 2H), 2.18 (s, 3H), 2.13 (s, 3H), 1.87 (m, 2H), 1.76 (m, 2H). $^{13}$C NMR (126 MHz, CDCl$_3$+CH$_3$OH) δ 159.63, 155.83, 148.66, 139.68, 132.35, 130.88, 130.37, 129.01, 126.56, 124.86, 122.61, 122.55, 121.68, 114.70, 113.85, 110.46, 71.83, 51.86, 45.59, 42.44, 29.99, 8.00. HRMS (ESI$^+$) m/z [M+H$^+$] calcd for $C_{24}H_{26}Cl_2N_3O_4$ 490.1300; found 490.1297.

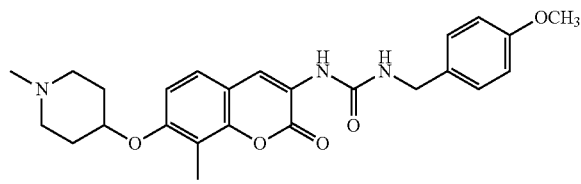 [SMILES: COc1ccc(CNC(=O)Nc2cc3ccc(OC4CCN(C)CC4)c(C)c3oc2=O)cc1]

1-(4-methoxybenzyl)-3-(8-methyl-7-((1-methylpiperidin-4-yl)oxy)-2-oxo-2H-chromen-3-yl)urea HRMS (ESI+) m/z [M+H+] calcd for $C_{25}H_{30}N_3O_5$ 452.2185; found 452.2180.

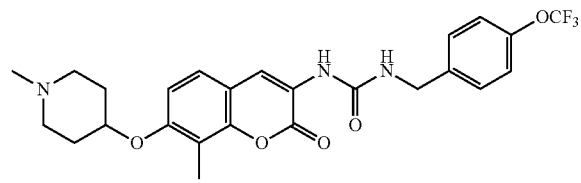 [SMILES: Cc1c(OC2CCN(C)CC2)ccc2cc(NC(=O)NCc3ccc(OC(F)(F)F)cc3)c(=O)oc12]

1-(8-methyl-7-((1-methylpiperidin-4-yl)oxy)-2-oxo-2H-chromen-3-yl)-3-(4-(trifluoromethoxy)benzyl)urea $^1$H NMR (500 MHz, CDCl$_3$) δ 8.17 (s, 1H), 7.20 (d, J=7.3 Hz, 2H), 7.10 (d, J=8.4 Hz, 1H), 7.01 (d, J=7.9 Hz, 2H), 6.70 (d, J=8.5 Hz, 1H), 5.16 (s, 2H), 4.36 (m, 1H), 4.26 (s, 2H), 2.60 (m, 2H), 2.41 (m, 2H), 2.24 (s, 3H), 2.13 (s, 3H), 1.90 (m, 2H), 1.80 (m, 2H). $^{13}$C NMR (126 MHz, DMSO) δ 158.26, 155.27, 154.99, 147.98, 147.13, 139.49, 128.88, 124.93, 122.97, 121.07, 121.02, 119.67, 113.42, 113.33, 110.90, 71.74, 51.78, 41.94, 30.07, 8.11. HRMS (ESI) m/z [M+H+] calcd for $C_{25}H_{27}FN_3O_5$ 506.1903; found 506.1899.

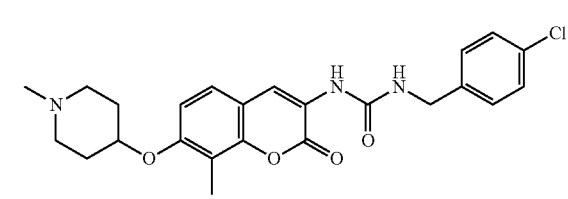 [SMILES: Cc1c(OC2CCN(C)CC2)ccc2cc(NC(=O)NCc3ccc(Cl)cc3)c(=O)oc12]

1-(4-chlorobenzyl)-3-(8-methyl-7-((1-methylpiperidin-4-yl)oxy)-2-oxo-2H-chromen-3-yl)urea 1-(8-methyl-7-((1-methylpiperidin-4-yl)oxy)-2-oxo-2H-chromen-3-yl)-3-(4-methylbenzyl)urea HRMS (ESI+) m/z [M+H+] calcd for $C_{25}H_{30}N_3O_4$ 436.2236; found 436.2234.

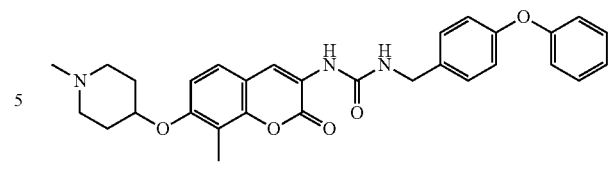

1-(8-methy-7-((1-methylpiperidin-4-yl)oxy)-2-oxo-2-chromen-3-yl)-3-(4-phenoxybenzyl)urea $^1$H NMR (500 MHz, DMSO) δ 8.51 (s, 1H, NH), 8.35 (s, 1H), 7.48 (t, J=5.8 Hz, 1H), 7.43 (d, J=8.6 Hz, 1H), 7.40-7.35 (m, 2H), 7.32 (d, J=8.6 Hz, 2H), 7.11 (tt, J=7.6, 1.1 Hz, 1H), 7.06 (d, J=8.8 Hz, 1H), 7.01 (s, 1H, NH), 7.00-6.99 (m, 2H), 6.99-6.97 (m, 1H), 4.55 (m, 1H), 4.29 (d, J=5.7 Hz, 2H), 2.66~2.64, 2.40~2.36, 2.29 (s, 3H), 2.22 (s, 3H), 1.97~1.94 (m, 2H), 1.75 (m, 2H). $^{13}$C NMR (126 MHz, DMSO) δ 158.27, 156.86, 155.34, 155.20, 154.94, 147.96, 135.01, 129.98, 128.88, 124.91, 123.23, 123.05, 119.53, 118.77, 118.27, 113.48, 113.35, 110.89, 71.76, 51.67, 45.28, 42.08, 29.97, 8.11. HRMS (ESI+) m/z [M+H+] calcd for $C_{30}H_{32}N_3O_5$ 514.2342; found 514.2346.

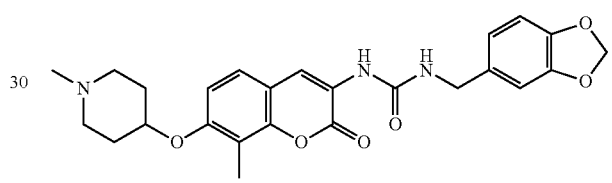

1-(benzo[d][1,3]dioxol-5-ylmethyl)-3-(8-methyl-7-((1-methylpiperidin-4-yl)oxy)-2-oxo-2H-chromen-3-yl)urea $^1$H NMR (500 MHz, CDCl$_3$+CH$_3$OH) δ 8.30 (s, 1H), 7.48 (s, 1H), 7.25 (d, J=8.6 Hz, 1H), 6.86 (d, J=8.7 Hz, 1H), 6.81-6.67 (m, 2H), 5.90 (s, 2H), 4.53 (m, 1H), 4.28 (s, 2H), 2.78 (m, 2H), 2.60 (m, 2H), 2.41 (s, 3H), 2.27 (s, 3H), 2.06 (m, 2H), 1.95 (m, 2H). $^{13}$C NMR (126 MHz, CDCl$_3$+CH$_3$OH) δ 159.47, 155.81, 155.49, 148.51, 147.66, 146.57, 132.76, 124.76, 122.66, 121.26, 120.30, 114.51, 113.93, 110.29, 107.92, 107.67, 100.78, 70.50, 51.51, 45.02, 43.15, 29.42, 7.80. HRMS (ESI+) m/z [M+H+] calcd for $C_{25}H_{28}N_3O_6$ 466.1978; found 466.1975.

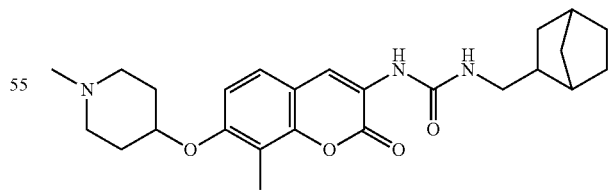

1-(bicyclo[2.2.1]heptan-2-ylmethyl)-3-(8-methyl-7-((1-methylpiperidin-4-yl)oxy)-2-oxo-2H-chromen-3-yl)urea HRMS (ESI+) m/z [M+H+] calcd for $C_{25}H_{34}N_3O_4$ 440.2549; found 440.2549.

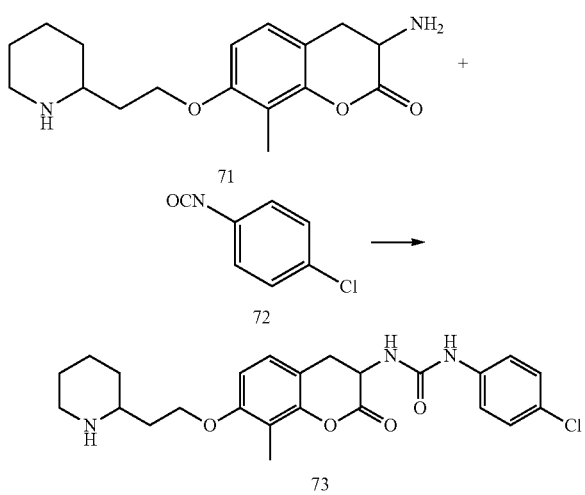

1-(4-chlorophenyl)-3-(8-methyl-2-oxo-7-(2-(piperidin-2-yl)ethoxy)chroman-3-yl)urea 4-Chlorophenyl isocyanate, 72, (0.20 mmol) was added to a solution of 3-amino-8-methyl-7-(2-(piperidin-2-yl)ethoxy)-2H-chromen-2-one, 71, (0.10 mmol) in dichloromethane (2 mL) and stirred at room temperature overnight. The resulting mixture was purified via column chromatography (SiO$_2$, 10:1 CH$_2$Cl$_2$:methanol) to afford desired product, 73 in 69% yield. $^{13}$C NMR (126 MHz, DMSO) δ 157.67, 155.78, 151.47, 146.94, 136.70, 127.47, 125.33, 124.09, 121.17, 120.26, 118.63, 112.41, 111.73, 107.91, 63.28, 53.19, 43.39, 31.56, 26.95, 20.64, 20.55, 6.76

* * *

All of the compounds, formulations, and methods disclosed and claimed herein can be made and executed without undue experimentation in light of the present disclosure. While the compounds, formulations, and methods of this invention have been described in terms of preferred embodiments, it will be apparent to those of skill in the art that variations may be applied to the compounds, formulations, and methods, as well as in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

Burlison, et al., *J. Am. Chem. Soc.*, 128:15529, 2006.
Burlison, et al., *J. Org. Chem.*, 73:2130, 2008.
Conde, et al., *Biochem. Cell Biol.*, 87:845-851, 2009.
Cox and Johnson, *Methods Mol. Biol.* (New York City, N.Y.), 787:45, 2011.
Donnelly, et al., *J. Org. Chem.*, 73:8901, 2008.
Donnelly, et al., *Med. Chem. Commun.*, 1:165, 2010.
Eskew, et al., *BMC Cancer*, 11:468, 2011.
Hanahan and Weinberg, *Cell*, 144:646-674, 2011.
*Handbook of Pharmaceutical Salts: Properties, and Use*, Stahl and Wermuth Eds.), Verlag Helvetica Chimica Acta, 2002.
*March's Advanced Organic Chemistry: Reactions, Mechanisms, and Structure*, 2007.
Marcu, et al., *J. Biol. Chem.*, 275:37181, 2000.
Marcu, et al., *J. Natl. Cancer Inst.*, 92:242-248, 2000.
Neckers and Workman, *Clin. Cancer Res.*, 1:64-76, 2012.
Robson and James, *Drug Discovery Today*, 17:544, 2012.
Shelton, et al., *Mol. Pharmacol.*, 76:1314-1322, 2009.
Taipale, et al., *Nat. Rev. Mol. Cell. Biol.*, 11:515-528, 2010.
Tran, et al., *BMC Cancer*, 10:276, 2010.
Whitesell, et al., *Curr. Mol. Med.*, 12:11108-1124, 2012.
Yu, et al., *J. Am. Chem. Soc.*, 127:12778, 2005.
Zhang, et al., *J. Proteome Research*, 11:2581, 2012.
Zhao and Blagg, *ACS Med. Chem. Lett.*, 1:311, 2010.
Zhao, et al., *J. Med. Chem.*, 2011.
Zhao, et al., *Bioorg. Med. Chem. Lett.*, 21:2659-2664, 2011.
Zhao, et al., *ACS Med. Chem. Lett.*, 3:327-331, 2012.
Zhao, et al., *ACS Med. Chem. Lett.*, 4:57-62, 2013.

What is claimed is:

1. A compound of the formula:

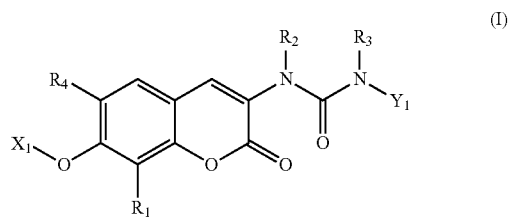

wherein:
R$_1$ and R$_2$ are each independently selected from hydrogen, alkyl$_{(C≤12)}$, or substituted alkyl$_{(C≤12)}$;
R$_3$ is hydrogen, alkyl$_{(C≤12)}$, aralkyl$_{(C≤12)}$, substituted alkyl$_{(C≤12)}$, or substituted aralkyl$_{(C≤12)}$; or R$_3$ and Y$_1$ are taken together as defined below;
R$_4$ is hydrogen, alkyl$_{(C≤12)}$, alkoxy$_{(C≤12)}$, substituted alkyl$_{(C≤12)}$, or substituted alkoxy$_{(C≤12)}$;
X$_1$ is -alkanediyl$_{(C≤8)}$-heterocycloalkyl$_{(C≤12)}$, -alkanediyl$_{(C≤8)}$-amino$_{(C≤12)}$, -alkanediyl$_{(C≤8)}$-alkylamino$_{(C≤12)}$, -alkanediyl$_{(C≤8)}$-dialkylamino$_{(C≤12)}$, heterocycloalkyl$_{(C≤12)}$, or a substituted version of any of these groups; and
Y$_1$ is alkyl$_{(C≤12)}$, cycloalkyl$_{(C≤12)}$, adamantyl$_{(C≤18)}$, aryl$_{(C≤18)}$, aralkyl$_{(C≤18)}$, acyl$_{(C≤12)}$, -alkanediyl$_{(C≤8)}$-cycloalkyl$_{(C≤12)}$, -arenediyl$_{(C≤12)}$-alkene$_{(C≤8)}$, -arenediyl$_{(C≤12)}$-aryl$_{(C≤12)}$, -arenediyl$_{(C≤12)}$-aralkyl$_{(C≤12)}$, -arenediyl$_{(C≤12)}$-aryloxy$_{(C≤12)}$, or a substituted version of any of these groups; or R$_3$ and Y$_1$ are taken together and are alkanediyl$_{(C≤8)}$, alkylaminodiyl$_{(C≤8)}$, alkoxydiyl$_{(C≤8)}$, or a substituted version of any of these groups; or

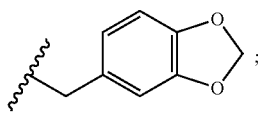 [SMILES: *Cc1ccc2c(c1)OCO2]

wherein the compound is not selected from:

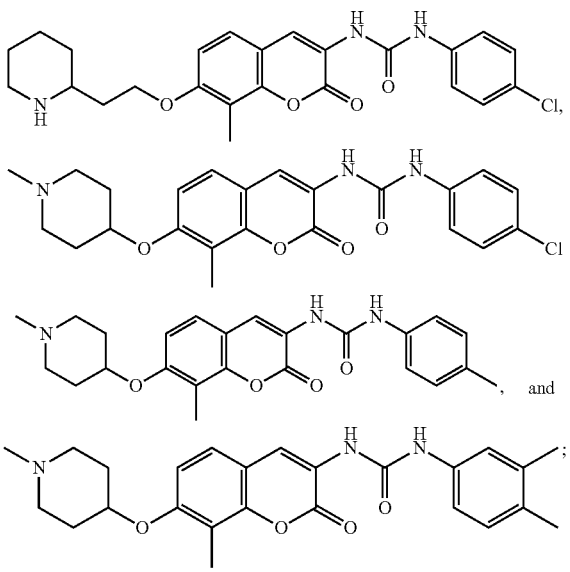

or a pharmaceutically acceptable salt thereof.

2. The compound of claim 1 further defined as:

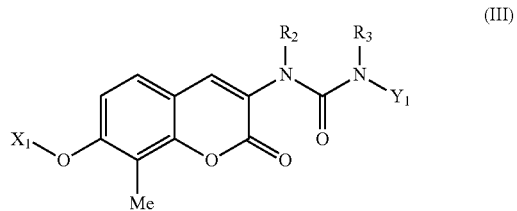

wherein:
R$_1$ and R$_2$ are each independently selected from hydrogen, alkyl$_{(C\leq12)}$, or substituted alkyl$_{(C\leq12)}$;
R$_3$ is hydrogen, alkyl$_{(C\leq12)}$, aralkyl$_{(C\leq12)}$, substituted alkyl$_{(C\leq12)}$, or substituted aralkyl$_{(C\leq12)}$; or R$_3$ and Y$_1$ are taken together as defined below;
X$_1$ is -alkanediyl$_{(C\leq8)}$-heterocycloalkyl$_{(C\leq12)}$, -alkanediyl$_{(C\leq8)}$-amino$_{(C\leq12)}$, -alkanediyl$_{(C\leq8)}$-alkylamino$_{(C\leq12)}$, -alkanediyl$_{(C\leq8)}$-dialkylamino$_{(C\leq12)}$, heterocycloalkyl$_{(C\leq12)}$, or a substituted version of any of these groups; and
Y$_1$ is alkyl$_{(C\leq12)}$, cycloalkyl$_{(C\leq12)}$, adamantyl$_{(C\leq18)}$, aryl$_{(C\leq18)}$, aralkyl$_{(C\leq18)}$, acyl$_{(C\leq12)}$, -alkanediyl$_{(C\leq8)}$-cycloalkyl$_{(C\leq12)}$, -arenediyl$_{(C\leq12)}$-alkene$_{(C\leq8)}$, -arenediyl$_{(C\leq12)}$-aryl$_{(C\leq12)}$, -arenediyl$_{(C\leq12)}$-aralkyl$_{(C\leq12)}$, -arenediyl$_{(C\leq12)}$-aryloxy$_{(C\leq12)}$, or a substituted version of any of these groups; or R$_3$ and Y$_1$ are taken together and are alkanediyl$_{(C\leq8)}$, alkyl aminodiyl$_{(C\leq8)}$, alkoxydiyl$_{(C\leq8)}$, or a substituted version of any of these groups; or

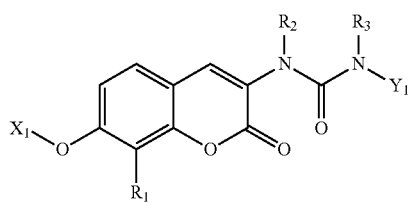

or a pharmaceutically acceptable salt thereof.

3. The compound of claim 1 further defined as:

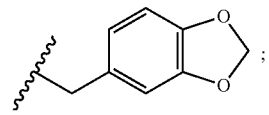

wherein:
R$_2$ is hydrogen, alkyl$_{(C\leq12)}$, or substituted alkyl$_{(C\leq12)}$;
R$_3$ is hydrogen, alkyl$_{(C\leq12)}$, aralkyl$_{(C\leq12)}$, substituted alkyl$_{(C\leq12)}$, or substituted aralkyl$_{(C\leq12)}$; or R$_3$ and Y$_1$ are taken together as defined below;
X$_1$ is -alkanediyl$_{(C\leq8)}$-heterocycloalkyl$_{(C\leq12)}$, -alkanediyl$_{(C\leq8)}$-amino$_{(C\leq12)}$, -alkanediyl$_{(C\leq8)}$-alkylamino$_{(C\leq12)}$, -alkanediyl$_{(C\leq8)}$-dialkylamino$_{(C\leq12)}$, heterocycloalkyl$_{(C\leq12)}$, or a substituted version of any of these groups; and
Y$_1$ is alkyl$_{(C\leq12)}$, cycloalkyl$_{(C\leq12)}$, adamantyl$_{(C\leq18)}$, aryl$_{(C\leq18)}$, aralkyl$_{(C\leq18)}$, acyl$_{(C\leq12)}$, -alkanediyl$_{(C\leq8)}$-cycloalkyl$_{(C\leq12)}$, -arenediyl$_{(C\leq12)}$-alkene$_{(C\leq8)}$, -arenediyl$_{(C\leq12)}$-aryl$_{(C\leq12)}$, -arenediyl$_{(C\leq12)}$-aralkyl$_{(C\leq12)}$, -arenediyl$_{(C\leq12)}$-aryloxy$_{(C\leq12)}$, or a substituted version of any of these groups; or R$_3$ and Y$_1$ are taken together and are alkanediyl$_{(C\leq8)}$, alkyl aminodiyl$_{(C\leq18)}$, alkoxydiyl$_{(C\leq8)}$, or a substituted version of any of these groups; or

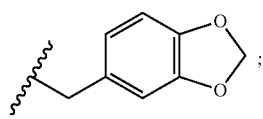 [SMILES: *Cc1ccc2c(c1)OCO2]

or a pharmaceutically acceptable salt thereof.

4. The compound of claim 1 further defined as:

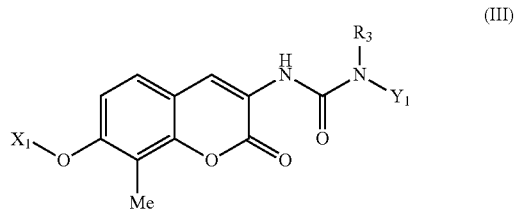

wherein:
R$_3$ is hydrogen, alkyl$_{(C\leq12)}$, aralkyl$_{(C\leq12)}$, substituted alkyl$_{(C\leq12)}$, or substituted aralkyl$_{(C\leq12)}$; or R$_3$ and Y$_1$ are taken together as defined below;
X$_1$ is -alkanediyl$_{(C\leq8)}$-heterocycloalkyl$_{(C\leq12)}$, -alkanediyl$_{(C\leq8)}$-amino$_{(C\leq12)}$, -alkanediyl$_{(C\leq8)}$-alkylamino$_{(C\leq12)}$, -alkanediyl$_{(C\leq8)}$-dialkylamino$_{(C\leq12)}$, heterocycloalkyl$_{(C\leq12)}$, or a substituted version of any of these groups; and
Y$_1$ is alkyl$_{(C\leq12)}$, cycloalkyl$_{(C\leq12)}$, adamantyl$_{(C\leq18)}$, aryl$_{(C\leq18)}$, aralkyl$_{(C\leq18)}$, acyl$_{(C\leq12)}$, -alkanediyl$_{(C\leq8)}$-cycloalkyl$_{(C\leq12)}$, -arenediyl$_{(C\leq12)}$-alkene$_{(C\leq8)}$, -arenediyl$_{(C\leq12)}$-aryl$_{(C\leq12)}$, -arenediyl$_{(C\leq12)}$ -aralkyl$_{(C≤12)}$, -arenediyl$_{(C≤12)}$-aryloxy$_{(C≤12)}$, or a substituted version of any of these groups; or $R_3$ and $Y_1$ are taken together and are alkanediyl$_{(C≤8)}$, alkyl aminodiyl$_{(C≤8)}$, alkoxydiyl$_{(C≤8)}$, or a substituted version of any of these groups; or

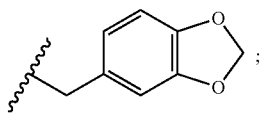 [SMILES: *Cc1ccc2c(c1)OCO2]

or a pharmaceutically acceptable salt thereof.

5. The compound of claim 1 further defined as:

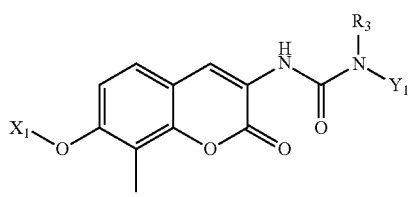

(III)

wherein:

$R_3$ is hydrogen, alkyl$_{(C≤12)}$, substituted alkyl$_{(C≤12)}$, aralkyl$_{(C≤12)}$, or substituted aralkyl$_{(C≤12)}$; or $R_3$ and $Y_1$ are taken together as defined below;

$X_1$ is heterocycloalkyl$_{(C≤12)}$ or substituted heterocycloalkyl$_{(C≤12)}$; and $Y_1$ is alkyl$_{(C≤12)}$, cycloalkyl$_{(C≤12)}$, adamantyl$_{(C≤18)}$, aryl$_{(C≤18)}$, aralkyl$_{(C≤18)}$, acyl$_{(C≤12)}$, -alkanediyl$_{(C≤8)}$-cycloalkyl$_{(C≤12)}$, -arenediyl$_{(C≤12)}$-alkene$_{(C≤8)}$, -arenediyl$_{(C≤12)}$-aryl$_{(C≤12)}$, -arenediyl$_{(C≤12)}$-aralkyl$_{(C≤12)}$, -arenediyl$_{(C≤12)}$-aryloxy$_{(C≤12)}$, or a substituted version of any of these groups; or $R_3$ and $Y_1$ are taken together and are alkanediyl$_{(C≤8)}$, alkyl aminodiyl$_{(C≤8)}$, alkoxydiyl$_{(C≤8)}$, or a substituted version of any of these groups; or

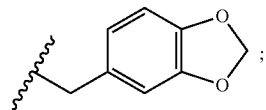 [SMILES: *Cc1ccc2c(c1)OCO2]

or a pharmaceutically acceptable salt thereof.

6. The compound of claim 1, wherein $R_3$ is hydrogen.

7. The compound of claim 1, wherein $R_3$ is alkyl$_{(C≤6)}$.

8. The compound of claim 1, wherein $X_1$ is heterocycloalkyl$_{(C≤8)}$ or substituted heterocycloalkyl$_{(C≤8)}$.

9. The compound of claim 8, wherein $X_1$ is:

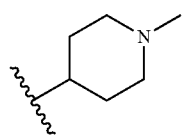

10. The compound of claim 1, wherein $Y_1$ is aryl$_{(C≤18)}$ or substituted aryl$_{(C≤18)}$.

11. The compound of claim 10, wherein $Y_1$ is aryl$_{(C≤12)}$.

12. The compound of claim 10, wherein $Y_1$ is biphenyl$_{(C≤12)}$.

13. The compound of claim 10, wherein $Y_1$ is substituted aryl$_{(C≤12)}$.

14. The compound of claim 10, wherein $Y_1$ is substituted biphenyl$_{(C≤18)}$.

15. The compound of claim 1, wherein $Y_1$ is aralkyl$_{(C≤18)}$ or substituted aralky$_{(C≤18)}$.

16. The compound of claim 1, wherein the compound is further defined as:

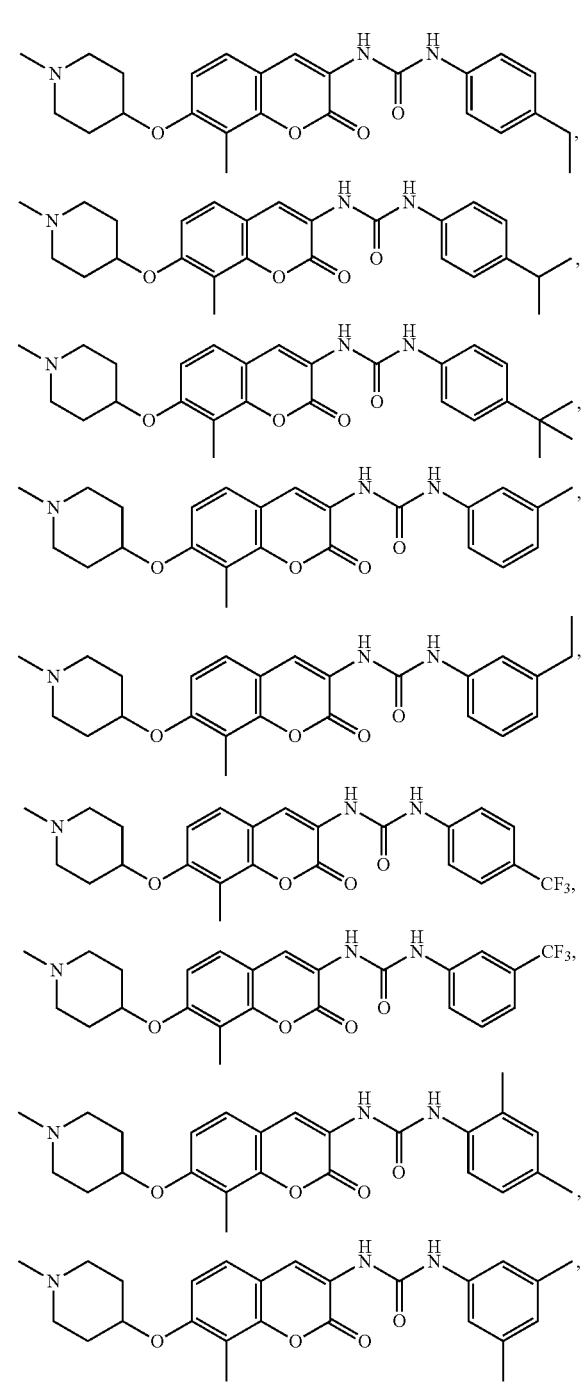

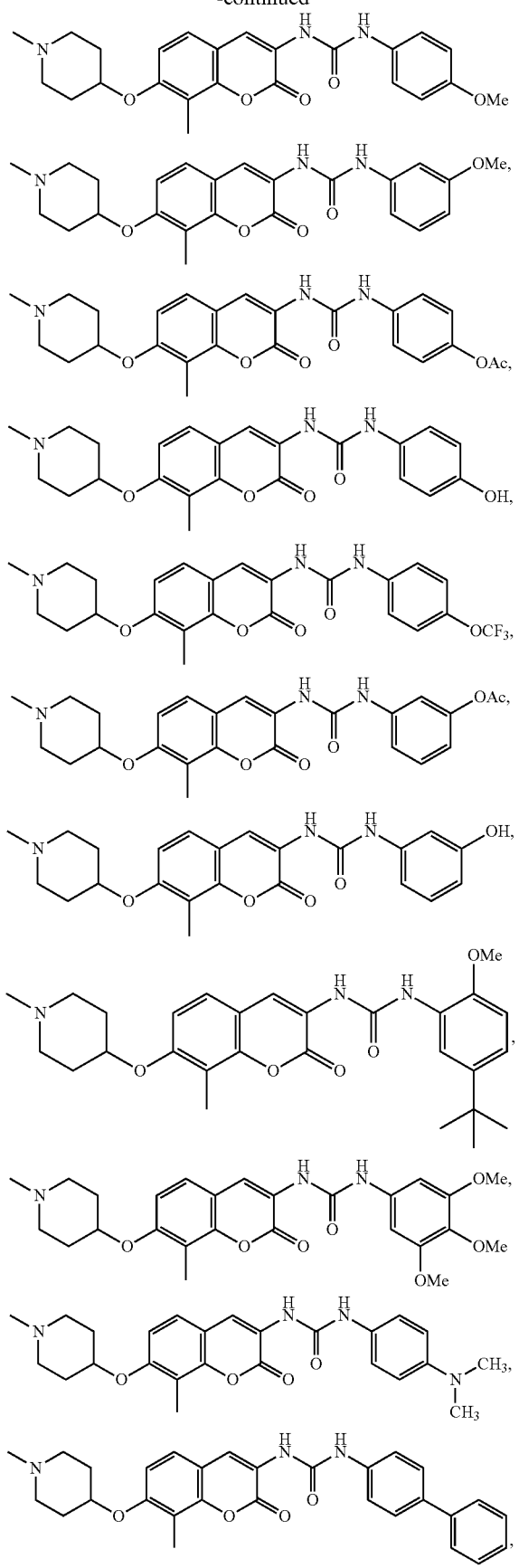
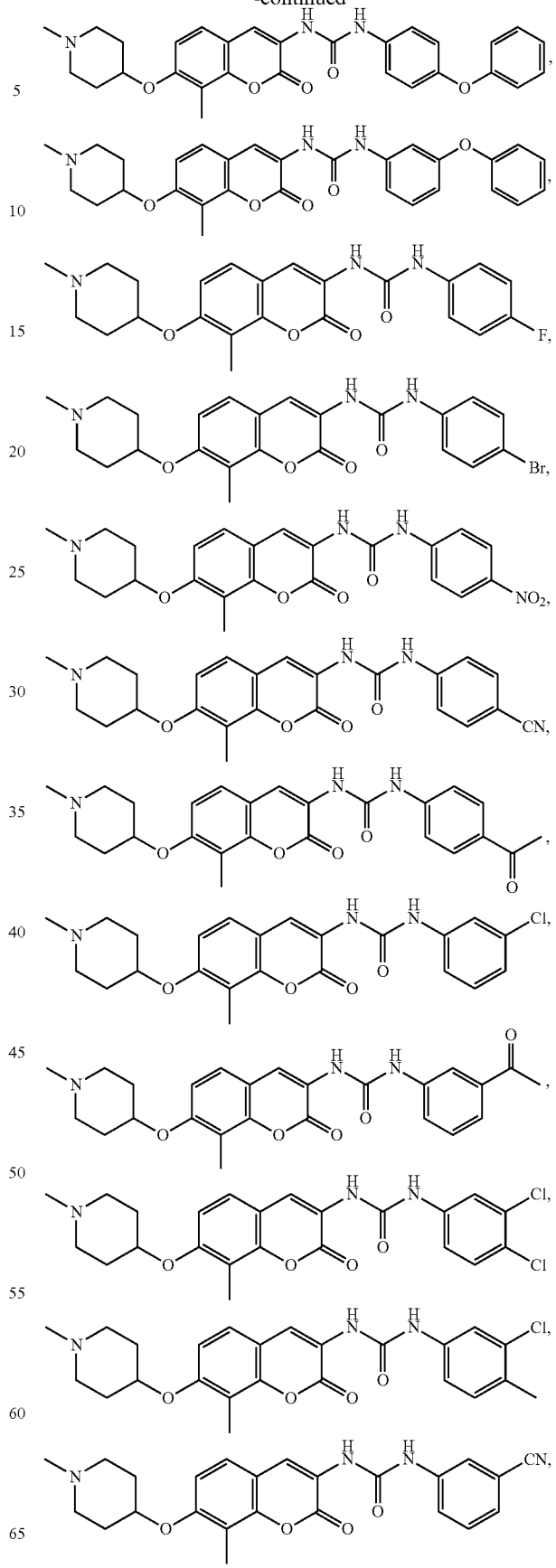

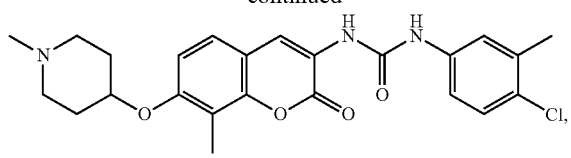
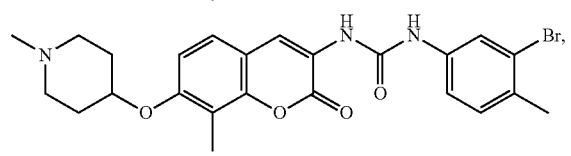
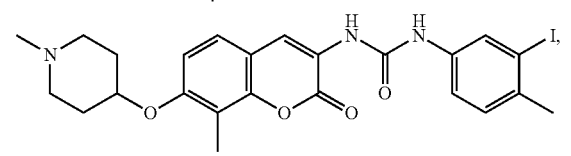
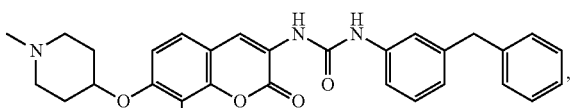
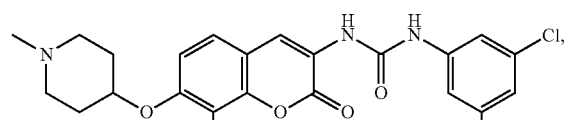
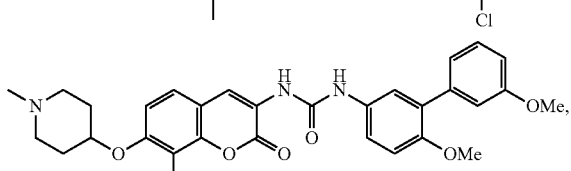
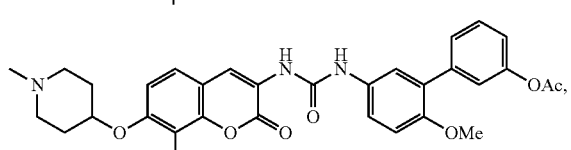
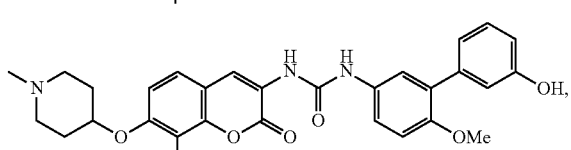
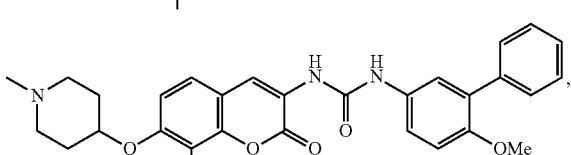
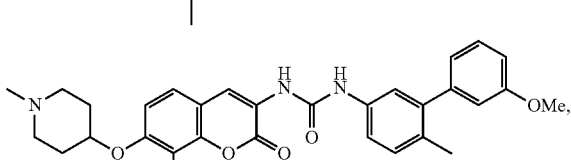
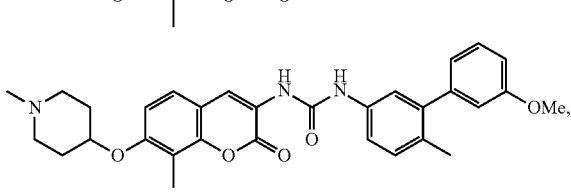
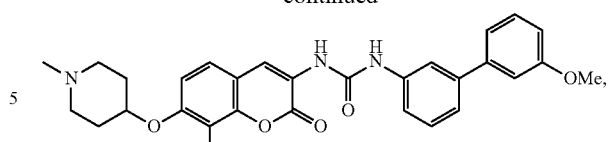
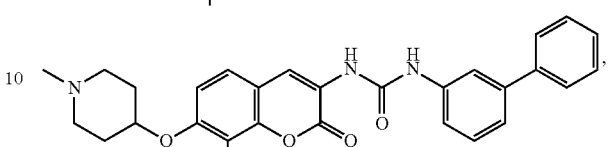
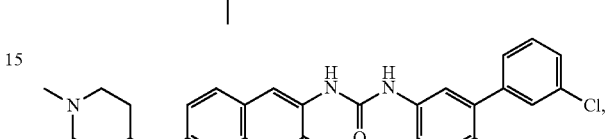
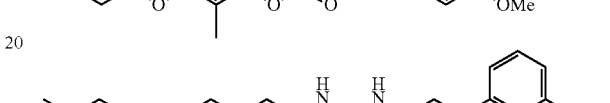
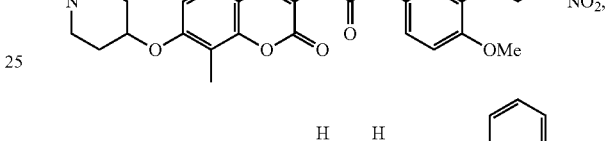
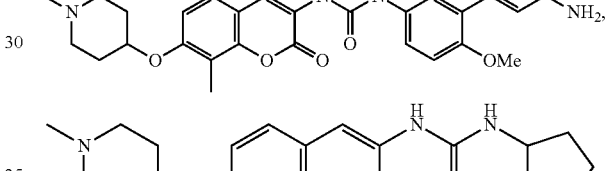
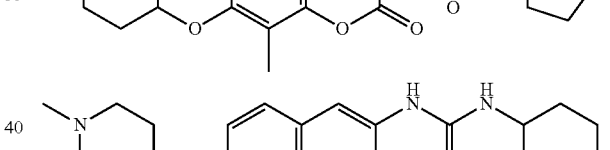
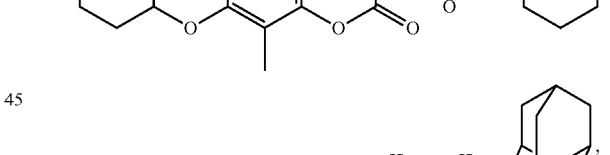
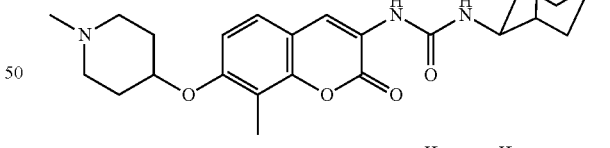
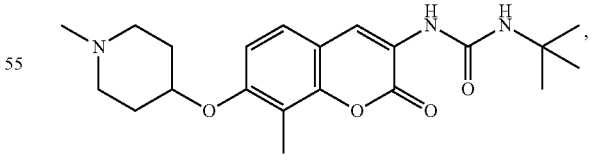
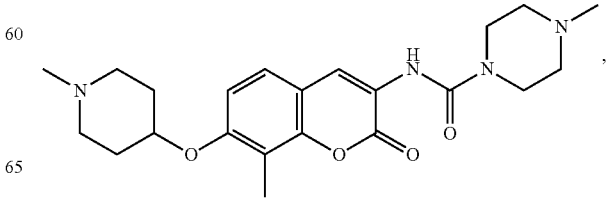

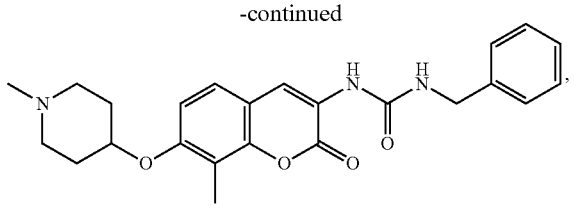
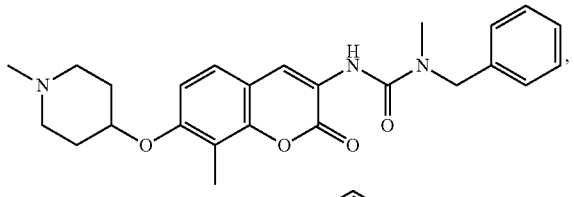
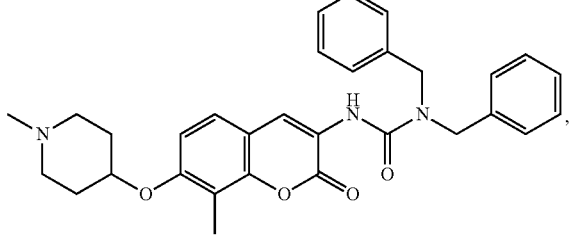
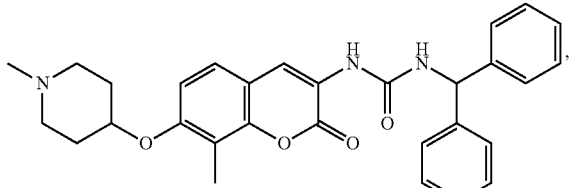
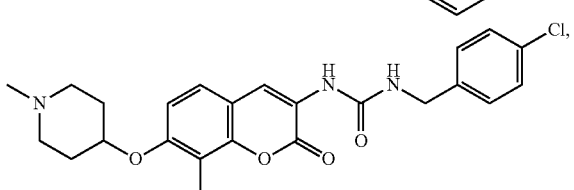
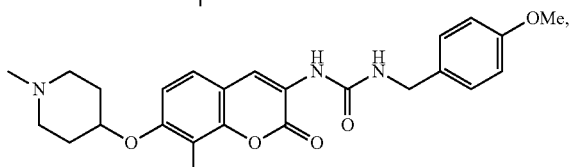
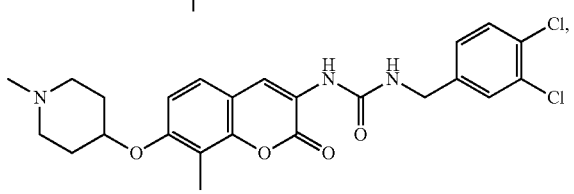
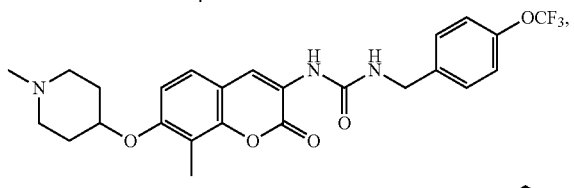
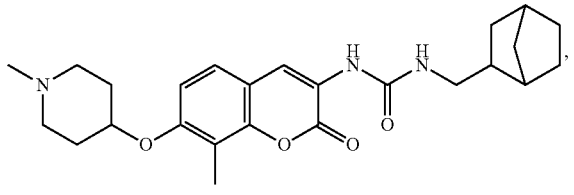
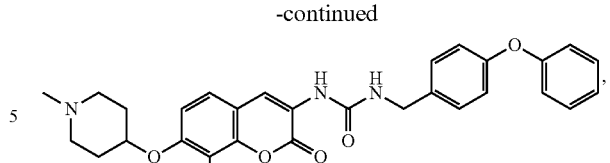
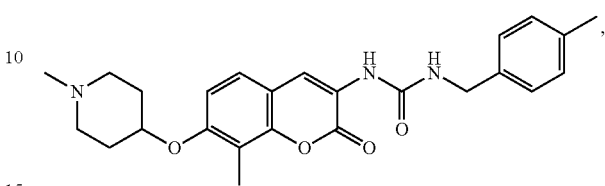
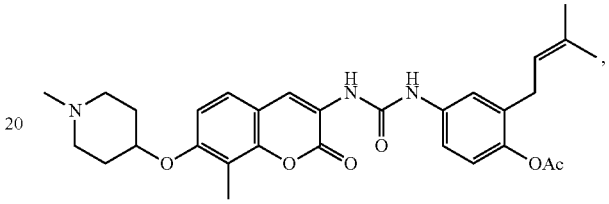
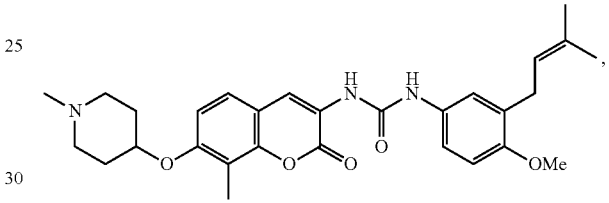
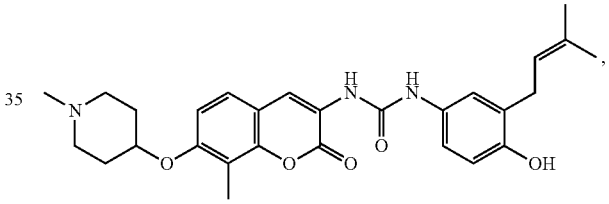
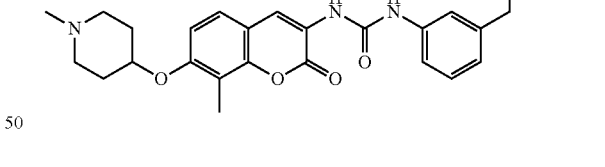
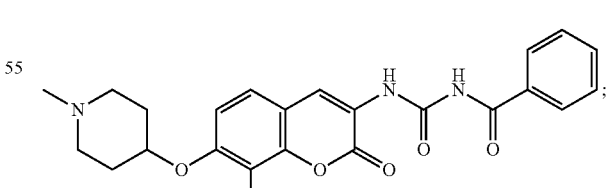
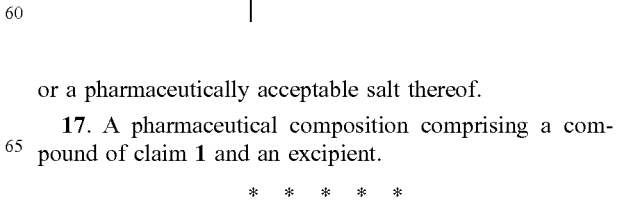
or a pharmaceutically acceptable salt thereof.
17. A pharmaceutical composition comprising a compound of claim 1 and an excipient.
* * * * *

UNITED STATES PATENT AND TRADEMARK OFFICE
CERTIFICATE OF CORRECTION

PATENT NO. : 10,030,006 B2
APPLICATION NO. : 15/035610
DATED : July 24, 2018
INVENTOR(S) : Brian S. J. Blagg and Huiping Zhao It is certified that error appears in the above-identified patent and that said Letters Patent is hereby corrected as shown below:

In the Claims

In Claim 16, Column 147, please delete the compound at Line 5.

Signed and Sealed this
Thirteenth Day of August, 2019

Andrei Iancu
*Director of the United States Patent and Trademark Office*

UNITED STATES PATENT AND TRADEMARK OFFICE
CERTIFICATE OF CORRECTION

PATENT NO. : 10,030,006 B2
APPLICATION NO. : 15/035610
DATED : July 24, 2018
INVENTOR(S) : Brian S. J. Blagg and Huiping Zhao It is certified that error appears in the above-identified patent and that said Letters Patent is hereby corrected as shown below:

In the Specification

Column 1, Lines 10-14, delete the entire contents and insert --This invention was made with government support under CA120458 awarded by the National Institutes of Health and W81XWH-05-1-0594 awarded by the Department of Defense. The government has certain rights in the invention.-- therefor.

Signed and Sealed this
Twenty-seventh Day of October, 2020

Andrei Iancu
*Director of the United States Patent and Trademark Office*